United States Patent
Zawistoski et al.

(10) Patent No.: US 9,944,603 B2
(45) Date of Patent: *Apr. 17, 2018

(54) COMPOUNDS AND METHODS FOR THE TREATMENT OF CYSTIC FIBROSIS

(71) Applicant: Flatley Discovery Lab, LLC, Charlestown, MA (US)

(72) Inventors: Michael P. Zawistoski, West Warwick, RI (US); Yevgen Barsukov, Brookline, MA (US); Bridget M. Cole, Quincy, MA (US); Richard A. Nugent, Ashland, MA (US)

(73) Assignee: FLATLEY DISCOVERY LAB, LLC, Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,413

(22) Filed: Apr. 10, 2017

(65) Prior Publication Data

US 2017/0313659 A1 Nov. 2, 2017

Related U.S. Application Data

(63) Continuation of application No. 14/210,238, filed on Mar. 13, 2014, now abandoned.

(60) Provisional application No. 61/778,883, filed on Mar. 13, 2013.

(51) Int. Cl.

| | |
|---|---|
| C07D 401/14 | (2006.01) |
| A61K 31/437 | (2006.01) |
| C07D 211/96 | (2006.01) |
| C07D 401/12 | (2006.01) |
| A61K 31/4525 | (2006.01) |
| A61K 31/4725 | (2006.01) |
| A61K 31/7036 | (2006.01) |
| A61K 45/06 | (2006.01) |
| A61K 31/506 | (2006.01) |
| C07D 417/12 | (2006.01) |
| A61K 31/454 | (2006.01) |
| C07D 413/12 | (2006.01) |
| C07D 405/14 | (2006.01) |
| A61K 31/4545 | (2006.01) |
| C07D 471/04 | (2006.01) |
| A61K 31/4245 | (2006.01) |
| A61K 31/443 | (2006.01) |
| A61K 31/497 | (2006.01) |
| A61K 31/4468 | (2006.01) |

(52) U.S. Cl.
CPC ........ *C07D 211/96* (2013.01); *A61K 31/4245* (2013.01); *A61K 31/437* (2013.01); *A61K 31/443* (2013.01); *A61K 31/4468* (2013.01); *A61K 31/454* (2013.01); *A61K 31/4525* (2013.01); *A61K 31/4545* (2013.01); *A61K 31/4725* (2013.01); *A61K 31/497* (2013.01); *A61K 31/506* (2013.01); *A61K 31/7036* (2013.01); *A61K 45/06* (2013.01); *C07D 401/12* (2013.01); *C07D 401/14* (2013.01); *C07D 405/14* (2013.01); *C07D 413/12* (2013.01); *C07D 417/12* (2013.01); *C07D 471/04* (2013.01)

(58) Field of Classification Search
CPC ........................... C07D 401/14; A61K 31/437
USPC ............................................ 546/119; 514/303
See application file for complete search history.

(56) References Cited

U.S. PATENT DOCUMENTS 9,771,327 B2 * 9/2017 Zawistoski ........ A61K 31/4245

* cited by examiner

*Primary Examiner* — Niloofar Rahmani
(74) *Attorney, Agent, or Firm* — Elmore Patent Law Group, P.C.; Edgar Harlan; Carolyn Elmore

(57) ABSTRACT

The invention relates to a compound of Formula I and methods of treating cystic fibrosis comprising the step of administering a therapeutically effective amount of a compound of Formula I or IA to a patient in need thereof.

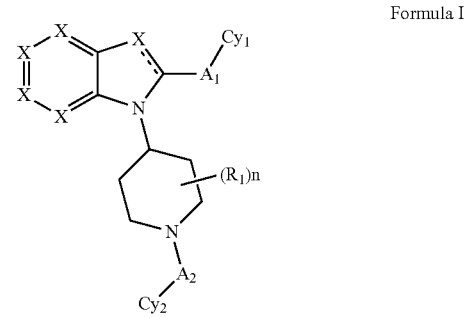

Formula I

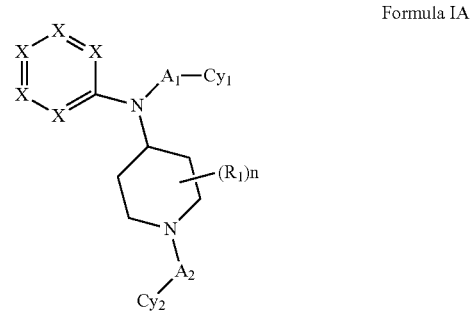

Formula IA

2 Claims, No Drawings

COMPOUNDS AND METHODS FOR THE TREATMENT OF CYSTIC FIBROSIS

RELATED APPLICATIONS

This application is a continuation of application Ser. No. 14/210,238 filed on Mar. 13, 2014, which claims the benefit of U.S. Provisional Application No. 61/778,883, filed on Mar. 13, 2013. The entire teachings of the above applications are incorporated herein by reference.

BACKGROUND

Cystic fibrosis (CF) is a lethal, recessive, genetic disease affecting approximately 1 in 2500 live births among Caucasians. (Cohen-Cymberknoh M, Shoseyov D, Kerem E. Managing cystic fibrosis: strategies that increase life expectancy and improve quality of life. Am J Respir Crit Care Med (2011); 183: 1463-1471; Boat T F, Welsh M J and Beaudet A L. Cystic fibrosis. (1989) IN "The Metabolic Basis of Inherited Disease" (C L Scriver, A L Beaudet, W S Sly and D Valee, eds.), $6^{th}$ Ed., pp. 2649-2680. McGraw-Hill, New York). Approximately 1 in 25 persons are carriers of the genetic defect associated with the disease. The major symptoms of cystic fibrosis include chronic pulmonary disease, pancreatic exocrine insufficiency, infertility in males, and elevated sweat electrolyte levels. The symptoms are consistent with cystic fibrosis being an exocrine disorder. (Hantash F: U.S. Patent Application No. 20060057593. Method for detecting cystic fibrosis. (2004). Published Mar. 16, 2006).

The CF gene codes for a cAMP/PKA-dependent, ATP-requiring, membrane-bound chloride ion channel known as CFTR (cystic fibrosis transmembrane conductance regulator), and is generally localized to the apical membranes of many secreting epithelia There are currently over 1700 known mutations affecting CFTR, many of which give rise to a disease phenotype. Around 75% of CF alleles contain the ⇋F508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cutbert A W. New horizons in the treatment of cystic fibrosis. British J Pharm, (2011), 163: 173-183).

Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, Deficiency in bicarbonate secretion due to loss of CFTR function also results in a lower pH at the airway surface which impairs anti-bacterial killing activity and increases susceptibility to infection. An exaggerated inflammatory response in response to chronic lung infections leads to the development of bronchiectasis and progressive obstructive airways disease. Pulmonary insufficiency is responsible for most CF-related deaths. (Cohen-Cymberknoh M, Shoseyov D, Kerem E. Managing cystic fibrosis: strategies that increase life expectancy and improve quality of life. Am J Respir Crit Care Med (2011); 183: 1463-1471).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C, Smyth A. Treatment strategies for cystic fibrosis: what's in the pipeline? Pharmacotherapy (2009), 10: 1191-1202).

SUMMARY

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I or IA to a patient in need thereof:

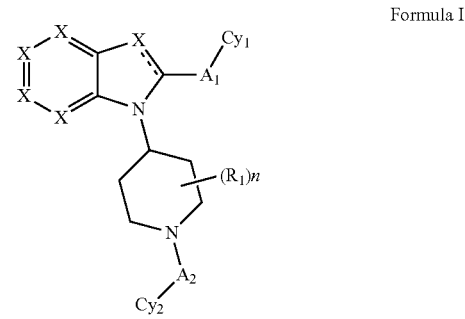

Formula I

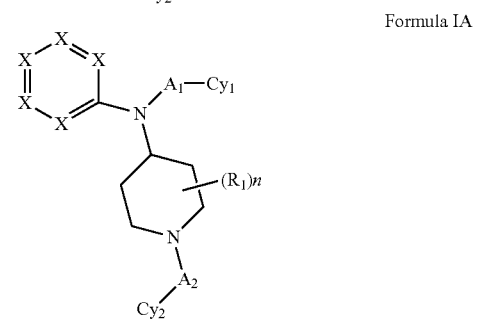

Formula IA

Wherein n is 0, 1, 2, 3, 4, 5, 6 or 7;
Each X is independently selected from —$CR_{100}$, —N—, —$COR_{100}$, —$CN(R_{100})(R_{101})$, —$CSR_{100}$, —C—C(O)$NR_{100}$, and —$CN(R_{100})C(O)R_{101}$;
$A_1$ is absent, —[$C(R_{100})(R_{101})$]$_m$— —C(O)—, —C(S)—, —S(O)—, —C(O)N($R_{100}$)—, —S(O)$_2$N($R_{100}$)($R_{101}$) or —S(O)$_2$—, —N[$C(R_{100})(R_{101})$]$_m$—, —N($R_{100}$)C(O)—, —N($R_{100}$)C(S)—, —N($R_{100}$)S(O)—, —N($R_{101}$)C(O)N($R_{100}$)— or —N($R_{100}$)S(O)$_2$—, —N($R_{100}$)S(O)$_2$N($R_{100}$)($R_{101}$);
Wherein m is 0, 1, 2, 3, 4, 5, 6 or 7;
Wherein each $R_{100}$ and $R_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent, $-[C(R_{100})(R_{101})]_m-$ $-C(O)-$, $-C(S)-$, $-S(O)-$, $-C(O)N(R_{100})-$, $-S(O)_2N(R_{100})(R_{101})$ or $-S(O)_2-$;

Each $R_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl $-OR_{100}$, $-SR_{100}$, $-S(O)-$, $S(O)_2-$, $-S(O)_2N(R_{100})(R_{101})-NR_{100}R_{101}$, $-C(O)R_{100}$, $-C(O)OR_{100}$, $-C(O)NR_{100}R_{101}$, $-N(R_{100})C(O)R_{101}$, $-CF_3$, $-CN$, $-NO_2$, $-N_3$, acyl, alkoxy, substituted alkoxy, alkylamino, substituted alkylamino, dialkylamino, substituted dialkylamino, alkylthio or substituted alkylthio; alternatively two of $R_1$ groups together with the atoms to which they are attached and any intervening atoms may form an additional optionally substituted 3, 4, 5, 6 or 7 membered ring;

$Cy_1$ is absent, alkyl, cycloalkyl, substituted cycloalkyl, aryl, substituted aryl, heteroaryl or substituted heteroaryl;

$Cy_2$ is alkyl, cycloalkyl, substituted cycloalkyl, aryl, substituted aryl, heteroaryl or substituted heteroaryl.

DETAILED DESCRIPTION OF THE INVENTION

The invention relates to a compound of Formula I and methods of treating cystic fibrosis comprising the step of administering a therapeutically effective amount of a compound of Formula I or IA to a patient in need thereof:

Formula I

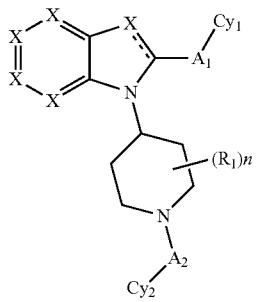

Formula IA

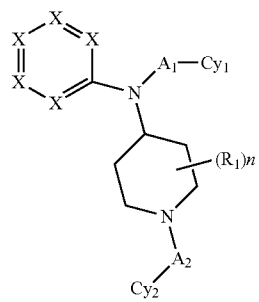

Wherein n is 0, 1, 2, 3, 4, 5, 6 or 7;

Each X is independently selected from $-CR_{100}-$, $-N-$, $-COR_{100}$, $-CN(R_{100})(R_{101})$, $-CSR_{100}$, $-C-C(O)NR_{100}$, and $-CN(R_{100})C(O)R_{101}$;

$A_1$ is absent, $-[C(R_{100})(R_{101})]_m-$ $-C(O)-$, $-C(S)-$, $-S(O)-$, $-C(O)N(R_{100})-$ or $-S(O)_2-$, $-S(O)_2N(R_{100})(R_{101})$, $-N[C(R_{100})(R_{101})]_m-$, $-N(R_{100})C(O)-$, $-N(R_{100})C(S)-$, $-N(R_{100})S(O)-$, $-N(R_{101})C(O)N(R_{100})-$ or $-N(R_{100})S(O)_2-$, $-N(R_{100})S(O)_2N(R_{100})(R_{101})$;

Wherein m is 0, 1, 2, 3, 4, 5, 6 or 7;

Wherein each $R_{100}$ and $R_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent, $-[C(R_{100})(R_{101})]_m-$ $-C(O)-$, $-C(S)-$, $-S(O)-$, $-C(O)N(R_{100})-$ or $-S(O)_2-$, $-S(O)_2N(R_{100})(R_{101})$;

Each $R_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl $-OR_{100}$, $-SR_{100}$, $-S(O)-$, $S(O)_2-$, $-S(O)_2N(R_{100})(R_{101})-NR_{100}R_{101}$, $-C(O)R_{100}$, $-C(O)OR_{100}$, $-C(O)NR_{100}R_{101}$, $-N(R_{100})C(O)R_{101}$, $-CF_3$, $-CN$, $-NO_2$, $-N_3$, acyl, alkoxy, substituted alkoxy, alkylamino, substituted alkylamino, dialkylamino, substituted dialkylamino, alkylthio or substituted alkylthio; alternatively two of $R_1$ groups together with the atoms to which they are attached and any intervening atoms may form an additional optionally substituted 3, 4, 5, 6 or 7 membered ring;

$Cy_1$ is absent, alkyl, cycloalkyl, substituted cycloalkyl, aryl, substituted aryl, heteroaryl or substituted heteroaryl;

$Cy_2$ is alkyl, cycloalkyl, substituted cycloalkyl aryl, substituted aryl, heteroaryl or substituted heteroaryl.

In a preferred embodiment, the invention relates to a compound having the Formula II or IIA:

Formula II

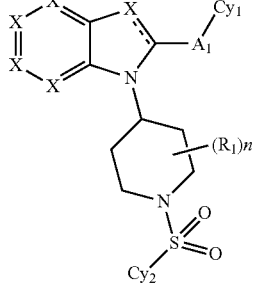

Formula IIA

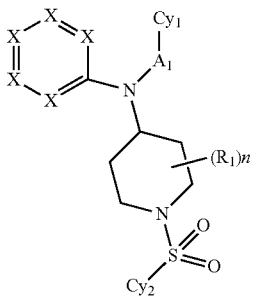

Wherein n is 0, 1, 2, 3, 4, 5, 6 or 7;

Each X is independently selected from $-CR_{100}-$, $-N-$, $-COR_{100}$, $-CN(R_{100})(R_{101})$, $-CSR_{100}-C-C(O)NR_{100}$, and $-CN(R_{100})C(O)R_{101}$;

$A_1$ is absent, —[C($R_{100}$)($R_{101}$)]$_m$—, —C(O)—, —C(S)—, —S(O)—, —C(O)N($R_{100}$)— or —S(O)$_2$—, —S(O)$_2$N($R_{100}$)($R_{101}$), —N[C($R_{100}$)($R_{101}$)]$_m$—, —N($R_{100}$)C(O)—, —N($R_{100}$)C(S)—, —N($R_{100}$)S(O)—, —N($R_{101}$)C(O)N($R_{100}$)— or —N($R_{100}$)S(O)$_2$—, —N($R_{100}$)S(O)$_2$N($R_{100}$)($R_{101}$);

Wherein m is 0, 1, 2, 3, 4, 5, 6 or 7;

Wherein each $R_{100}$ and $R_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl; alternatively two of $R_{100}$ and $R_{101}$ groups together with the atoms to which they are attached and any intervening atoms may form an additional optionally substituted, 3, 4, 5, 6 or 7 membered ring;

Each $R_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —O$R_{100}$, —S$R_{100}$, —S(O)—, S(O)$_2$—, —S(O)$_2$N($R_{100}$)($R_{101}$)—N$R_{100}$$R_{101}$, —C(O)$R_{100}$, —C(O)O$R_{100}$, —C(O)N$R_{100}$$R_{101}$, —N($R_{100}$)C(O)$R_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio;

Alternatively two of $R_1$ groups together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group;

$Cy_1$ is absent, cycloalkyl, substituted cycloalkyl, aryl, substituted aryl, heteroaryl or substituted heteroaryl;

$Cy_2$ is aryl, substituted aryl, heteroaryl or substituted heteroaryl.

In one embodiment, the —C($R_{100}$) from X and an $R_{100}$ group from $A_1$ together with the atoms to which they are attached and any intervening atoms form a $C_3$-$C_7$ fused or bridged ring; preferably a $C_3$-$C_7$ heterocyclic or heteroaryl ring.

In a preferred embodiment, the invention relates to a compound having the Formula III or IIIA:

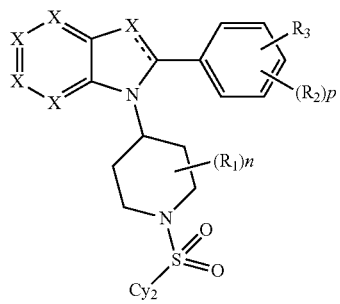

Formula III

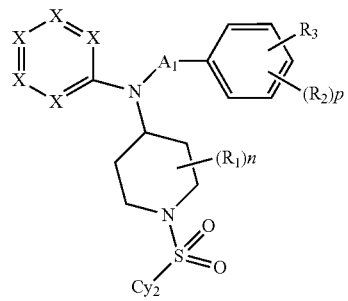

Formula IIIA

Wherein p is 0, 1, 2 or 3;

Each $R_2$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —O$R_{100}$, —S$R_{100}$, —S(O)—, S(O)$_2$—, —S(O)$_2$N($R_{100}$)($R_{101}$), —N$R_{100}$$R_{101}$, —C(O)$R_{100}$, —C(O)O$R_{100}$, —C(O)N$R_{100}$$R_{101}$, —N($R_{100}$)C(O)$R_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio; and, $R_3$ is selected from halogen, deuterium, alkyl, substituted alkyl, cycloalkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —O$R_{100}$, —S$R_{100}$, —S(O)—, S(O)$_2$—, —S(O)$_2$N($R_{100}$)($R_{101}$), —N$R_{100}$$R_{101}$, —C(O)$R_{100}$, —C(O)O$R_{100}$, —C(O)N$R_{100}$$R_{101}$, —N($R_{100}$)C(O)$R_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio;

alternatively two of $R_2$ groups or an $R_2$ group with an $R_3$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, the invention relates to a compound having the Formula IV or IVA:

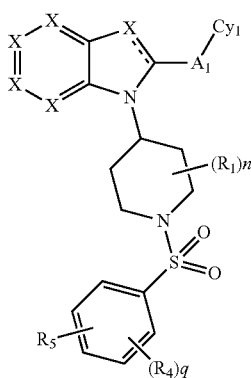

Formula IV

Formula IVA

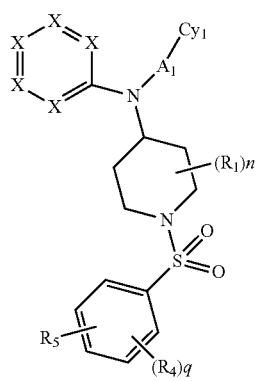

Wherein q is 0, 1, 2 or 3;

Each $R_4$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —$S(O)$—, $S(O)_2$—, —$S(O)_2N(R_{100})(R_{101})$, —$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio; and, $R_5$ is selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —$S(O)$—, $S(O)_2$—, —$S(O)_2N(R_{100})(R_{101})$, —$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio;

alternatively two of $R_4$ groups or an $R_4$ group with an $R_5$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, the invention relates to a compound having the Formula V or VA:

Formula V

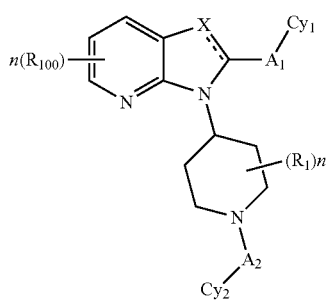

Formula VA

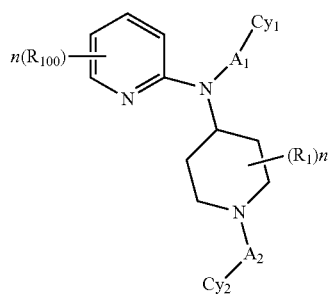

In a preferred embodiment, $Cy_1$ is selected from:

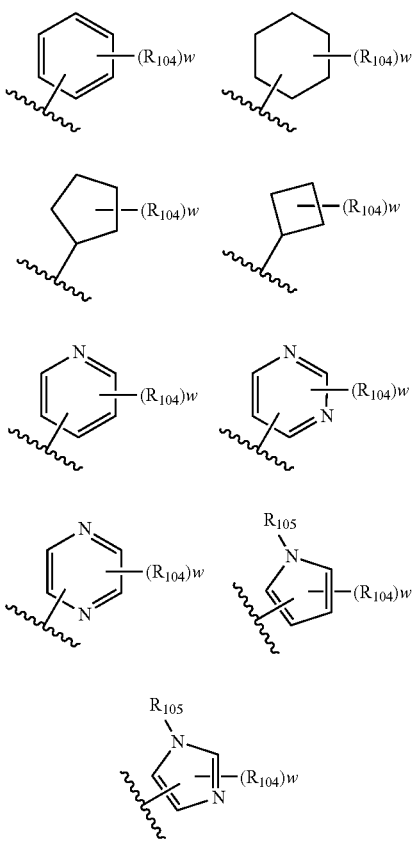

Wherein w is 0, 1, 2, 3 or 4;

Each $R_{104}$ and $R_{105}$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —$S(O)$—, $S(O)_2$—, —$S(O)_2N(R_{100})(R_{101})$, —$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, substituted alkoxy, alkylamino, substituted alkylamino, dialkylamino, substituted dialkylamino, alkylthio or substituted alkylthio;

Alternatively, two of $R_{104}$ groups or an $R_{104}$ group with an $R_{105}$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, $Cy_2$ is selected from:

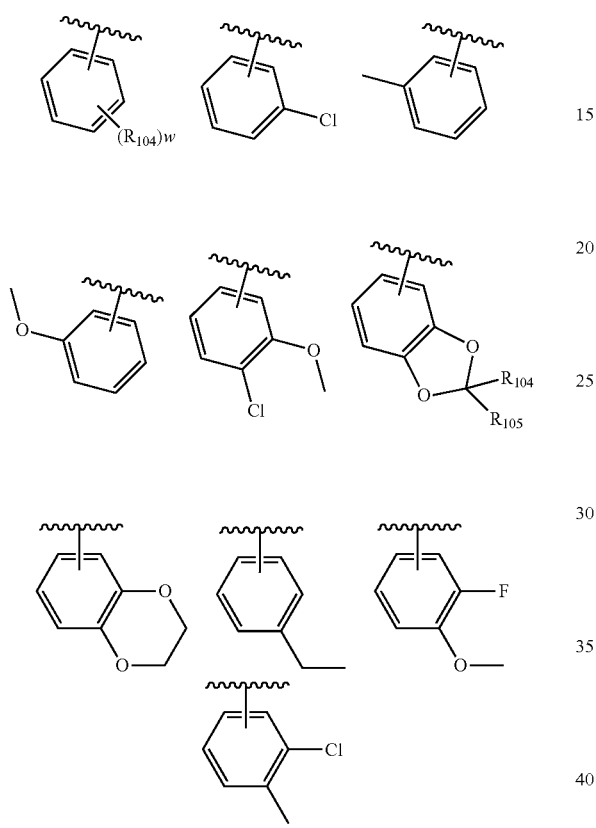

In a more preferred embodiment, a compound of formula I is selected from Table 1:

TABLE 1

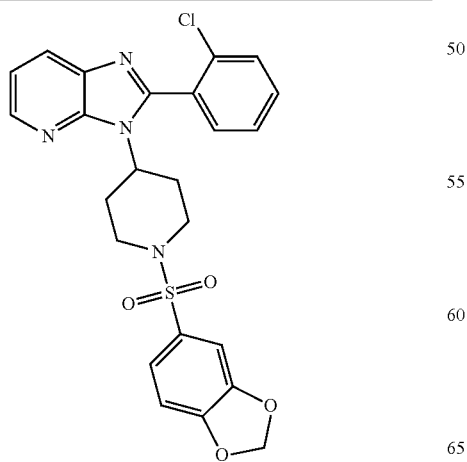

TABLE 1-continued

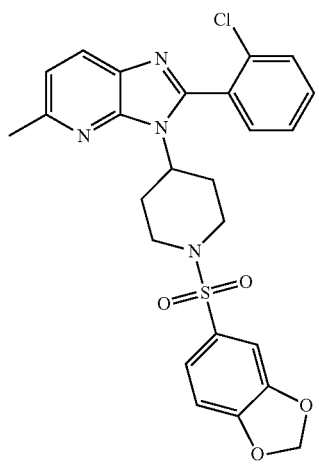 [SMILES: Cc1ccc2nc(-c3ccccc3Cl)n(C3CCN(S(=O)(=O)c4ccc5c(c4)OCO5)CC3)c2n1]

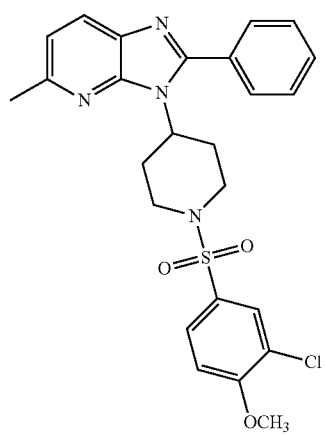 [SMILES: COc1ccc(S(=O)(=O)N2CCC(n3c(-c4ccccc4)nc4ccc(C)nc43)CC2)cc1Cl]

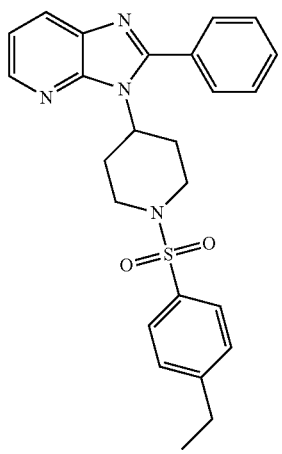 [SMILES: CCc1ccc(S(=O)(=O)N2CCC(n3c(-c4ccccc4)nc4cccnc43)CC2)cc1]

TABLE 1-continued
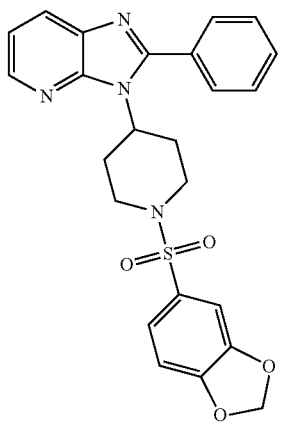 [SMILES: O=S(=O)(c1ccc2c(c1)OCO2)N1CCC(n2c(-c3ccccc3)nc3cccnc32)CC1]
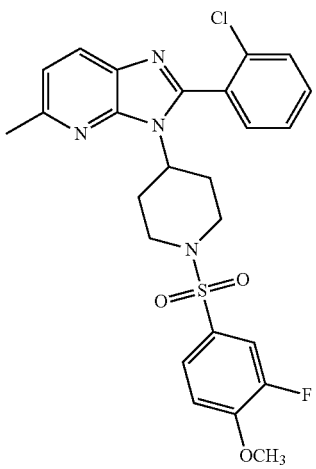
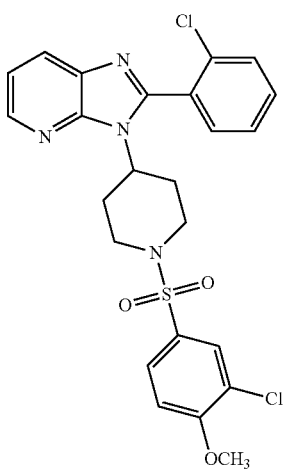
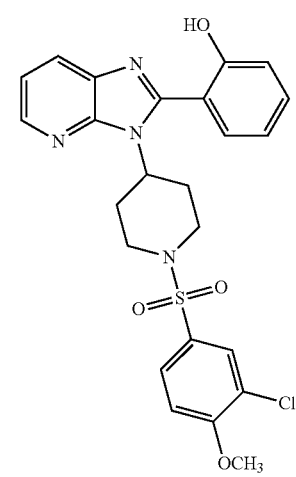
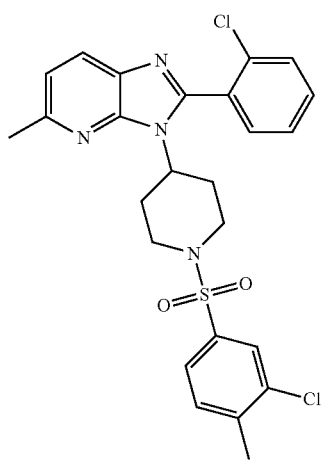 [SMILES: Cc1ccc2nc(-c3ccccc3Cl)n(C3CCN(S(=O)(=O)c4ccc(C)c(Cl)c4)CC3)c2n1]
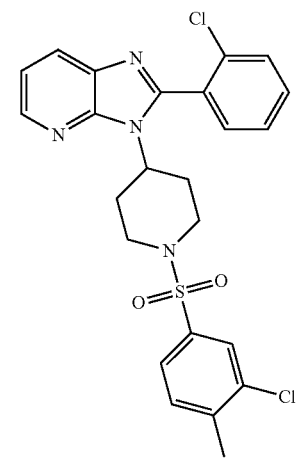 [SMILES: Cc1ccc(S(=O)(=O)N2CCC(n3c(-c4ccccc4Cl)nc4cccnc43)CC2)cc1Cl]

TABLE 1-continued
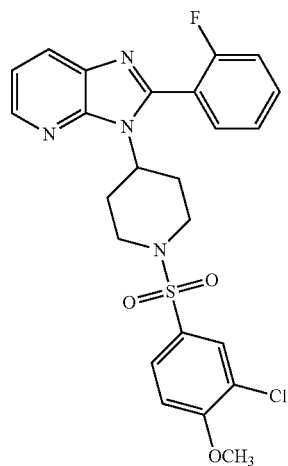
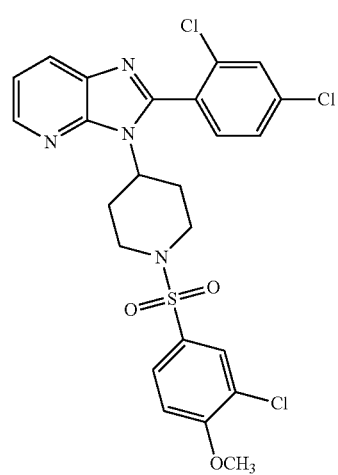 [SMILES: COc1ccc(S(=O)(=O)N2CCC(n3c(-c4ccc(Cl)cc4Cl)nc4cccnc43)CC2)cc1Cl]
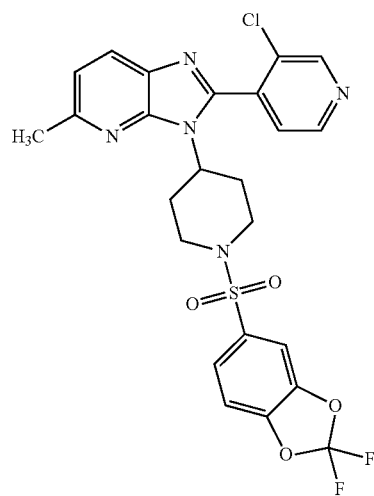 [SMILES: Cc1ccc2nc(-c3ccncc3Cl)n(C3CCN(S(=O)(=O)c4ccc5c(c4)OC(F)(F)O5)CC3)c2n1]
TABLE 1-continued
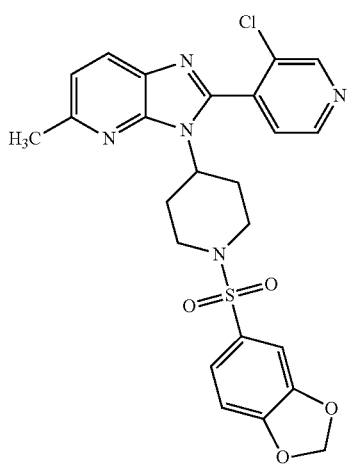 [SMILES: Cc1ccc2nc(-c3ccncc3Cl)n(C3CCN(S(=O)(=O)c4ccc5c(c4)OCO5)CC3)c2n1]
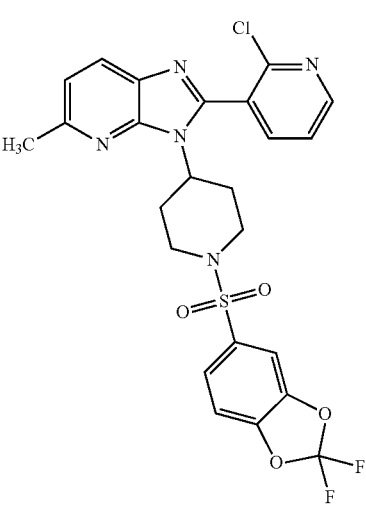 [SMILES: Cc1ccc2nc(-c3cccnc3Cl)n(C3CCN(S(=O)(=O)c4ccc5c(c4)OC(F)(F)O5)CC3)c2n1]
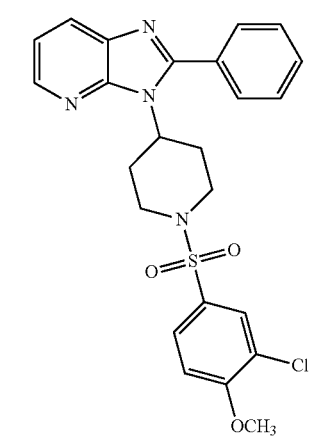

TABLE 1-continued
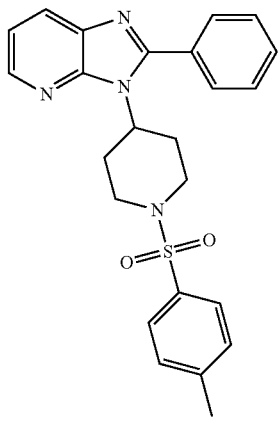 [SMILES: Cc1ccc(S(=O)(=O)N2CCC(n3c(-c4ccccc4)nc4cccnc43)CC2)cc1]
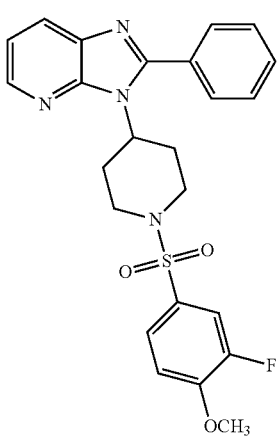 [SMILES: COc1ccc(S(=O)(=O)N2CCC(n3c(-c4ccccc4)nc4cccnc43)CC2)cc1F]
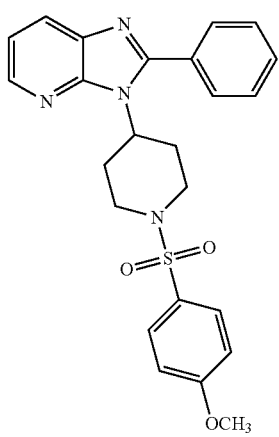 [SMILES: COc1ccc(S(=O)(=O)N2CCC(n3c(-c4ccccc4)nc4cccnc43)CC2)cc1]
TABLE 1-continued
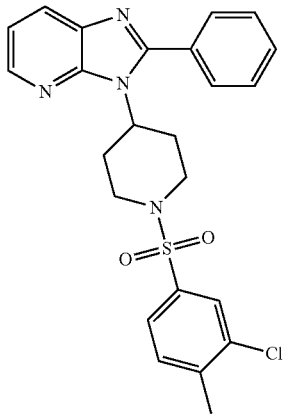 [SMILES: Cc1ccc(S(=O)(=O)N2CCC(n3c(-c4ccccc4)nc4cccnc43)CC2)cc1Cl]
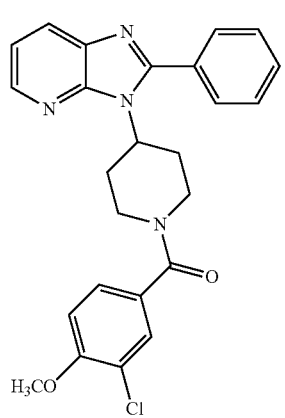 [SMILES: COc1ccc(C(=O)N2CCC(n3c(-c4ccccc4)nc4cccnc43)CC2)cc1Cl]
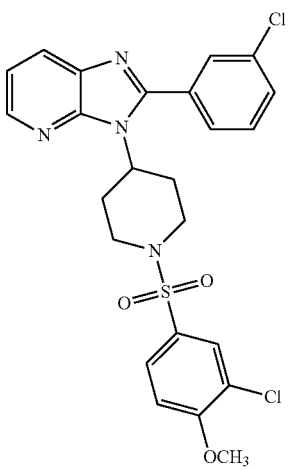 [SMILES: COc1ccc(S(=O)(=O)N2CCC(n3c(-c4cccc(Cl)c4)nc4cccnc43)CC2)cc1Cl]

TABLE 1-continued
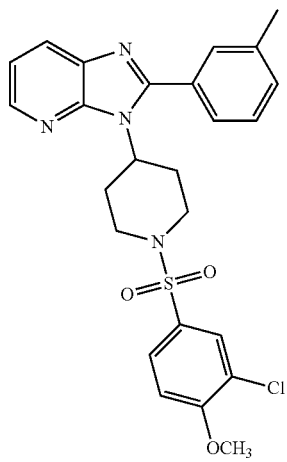 [SMILES: COc1ccc(S(=O)(=O)N2CCC(n3c(-c4cccc(C)c4)nc4cccnc43)CC2)cc1Cl]
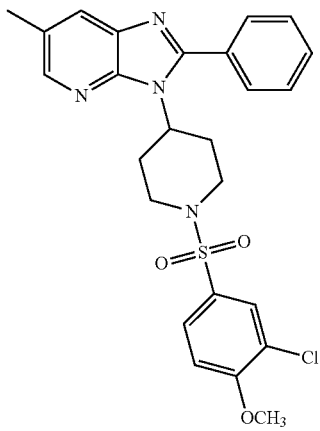
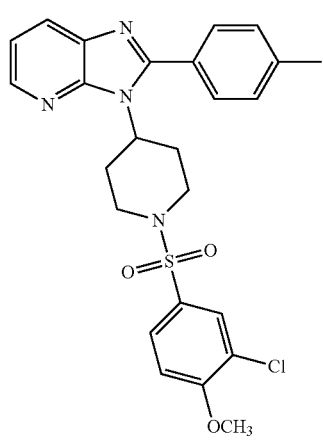 [SMILES: COc1ccc(S(=O)(=O)N2CCC(n3c(-c4ccc(C)cc4)nc4cccnc43)CC2)cc1Cl]
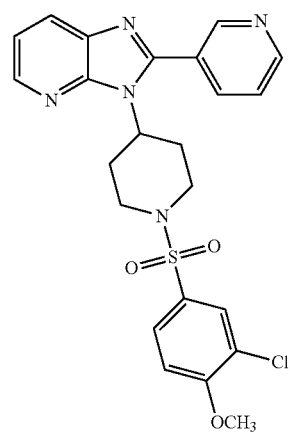
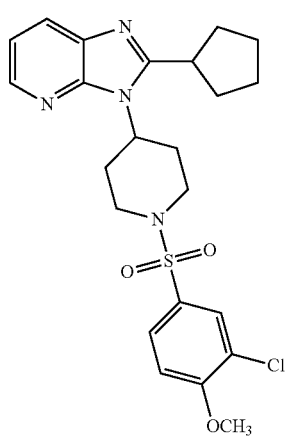 [SMILES: COc1ccc(S(=O)(=O)N2CCC(n3c(C4CCCC4)nc4cccnc43)CC2)cc1Cl]
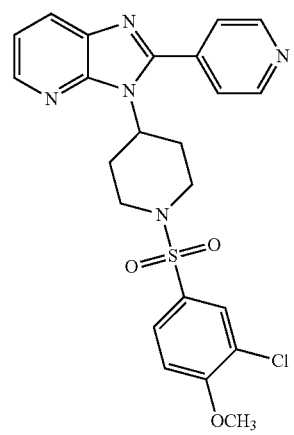

TABLE 1-continued
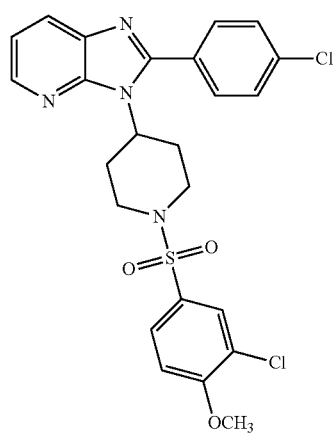 [SMILES: COc1ccc(S(=O)(=O)N2CCC(n3c(-c4ccc(Cl)cc4)nc4cccnc43)CC2)cc1Cl]
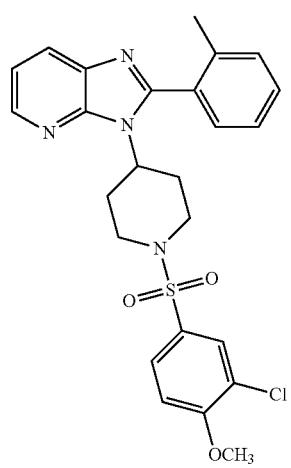 [SMILES: COc1ccc(S(=O)(=O)N2CCC(n3c(-c4ccccc4C)nc4cccnc43)CC2)cc1Cl]
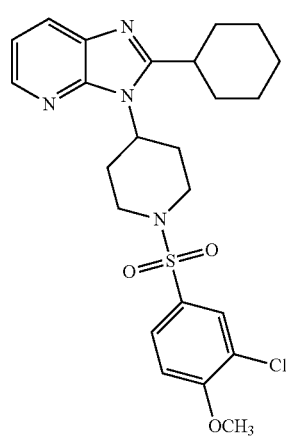 [SMILES: COc1ccc(S(=O)(=O)N2CCC(n3c(C4CCCCC4)nc4cccnc43)CC2)cc1Cl]
TABLE 1-continued
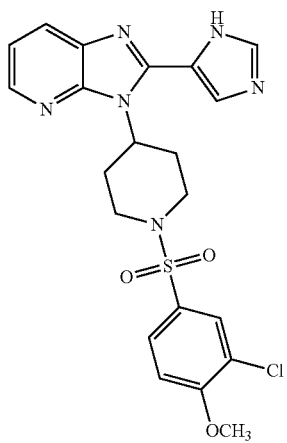 [SMILES: COc1ccc(S(=O)(=O)N2CCC(n3c(-c4cnc[nH]4)nc4cccnc43)CC2)cc1Cl]
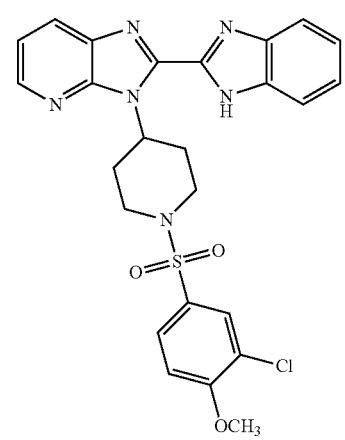 [SMILES: COc1ccc(S(=O)(=O)N2CCC(n3c(-c4nc5ccccc5[nH]4)nc4cccnc43)CC2)cc1Cl]
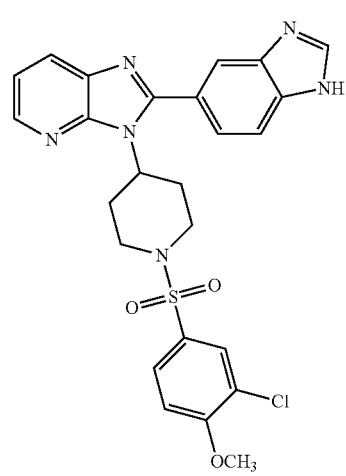 [SMILES: COc1ccc(S(=O)(=O)N2CCC(n3c(-c4ccc5[nH]cnc5c4)nc4cccnc43)CC2)cc1Cl]

TABLE 1-continued
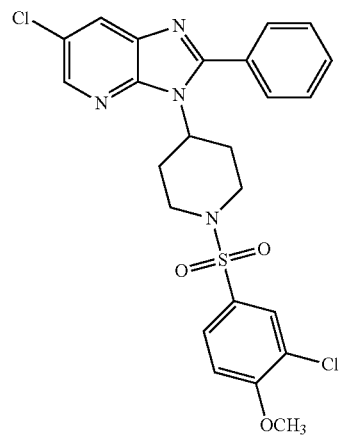 [SMILES: COc1ccc(S(=O)(=O)N2CCC(n3c(-c4ccccc4)nc4cc(Cl)cnc43)CC2)cc1Cl]
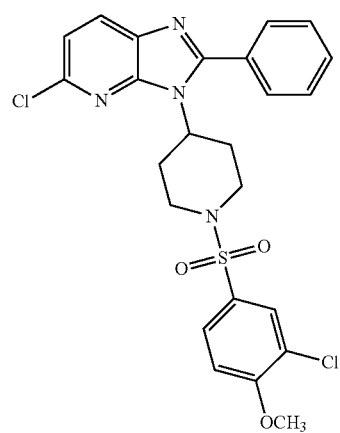 [SMILES: COc1ccc(S(=O)(=O)N2CCC(n3c(-c4ccccc4)nc4ccc(Cl)nc43)CC2)cc1Cl]
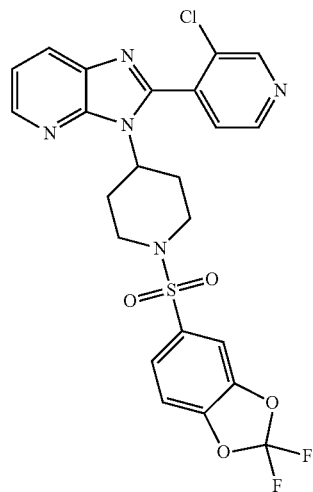 [SMILES: O=S(=O)(c1ccc2c(c1)OC(F)(F)O2)N1CCC(n2c(-c3ccncc3Cl)nc3cccnc32)CC1]
TABLE 1-continued
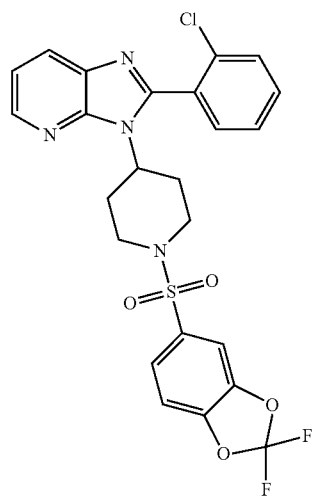 [SMILES: O=S(=O)(c1ccc2c(c1)OC(F)(F)O2)N1CCC(n2c(-c3ccccc3Cl)nc3cccnc32)CC1]
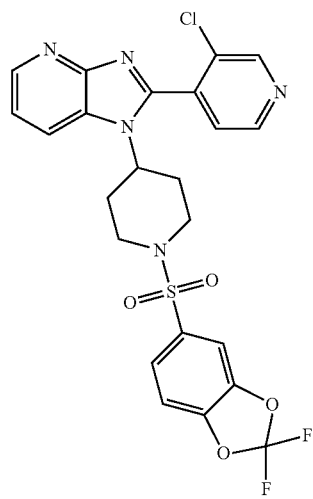 [SMILES: O=S(=O)(c1ccc2c(c1)OC(F)(F)O2)N1CCC(n2c(-c3ccncc3Cl)nc3ncccc32)CC1]

TABLE 1-continued
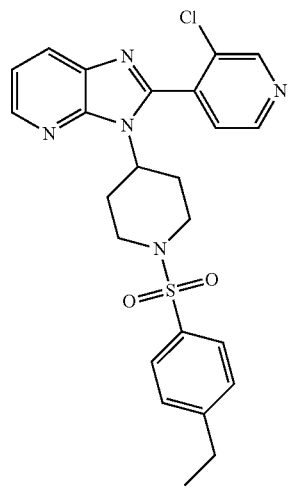 [SMILES: CCc1ccc(S(=O)(=O)N2CCC(n3c(-c4ccncc4Cl)nc4cccnc43)CC2)cc1]
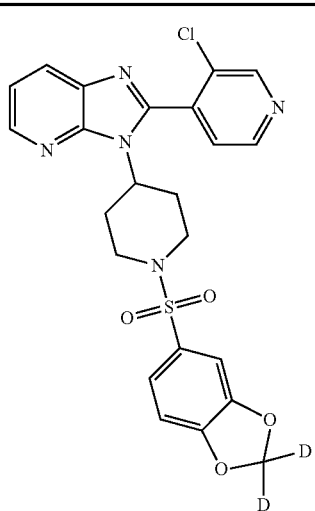
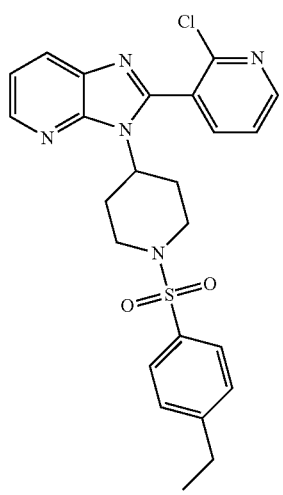 [SMILES: CCc1ccc(S(=O)(=O)N2CCC(n3c(-c4cccnc4Cl)nc4cccnc43)CC2)cc1]
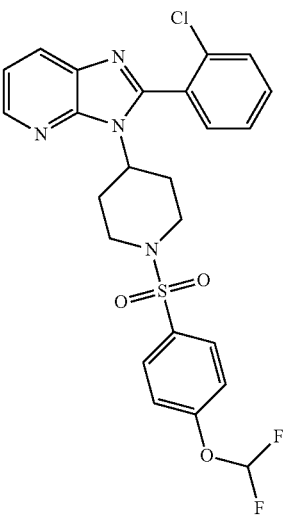 [SMILES: O=S(=O)(c1ccc(OC(F)F)cc1)N1CCC(n2c(-c3ccccc3Cl)nc3cccnc32)CC1]

TABLE 1-continued
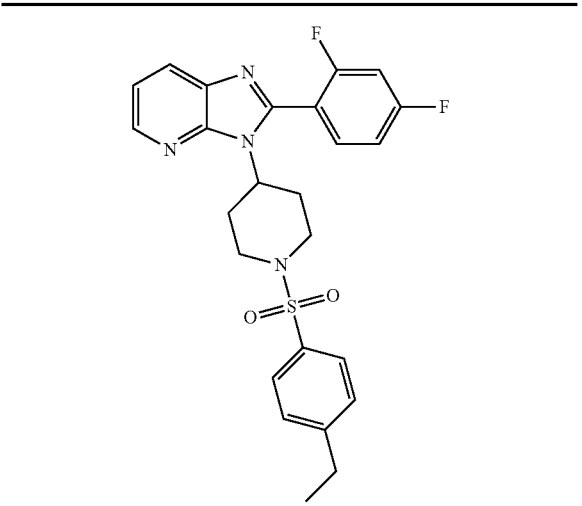
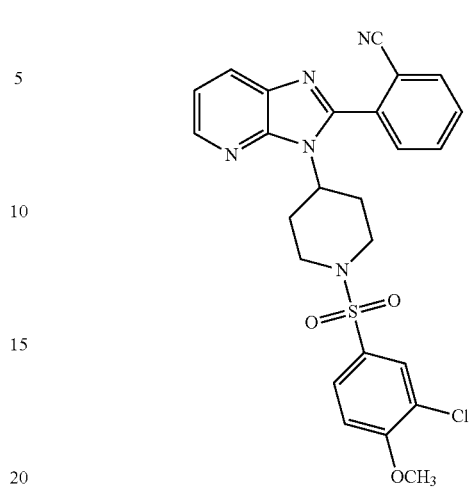
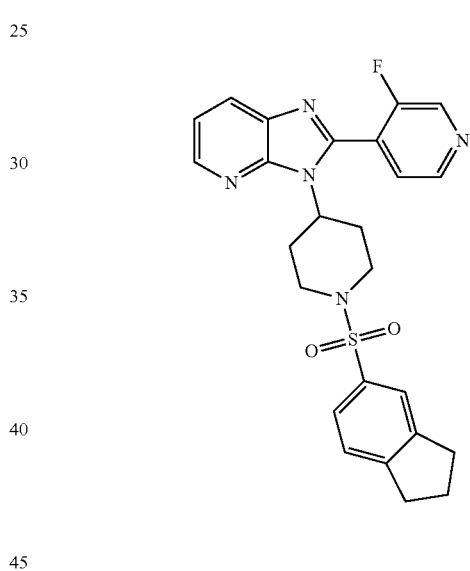
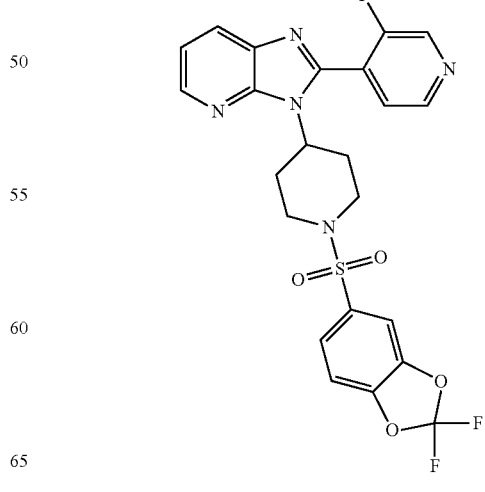

TABLE 1-continued
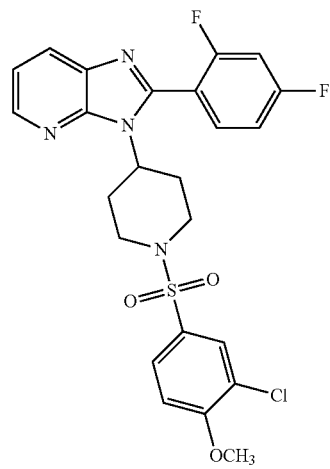 [SMILES: COc1ccc(S(=O)(=O)N2CCC(n3c(-c4ccc(F)cc4F)nc4cccnc43)CC2)cc1Cl]
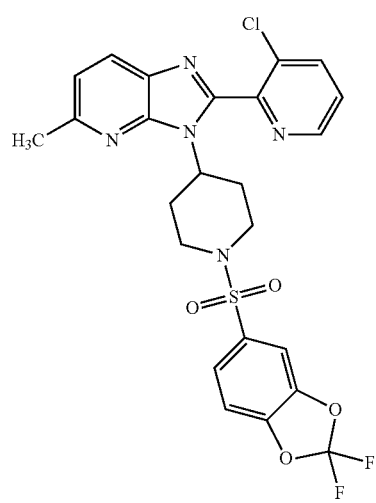 [SMILES: Cc1ccc2nc(-c3ncccc3Cl)n(C3CCN(S(=O)(=O)c4ccc5c(c4)OC(F)(F)O5)CC3)c2n1]
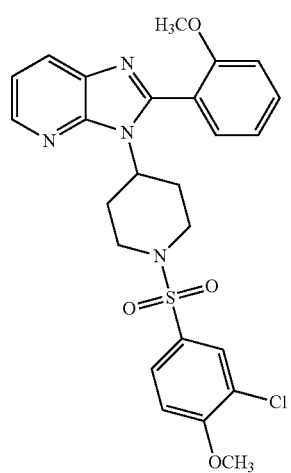
TABLE 1-continued
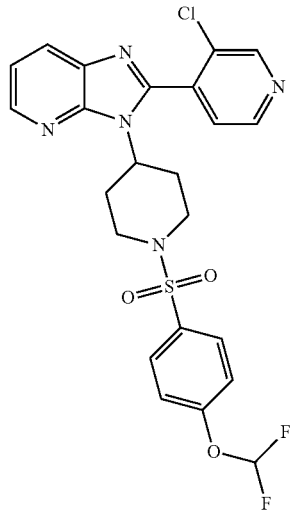
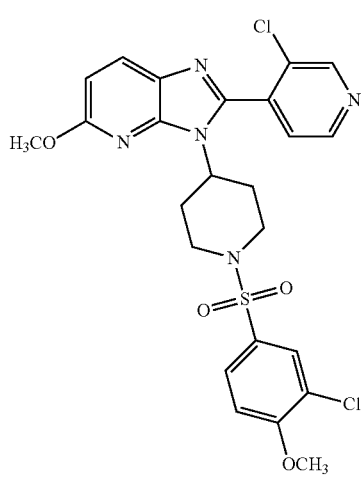 [SMILES: COc1ccc2nc(-c3ccncc3Cl)n(C3CCN(S(=O)(=O)c4ccc(OC)c(Cl)c4)CC3)c2n1]

TABLE 1-continued
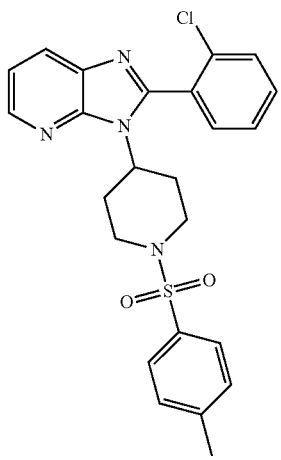 [SMILES: Cc1ccc(S(=O)(=O)N2CCC(n3c(-c4ccccc4Cl)nc4cccnc43)CC2)cc1]
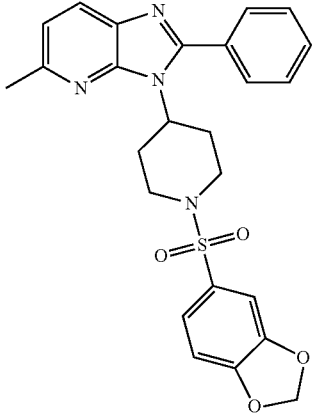
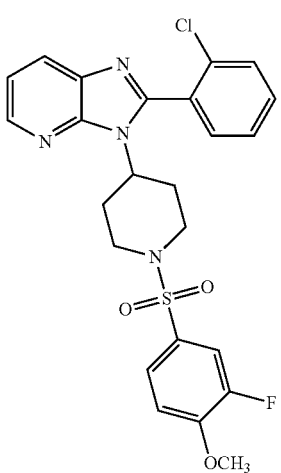 [SMILES: COc1ccc(S(=O)(=O)N2CCC(n3c(-c4ccccc4Cl)nc4cccnc43)CC2)cc1F]
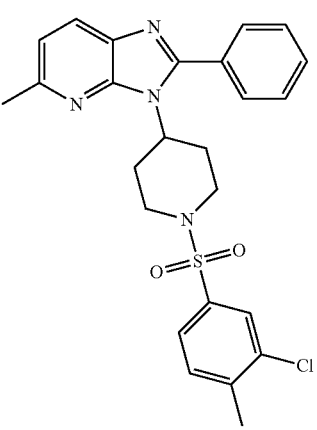
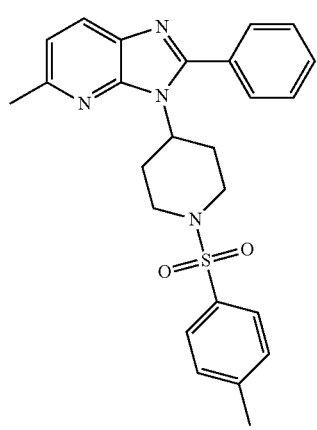 [SMILES: Cc1ccc(S(=O)(=O)N2CCC(n3c(-c4ccccc4)nc4ccc(C)nc43)CC2)cc1]
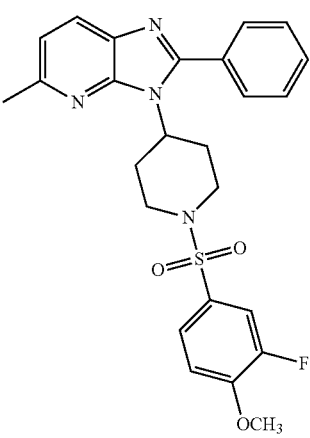 [SMILES: COc1ccc(S(=O)(=O)N2CCC(n3c(-c4ccccc4)nc4ccc(C)nc43)CC2)cc1F]

TABLE 1-continued
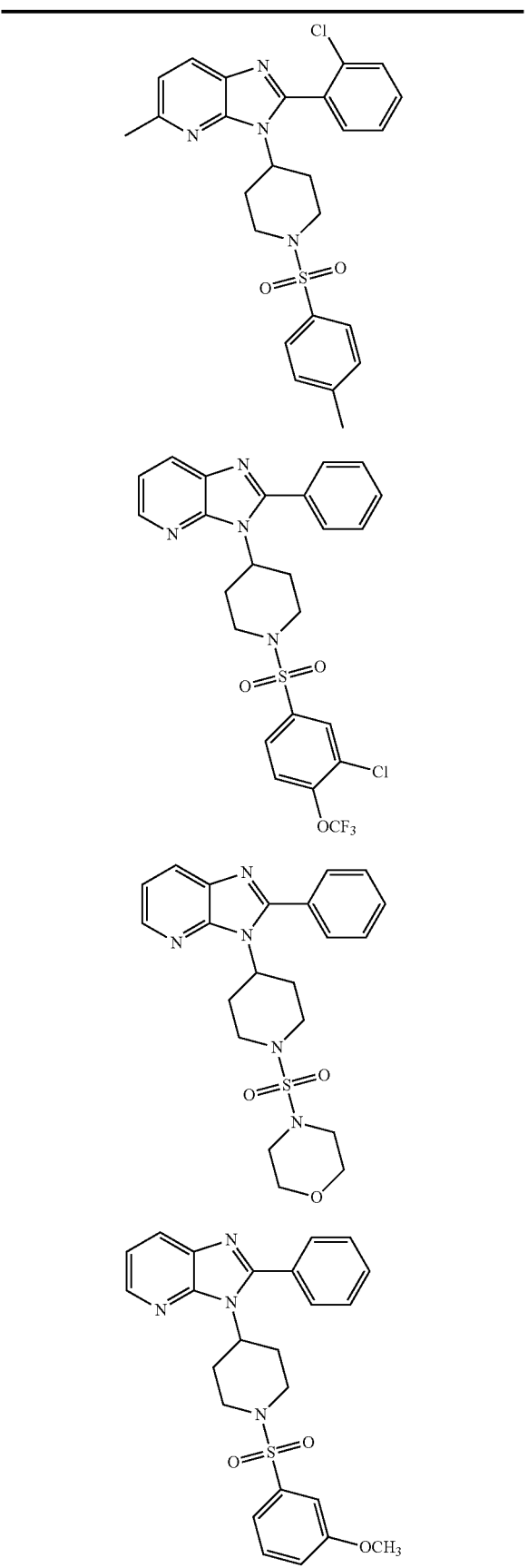
TABLE 1-continued
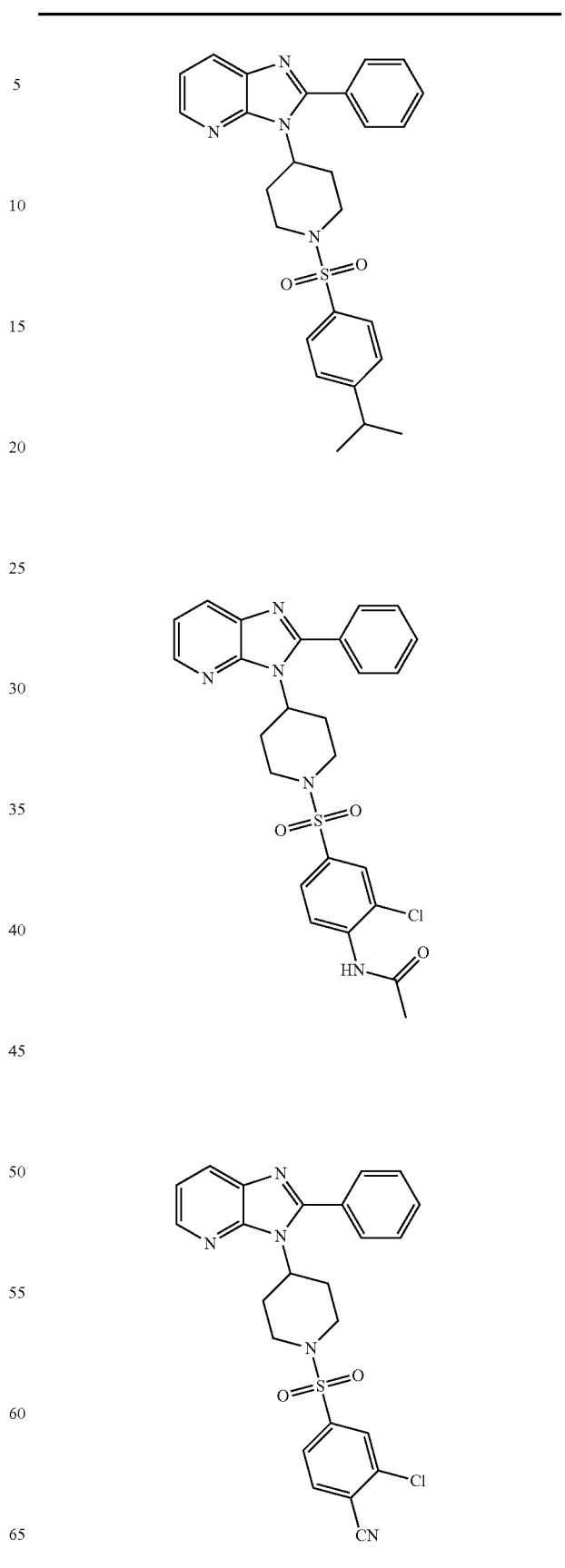

TABLE 1-continued
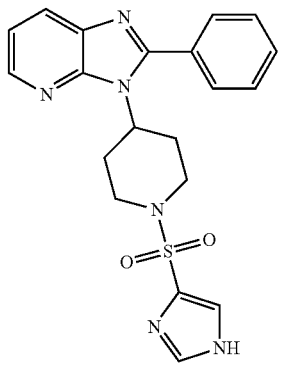 [SMILES: O=S(=O)(c1c[nH]cn1)N1CCC(n2c(-c3ccccc3)nc3cccnc32)CC1]
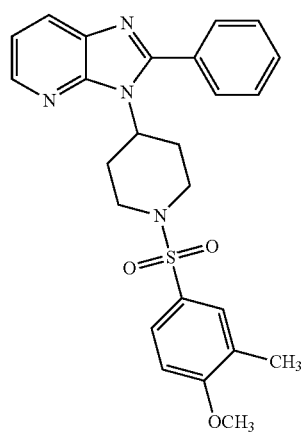 [SMILES: COc1ccc(S(=O)(=O)N2CCC(n3c(-c4ccccc4)nc4cccnc43)CC2)cc1C]
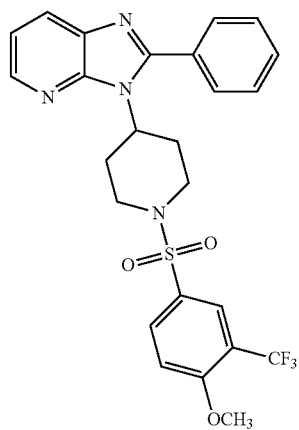 [SMILES: COc1ccc(S(=O)(=O)N2CCC(n3c(-c4ccccc4)nc4cccnc43)CC2)cc1C(F)(F)F]
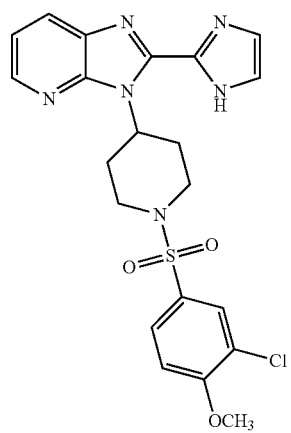 [SMILES: COc1ccc(S(=O)(=O)N2CCC(n3c(-c4ncc[nH]4)nc4cccnc43)CC2)cc1Cl]
TABLE 1-continued
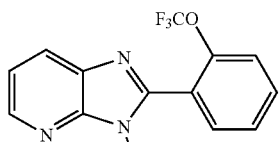
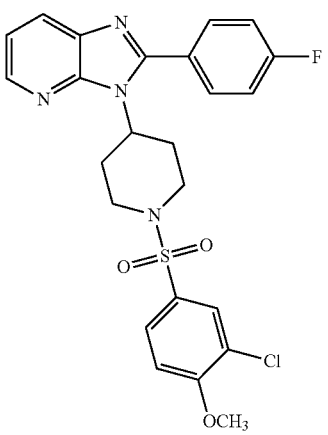 [SMILES: COc1ccc(S(=O)(=O)N2CCC(n3c(-c4ccc(F)cc4)nc4cccnc43)CC2)cc1Cl]
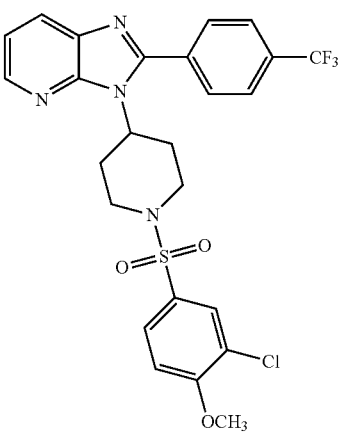 [SMILES: COc1ccc(S(=O)(=O)N2CCC(n3c(-c4ccc(C(F)(F)F)cc4)nc4cccnc43)CC2)cc1Cl]

TABLE 1-continued
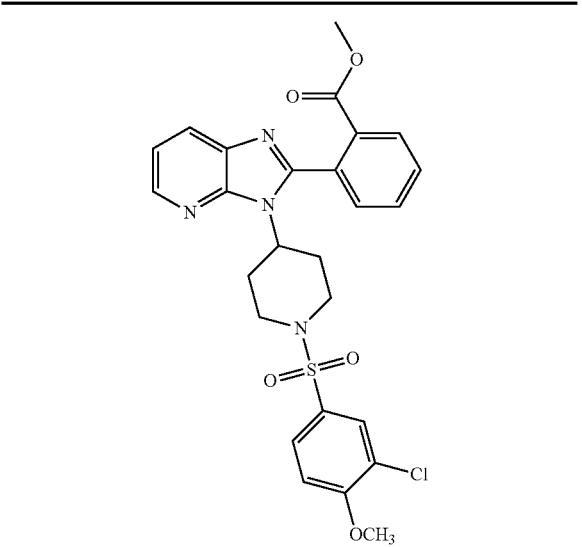
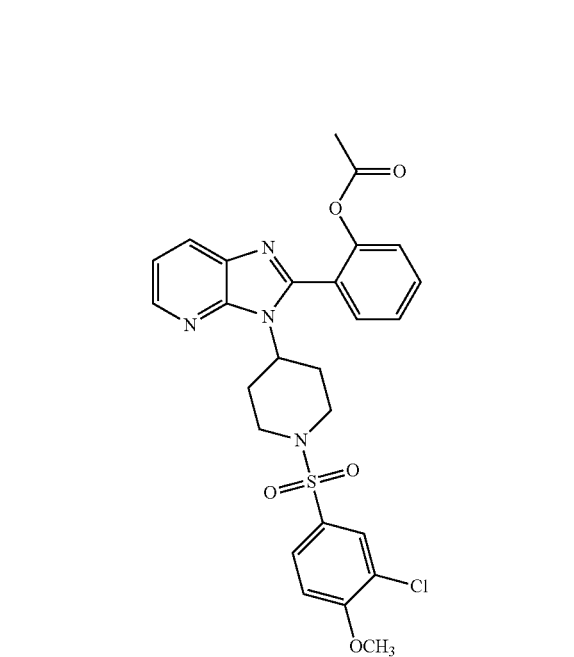 [SMILES: COc1ccc(S(=O)(=O)N2CCC(n3c(-c4ccccc4OC(C)=O)nc4cccnc43)CC2)cc1Cl]
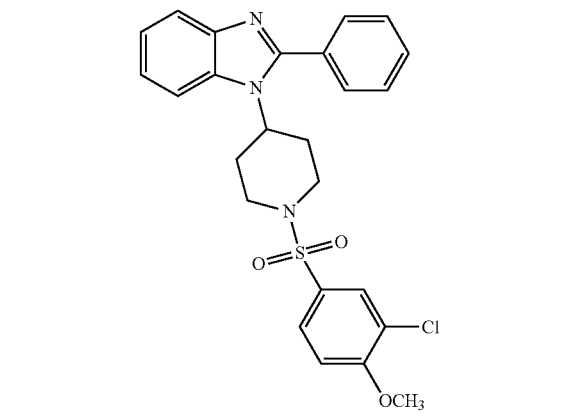 [SMILES: COc1ccc(S(=O)(=O)N2CCC(n3c(-c4ccccc4)nc4ccccc43)CC2)cc1Cl]
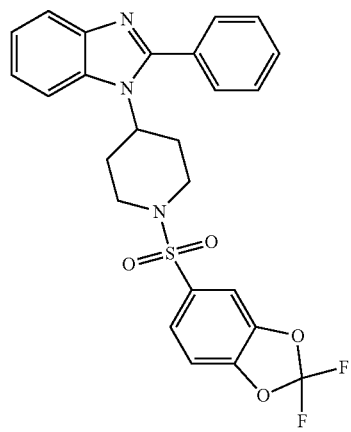 [SMILES: O=S(=O)(c1ccc2c(c1)OC(F)(F)O2)N1CCC(n2c(-c3ccccc3)nc3ccccc32)CC1]
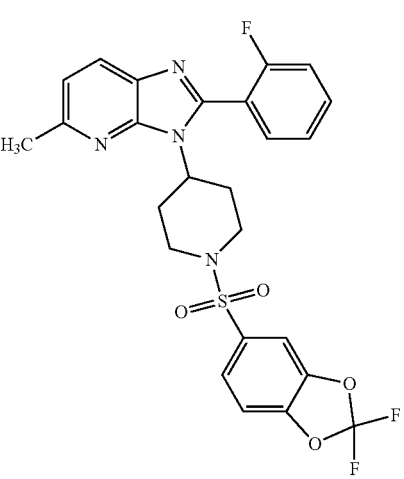 [SMILES: Cc1ccc2nc(-c3ccccc3F)n(C3CCN(S(=O)(=O)c4ccc5c(c4)OC(F)(F)O5)CC3)c2n1]
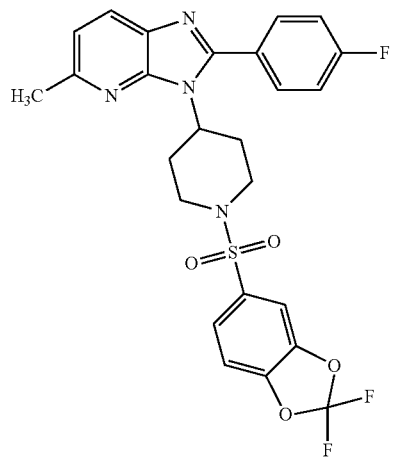 [SMILES: Cc1ccc2nc(-c3ccc(F)cc3)n(C3CCN(S(=O)(=O)c4ccc5c(c4)OC(F)(F)O5)CC3)c2n1]

TABLE 1-continued
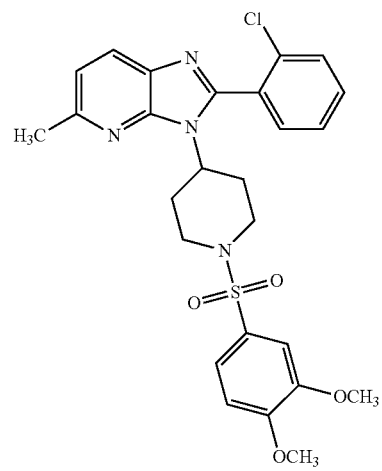 [SMILES: COc1ccc(S(=O)(=O)N2CCC(n3c(-c4ccccc4Cl)nc4ccc(C)nc43)CC2)cc1OC]
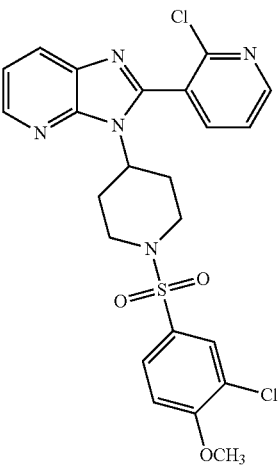
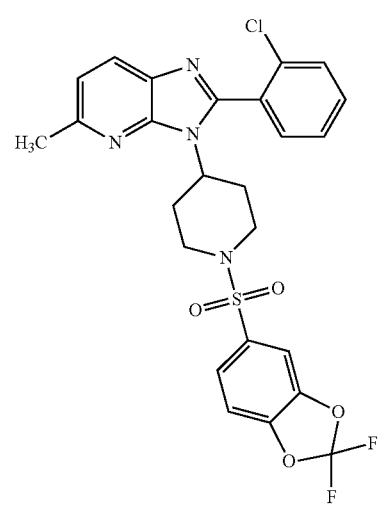
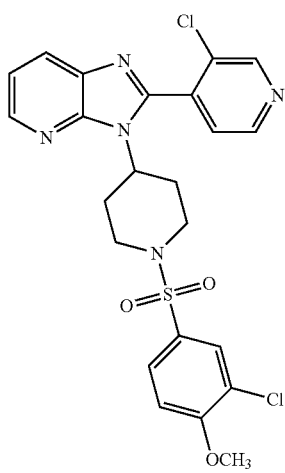
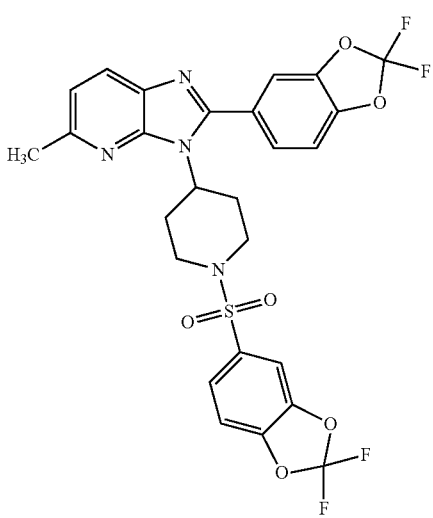 [SMILES: Cc1ccc2nc(-c3ccc4c(c3)OC(F)(F)O4)n(C3CCN(S(=O)(=O)c4ccc5c(c4)OC(F)(F)O5)CC3)c2n1]
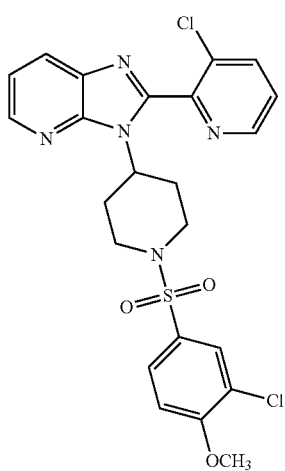 [SMILES: COc1ccc(S(=O)(=O)N2CCC(n3c(-c4ncccc4Cl)nc4cccnc43)CC2)cc1Cl]

TABLE 1-continued
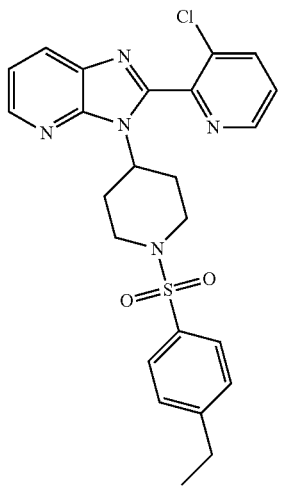 [SMILES: CCc1ccc(S(=O)(=O)N2CCC(n3c(-c4ncccc4Cl)nc4cccnc43)CC2)cc1]
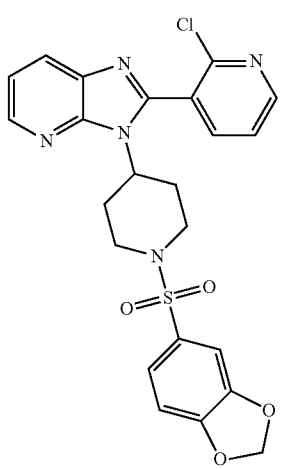
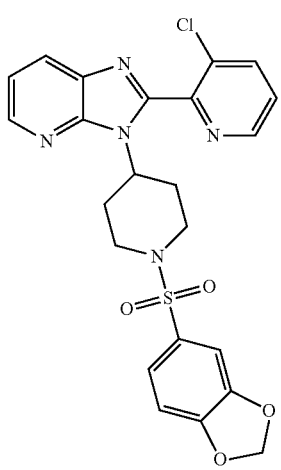 [SMILES: O=S(=O)(c1ccc2c(c1)OCO2)N1CCC(n2c(-c3ncccc3Cl)nc3cccnc32)CC1]
TABLE 1-continued
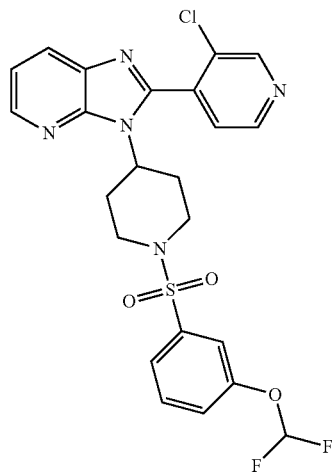 [SMILES: O=S(=O)(c1cccc(OC(F)F)c1)N1CCC(n2c(-c3ccncc3Cl)nc3cccnc32)CC1]
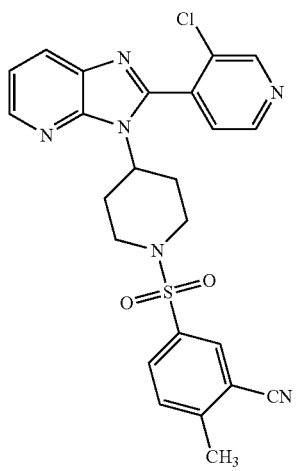 [SMILES: Cc1ccc(S(=O)(=O)N2CCC(n3c(-c4ccncc4Cl)nc4cccnc43)CC2)cc1C#N]
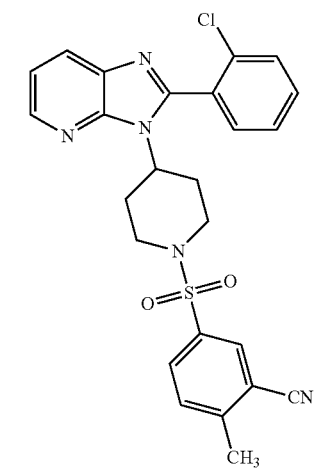

TABLE 1-continued
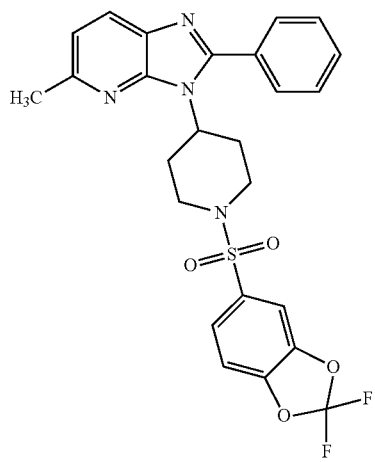 [SMILES: Cc1ccc2nc(-c3ccccc3)n(C3CCN(S(=O)(=O)c4ccc5c(c4)OC(F)(F)O5)CC3)c2n1]
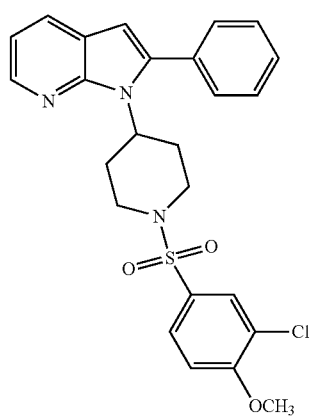 [SMILES: COc1ccc(S(=O)(=O)N2CCC(n3c(-c4ccccc4)cc4cccnc43)CC2)cc1Cl]
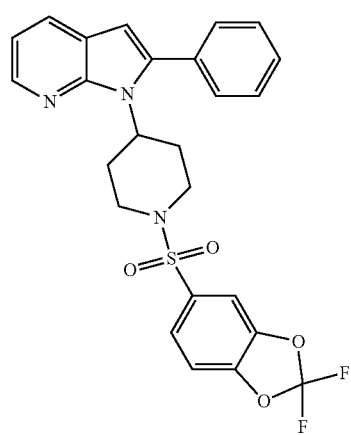 [SMILES: O=S(=O)(c1ccc2c(c1)OC(F)(F)O2)N1CCC(n2c(-c3ccccc3)cc3cccnc32)CC1]
TABLE 1-continued
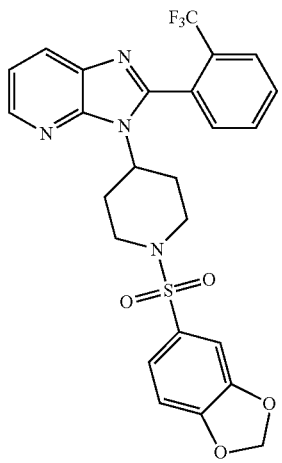
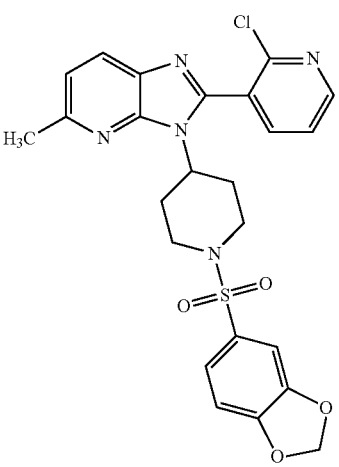 [SMILES: Cc1ccc2nc(-c3cccnc3Cl)n(C3CCN(S(=O)(=O)c4ccc5c(c4)OCO5)CC3)c2n1]
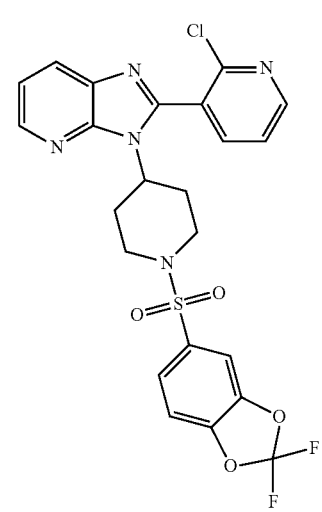

TABLE 1-continued
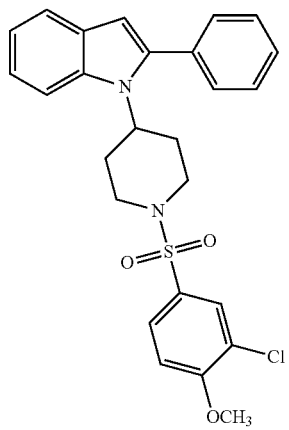
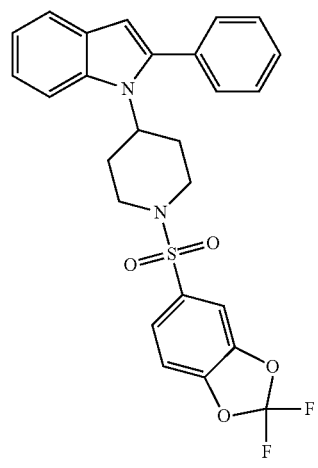 [SMILES: O=S(=O)(c1ccc2c(c1)OC(F)(F)O2)N1CCC(n2c(-c3ccccc3)cc3ccccc32)CC1]
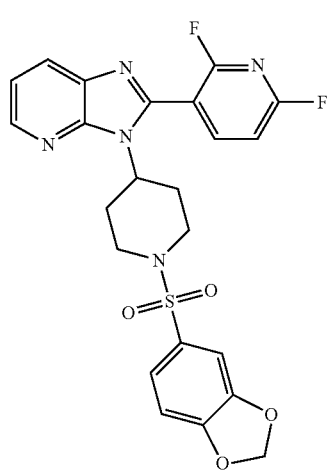 [SMILES: O=S(=O)(c1ccc2c(c1)OCO2)N1CCC(n2c(-c3ccc(F)nc3F)nc3cccnc32)CC1]
TABLE 1-continued
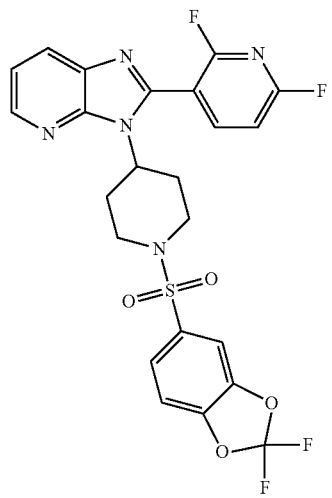 [SMILES: O=S(=O)(c1ccc2c(c1)OC(F)(F)O2)N1CCC(n2c(-c3ccc(F)nc3F)nc3cccnc32)CC1]
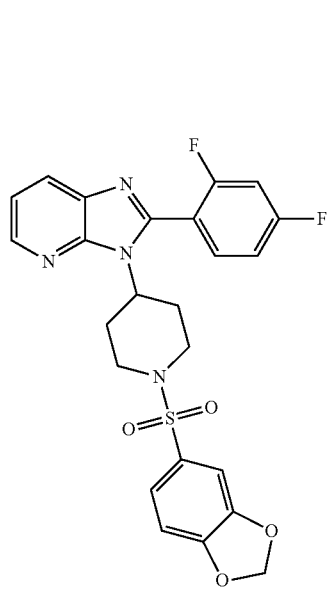

TABLE 1-continued
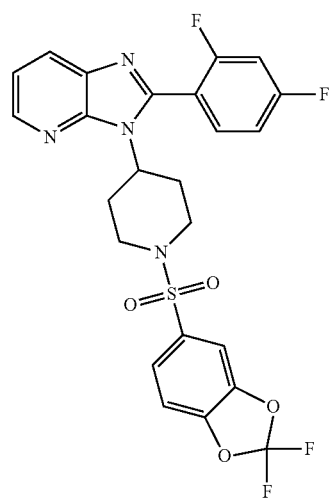 [SMILES: O=S(=O)(c1ccc2c(c1)OC(F)(F)O2)N1CCC(n2c(-c3ccc(F)cc3F)nc3cccnc32)CC1]
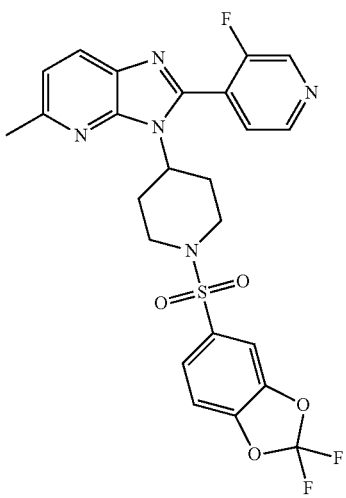 [SMILES: Cc1ccc2nc(-c3ccncc3F)n(C3CCN(S(=O)(=O)c4ccc5c(c4)OC(F)(F)O5)CC3)c2n1]

TABLE 1-continued
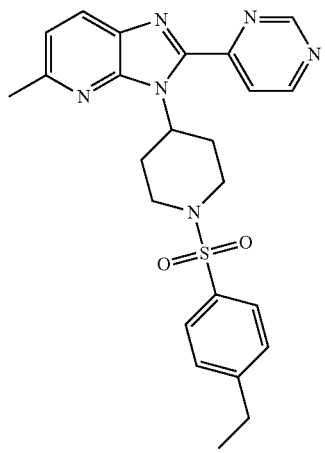 [SMILES: CCc1ccc(S(=O)(=O)N2CCC(n3c(-c4ccncn4)nc4ccc(C)nc43)CC2)cc1]
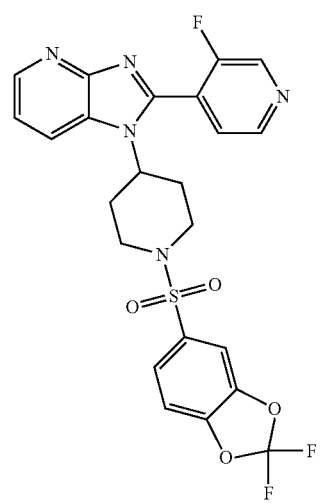 [SMILES: O=S(=O)(c1ccc2c(c1)OC(F)(F)O2)N1CCC(n2c(-c3ccncc3F)nc3ncccc32)CC1]
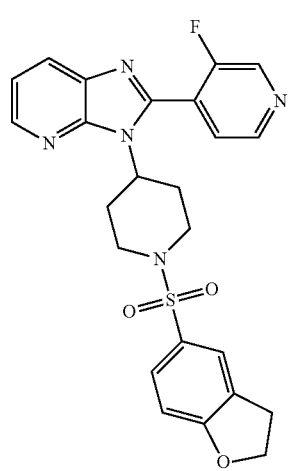 [SMILES: O=S(=O)(c1ccc2c(c1)CCO2)N1CCC(n2c(-c3ccncc3F)nc3cccnc32)CC1]
TABLE 1-continued
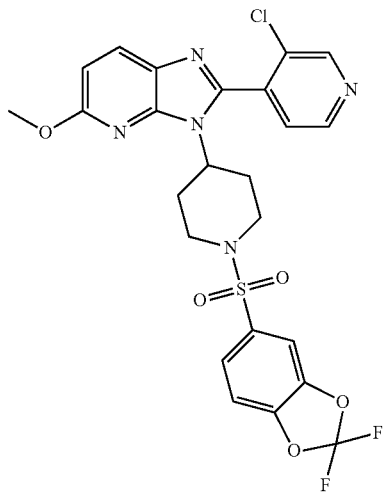 [SMILES: COc1ccc2nc(-c3ccncc3Cl)n(C3CCN(S(=O)(=O)c4ccc5c(c4)OC(F)(F)O5)CC3)c2n1]
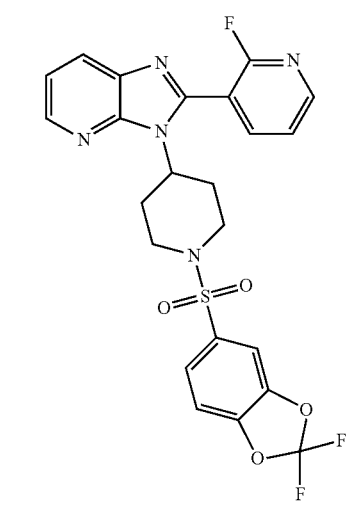
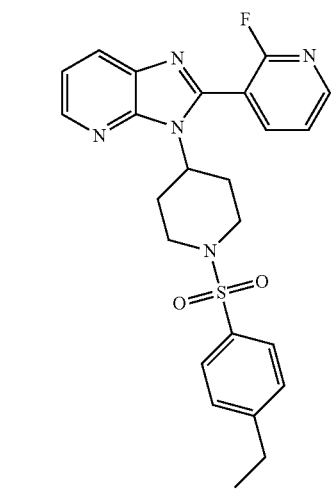 [SMILES: CCc1ccc(S(=O)(=O)N2CCC(n3c(-c4cccnc4F)nc4cccnc43)CC2)cc1]

TABLE 1-continued
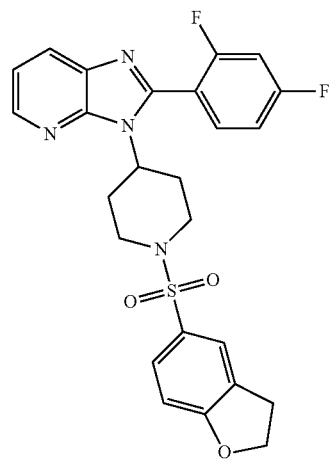
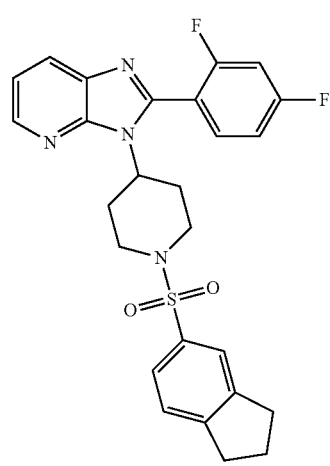 [SMILES: O=S(=O)(c1ccc2c(c1)CCC2)N1CCC(n2c(-c3ccc(F)cc3F)nc3cccnc32)CC1]
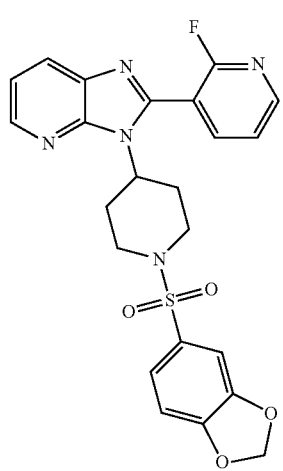 [SMILES: O=S(=O)(c1ccc2c(c1)OCO2)N1CCC(n2c(-c3cccnc3F)nc3cccnc32)CC1]
TABLE 1-continued
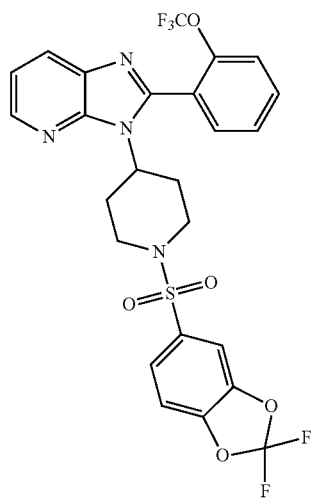 [SMILES: O=S(=O)(c1ccc2c(c1)OC(F)(F)O2)N1CCC(n2c(-c3ccccc3OC(F)(F)F)nc3cccnc32)CC1]
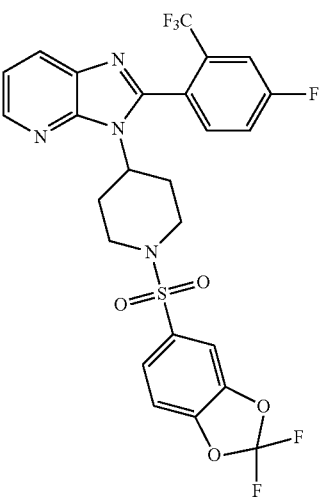 [SMILES: O=S(=O)(c1ccc2c(c1)OC(F)(F)O2)N1CCC(n2c(-c3ccc(F)cc3C(F)(F)F)nc3cccnc32)CC1]
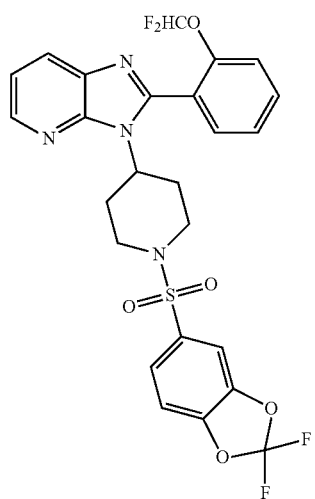 [SMILES: O=S(=O)(c1ccc2c(c1)OC(F)(F)O2)N1CCC(n2c(-c3ccccc3OC(F)F)nc3cccnc32)CC1]

TABLE 1-continued
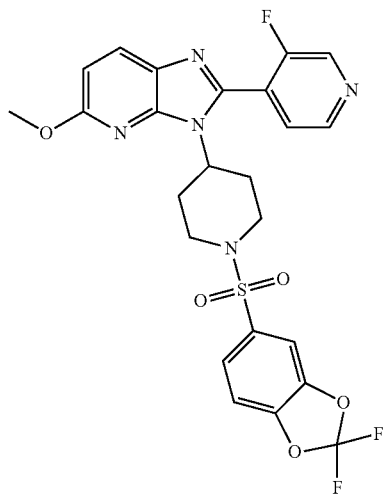 [SMILES: COc1ccc2nc(-c3ccncc3F)n(C3CCN(S(=O)(=O)c4ccc5c(c4)OC(F)(F)O5)CC3)c2n1]
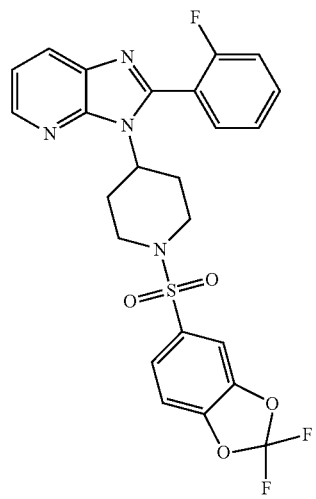
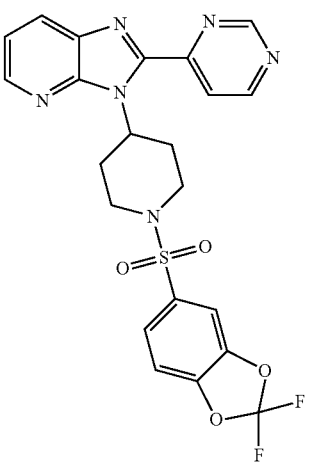 [SMILES: O=S(=O)(c1ccc2c(c1)OC(F)(F)O2)N1CCC(n2c(-c3ccncn3)nc3cccnc32)CC1]
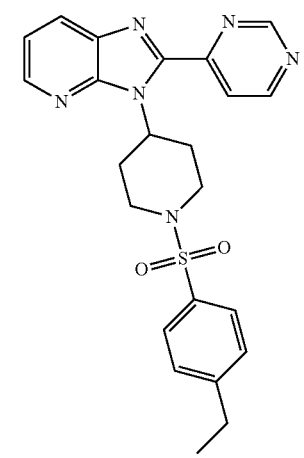
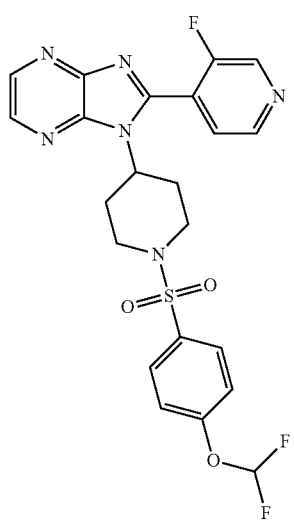 [SMILES: O=S(=O)(c1ccc(OC(F)F)cc1)N1CCC(n2c(-c3ccncc3F)nc3nccnc32)CC1]
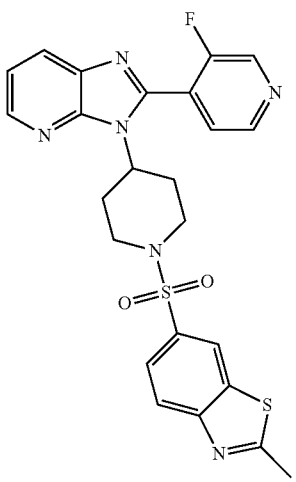 [SMILES: Cc1nc2ccc(S(=O)(=O)N3CCC(n4c(-c5ccncc5F)nc5cccnc54)CC3)cc2s1]

TABLE 1-continued
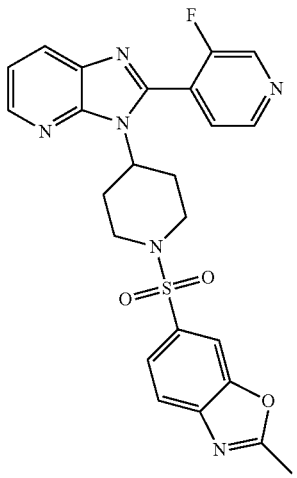 [SMILES: Cc1nc2ccc(S(=O)(=O)N3CCC(n4c(-c5ccncc5F)nc5cccnc54)CC3)cc2o1]
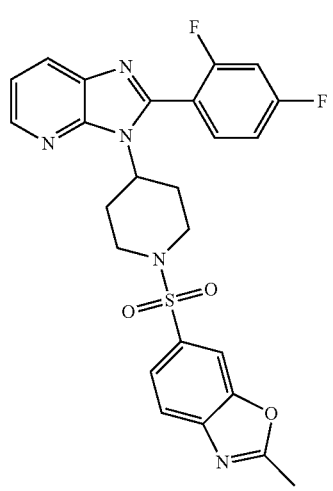 [SMILES: Cc1nc2ccc(S(=O)(=O)N3CCC(n4c(-c5ccc(F)cc5F)nc5cccnc54)CC3)cc2o1]
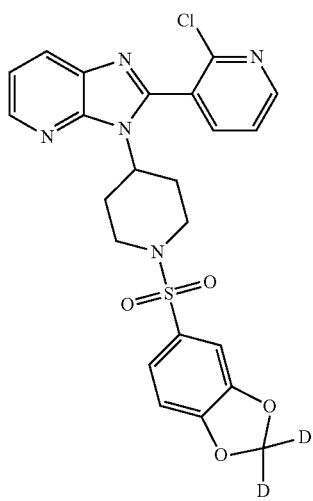 [SMILES: [2H]C1([2H])Oc2ccc(S(=O)(=O)N3CCC(n4c(-c5cccnc5Cl)nc5cccnc54)CC3)cc2O1]
TABLE 1-continued
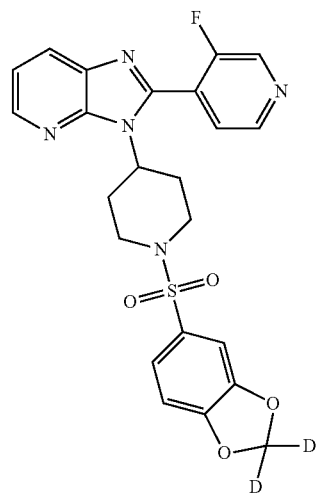 [SMILES: [2H]C1([2H])Oc2ccc(S(=O)(=O)N3CCC(n4c(-c5ccncc5F)nc5cccnc54)CC3)cc2O1]
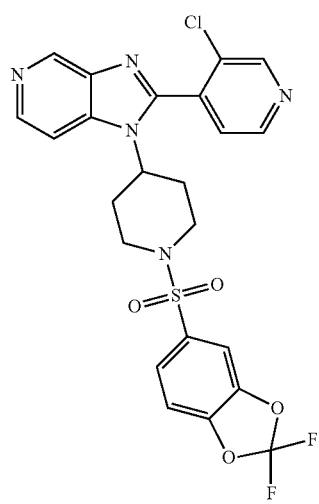 [SMILES: O=S(=O)(c1ccc2c(c1)OC(F)(F)O2)N1CCC(n2c(-c3ccncc3Cl)nc3cnccc32)CC1]
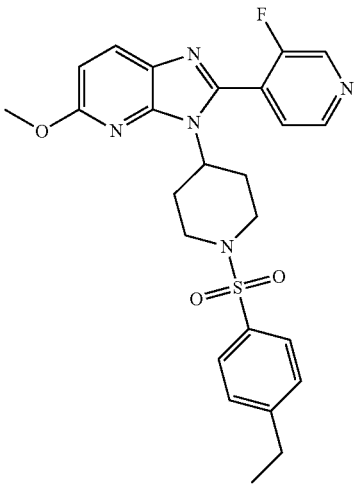 [SMILES: CCc1ccc(S(=O)(=O)N2CCC(n3c(-c4ccncc4F)nc4ccc(OC)nc43)CC2)cc1]

TABLE 1-continued
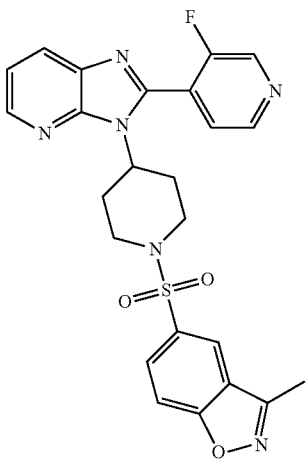 [SMILES: Cc1noc2ccc(S(=O)(=O)N3CCC(n4c(-c5ccncc5F)nc5cccnc54)CC3)cc12]
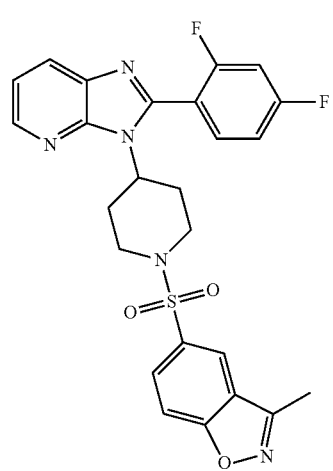 [SMILES: Cc1noc2ccc(S(=O)(=O)N3CCC(n4c(-c5ccc(F)cc5F)nc5cccnc54)CC3)cc12]
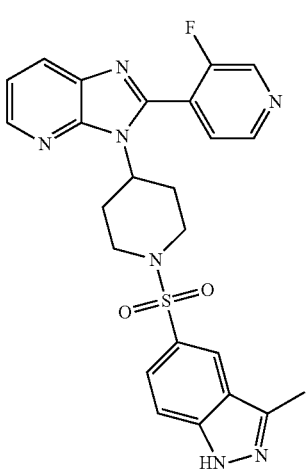 [SMILES: Cc1n[nH]c2ccc(S(=O)(=O)N3CCC(n4c(-c5ccncc5F)nc5cccnc54)CC3)cc12]
TABLE 1-continued
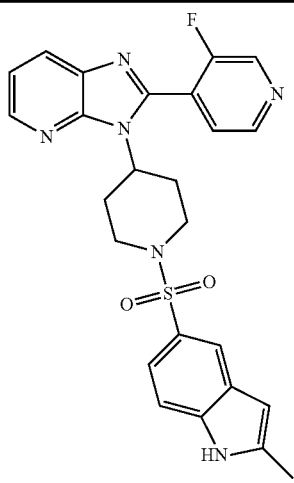
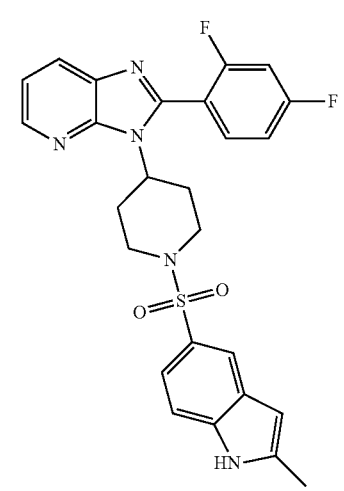 [SMILES: Cc1cc2cc(S(=O)(=O)N3CCC(n4c(-c5ccc(F)cc5F)nc5cccnc54)CC3)ccc2[nH]1]
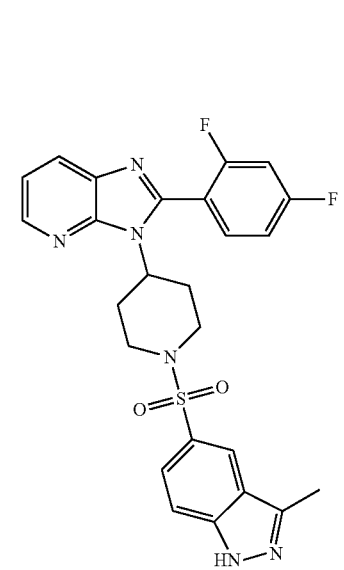 [SMILES: Cc1n[nH]c2ccc(S(=O)(=O)N3CCC(n4c(-c5ccc(F)cc5F)nc5cccnc54)CC3)cc12]

TABLE 1-continued
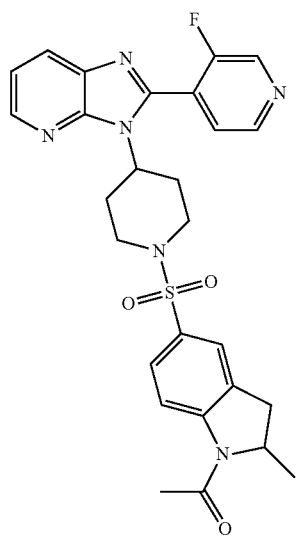 [SMILES: CC(=O)N1c2ccc(S(=O)(=O)N3CCC(n4c(-c5ccncc5F)nc5cccnc54)CC3)cc2CC1C]
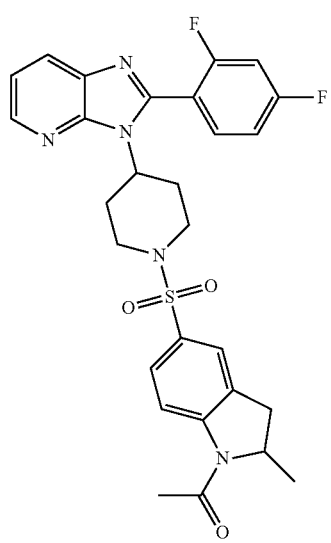 [SMILES: CC(=O)N1c2ccc(S(=O)(=O)N3CCC(n4c(-c5ccc(F)cc5F)nc5cccnc54)CC3)cc2CC1C]
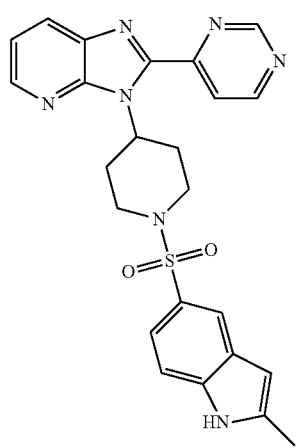 [SMILES: Cc1cc2cc(S(=O)(=O)N3CCC(n4c(-c5ccncn5)nc5cccnc54)CC3)ccc2[nH]1]
TABLE 1-continued
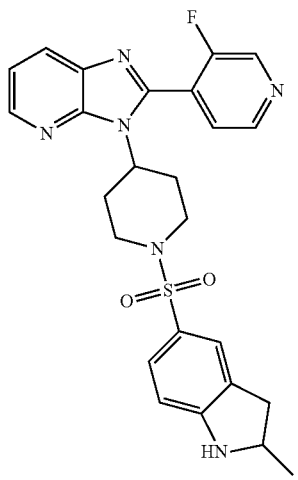 [SMILES: CC1Cc2cc(S(=O)(=O)N3CCC(n4c(-c5ccncc5F)nc5cccnc54)CC3)ccc2N1]
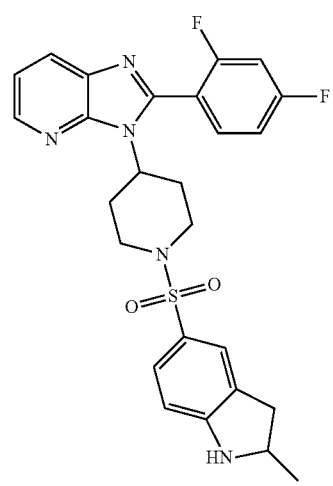 [SMILES: CC1Cc2cc(S(=O)(=O)N3CCC(n4c(-c5ccc(F)cc5F)nc5cccnc54)CC3)ccc2N1]
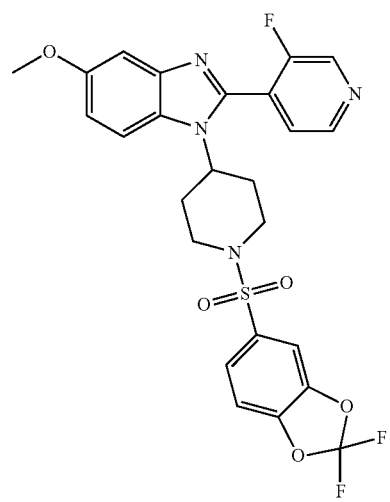 [SMILES: COc1ccc2c(c1)nc(-c1ccncc1F)n2C1CCN(S(=O)(=O)c2ccc3c(c2)OC(F)(F)O3)CC1]

TABLE 1-continued
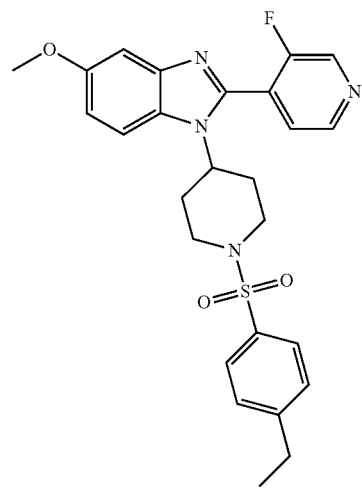 [SMILES: CCc1ccc(S(=O)(=O)N2CCC(n3c(-c4ccncc4F)nc4cc(OC)ccc43)CC2)cc1]
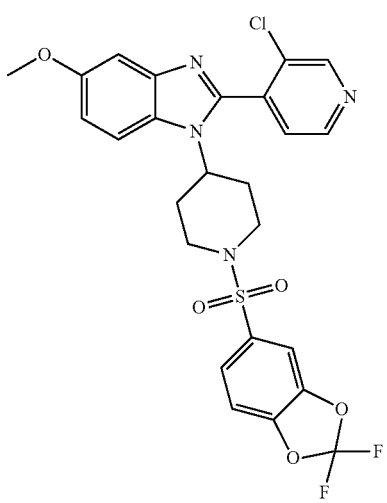
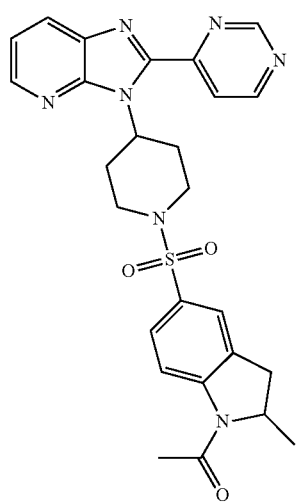 [SMILES: CC(=O)N1c2ccc(S(=O)(=O)N3CCC(n4c(-c5ccncn5)nc5cccnc54)CC3)cc2CC1C]
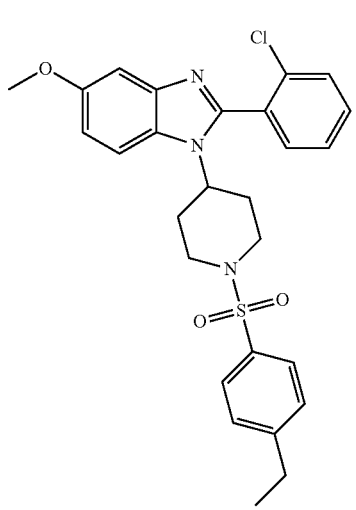
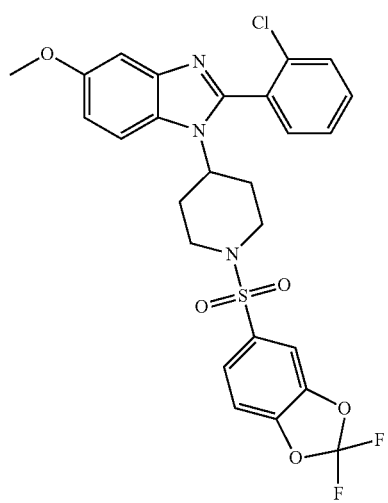 [SMILES: COc1ccc2c(c1)nc(-c1ccccc1Cl)n2C1CCN(S(=O)(=O)c2ccc3c(c2)OC(F)(F)O3)CC1]
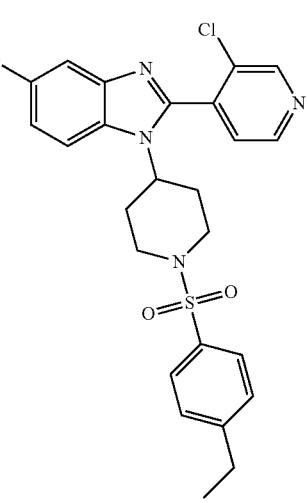

TABLE 1-continued
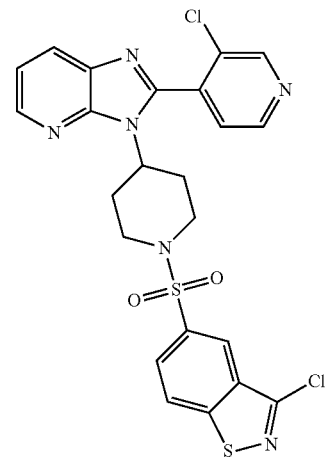
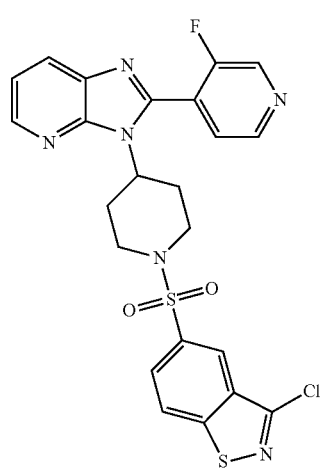 [SMILES: O=S(=O)(c1ccc2snc(Cl)c2c1)N1CCC(n2c(-c3ccncc3F)nc3cccnc32)CC1]
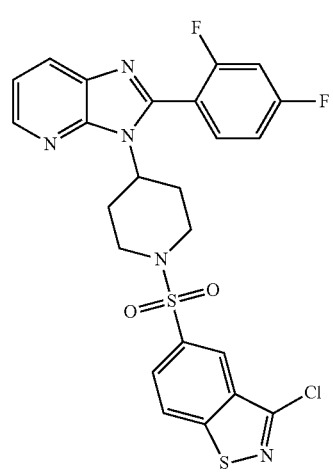 [SMILES: O=S(=O)(c1ccc2snc(Cl)c2c1)N1CCC(n2c(-c3ccc(F)cc3F)nc3cccnc32)CC1]
TABLE 1-continued
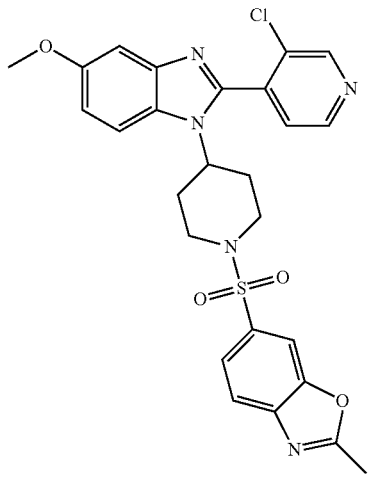
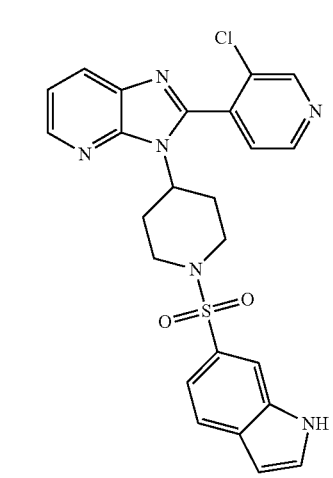
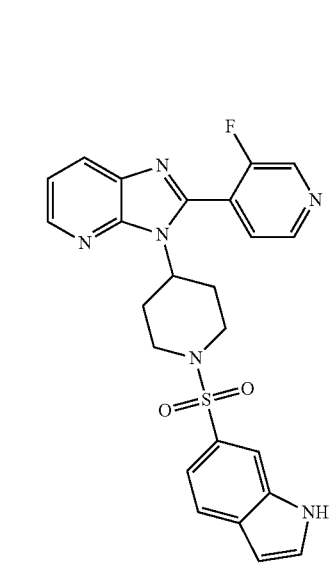 [SMILES: O=S(=O)(c1ccc2cc[nH]c2c1)N1CCC(n2c(-c3ccncc3F)nc3cccnc32)CC1]

TABLE 1-continued
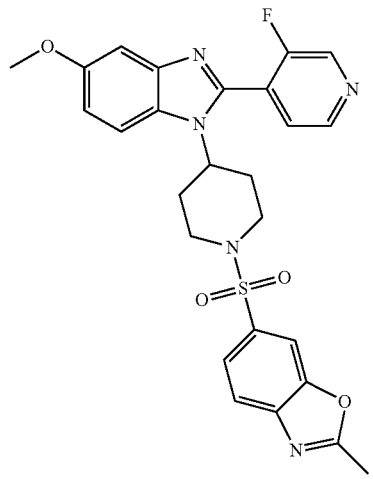
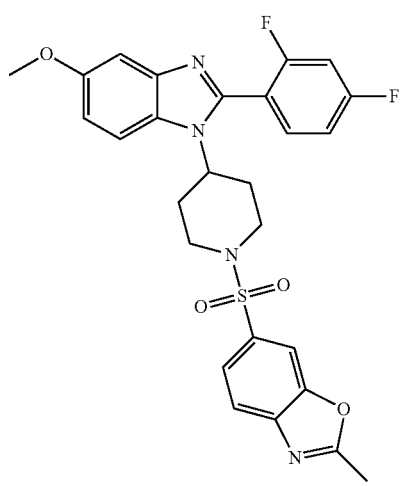 [SMILES: COc1ccc2c(c1)nc(-c1ccc(F)cc1F)n2C1CCN(S(=O)(=O)c2ccc3nc(C)oc3c2)CC1]
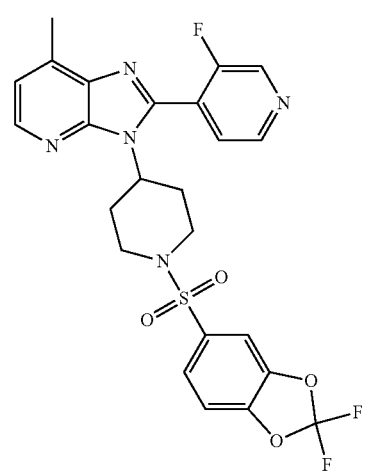 [SMILES: Cc1ccnc2c1nc(-c1ccncc1F)n2C1CCN(S(=O)(=O)c2ccc3c(c2)OC(F)(F)O3)CC1]
TABLE 1-continued
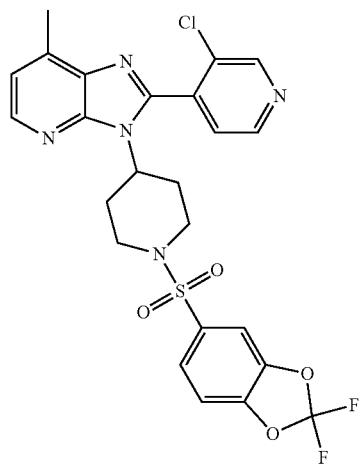
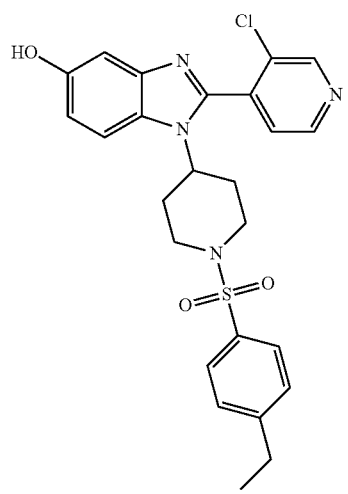 [SMILES: CCc1ccc(S(=O)(=O)N2CCC(n3c(-c4ccncc4Cl)nc4cc(O)ccc43)CC2)cc1]

TABLE 1-continued
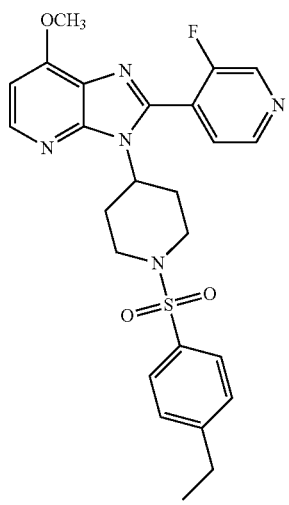 [SMILES: CCc1ccc(S(=O)(=O)N2CCC(n3c(-c4ccncc4F)nc4c(OC)ccnc43)CC2)cc1]
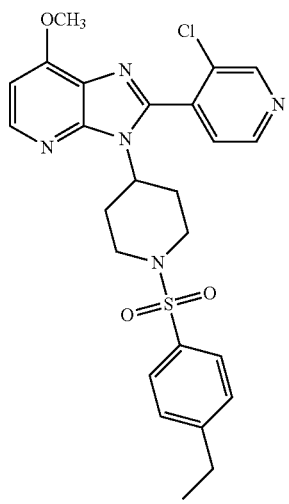
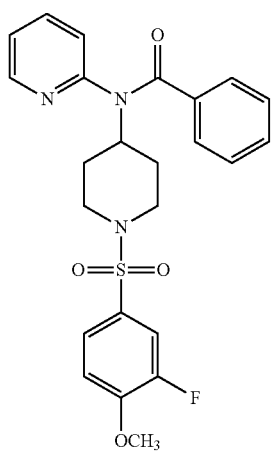 [SMILES: COc1ccc(S(=O)(=O)N2CCC(N(C(=O)c3ccccc3)c3ccccn3)CC2)cc1F]
TABLE 1-continued
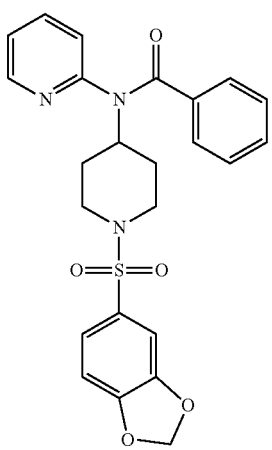 [SMILES: O=C(c1ccccc1)N(c1ccccn1)C1CCN(S(=O)(=O)c2ccc3c(c2)OCO3)CC1]
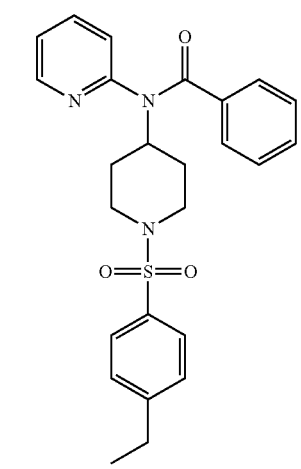 [SMILES: CCc1ccc(S(=O)(=O)N2CCC(N(C(=O)c3ccccc3)c3ccccn3)CC2)cc1]
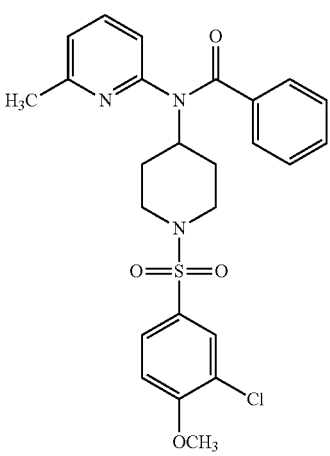 [SMILES: COc1ccc(S(=O)(=O)N2CCC(N(C(=O)c3ccccc3)c3cccc(C)n3)CC2)cc1Cl]

TABLE 1-continued
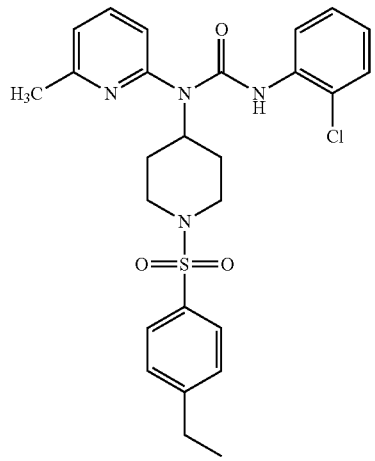 [SMILES: CCc1ccc(S(=O)(=O)N2CCC(N(C(=O)Nc3ccccc3Cl)c3cccc(C)n3)CC2)cc1]
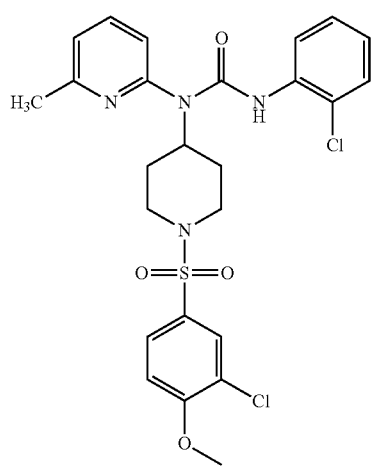 [SMILES: COc1ccc(S(=O)(=O)N2CCC(N(C(=O)Nc3ccccc3Cl)c3cccc(C)n3)CC2)cc1Cl]
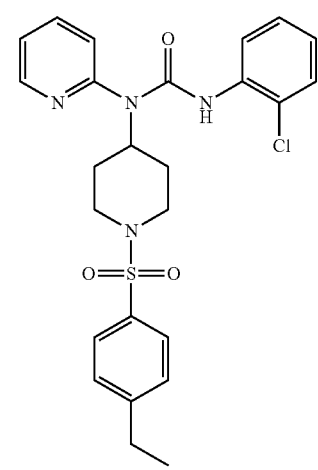 [SMILES: CCc1ccc(S(=O)(=O)N2CCC(N(C(=O)Nc3ccccc3Cl)c3ccccn3)CC2)cc1]
TABLE 1-continued
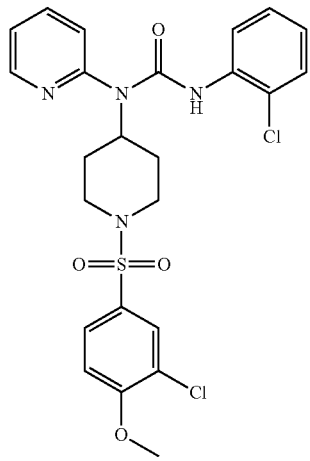 [SMILES: COc1ccc(S(=O)(=O)N2CCC(N(C(=O)Nc3ccccc3Cl)c3ccccn3)CC2)cc1Cl]
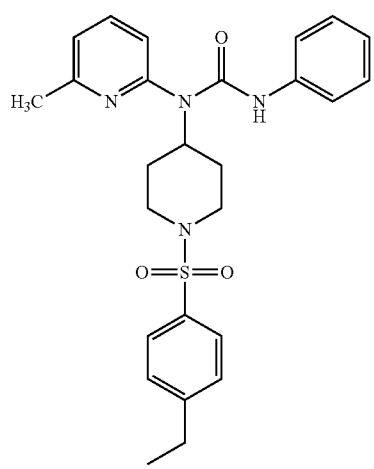 [SMILES: CCc1ccc(S(=O)(=O)N2CCC(N(C(=O)Nc3ccccc3)c3cccc(C)n3)CC2)cc1]
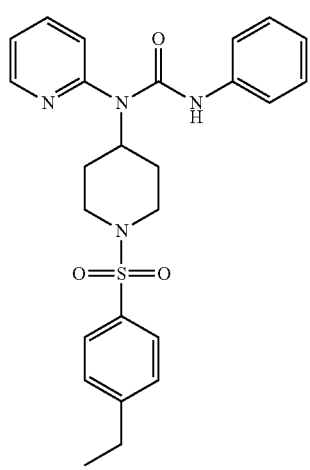 [SMILES: CCc1ccc(S(=O)(=O)N2CCC(N(C(=O)Nc3ccccc3)c3ccccn3)CC2)cc1]

TABLE 1-continued
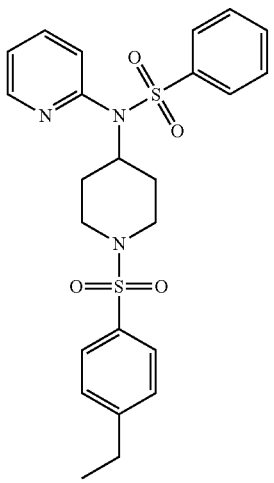 [SMILES: CCc1ccc(S(=O)(=O)N2CCC(N(c3ccccn3)S(=O)(=O)c3ccccc3)CC2)cc1]
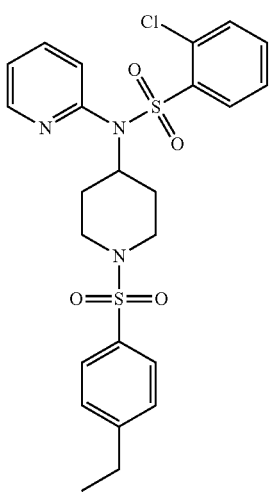 [SMILES: CCc1ccc(S(=O)(=O)N2CCC(N(c3ccccn3)S(=O)(=O)c3ccccc3Cl)CC2)cc1]
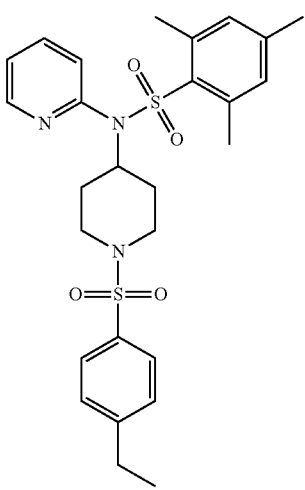 [SMILES: CCc1ccc(S(=O)(=O)N2CCC(N(c3ccccn3)S(=O)(=O)c3c(C)cc(C)cc3C)CC2)cc1]
TABLE 1-continued
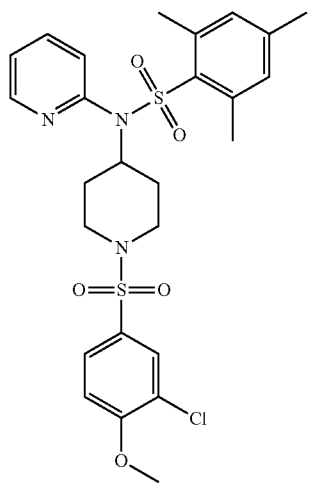 [SMILES: COc1ccc(S(=O)(=O)N2CCC(N(c3ccccn3)S(=O)(=O)c3c(C)cc(C)cc3C)CC2)cc1Cl]
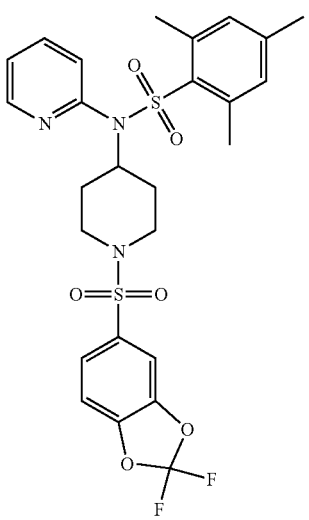 [SMILES: Cc1cc(C)c(S(=O)(=O)N(c2ccccn2)C2CCN(S(=O)(=O)c3ccc4c(c3)OC(F)(F)O4)CC2)c(C)c1]
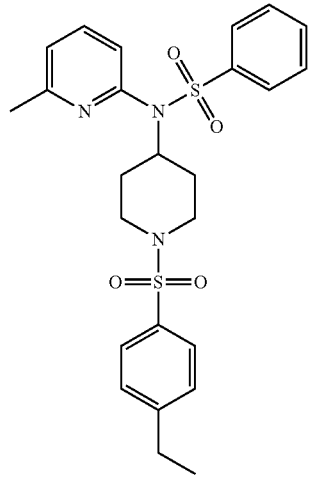 [SMILES: CCc1ccc(S(=O)(=O)N2CCC(N(c3cccc(C)n3)S(=O)(=O)c3ccccc3)CC2)cc1]

TABLE 1-continued
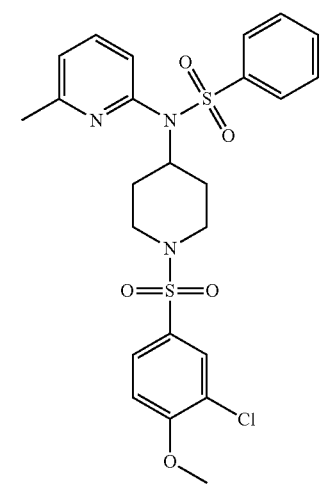
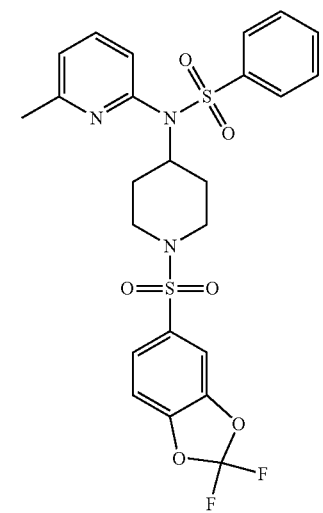 [SMILES: Cc1cccc(N(C2CCN(S(=O)(=O)c3ccc4c(c3)OC(F)(F)O4)CC2)S(=O)(=O)c2ccccc2)n1]
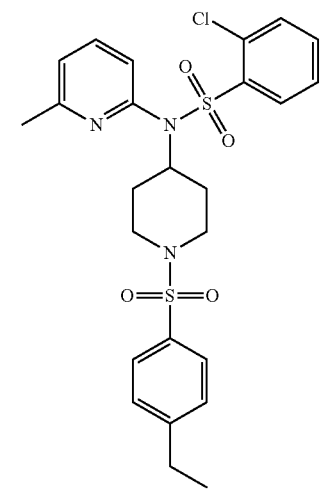 [SMILES: CCc1ccc(S(=O)(=O)N2CCC(N(c3cccc(C)n3)S(=O)(=O)c3ccccc3Cl)CC2)cc1]
TABLE 1-continued
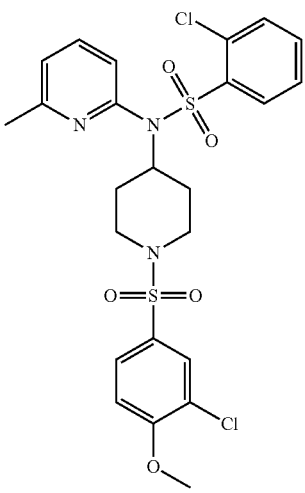
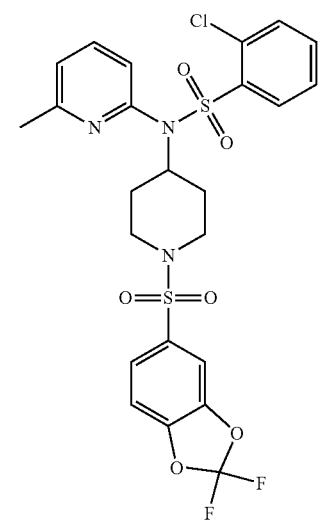 [SMILES: Cc1cccc(N(C2CCN(S(=O)(=O)c3ccc4c(c3)OC(F)(F)O4)CC2)S(=O)(=O)c2ccccc2Cl)n1]
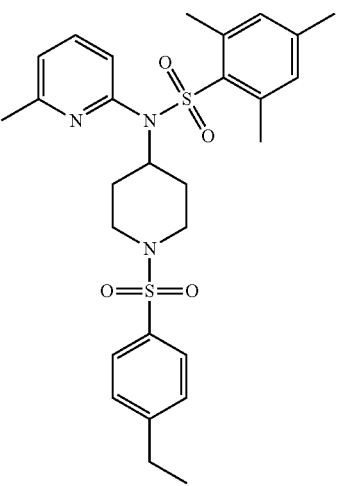

TABLE 1-continued
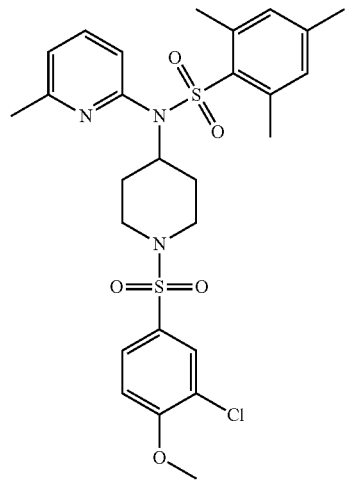
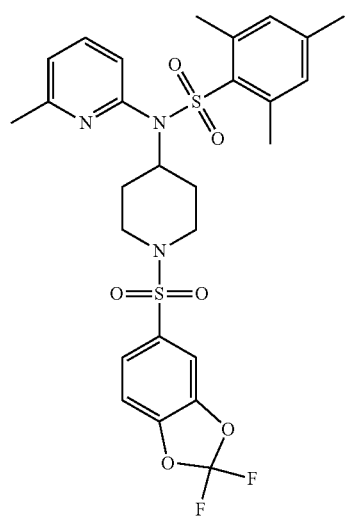
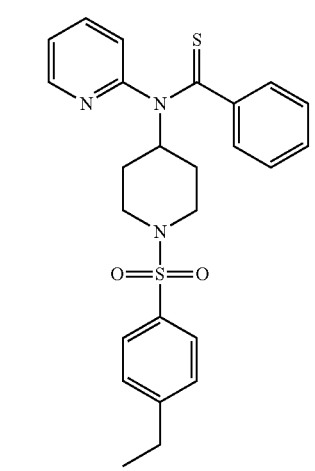 [SMILES: CCc1ccc(S(=O)(=O)N2CCC(N(C(=S)c3ccccc3)c3ccccn3)CC2)cc1]
TABLE 1-continued
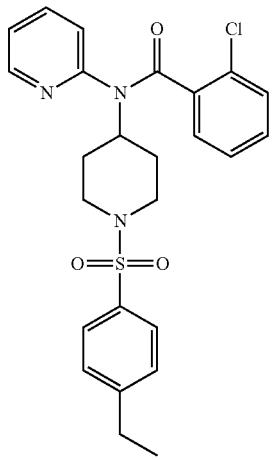 [SMILES: CCc1ccc(S(=O)(=O)N2CCC(N(C(=O)c3ccccc3Cl)c3ccccn3)CC2)cc1]
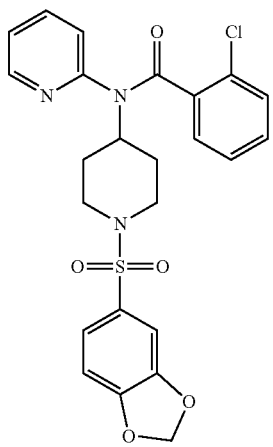 [SMILES: O=C(c1ccccc1Cl)N(c1ccccn1)C1CCN(S(=O)(=O)c2ccc3c(c2)OCO3)CC1]
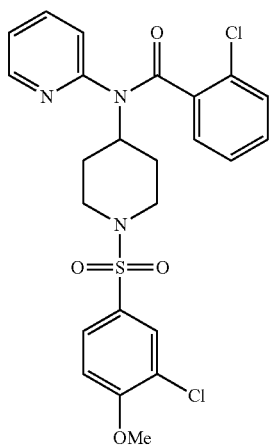

TABLE 1-continued
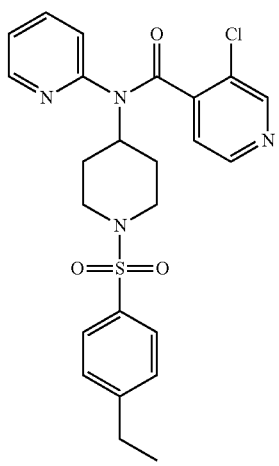 [SMILES: CCc1ccc(S(=O)(=O)N2CCC(N(C(=O)c3ccncc3Cl)c3ccccn3)CC2)cc1]
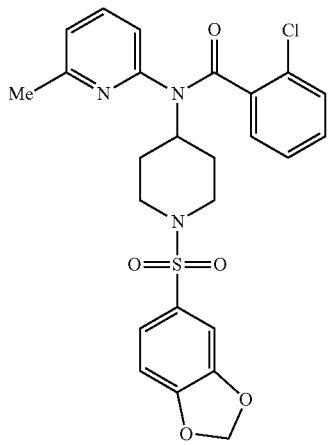
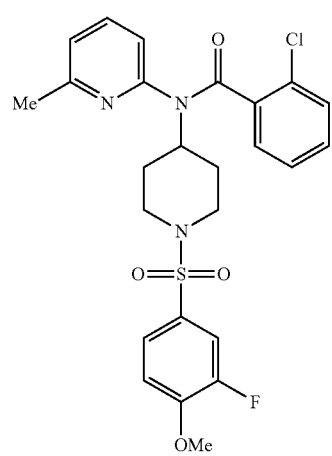 [SMILES: COc1ccc(S(=O)(=O)N2CCC(N(C(=O)c3ccccc3Cl)c3cccc(C)n3)CC2)cc1F]
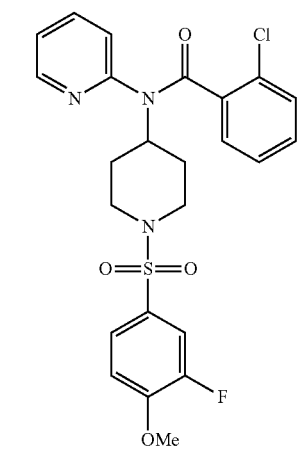
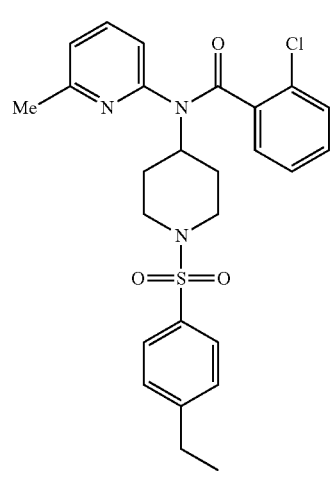 [SMILES: CCc1ccc(S(=O)(=O)N2CCC(N(C(=O)c3ccccc3Cl)c3cccc(C)n3)CC2)cc1]
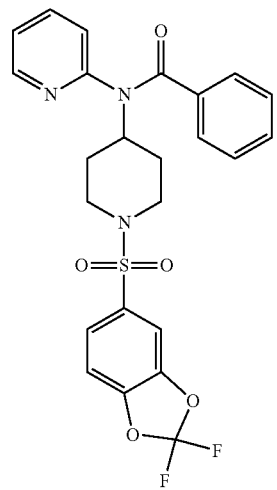 [SMILES: O=C(c1ccccc1)N(c1ccccn1)C1CCN(S(=O)(=O)c2ccc3c(c2)OC(F)(F)O3)CC1]

TABLE 1-continued
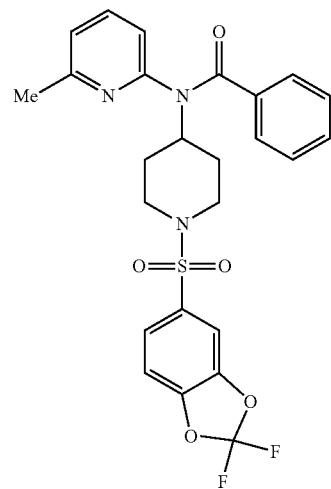 [SMILES: Cc1cccc(N(C(=O)c2ccccc2)C2CCN(S(=O)(=O)c3ccc4c(c3)OC(F)(F)O4)CC2)n1]
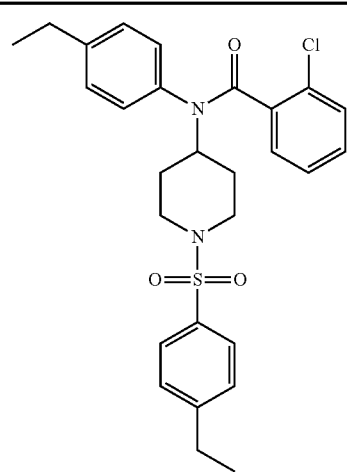
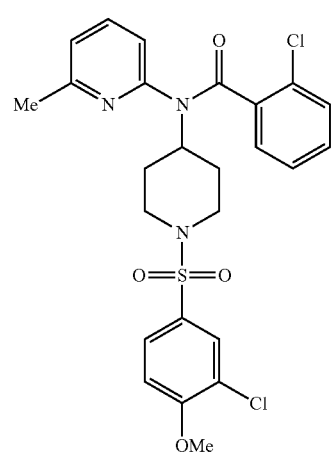 [SMILES: COc1ccc(S(=O)(=O)N2CCC(N(C(=O)c3ccccc3Cl)c3cccc(C)n3)CC2)cc1Cl]
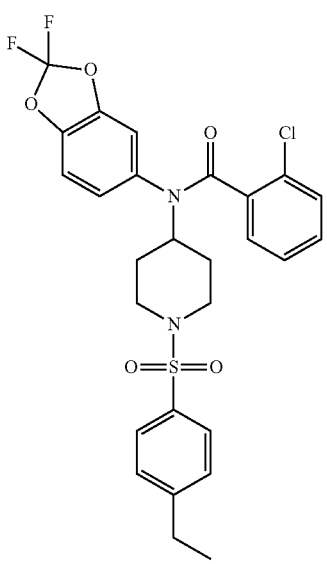
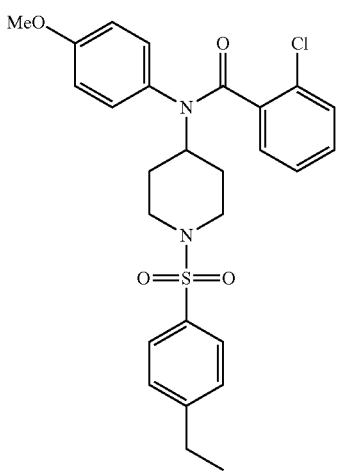 [SMILES: CCc1ccc(S(=O)(=O)N2CCC(N(C(=O)c3ccccc3Cl)c3ccc(OC)cc3)CC2)cc1]
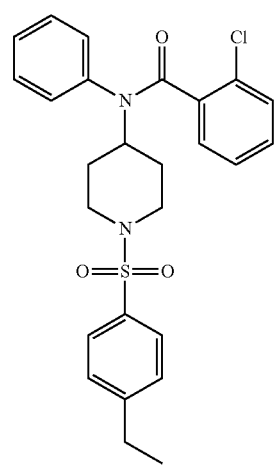 [SMILES: CCc1ccc(S(=O)(=O)N2CCC(N(C(=O)c3ccccc3Cl)c3ccccc3)CC2)cc1]

TABLE 1-continued
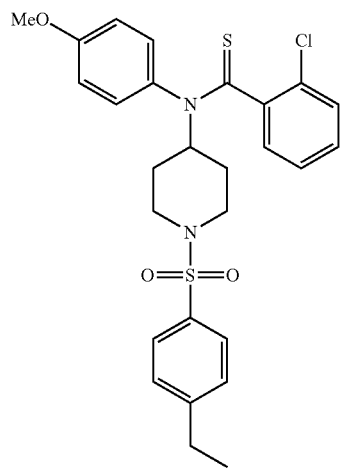
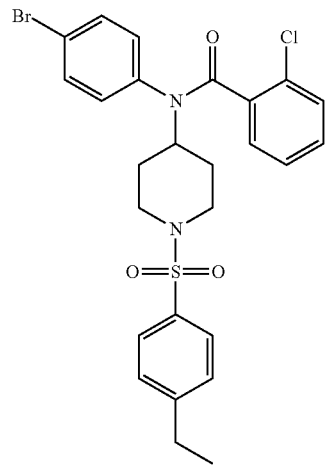 [SMILES: CCc1ccc(S(=O)(=O)N2CCC(N(C(=O)c3ccccc3Cl)c3ccc(Br)cc3)CC2)cc1]
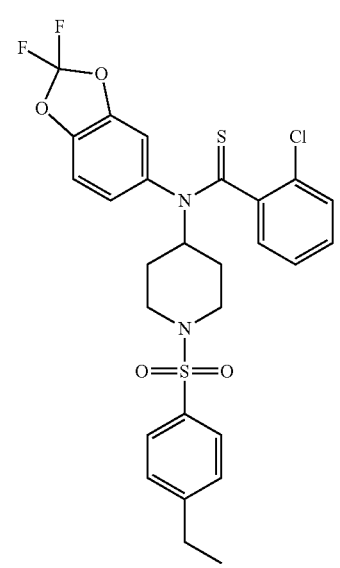
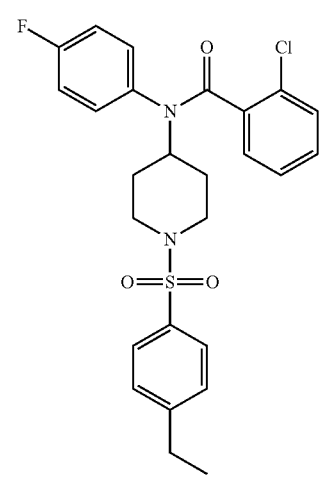 [SMILES: CCc1ccc(S(=O)(=O)N2CCC(N(C(=O)c3ccccc3Cl)c3ccc(F)cc3)CC2)cc1]
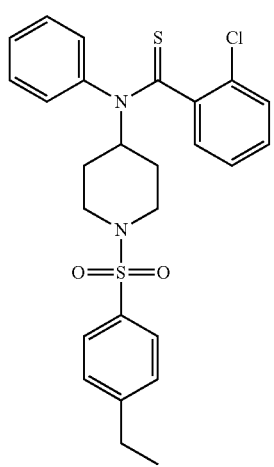
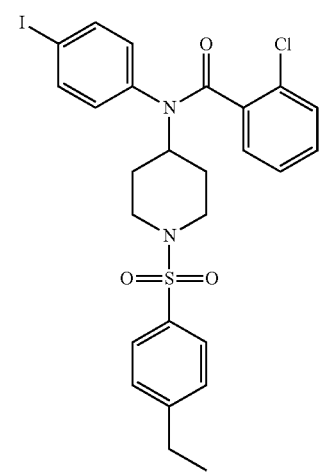

TABLE 1-continued
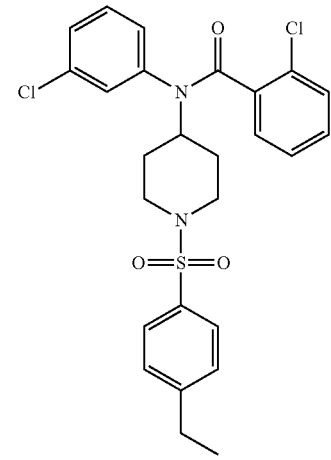 [SMILES: CCc1ccc(S(=O)(=O)N2CCC(N(C(=O)c3ccccc3Cl)c3cccc(Cl)c3)CC2)cc1]
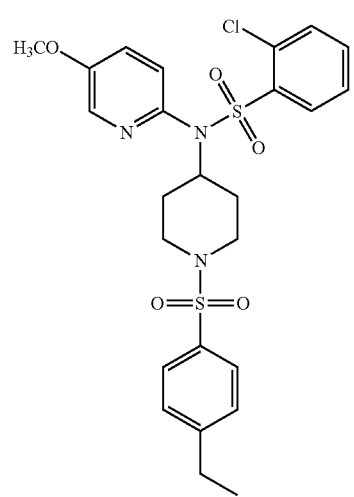 [SMILES: CCc1ccc(S(=O)(=O)N2CCC(N(c3ccc(OC)cn3)S(=O)(=O)c3ccccc3Cl)CC2)cc1]
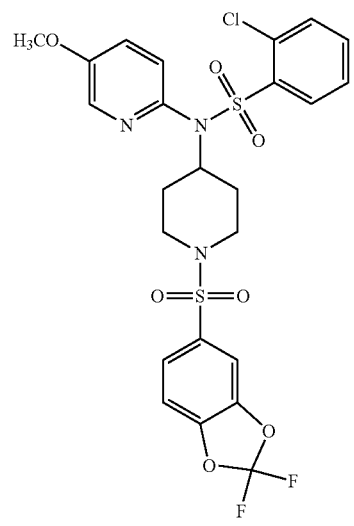 [SMILES: COc1ccc(N(C2CCN(S(=O)(=O)c3ccc4c(c3)OC(F)(F)O4)CC2)S(=O)(=O)c2ccccc2Cl)nc1]
TABLE 1-continued
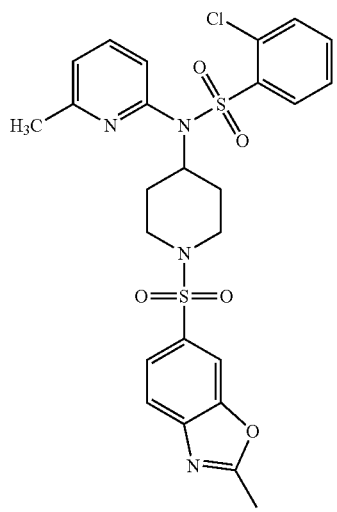 [SMILES: Cc1cccc(N(C2CCN(S(=O)(=O)c3ccc4nc(C)oc4c3)CC2)S(=O)(=O)c2ccccc2Cl)n1]
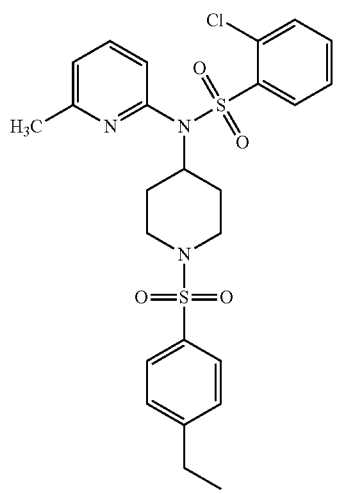 [SMILES: CCc1ccc(S(=O)(=O)N2CCC(N(c3cccc(C)n3)S(=O)(=O)c3ccccc3Cl)CC2)cc1]
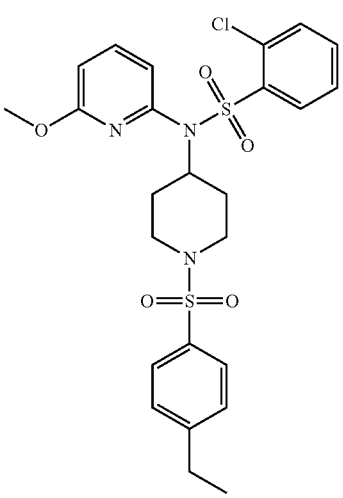 [SMILES: CCc1ccc(S(=O)(=O)N2CCC(N(c3cccc(OC)n3)S(=O)(=O)c3ccccc3Cl)CC2)cc1]

TABLE 1-continued
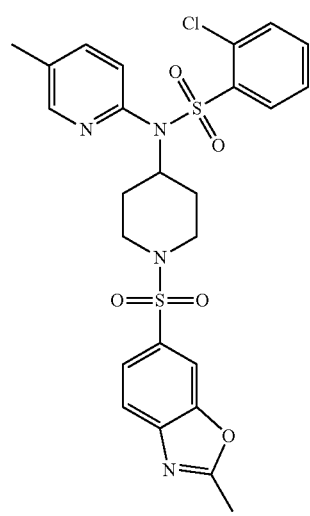 [SMILES: Cc1ccc(N(C2CCN(S(=O)(=O)c3ccc4nc(C)oc4c3)CC2)S(=O)(=O)c2ccccc2Cl)nc1]
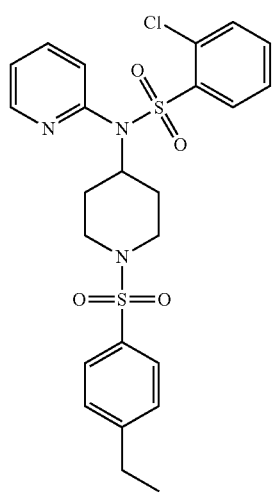 [SMILES: CCc1ccc(S(=O)(=O)N2CCC(N(c3ccccn3)S(=O)(=O)c3ccccc3Cl)CC2)cc1]
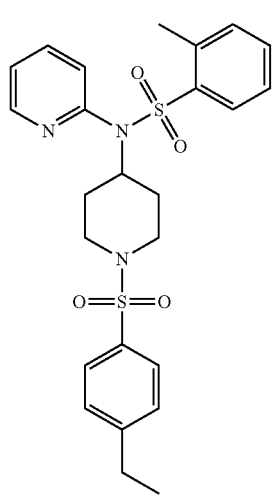 [SMILES: CCc1ccc(S(=O)(=O)N2CCC(N(c3ccccn3)S(=O)(=O)c3ccccc3C)CC2)cc1]
TABLE 1-continued
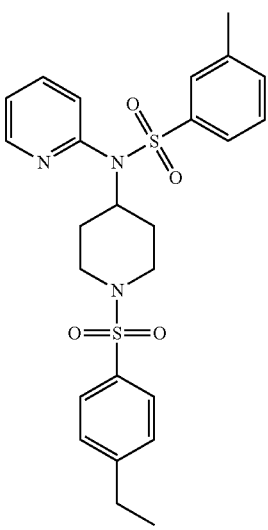 [SMILES: CCc1ccc(S(=O)(=O)N2CCC(N(c3ccccn3)S(=O)(=O)c3cccc(C)c3)CC2)cc1]
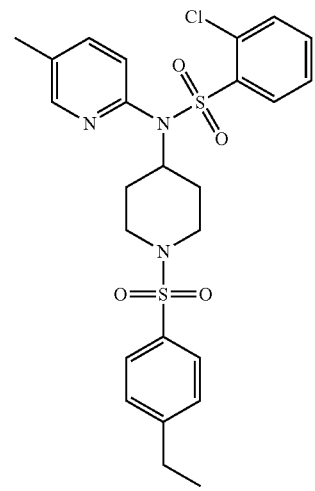 [SMILES: CCc1ccc(S(=O)(=O)N2CCC(N(c3ccc(C)cn3)S(=O)(=O)c3ccccc3Cl)CC2)cc1]
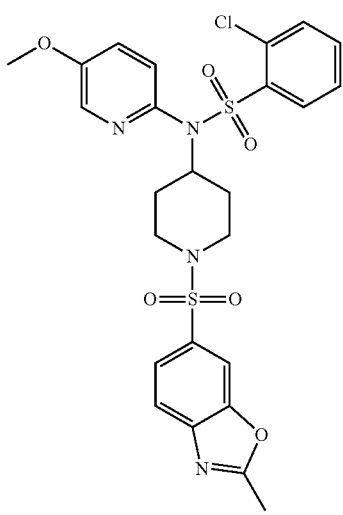 [SMILES: COc1ccc(N(C2CCN(S(=O)(=O)c3ccc4nc(C)oc4c3)CC2)S(=O)(=O)c2ccccc2Cl)nc1]

TABLE 1-continued
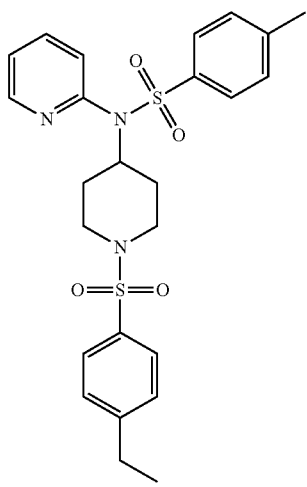 [SMILES: CCc1ccc(S(=O)(=O)N2CCC(N(c3ccccn3)S(=O)(=O)c3ccc(C)cc3)CC2)cc1]
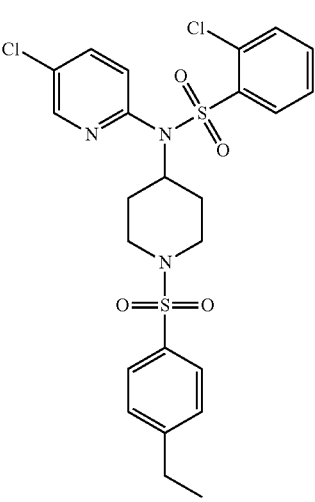 [SMILES: CCc1ccc(S(=O)(=O)N2CCC(N(c3ccc(Cl)cn3)S(=O)(=O)c3ccccc3Cl)CC2)cc1]
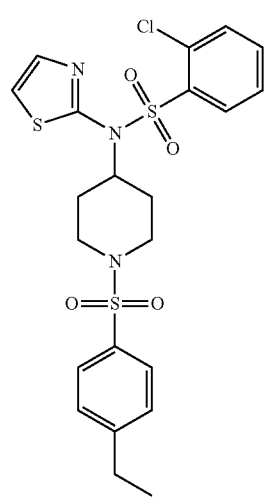 [SMILES: CCc1ccc(S(=O)(=O)N2CCC(N(c3nccs3)S(=O)(=O)c3ccccc3Cl)CC2)cc1]
TABLE 1-continued
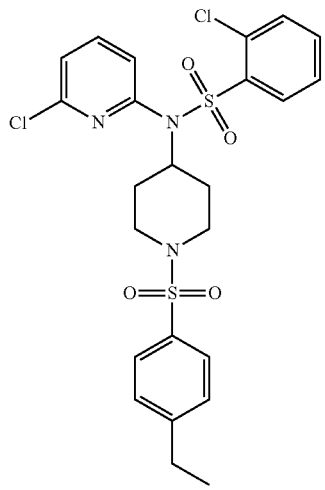 [SMILES: CCc1ccc(S(=O)(=O)N2CCC(N(c3cccc(Cl)n3)S(=O)(=O)c3ccccc3Cl)CC2)cc1]
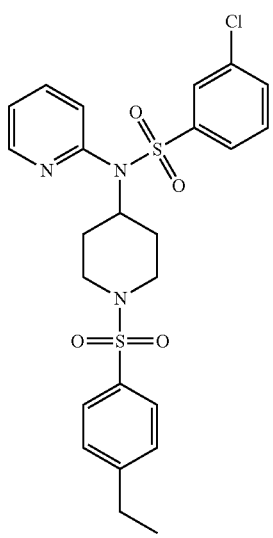 [SMILES: CCc1ccc(S(=O)(=O)N2CCC(N(c3ccccn3)S(=O)(=O)c3cccc(Cl)c3)CC2)cc1]

TABLE 1-continued
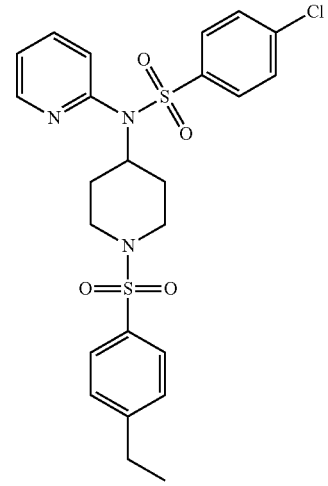 [SMILES: CCc1ccc(S(=O)(=O)N2CCC(N(c3ccccn3)S(=O)(=O)c3ccc(Cl)cc3)CC2)cc1]
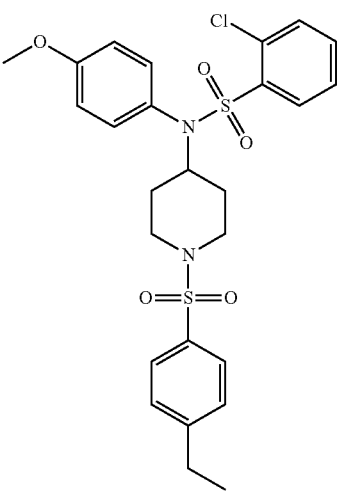 [SMILES: CCc1ccc(S(=O)(=O)N2CCC(N(c3ccc(OC)cc3)S(=O)(=O)c3ccccc3Cl)CC2)cc1]
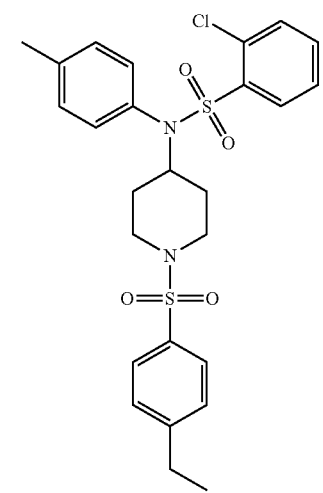 [SMILES: CCc1ccc(S(=O)(=O)N2CCC(N(c3ccc(C)cc3)S(=O)(=O)c3ccccc3Cl)CC2)cc1]
TABLE 1-continued
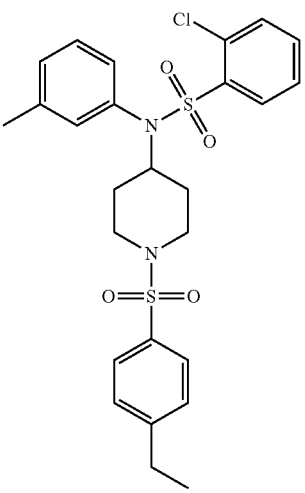
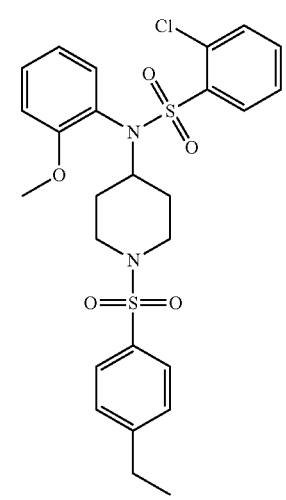 [SMILES: CCc1ccc(S(=O)(=O)N2CCC(N(c3ccccc3OC)S(=O)(=O)c3ccccc3Cl)CC2)cc1]
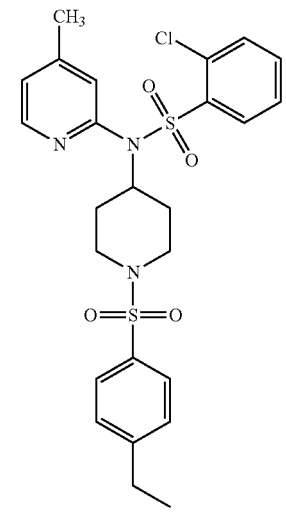 [SMILES: CCc1ccc(S(=O)(=O)N2CCC(N(c3cc(C)ccn3)S(=O)(=O)c3ccccc3Cl)CC2)cc1]

TABLE 1-continued
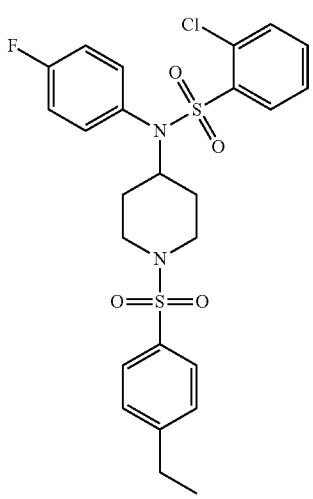 [SMILES: CCc1ccc(S(=O)(=O)N2CCC(N(c3ccc(F)cc3)S(=O)(=O)c3ccccc3Cl)CC2)cc1]
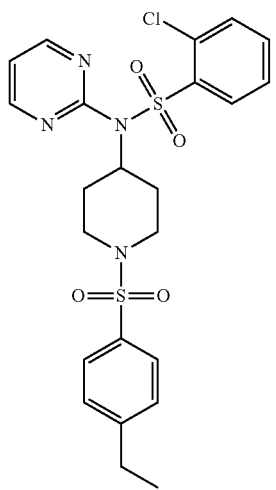 [SMILES: CCc1ccc(S(=O)(=O)N2CCC(N(c3ncccn3)S(=O)(=O)c3ccccc3Cl)CC2)cc1]
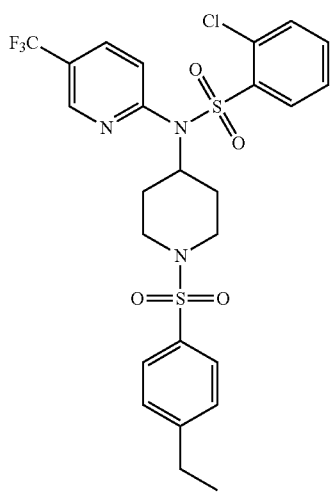 [SMILES: CCc1ccc(S(=O)(=O)N2CCC(N(c3ccc(C(F)(F)F)cn3)S(=O)(=O)c3ccccc3Cl)CC2)cc1]
TABLE 1-continued
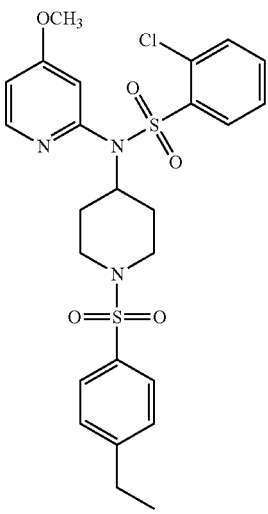 [SMILES: CCc1ccc(S(=O)(=O)N2CCC(N(c3cc(OC)ccn3)S(=O)(=O)c3ccccc3Cl)CC2)cc1]
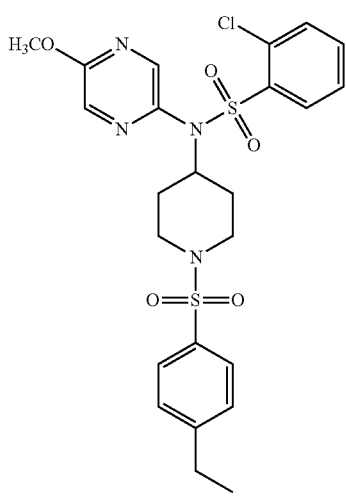 [SMILES: CCc1ccc(S(=O)(=O)N2CCC(N(c3cnc(OC)cn3)S(=O)(=O)c3ccccc3Cl)CC2)cc1]
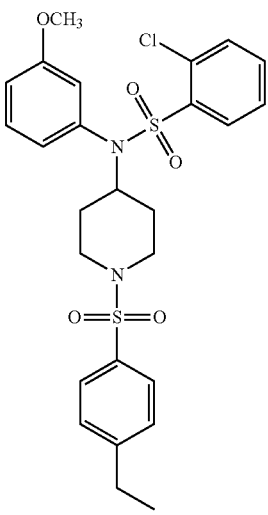 [SMILES: CCc1ccc(S(=O)(=O)N2CCC(N(c3cccc(OC)c3)S(=O)(=O)c3ccccc3Cl)CC2)cc1]

TABLE 1-continued
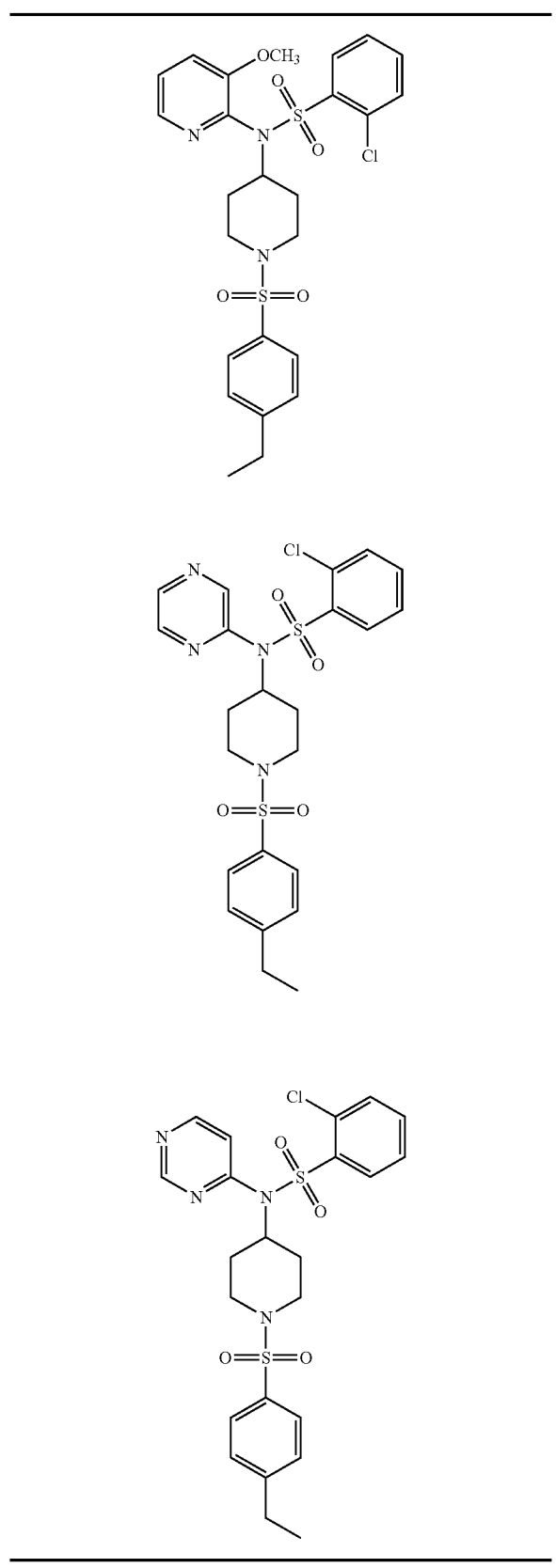
General synthetic schemes to prepare compounds of the invention:
SCHEME 1:
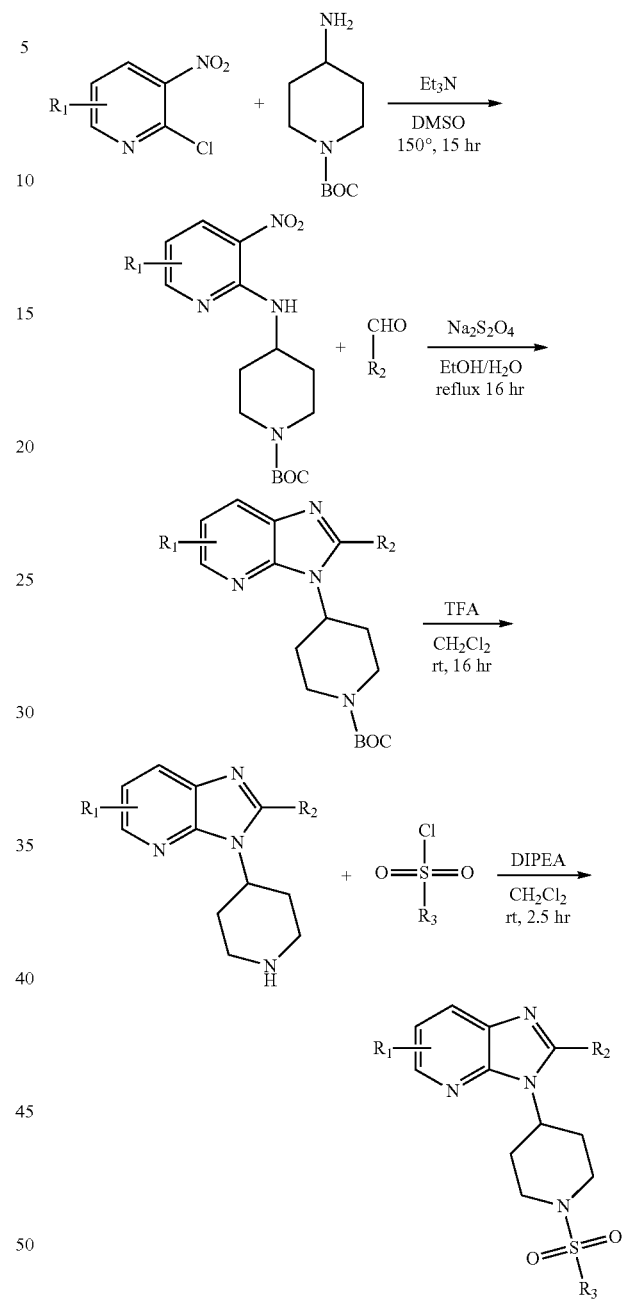
SCHEME 1a:
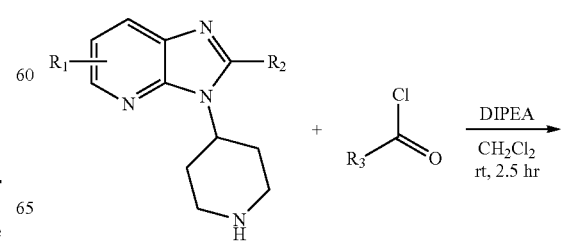

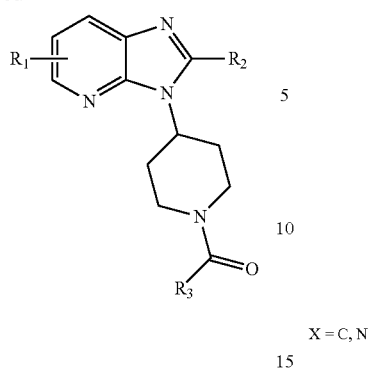
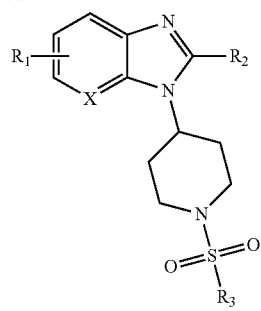
X = C, N
SCHEME 1b:
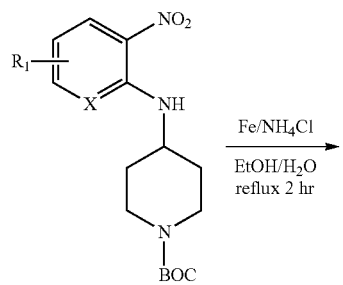
SCHEME 1c:
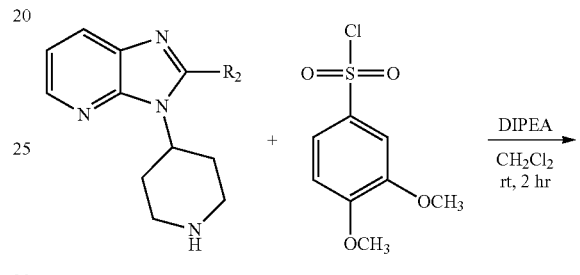
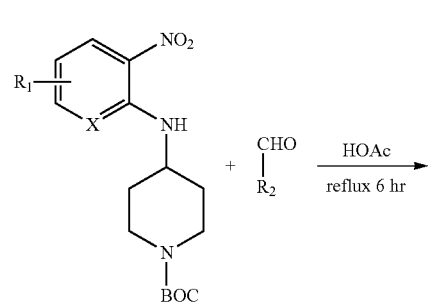
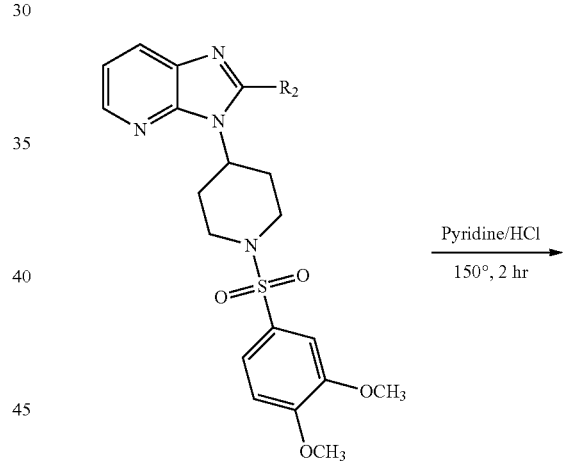
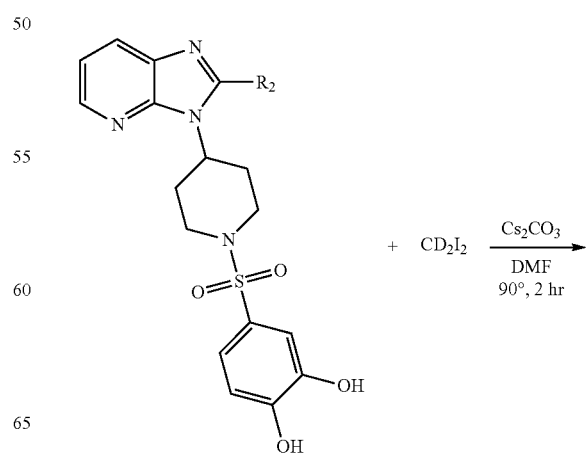

-continued
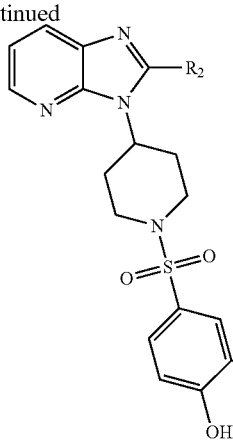
SCHEME 2:
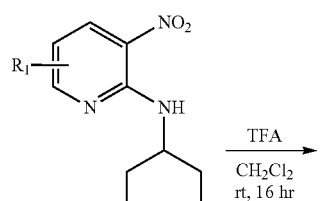
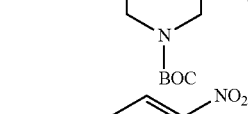
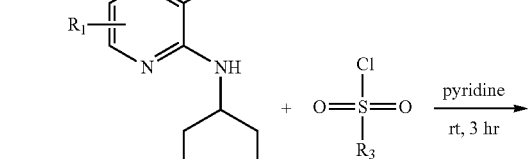
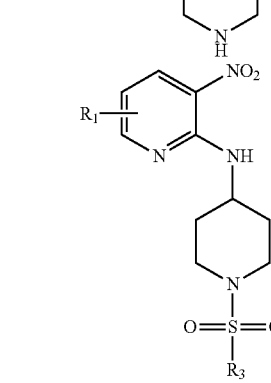
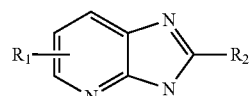
SCHEME 3:
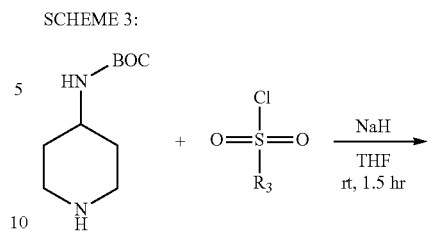
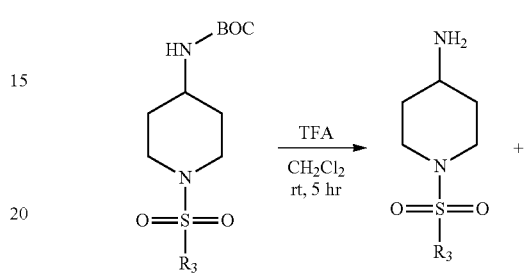
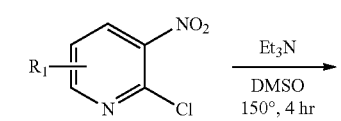
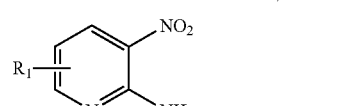
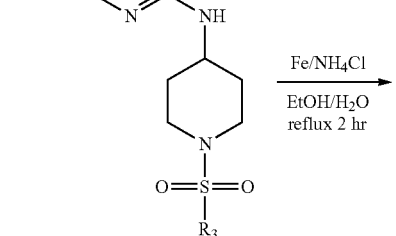
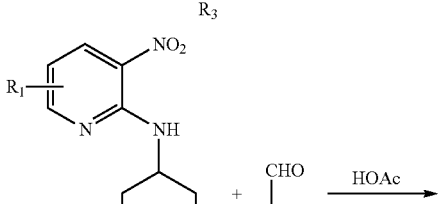
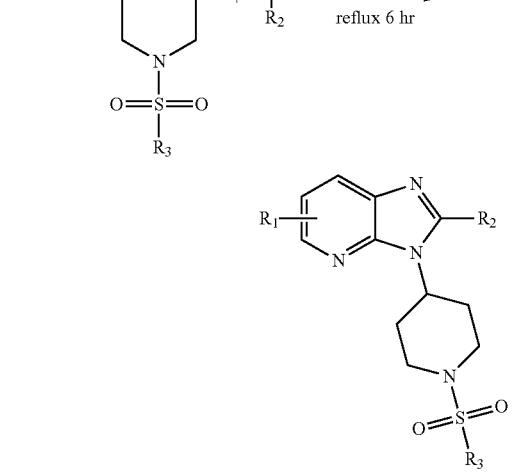

SCHEME 3a:
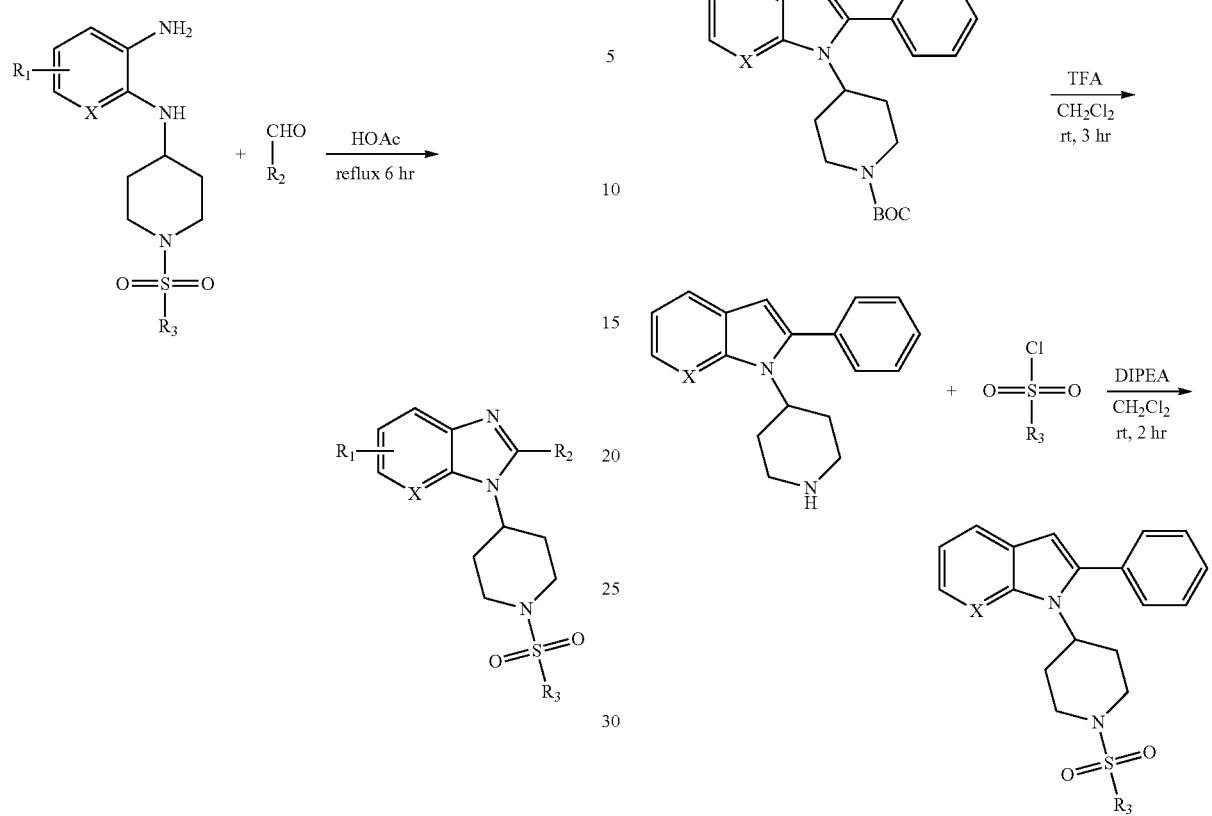
X = C, N
SCHEME 4:
SCHEME 5:
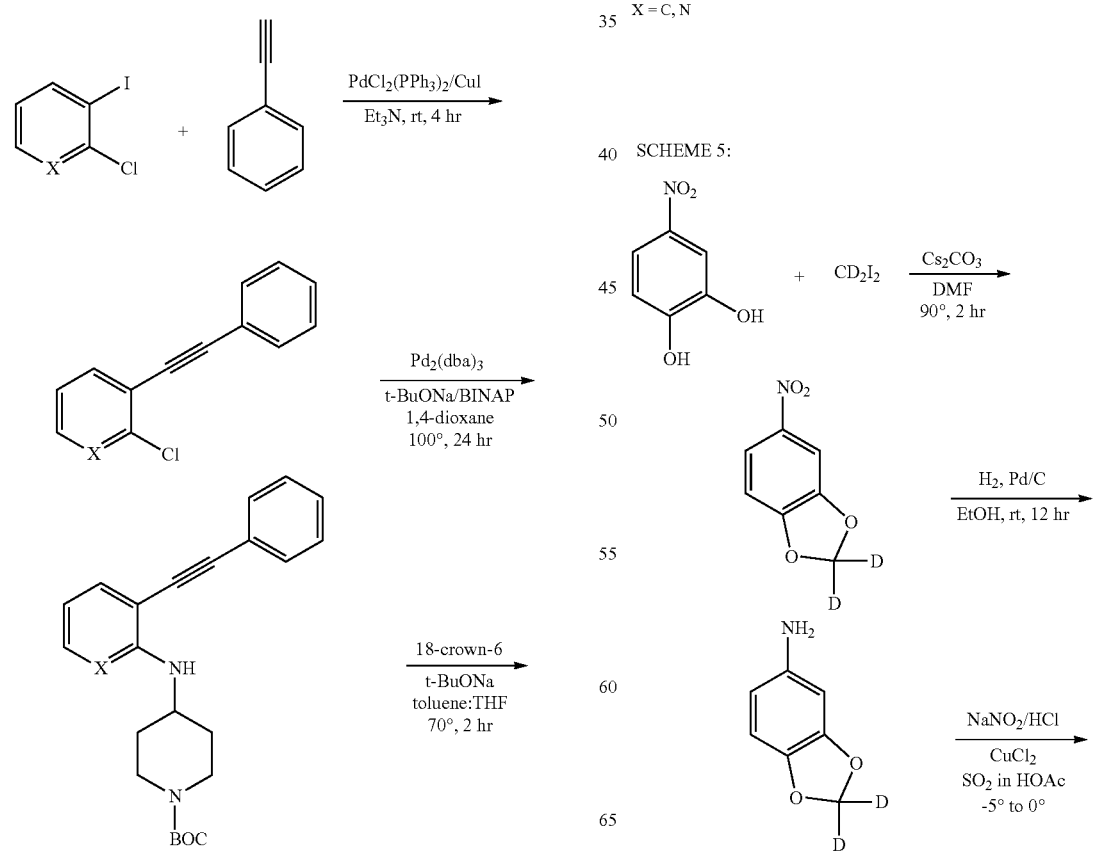

-continued
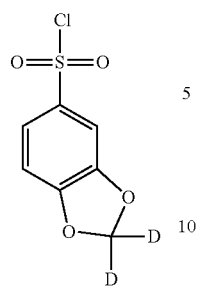
SCHEME 8:
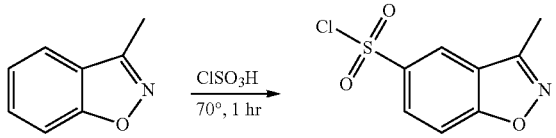
SCHEME 6:
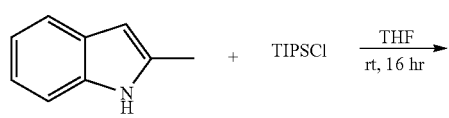
SCHEME 9:
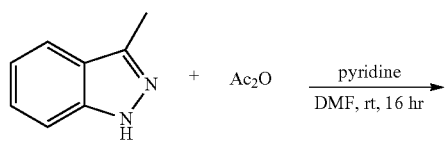
SCHEME 7:
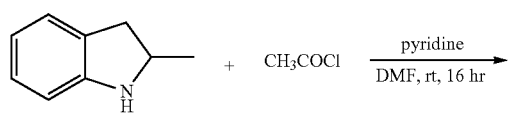
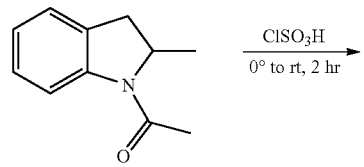
SCHEME 10:
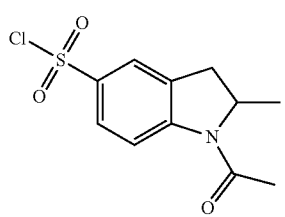

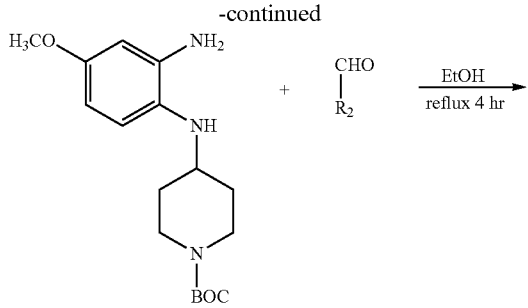
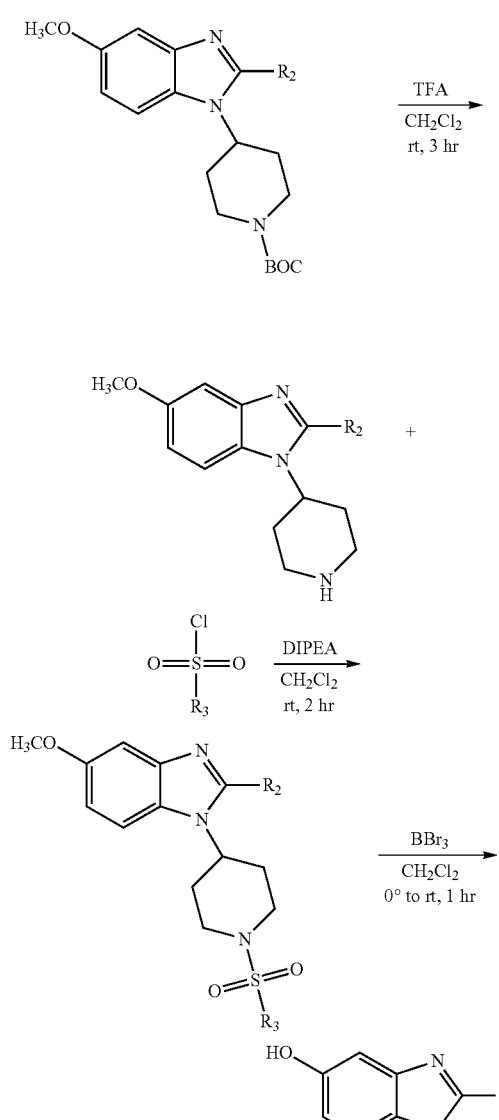
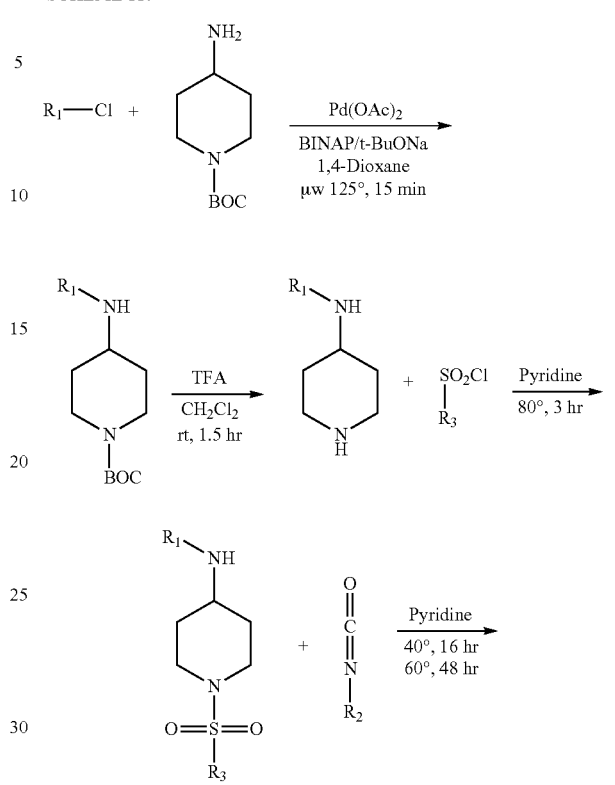
SCHEME 12:
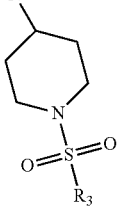
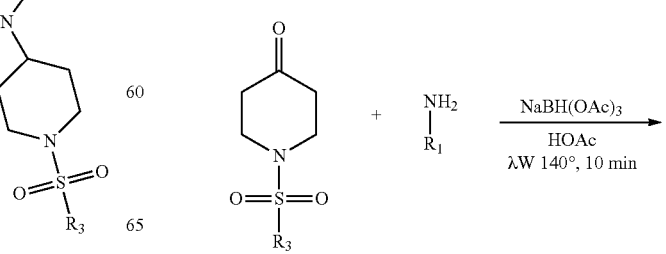

103

-continued

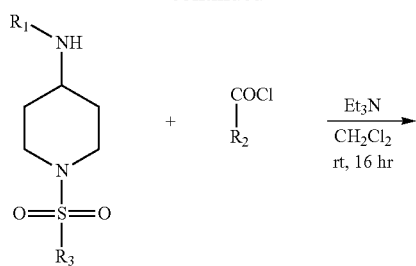

104

-continued

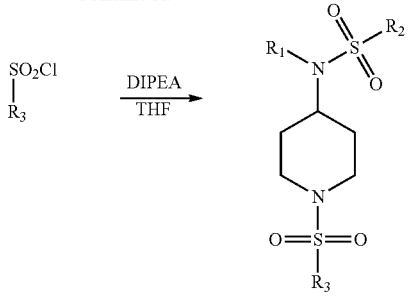

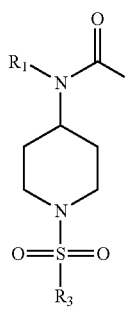

SCHEME 14:

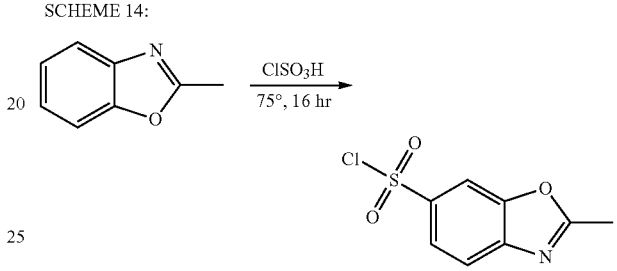

SCHEME 12a:

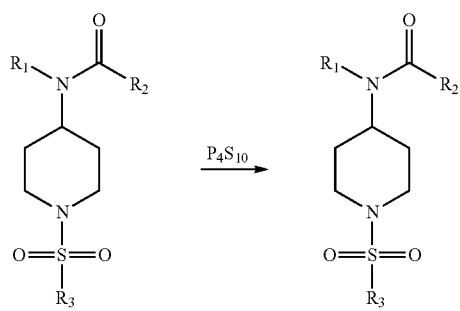

SCHEME 13:

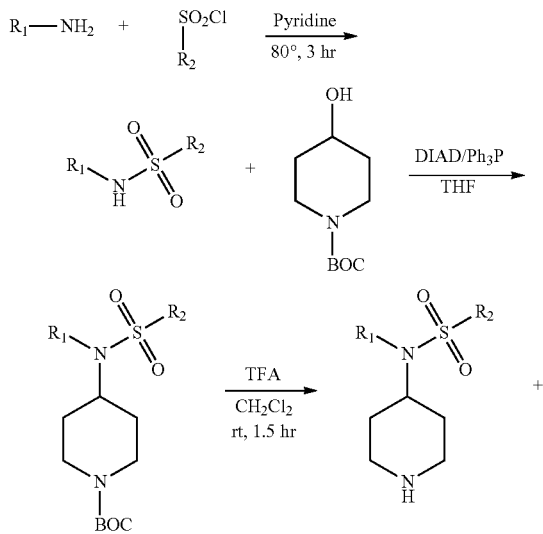

Compounds of the invention are useful as modulators of CFTR and treating diseases or disorders mediated by CFTR such as for the treatment of disease, disorders or conditions such as Cystic fibrosis, Hereditary emphysema, Hereditary hemochromatosis, Coagulation-Fibrinolysis deficiencies such as Protein C deficiency, Type 1 hereditary angioedema, Lipid processing deficiencies such as Familial hypercholesterolemia, Type 1 chylomicronemia, Abetalipoproteinemia, Lysosomal storage diseases such as I-cell disease/Pseudo-Hurler, Mucopolysaccharidosis, Sandhof/Tay-Sachs, Crigler-Najjar type II, Polyendocrinopathy/Hyperinsulemia, Diabetes mellitus, Laron dwarfism, Myeloperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, progressive supranuclear palsy, Pick's disease, several polyglutamine neurological disorders such as Huntington's disease, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome, secretory diarrhea, polycistic kidney disease, chronic obstructive pulmonary disease (COPD), dry eye disease or Sjogren's syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases. Mucolytics or mucus thinning medicines can also be used in combination with the invention. Examples include carbocisteine (trade name MUCODYNE®), erdosteine (trade name ERDOTIN®) and mecysteine (trade name VISCLAIR®). Another type of mucolytic that can be used is dornase alfa (trade name PULMOZYME®). These drugs can be used as inhaled or nebulized formulations, capsules, tablets or oral liquids.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention. In one embodiment, the invention relates to the administration of a compound of the invention to a patient currently undergoing treatment with a second pharmaceutical agent for the treatment of a disease or disorder mediated by CFTR.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused.

The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms.

Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: deutero, halo, alkyl, cycloalkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

Abbreviations:
All temperatures are in degrees Centigrade
rt—room temperature
hr—hours
$Et_3N$—triethylamine
DMSO—dimethylsulfoxide
EtOAc—ethyl acetate
$Na_2SO_4$—sodium sulfate
$MgSO_4$—magnesium sulfate
$K_2CO_3$—potassium carbonate
$Et_2O$—diethyl ether
TFA—trifluoroacetic acid
$CH_2Cl_2$—methylene chloride
$CHCl_3$—chloroform
$Na_2S_2O_4$—sodium dithionite
$NaHCO_3$—sodium bicarbonate
$H_2O$—water
DIPEA—diisopropylethylamine
HCl—hydrochloric acid
NaH—sodium hydride
THF—tetrahydrofuran
$NH_4Cl$—ammonium chloride
HOAc—acetic acid
n-BuLi—n-butyl lithium
$SO_2Cl_2$—sulfuryl chloride
Fe—iron powder
$Cs_2CO_3$—cesium carbonate
$PdCl_2(PPh_3)_2$—bis(triphenylphosphine)palladium(II) dichloride
CuI—copper(I) iodide
$Pd_2(dba)_3$—tris(dibenzylideneacetone)dipalladium(O)
t-BuONa—sodium tert-butoxide
BINAP—(2,2'-bis(diphenylphosphino)-1,1'-binaphthyl)
18-crown-6-18-crown-6 ether
$CD_2I_2$—diiodomethane-$D_2$
$NaNO_2$—sodium nitrite
TIPSCl—triisopropylsilyl chloride
$ClSO_3H$—chlorosulfonic acid
$CH_3COCl$—acetyl chloride
$Ac_2O$—acetic anhydride
Xantphos—4,5-bis(diphenylphosphino)-9,9-dimethyxanthene
$BBr_3$—boron tribromide
$NaBH(OAc)_3$—sodium triacetoxyborohydride
DCE—dichloroethane
$Pd(OAc)_2$—palladium acetate
$P_4S_{10}$—phosphorous pentasulfide
DIAD—diisopropyl azodicarboxylate
$Ph_3P$—triphenylphosphine
$CuCl_2$—copper(II) chloride.

EXAMPLES

Example 1

3-(1-(Benzo[d][1,3]dioxol-5-ylsulfonyl)piperidin-4-yl)-2-(2-chlorophenyl)-3H-imidazo[4,5-b]pyridine (8)

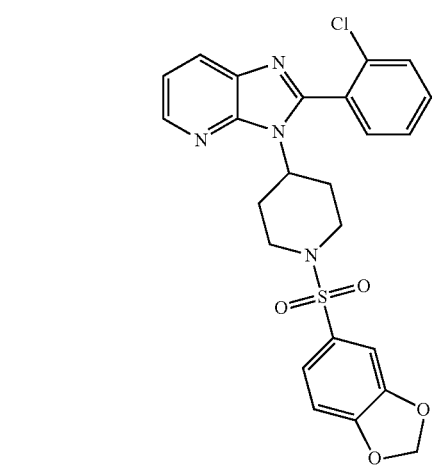

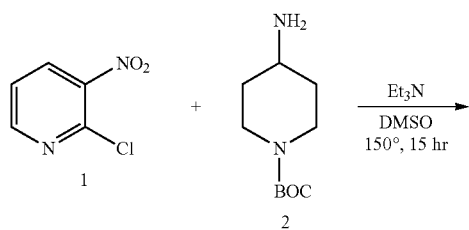

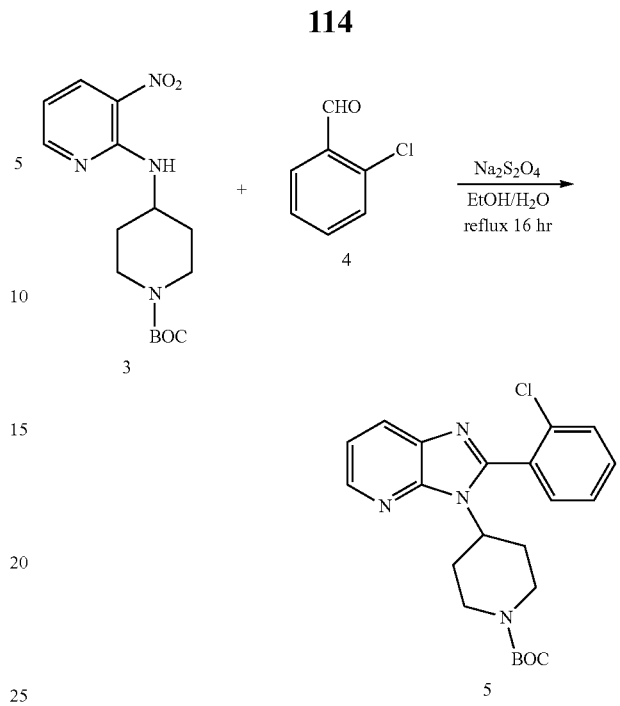

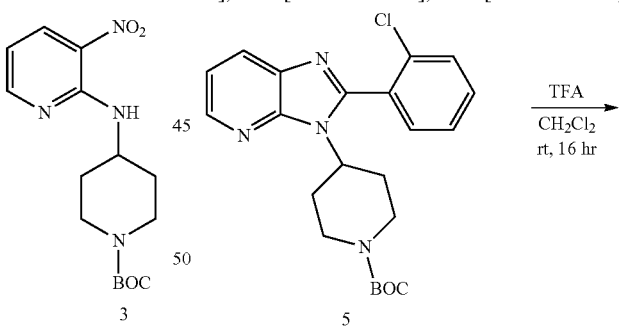

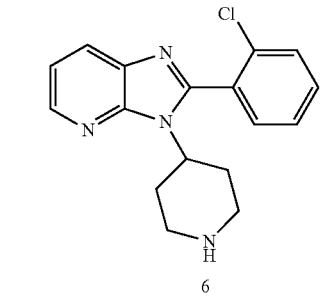

tert-Butyl 4-((3-nitropyridin-2-yl)amino)piperidin-1-carboxylate (3). Et₃N (2.6 mL, 19.26 mmol) was added to a stirred solution of 1 (2.35 g, 14.822 mmol) and 2 (2.97 g, 14.822 mmol) in anhydrous DMSO (30 mL) at room temperature (rt). The resulting reaction mixture was stirred at 150° C. for 15 hr. After the reaction was complete, it was cooled to rt and ice-cold H₂O was added. The resulting mixture was extracted with EtOAc (2×30 mL). The combined organic layers were dried over anhydrous Na₂SO₄ and concentrated in vacuo to give the crude compound as a thick brown liquid. This was triturated with hexanes to give 3.3 g (69% yield) of 3 as a yellow solid. LCMS m/z 267 [M−56+H], 223 [M−100+H].

tert-Butyl 4-(2-(2-chlorophenyl)-3H-imidazo[4,5-b]pyridin-3-yl)piperidine-1-carboxylate (5). Saturated sodium dithionite (8.91 g, 51.18 mmol) solution was added to a stirred solution of 3 (3.3 g, 10.23 mmol) and 4 (1.43 g, 10.237 mmol) in EtOH (33 mL) at rt. The reaction mixture was heated to 110° and stirred for 16 hr. After the reaction was complete, the reaction mixture was cooled to rt and ice-cold H₂O was added. The resulting mixture was extracted with EtOAc (2×75 mL). The combined organic layers were dried over anhydrous Na₂SO₄ and concentrated in vacuo to give the crude product. This was washed with Et₂O and n-hexane (1:10) to give 2.45 g (58% yield) of pale yellow solid 5 which was used in the next step without any further purification. LCMS m/z 413 [M+H−1], 415 [M+H+1], 313 [M+H−100−1], 315 [M+H−100+1].

2-(2-Chlorophenyl)-3-(piperidin-4-yl)-3H-imidazo[4,5-b]pyridine (6). TFA (7.5 mL) was added to a stirred solution of 5 (2.45 g, 5.93 mmol) in anhydrous CH$_2$Cl$_2$ (25 mL) at 0°. The reaction mixture was allowed to warm to rt and stirred for 16 hr. The reaction mixture was basified with saturated NaHCO$_3$ solution, then extracted with CH$_2$Cl$_2$. The organic layer was washed with H$_2$O, followed by brine solution and dried over anhydrous Na$_2$SO$_4$. The organic layer concentrated in vacuo to give crude 6 as a pale yellow solid. This was triturated with Et$_2$O and n-hexanes (1:10) to give 1.5 g (81% yield) of 6 as a pale yellow solid. LCMS m/z 313 [M+H−1], 315 [M+H+1].

δ 8.42-8.41 (dd, J=4.8 Hz, J=1.6 Hz, 1H), 8.13-8.11 (dd, J=1.4 Hz, J=7.8 Hz, 1H), 7.67-7.59 (m, 3H), 7.54-7.48 (m, 1H), 7.36-7.33 (dd, J=7.8 Hz, J=5.0 Hz, 1H), 7.28-7.26 (dd, J=8.0 Hz, J=1.6 Hz, 1H), 7.21 (d, J=1.6 Hz, 1H), 7.11 (d, J=8.0 Hz, 1H), 6.18 (s, 2H), 4.00-3.90 (m, 1H), 3.80-3.66 (br m, 2H), 3.10-2.85 (br m, 2H), 2.38-2.26 (br m, 2H), 2.02-1.74 (br m, 2H). LCMS m/z 497 [M+H−1], 499 [M+H+1].

Example 2

3-(1-Benzo[d][1,3]dioxol-5-ylsulfonyl(piperidin-4-yl)-2-(2-chlorophenyl)-5-methyl-3H-imidazo[4,5-b]pyridine (13)

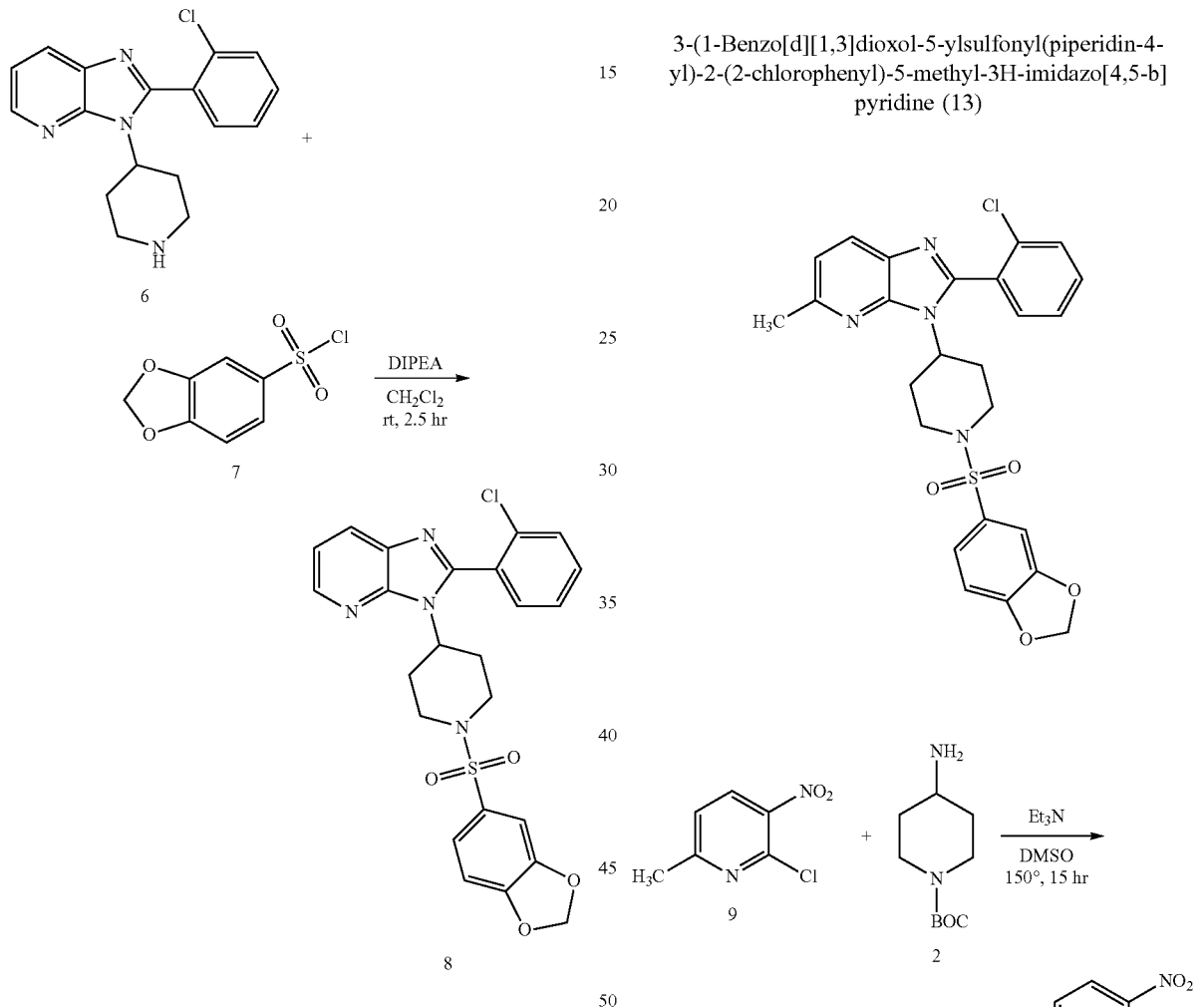

3-(1-(Benzo[d][1,3]dioxol-5-ylsulfonyl)piperidin-4-yl)-2-(2-chlorophenyl)-3H-imidazo[4,5-b]pyridine (8). DIPEA (0.19 mL, 1.15 mmol) was added to a stirred solution of 6 (0.12 g, 0.383 mmol) in anhydrous CH$_2$Cl$_2$ (3 mL) at 0°. The reaction mixture was stirred at this temperature for 2 hr and then 7 (0.084 g, 0.383 mmol) was added. The resulting mixture was allowed to warm to rt and stirred at rt for 30 min. The reaction mixture was basified using saturated NaHCO$_3$ solution then extracted with CH$_2$Cl$_2$. The organic layer was washed with H$_2$O, followed by brine solution and dried over anhydrous Na$_2$SO$_4$. The organic layer was concentrated in vacuo to give the crude product as a semi-solid. The crude product was purified by flash column chromatography using 100-200 mesh silica gel. The desired product was eluted in 50% EtOAc in pet-ether to obtain 0.075 g (39%) of pure 8 as a pale yellow solid. $^1$H NMR (DMSO-d$_6$)

tert-Butyl 4-((6-methyl-3-nitropyridin-2-yl)amino)piperidine-1-carboxylate (10). Et$_3$N (4.52 mL, 74.578 mmol) was added to a stirred solution of 9 (4.29 g, 24.859 mmol), 2 (5.0 g, 24.859 mmol) in anhydrous DMSO (45 mL) at rt. The resulting reaction mixture was stirred at 150° for 15 hr. After the reaction was complete, it was cooled to rt and ice-cold H₂O was added. The resulting mixture was extracted with EtOAc (2×50 mL). The combined organic layers were dried over anhydrous Na₂SO₄ and concentrated in vacuo in order to afford crude compound as a thick brown liquid. This was washed with n-hexane to give 4.50 g (54% yield) of 10 as a yellow solid. LCMS m/z 281 [M−56+H], 237 [M−100+H].

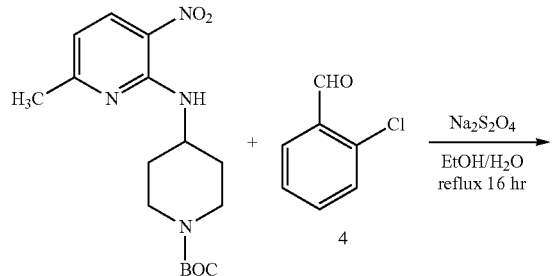

10

4

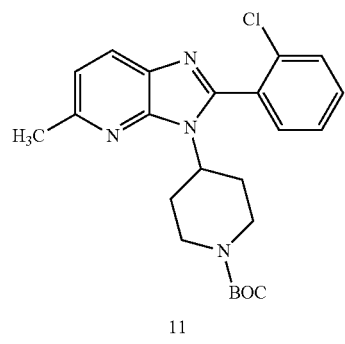

11 tert-Butyl 4-(2-(2-chlorophenyl)-5-methyl-3H-imidazo[4,5-b]pyridin-3-yl)piperidine-1-carboxylate (11). Sodium dithionite (8.28 g, 47.563 mmol) solution was added to a stirred solution of 10 (3.2 g, 9.512 mmol) and 4 (1.33 g, 9.512 mmol) in EtOH (33 mL) at rt. The reaction mixture was stirred at 110° for 16 hr. After the reaction was complete, it was cooled to rt and ice-cold H₂O was added. The resulting mixture was extracted with EtOAc (2×50 mL). The combined organic layers were dried over anhydrous Na₂SO₄ and concentrated in vacuo to give crude product. This was triturated with Et₂O and n-hexane (1:10) to give 2.5 g (65% yield) of 11 as a pale yellow solid. LCMS m/z 427 [M+H−1], 429 [M+H+1], 327 [M+H−100−1], 329 [M+H−100+1].

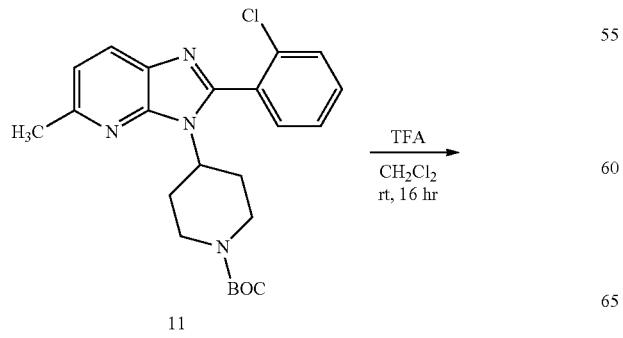

11

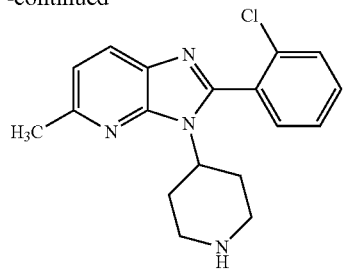

12

2-(2-Chlorophenyl)-5-methyl-3-(piperidin-4-yl)-3H-imidazo[4,5-b]pyridine (12). TFA (9 mL) was added to a stirred solution of 11 (2.5 g, 5.8556 mmol) in anhydrous CH₂Cl₂ (25 mL) at 0° C. The reaction mixture was allowed to warm to rt and stirred for 16 hr. After the reaction was complete, the reaction mixture was basified using saturated NaHCO₃ solution and extracted with CH₂Cl₂ (2×75 mL). The combined organic layers were washed with H₂O and brine solution. The organic layer was dried over anhydrous Na₂SO₄ and concentrated in vacuo to give crude 12 as a pale yellow solid. This was triturated with Et₂O and n-hexane (1:10) to give 1.5 g (78% yield) of 12 as a pale yellow solid. LCMS m/z 327 [M+H−1], 329 [M+H+1].

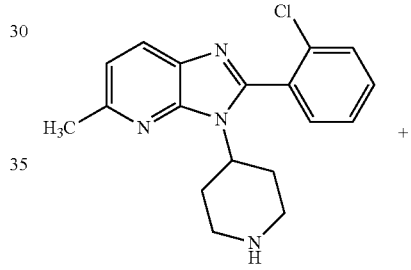

12

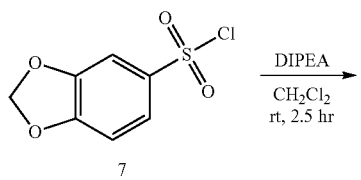

7

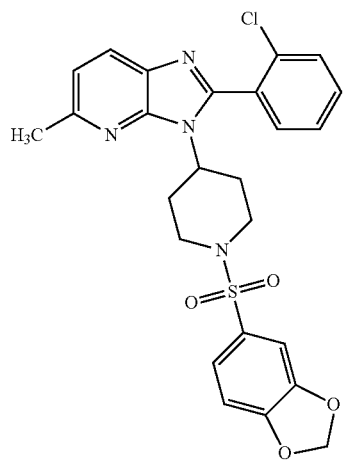

13

3-(1-Benzo[d][1,3]dioxol-5-ylsulfonyl(piperidin-4-yl)-2-(2-chlorophenyl)-5-methyl-3H-imidazo[4,5-b]pyridine (13). DIPEA (0.19 mL, 1.1013 mmol) was added to a stirred solution of 12 (0.12 g, 0.3671 mmol) in anhydrous CH$_2$Cl$_2$ (3 mL) at 0°. The reaction mixture was stirred at this temperature for 2 hr. and then 7 (0.081 g, 0.3671 mmol) was added. The resulting mixture was allowed to warm to rt and stirred at rt for 30 min. The reaction mixture was basified using saturated NaHCO$_3$ solution then extracted with CH$_2$Cl$_2$. The organic layer was washed with H$_2$O, followed by brine solution and dried over anhydrous Na$_2$SO$_4$. The organic layer was concentrated in vacuo to give crude product as a semi-solid. The crude product was purified by flash column chromatography using 100-200 mesh silica gel. The desired product was eluted in 50% EtOAc in pet-ether to obtain 0.057 g (30%) of pure 13 as a pale yellow solid. $^1$H NMR (DMSO-d$_6$) δ 7.98 (d, J=8.4 Hz, 1H), 7.66-7.61 (m, 2H), 7.59 (d, J=7.2 Hz, 1H), 7.52-7.48 (m, 1H), 7.27-7.25 (dd, J=8.2 Hz, J=1.8 Hz, 1H), 7.21 (d, J=6.4 Hz, 1H), 7.20 (d, J=2.8 Hz, 1H), 7.10 (d, J=7.6 Hz, 1H), 6.17 (s, 2H), 3.94-3.66 (br m, 1H), 3.60-3.34 (br m, 2H), 3.20-2.85 (br m, 2H), 2.63 (s, 3H), 2.66-2.40 (br m, 2H), 2.04-1.48 (br m, 2H). LCMS m/z 511 [M+H−1], 513 [M+H+1].

Example 3

3-(1-((3-Chloro-4-methoxyphenyl)sulfonyl)piperidin-4-yl)-5-methyl-2-phenyl-3H-imidazo[4,5-b]pyridine (18)

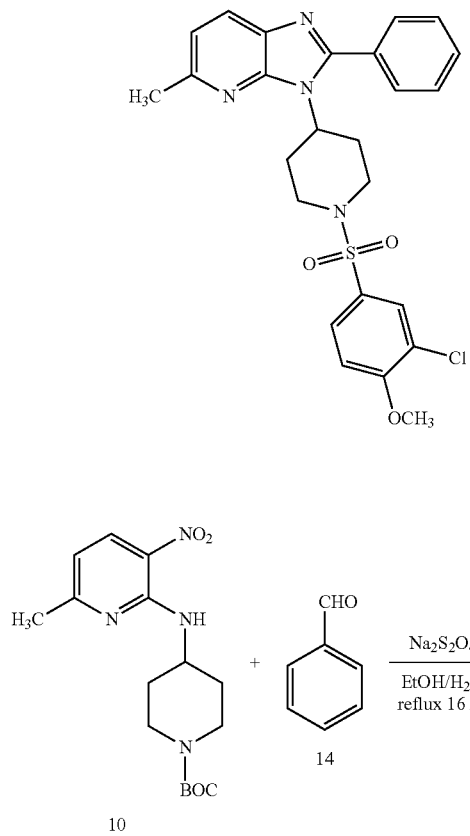

tert-Butyl 4-(5-methyl-2-phenyl-3H-imidazo[4,5-b]pyridin-3-yl)piperidine-1-carboxylate (15). Sodium dithionite (0.646 g, 3.715 mmol) solution was added to a stirred solution of 10 (0.250 g, 0.743 mmol) and 14 (0.780 g, 0.743 mmol) in EtOH (9 mL) at rt. The reaction mixture was stirred at 110° C. for 16 hr. After the reaction was complete, it was cooled to rt and ice-cold H$_2$O was added. The resulting mixture was extracted with EtOAc (3×50 mL). The combined organic layers were dried over anhydrous Na$_2$SO$_4$ and concentrated in vacuo to give 0.350 g of crude 15. This was used in the next step without any further purification. LCMS m/z 393 [M+H], 293 [M−100+H].

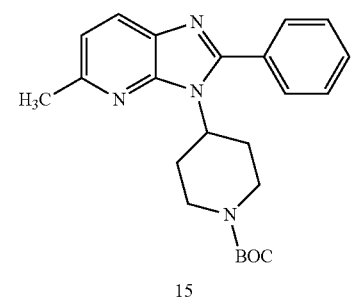

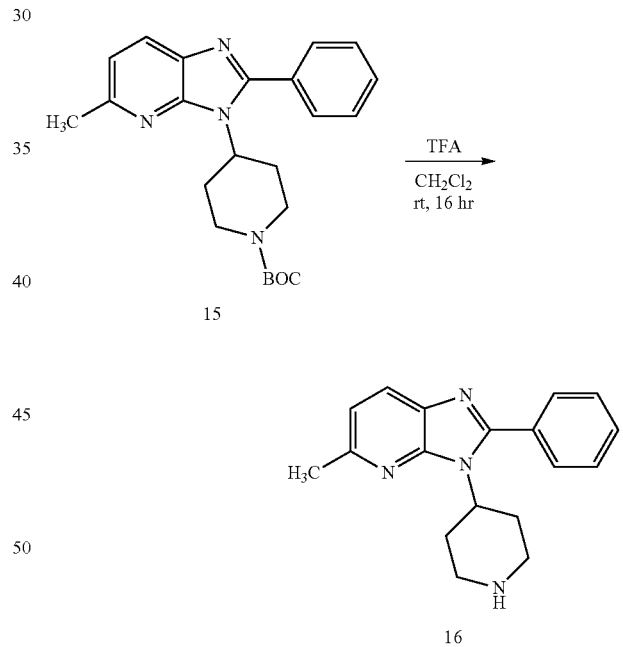

5-Methyl-2-phenyl-3-(piperidin-4-yl)-3H-imidazo[4,5-b]pyridine (16). TFA (1.5 mL) was added to a stirred solution of 15 (0.35 g, 0.892 mmol) in anhydrous CH$_2$Cl$_2$ (10 mL) at 0°. The reaction mixture was allowed to warm to rt and stirred for 16 hr. The reaction mixture was basified with saturated NaHCO$_3$ solution, then extracted with CH$_2$Cl$_2$ (3×20 mL). The combined organic layers were dried over anhydrous Na$_2$SO$_4$ and concentrated in vacuo to give 0.25 g (96% yield) of crude 16 as a pale yellow solid. LCMS m/z 293 [M+H].

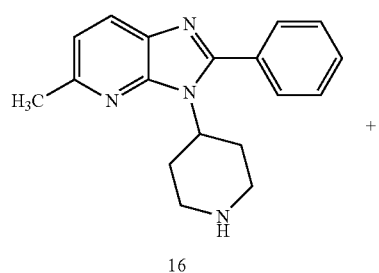

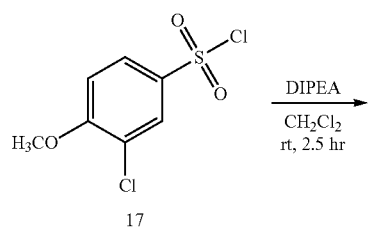

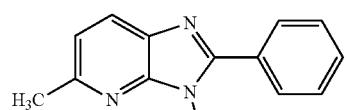

3-(1-((3-Chloro-4-methoxyphenyl)sulfonyl)piperidin-4-yl)-5-methyl-2-phenyl-3H-imidazo[4,5-b]pyridine (18). DIPEA (0.34 mL, 2.667 mmol) was added to a stirred solution of 16 (0.20 g, 0.684 mmol) in anhydrous $CH_2Cl_2$ (5 mL) at 0°. The reaction mixture was stirred at this temperature for 2 hr and then 17 (0.21 g, 0.889 mmol) was added. The resulting mixture was allowed to warm to rt and stirred at rt for 30 min. After the reaction was complete ice-cold $H_2O$ was added and the resulting mixture was extracted with $CH_2Cl_2$. The organic layer was washed with saturated $NaHCO_3$ solution followed by brine solution and dried over anhydrous $Na_2SO_4$, then concentrated in vacuo to give crude 18. The crude product was purified by flash column chromatography using 100-200 mesh silica gel. The desired product was eluted in 50% EtOAc in pet-ether to obtain 0.007 g (21%) of pure 18 as a pale yellow solid. $^1$H NMR (DMSO-$d_6$) δ 7.95 (d, J=10.8 Hz, 1H), 7.75 (d, J=3.2 Hz, 1H), 7.73-7.69 (dd, J=11.6 Hz, J=2.8 Hz, 1H), 7.66-7.62 (m, 2H), 7.56-7.51 (m, 3H), 7.37 (d, J=11.6 Hz, 1H), 7.17 (d, J=10.8 Hz, 1H), 4.34-4.23 (m, 1H), 3.96 (s, 3H), 3.84-3.75 (m, 2H), 3.02-2.90 (m, 2H), 2.61 (s, 3H), 2.48-2.33 (m, 2H), 1.98-1.89 (m, 2H). LCMS m/z 497 [M+H−1], 499 [M+H+1].

Example 4

3-(1-((4-Ethylphenyl)sulfonyl)piperidin-4-yl)-2-phenyl-3H-imidazo[4,5-b]pyridine (22)

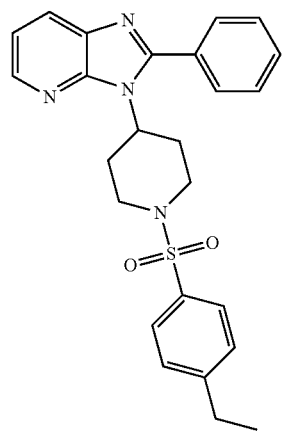 [SMILES: CCc1ccc(S(=O)(=O)N2CCC(n3c(-c4ccccc4)nc4cccnc43)CC2)cc1]

tert-Butyl 4-(2-phenyl-3H-imidazo[4,5-b]pyridin-3-yl)piperidine-1-carboxylate (19). Sodium dithionite (22.14 g, 127.18 mmol) solution in $H_2O$ (100 mL) was added to a stirred solution of 3 (8.2 g, 25.43 mmol) and benzaldehyde (14) (2.7 mL, 25.43 mmol) in EtOH (300 mL) at rt. The reaction mixture was refluxed for 16 hr. After the reaction was complete, the reaction mixture was cooled to rt and ice-cold $H_2O$ was added. The resulting mixture was extracted with EtOAc (3×50 mL). The combined organic layers were dried over anhydrous $Na_2SO_4$ and concentrated in vacuo to give 4.2 g (44% yield) of brown liquid 19 which was used in the next step without any further purification. LCMS m/z 379 [M+H], 279 [M−100+H].

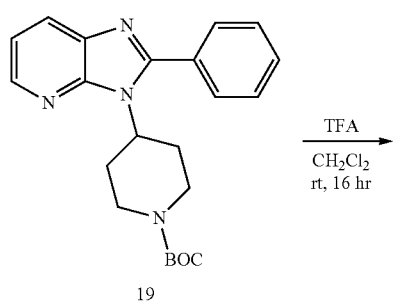

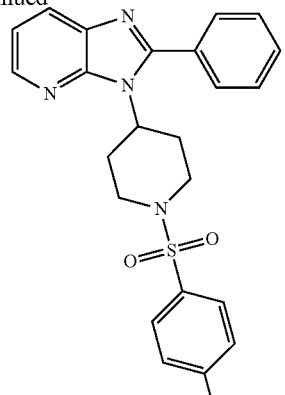

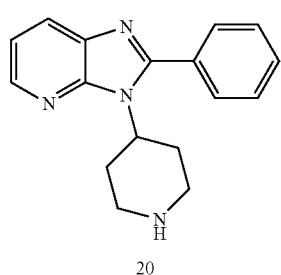

2-Phenyl-3-(piperidin-4-yl)-3H-imidazo[4,5-b]pyridine (20). TFA (10 mL) was added to a stirred solution of 19 (4.2 g, 11.09 mmol) in anhydrous CH$_2$Cl$_2$ (45 mL) at 0°. The reaction mixture was allowed to warm to rt and stirred for 16 hr. The reaction mixture was basified with saturated NaHCO$_3$ solution, then extracted with CH$_2$Cl$_2$ (3×20 mL). The combined organic layer were dried over anhydrous Na$_2$SO$_4$ and concentrated in vacuo to give 2.5 g (81% yield) of crude 20 as a yellow solid which was used in the next step without any further purification. LCMS m/z 279 [M+H].

3-(1-((4-Ethylphenyl)sulfonyl)piperidin-4-yl)-2-phenyl-3H-imidazo[4,5-b]pyridine (22). DIPEA (0.44 mL, 2.67 mmol) was added to a stirred solution of 20 (0.250 g, 0.89 mmol) in anhydrous CH$_2$Cl$_2$ (2.5 mL) at 0°. The reaction mixture was warmed to rt and stirred at rt for 2.5 hr, then cooled again to 0°. 21 (0.18 mL, 1.16 mmol) was added and the resulting mixture was allowed to warm to rt and stirred at rt for 30 min. The reaction mixture was basified using saturated NaHCO$_3$ solution then extracted with CH$_2$Cl$_2$. The organic layer was dried over anhydrous Na$_2$SO$_4$ then concentrated in vacuo to give the crude product. The crude product was purified by flash column chromatography using 100-200 mesh silica gel. The desired product was eluted in 50% EtOAc in pet-ether to obtain 0.170 g (42%) of pure 22 as a pale yellow solid.

$^1$H NMR (DMSO-d$_6$) δ 8.39-8.37 (dd, J=6.4 Hz, J=2.0 Hz, 1H), 8.11-8.07 (dd, J=10.8 Hz, J=2.0 Hz, 1H), 7.70-7.61 (m, 4H), 7.57-7.52 (m, 3H), 7.48 (d, J=11.2 Hz, 2H), 7.35-7.30 (dd, J=10.8 Hz, J=6.4 Hz, 1H), 4.41-4.28 (m, 1H), 3.84-3.74 (m, 2H), 3.08-2.90 (m, 2H), 2.76-2.67 (q, J=10.0 Hz, 2H), 2.42-2.29 (m, 2H), 2.01-1.90 (m, 2H), 1.21 (t, J=10.0 Hz, 3H). LCMS m/z 447 [M+H].

Example 5

3-(1-(Benzo[d][1,3]dioxol-5-ylsulfonyl)piperidin-4-yl)-2-phenyl-3H-imidazo[4,5-b]pyridine (23)

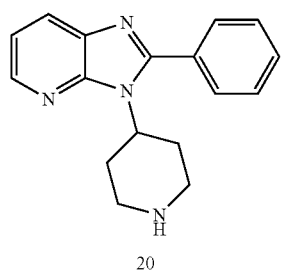

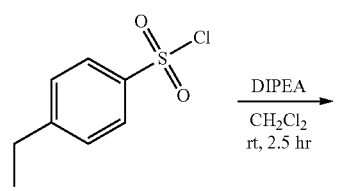

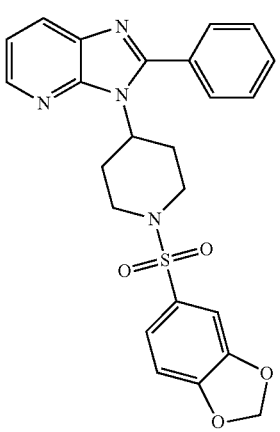 [SMILES: O=S(=O)(c1ccc2c(c1)OCO2)N1CCC(n2c(-c3ccccc3)nc3cccnc32)CC1]

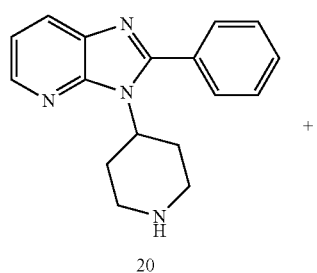

20

+

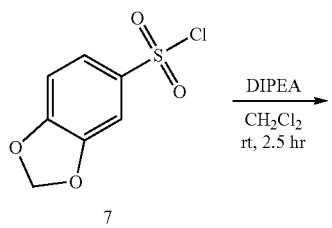

7

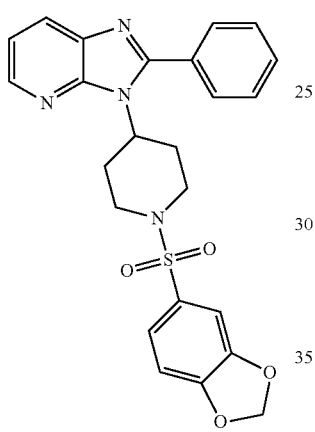

23

3-(1-(Benzo[d][1,3]dioxol-5-ylsulfonyl)piperidin-4-yl)-2-phenyl-3H-imidazo[4,5-b]pyridine (23). DIPEA (0.26 mL, 1.61 mmol) was added to a stirred solution of 20 (0.150 g, 0.53 mmol) in anhydrous CH$_2$Cl$_2$ (3.0 mL) at 0° C. The reaction mixture was warmed to rt and stirred at rt for 2.5 hr, then cooled again to 0° C. 7 (0.1545 g, 0.7 mmol) was added and the resulting mixture was allowed to warm to rt and stirred at rt for 30 min. The reaction mixture was basified using saturated NaHCO$_3$ solution then extracted with CH$_2$Cl$_2$. The organic layer was dried over anhydrous Na$_2$SO$_4$ then concentrated in vacuo to give the crude product. The crude product was purified by flash column chromatography using 100-200 mesh silica gel. The desired product was eluted in 50% EtOAc in pet-ether to obtain 0.75 g (30%) of pure 23 as an off-white solid.

$^1$H NMR (DMSO-d$_6$) δ 8.37-8.35 (dd, J=6.6 Hz, J=1.8 Hz, 1H), 8.09-8.06 (dd, J=10.8 Hz, J=1.2 Hz, 1H), 7.66 (d, J=3.2 Hz, 1H), 7.64 (d, J=4.8 Hz, 1H), 7.55 (d, J=3.2 Hz, 2H), 7.53 (d, J=1.6 Hz, 1H), 7.33-7.29 (dd, J=10.8 Hz, J=6.0 Hz, 1H), 7.30-7.26 (dd, J=10.8 Hz, J =2.0 Hz, 1H), 7.22 (d, J=2.0 Hz, 1H), 7.12 (d, J=10.8 Hz, 1H), 6.17 (s, 2H), 4.39-4.27 (m, 1H), 3.81-3.71 (m, 2H), 3.05-2.88 (m, 2H), 2.46-2.31 (m, 2H), 1.98-1.87 (m, 2H). LCMS m/z 463 [M+H].

Example 6

3-(1-((3-Chloro-4-methoxyphenyl)sulfonyl)piperidin-4-yl)-2-(2-chlorophenyl)-3H-imidazo[4,5-b]pyridine (26)

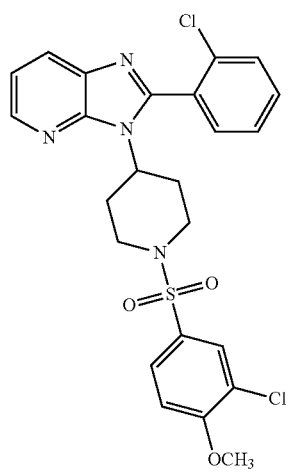

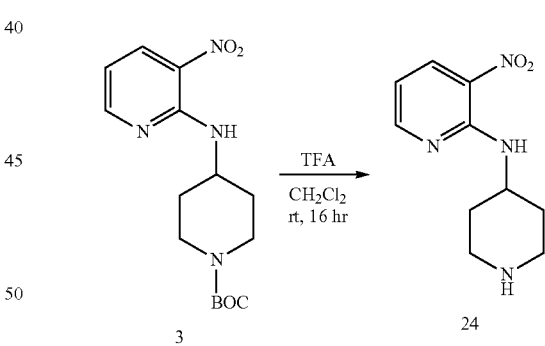

3-Nitro-N-(piperidin-4-yl)pyridin-2-amine (24). TFA (12.5 mL) was added to a stirred solution of 3 (2.5 g, 7.75 mmol) in anhydrous CH$_2$Cl$_2$ (20 mL) at 0°. The reaction mixture was allowed to warm to rt and stirred for 16 hr. The reaction mixture was evaporated in vacuo, basified with saturated NaHCO$_3$ solution, then extracted with EtOAc (3×20 mL). The combined organic layers were dried over anhydrous Na$_2$SO$_4$ and concentrated in vacuo to give crude 24 as a yellow solid which was used in the next step without any further purification. LCMS m/z 223 [M+H].

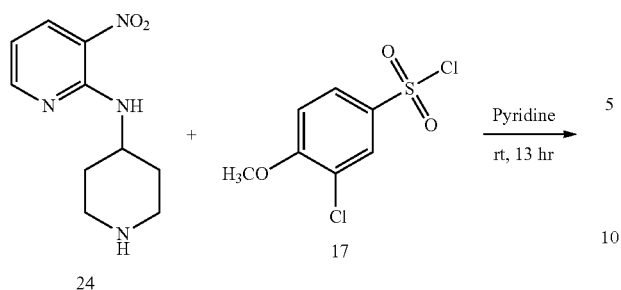

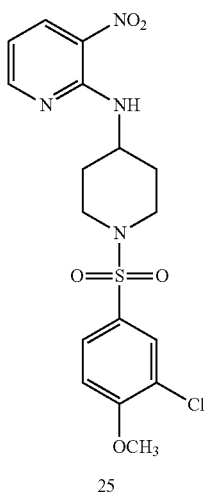

N-(1-((3-Chloro-4-methoxyphenyl)sulfonyl)piperidin-4-yl)-3-nitropyridin-2-amine (25). To a stirred solution of 24 (1.0 g, 4.499 mmol) in pyridine (12 mL) at 0° was added 17 (1.46 g, 5.848 mmol). The resulting mixture was allowed to warm to rt and stirred at rt for 3 hr. After the reaction was complete the reaction mixture was poured into 1N HCl solution and the resulting mixture was extracted with EtOAc. The organic layer was collected, dried over anhydrous $Na_2SO_4$ and concentrated in vacuo to give the crude product 25 as a yellow solid which was used in the next step without any further purification. LCMS m/z 427 [M+H−1], 429 [M+H+1].

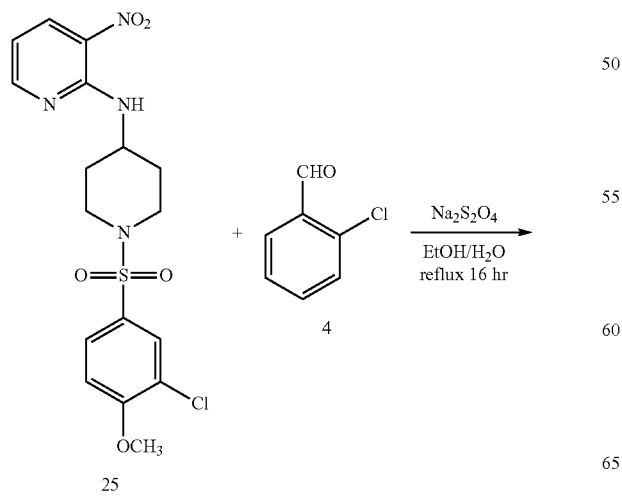

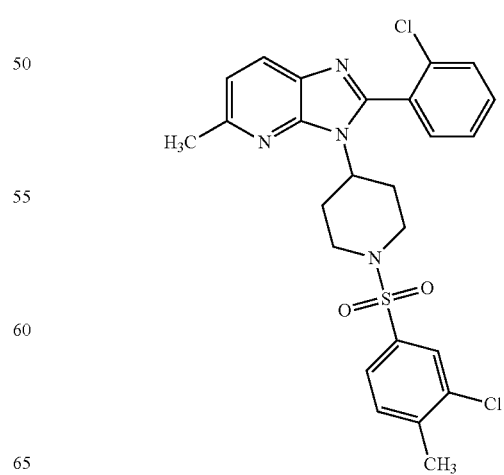

3-(1-((3-Chloro-4-methoxyphenyl)sulfonyl)piperidin-4-yl)-2-(2-chlorophenyl)-3H-imidazo[4,5-b]pyridine (26). Saturated sodium dithionite (407.8 mg, 2.342 mmol) solution was added to a stirred solution of 25 (200 mg, 0.468 mmol) and 4 (65.8 g, 0.468 mmol) in EtOH (10 mL) at rt. The reaction mixture was heated to 110° and stirred for 16 hr. After the reaction was complete, the reaction mixture was cooled to rt and ice-cold $H_2O$ was added. The resulting mixture was extracted with EtOAc (3×50 mL). The combined organic layers were dried over anhydrous $Na_2SO_4$ and concentrated in vacuo to give the crude product. This was purified by flash column chromatography using 100-200 mesh silica gel. The desired product was eluted in 40% EtOAc in pet-ether to give 0.060 g (27% yield) of off-white solid 26. $^1$H NMR (DMSO-$d_6$) δ 8.39-8.38 (dd, J=4.4 Hz, J=0.8 Hz, 1H), 8.13-8.10 (dd, J=7.8 Hz, J=1.2 Hz, 1H), 7.74 (d, J=2.0 Hz, 1H), 7.72-7.68 (m, 1H), 7.67-7.64 (m, 1H), 7.63-7.58 (m, 2H), 7.53-7.48 (m, 1H), 7.36 (d, J=8.4 Hz, 1H), 7.35 (d, J=7.6 Hz, 1H), 3.96 (s, 3H), 4.01-3.91 (br m, 1H), 3.84-3.70 (br m, 2H), 3.08-2.93 (br m, 2H), 2.44-2.36 (br m, 2H), 2.00-1.74 (br m, 2H). LCMS m/z 517 [M+H−1], 519 [M+H+1], 521 [M+H+3].

Example 7

3-(1-((3-Chloro-4-methylphenyl)sulfonyl)piperidin-4-yl)-2-(2-chlorophenyl)-5-methyl-3H-imidazo[4,5-b]pyridine (28)

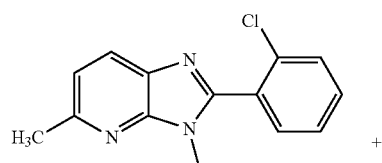

12

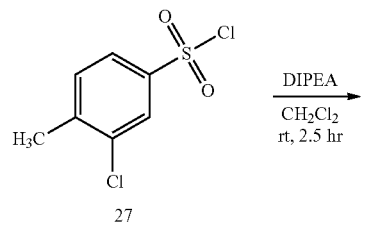

27

DIPEA
CH₂Cl₂
rt, 2.5 hr

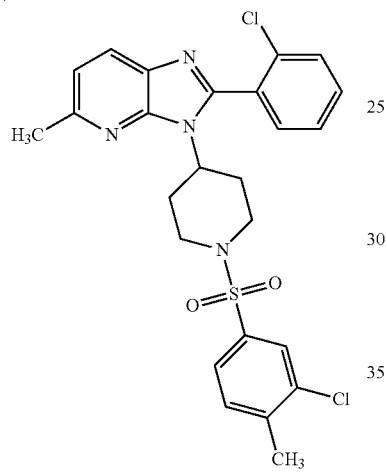

28

3-(1-((3-Chloro-4-methylphenyl)sulfonyl)piperidin-4-yl)-2-(2-chlorophenyl)-5-methyl-3H-imidazo[4,5-b]pyridine (28). DIPEA (0.19 mL, 1.101 mmol) was added to a stirred solution of 12 (0.12 g, 0.367 mmol) in anhydrous CH₂Cl₂ (3 mL) at 0° C. The reaction mixture was stirred at this temperature for 2 hr and then 27 (0.082 g, 0.367 mmol) was added. The resulting mixture was allowed to warm to rt and stirred at rt for 30 min. After the reaction was complete, ice-cold H₂O was added and the resulting mixture was extracted with CH₂Cl₂. The organic extract was washed with saturated NaHCO₃, followed by brine solution and dried over anhydrous Na₂SO₄, then concentrated in vacuo to give the crude product as a semi-solid. The crude product was purified by flash column chromatography using 100-200 mesh silica gel. The desired product was eluted in 40% EtOAc in pet-ether to obtain 0.041 g (22%) of pure 28 as a pale yellow solid.

¹H NMR (DMSO-d₆) δ 7.98-7.96 (d, J=8 Hz, 1H), 7.70 (s, 1H), 7.64-7.57 (m, 5H), 7.51-7.47 (t, J=7.2 Hz, 1H), 7.21-7.19 (d, J=8.4 Hz, 1H), 3.92-3.89 (d, J=12 Hz 1H), 3.76 (br s, 2H), 3.00 (br s, 2H), 2.62 (br s, 3H), 2.41 (br s, 3H), 2.33-2.28 (br d, J=19.6 Hz, 2H), 1.95-1.84 (br d, J=45.8 Hz, 2H). LCMS m/z 515 [M+H−1], 517 [M+H+1], 519 [M+H+3].

Example 8

2-(2-Chlorophenyl)-3-(1-((3-fluoro-4-methyloxyphenyl)sulfonyl)piperidin-4-yl)-5-methyl-3H-imidazo[4,5-b]pyridine (30)

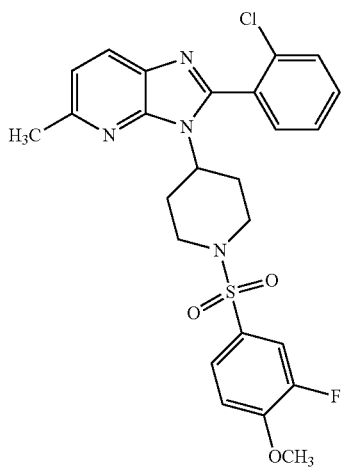 [SMILES: COc1ccc(S(=O)(=O)N2CCC(n3c(-c4ccccc4Cl)nc4ccc(C)nc43)CC2)cc1F]

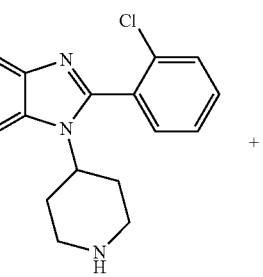

12

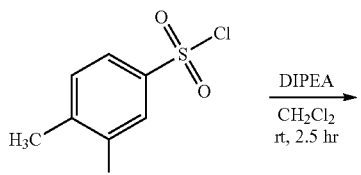

29

DIPEA
CH₂Cl₂
rt, 2.5 hr

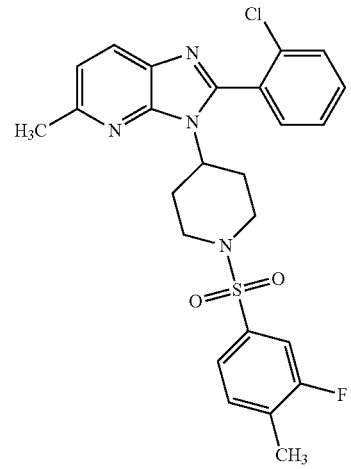

30

2-(2-Chlorophenyl)-3-(1-((3-fluoro-4-methyloxyphenyl)sulfonyl)piperidin-4-yl)-5-methyl-3H-imidazo[4,5-b]pyridine (30). DIPEA (0.19 mL, 1.101 mmol) was added to a stirred solution of 12 (0.12 g, 0.367 mmol) in anhydrous CH$_2$Cl$_2$ (3 mL) at 0° C. The reaction mixture was stirred at this temperature for 2 hr and then 29 (0.082 g, 0.367 mmol) was added. The resulting mixture was allowed to warm to rt and stirred at rt for 30 min. After the reaction was complete, ice-cold H$_2$O was added and the resulting mixture was extracted with CH$_2$Cl$_2$. The organic extract was washed with saturated NaHCO$_3$, followed by brine solution and dried over anhydrous Na$_2$SO$_4$, then concentrated in vacuo to give the crude product as a semi-solid. The crude product was purified by flash column chromatography using 100-200 mesh silica gel. The desired product was eluted in 40% EtOAc in pet-ether to obtain 0.040 g (21%) of pure 30 as a pale yellow solid. $^1$H NMR (DMSO-d$_6$) δ 7.98-7.96 (d, J=8.4 Hz, 1H), 7.65-7.47 (m, 6H), 7.40-7.36 (t, J=8.4 Hz, 1H), 7.21-7.19 (d, J=8 Hz, 1H), 3.93-3.86 (m, 4H), 3.74 (br s, 2H), 3.00 (br s, 2H), 2.62 (s, 3H), 2.33-2.32 (t, J=1.6 Hz, 2H), 1.94-1.82 (br d, J=48.8 Hz, 2H). LCMS m/z 515 [M+H−1], 517 [M+H+1].

Example 9

2-(3-(1-((3-Chloro-4-methoxyphenyl)sulfonyl)piperidin-4-yl)-3H-imidazo[4,5-b]pyridin-2-yl)phenol (32)

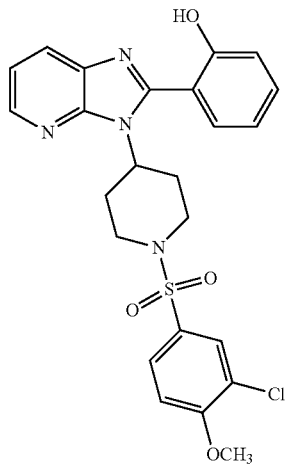 [SMILES: COc1ccc(S(=O)(=O)N2CCC(n3c(-c4ccccc4O)nc4cccnc43)CC2)cc1Cl]

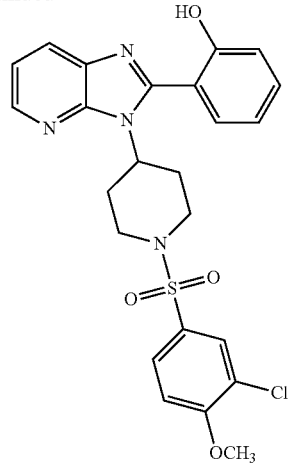

32

2-(3-(1-((3-Chloro-4-methoxyphenyl)sulfonyl)piperidin-4-yl)-3H-imidazo[4,5-b]pyridin-2-yl)phenol (32). Saturated sodium dithionite (203 mg, 1.171 mmol) solution was added to a stirred solution of 25 (100 mg, 0.234 mmol) and 31 (0.023 mL, 0.234 mmol) in EtOH (10 mL) at rt. The reaction mixture was heated to 110° C. and stirred for 16 hr. After the reaction was complete, the reaction mixture was cooled to rt and ice-cold H$_2$O was added. The resulting mixture was extracted with EtOAc (3×50 mL). The combined organic layers were dried over anhydrous Na$_2$SO$_4$ and concentrated in vacuo to give the crude product. This was purified by flash column chromatography using 100-200 mesh silica gel. The desired product was eluted in 40% EtOAc in pet-ether to give 0.023 g (20% yield) of off-white solid 32. $^1$H NMR (DMSO-d$_6$) δ 10.15 (br s, 1H), 8.32-8.31 (d, J=4.8 Hz, 1H), 8.06-8.03 (d, J=6.6 Hz, 1H), 7.76-7.76 (d, J=1.8 Hz, 1H), 7.73-7.72 (d, J=2.25 Hz, 1H), 7.38-7.27 (m, 4H), 6.98-6.91 (dd, J=7.2 Hz, 2H), 4.08-4.04 (m, 1H), 3.970 (s, 3H), 3.84-3.80 (d, J=12.3 Hz, 2H), 2.95-2.84 (m, 2H), 2.39-2.27 (q, J=11.85 Hz, 2H) 1.89-1.86 (d, J=10.2 Hz, 2H). LCMS m/z 499 [M+H−1], 501 [M+H+1].

Example 10

3-(1-((3-Chloro-4-methylphenyl)sulfonyl)piperidin-4-yl)-2-(2-chlorophenyl)-3H-imidazo[4,5-b]pyridine (33)

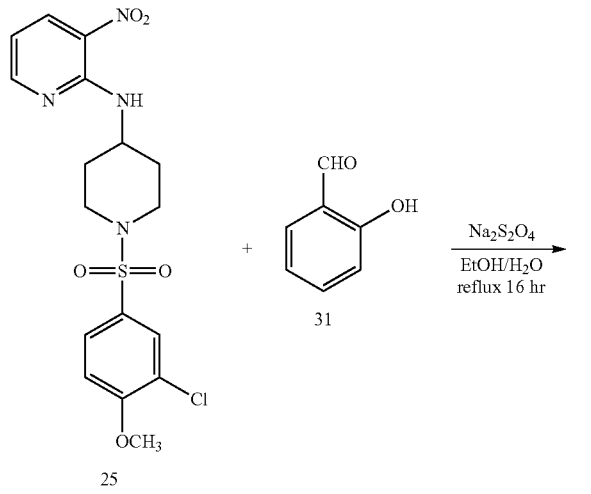

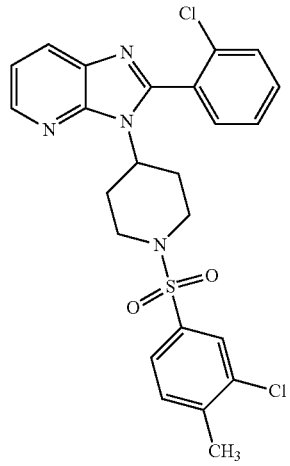 [SMILES: Cc1ccc(S(=O)(=O)N2CCC(n3c(-c4ccccc4Cl)nc4cccnc43)CC2)cc1Cl]

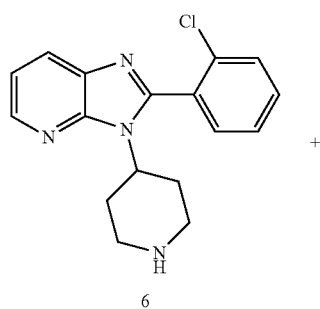

6

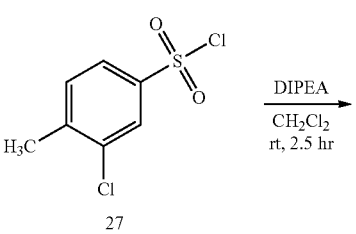

27

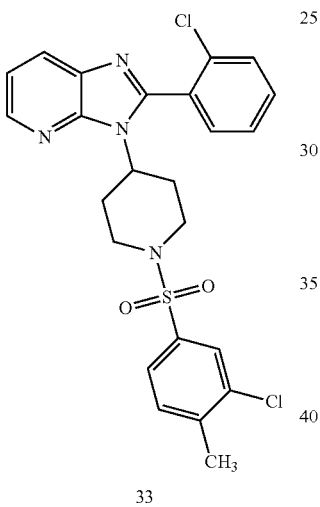

33

3-(1-((3-Chloro-4-methylphenyl)sulfonyl)piperidin-4-yl)-2-(2-chlorophenyl)-3H-imidazo[4,5-b]pyridine (33). DIPEA (0.2 mL, 1.150 mmol) was added to a stirred solution of 6 (0.12 g, 0.383 mmol) in anhydrous CH$_2$Cl$_2$ (3 mL) at 0° C. The reaction mixture was stirred at this temperature for 2 hr and then 27 (0.18 mL, 0.498 mmol) was added. The resulting mixture was allowed to warm to rt and stirred at rt for 30 min. The reaction mixture was washed with saturated NaHCO$_3$, H$_2$O was added, and the resulting mixture was extracted with CH$_2$Cl$_2$. The organic layer was dried over anhydrous Na$_2$SO$_4$, then concentrated in vacuo to give the crude product. This was purified by flash column chromatography using 100-200 mesh silica gel. The desired product was eluted in 50% EtOAc in pet-ether to obtain 0.93 g (48%) of pure 33 as an off-white solid. $^1$H NMR (DMSO-d$_6$) δ 8.41-8.39 (dd, J=4.8 Hz, 1H), 8.13-8.10 (dd, J=8.1 Hz, 1H), 7.71 (s, 1H), 7.67-7.58 (m, 5H), 7.53-7.50 (dd, J=6.75 Hz, 1H), 7.38-7.32 (dd, J=4.8 Hz, 1H), 4.02-3.94 (t, J=12 Hz, 1H), 3.80-3.77 (d, J=8.1 Hz, 2H), 3.0 (bs, 2H), 2.425 (br s, 5H), 2.16 (br s, 2H). LCMS m/z 501 [M+H−1], 503 [M+H+1] 505 [M+H+3].

Example 11

3-(1-((3-Chloro-4-methoxyphenyl)sulfonyl)piperidin-4-yl)-2-(2-fluorophenyl)-3H-imidazo[4,5-b]pyridine (37)

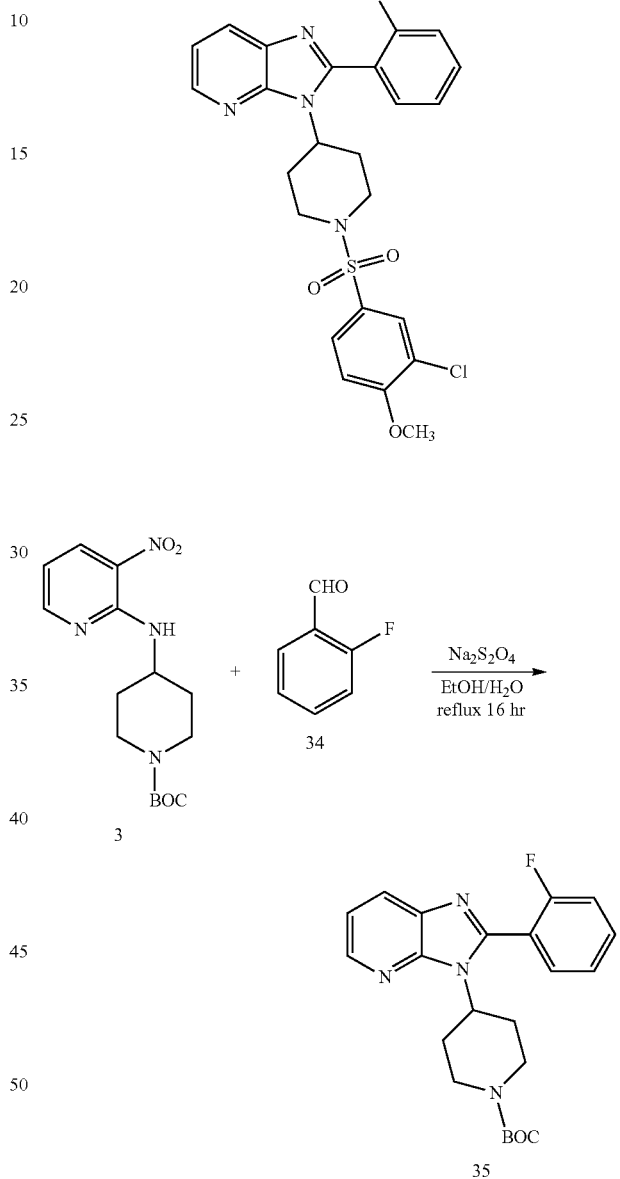

tert-Butyl 4-(2-(2-fluorophenyl)-3H-imidazo[4,5-b]pyridin-3-yl)piperidine-1-carboxylate (35). Saturated sodium dithionite (1.0 g, 6.20 mmol) solution was added to a stirred solution of 3 (0.4 g, 1.240 mmol) and 34 (0.154 g, 1.240 mmol) in EtOH (10 mL) and H$_2$O (2 mL) at rt. The reaction mixture was heated to 110° C. and stirred for 16 hr. After the reaction was complete, the reaction mixture was cooled to rt and ice-cold H$_2$O was added. The resulting mixture was extracted with EtOAc (2×75 mL). The combined organic layers were dried over anhydrous Na$_2$SO$_4$ and concentrated in vacuo to give the crude product. This was washed with Et$_2$O and n-hexane (1:10) to give 0.2 g (41% yield) of pale yellow solid 35 which was used in the next step without any further purification. LCMS m/z 397 [M+H].

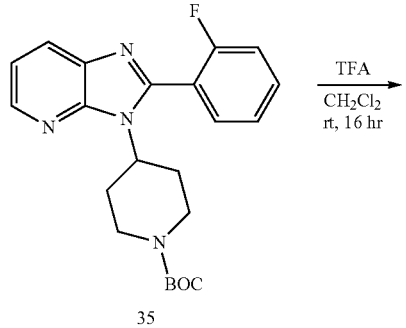

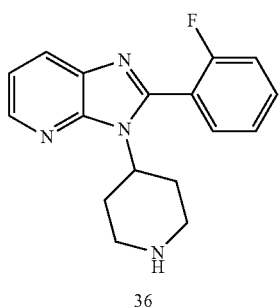

2-(2-Fluorophenyl)-3-(piperidin-4-yl)-3H-imidazo[4,5-b]pyridine (36). TFA (0.6 mL) was added to a stirred solution of 35 (0.2 g, 0.5044 mmol) in anhydrous CH$_2$Cl$_2$ (2 mL) at 0° C. The reaction mixture was allowed to warm to rt and stirred for 16 hr. The reaction mixture was basified with saturated NaHCO$_3$ solution then extracted with CH$_2$Cl$_2$. The organic layer was washed with H$_2$O, followed by brine solution and dried over anhydrous Na$_2$SO$_4$. The organic layer concentrated in vacuo to give 0.1 g (67% yield) of crude 36 as a pale yellow solid which was used in the next step without any further purification. LCMS m/z 297 [M+H].

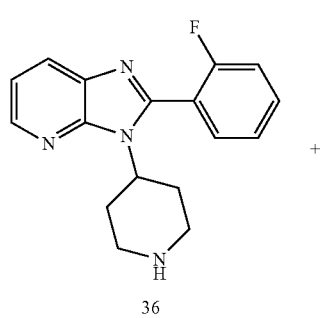

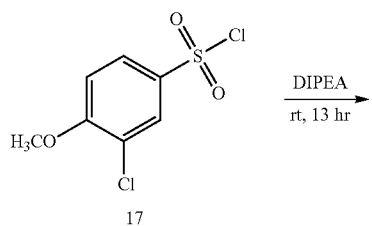

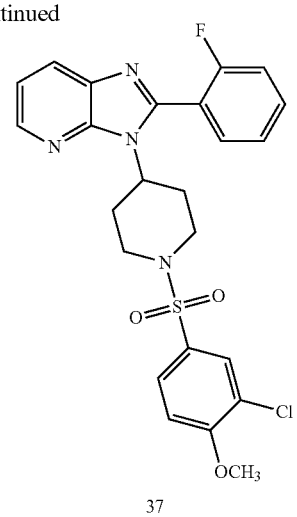

3-(1-((3-Chloro-4-methoxyphenyl)sulfonyl)piperidin-4-yl)-2-(2-fluorophenyl)-3H-imidazo[4,5-b]pyridine (37). DIPEA (0.17 mL, 1.012 mmol) was added to a stirred solution of 36 (0.1 g, 0.337 mmol) in anhydrous CH$_2$Cl$_2$ (3 mL) at 0°. The reaction mixture was stirred at this temperature for 2 hr and then 17 (0.1 mL, 0.438 mmol) was added. The resulting mixture was allowed to warm to rt and stirred at rt for 30 min. The reaction mixture was washed with saturated NaHCO$_3$, H$_2$O was added, and the resulting mixture was extracted with CH$_2$Cl$_2$. The organic layer was dried over anhydrous Na$_2$SO$_4$, then concentrated in vacuo to give the crude product. This was purified by flash column chromatography using 100-200 mesh silica gel. The desired product was eluted in 50% EtOAc in pet-ether to obtain 0.12 g (7%) of pure 37 as a pale yellow solid. $^1$H NMR (DMSO-d$_6$) δ 8.39-8.38 (d, J=3.9 Hz, 1H), 8.13-8.11 (d, J=6.9 Hz, 1H), 7.75-7.61 (m, 4H), 7.44-7.33 (m, 4H), 4.12 (br s, 1H), 3.96 (s, 3H), 3.81-3.77 (d, J=12 Hz, 2H), 2.96-2.85 (q, J=11.7 Hz, 2H), 2.44 (br s, 2H), 1.86-1.83 (d, J=10.8 Hz, 2H).
LCMS m/z 501 [M+H−1], 503 [M+H+1].

Example 12

3-(1-((3-Chloro-4-methoxyphenyl)sulfonyl)piperidin-4-yl)-2-(2,4-dichlorophenyl)-3H-imidazo[4,5-b]pyridine (43)

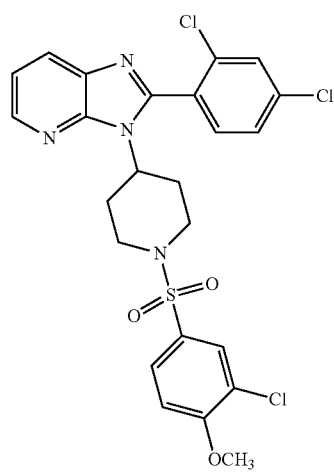 [SMILES: COc1ccc(S(=O)(=O)N2CCC(n3c(-c4ccc(Cl)cc4Cl)nc4cccnc43)CC2)cc1Cl]

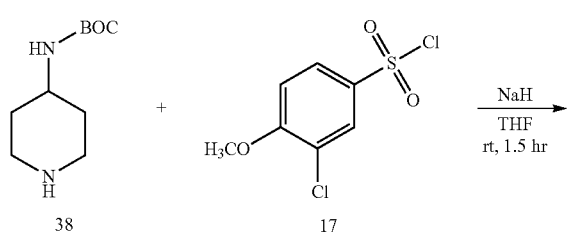

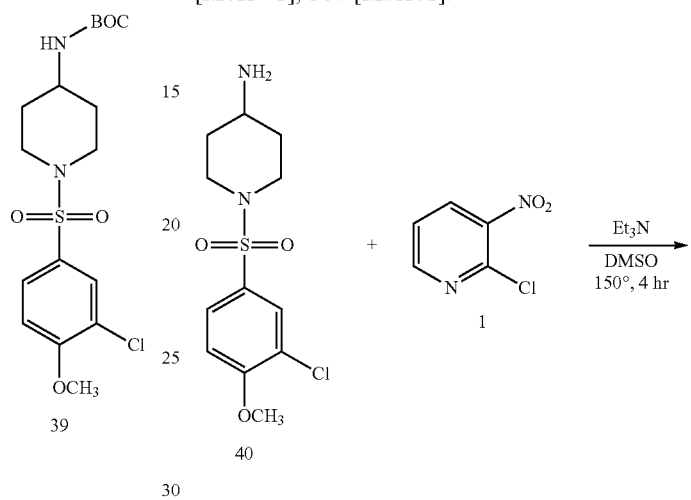

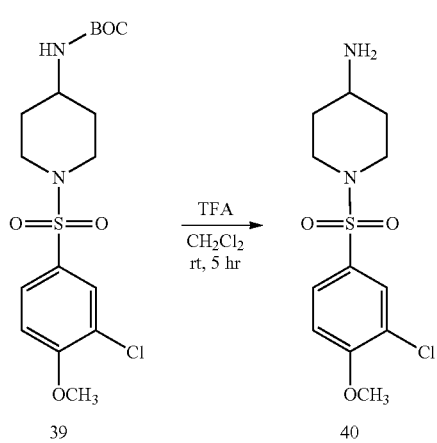 [SMILES: COc1ccc(S(=O)(=O)N2CCC(NC(=O)OC(C)(C)C)CC2)cc1Cl ; COc1ccc(S(=O)(=O)N2CCC(N)CC2)cc1Cl]

tert-Butyl (1-((3-chloro-4-methoxyphenyl)sulfonyl)piperidin-4-yl)carbamate (39). NaH (1.44 g, 29.94 mmol) was added to a stirred solution of 38 (3.0 g, 14.97 mmol) in anhydrous THF (30 mL) at 0°. The reaction mixture was stirred for 15 min, then 17 (3.67 g, 14.97 mmol) was added dropwise. The resulting mixture was warmed to rt and stirred at rt for 1 hr. Ice-cold H₂O was added and the resulting mixture was extracted with EtOAc. The combined organic layers were dried over Na₂SO₄ and concentrated in vacuo to give the crude product as an off white solid. This was washed with n-hexane to give pure 39 (3.3 g, 69% yield) as an off white solid. LCMS m/z 305 [M+H−100−1], 307 [M+H−100+1], 405 [M+H−1], 407 [M+H+1].

1-((3-Chloro-4-methoxyphenyl)sulfonyl)piperidin-4-amine (40). TFA (15 mL) was added to a stirred solution of 39 (5 g, 12.34 mmol) in anhydrous CH₂Cl₂ (50 mL) at 0°. The reaction mixture was allowed to warm to rt and stirred for 5 hr. The reaction mixture was basified with saturated NaHCO₃ solution, then extracted with CH₂Cl₂. The organic layer was washed with H₂O, followed by brine solution and dried over anhydrous Na₂SO₄. The organic layer concentrated in vacuo to give crude 40 as a pale yellow solid. This was triturated with Et₂O and n-hexanes (1:10) to give 3.2 g (85% yield) of 40 as an off white solid. LCMS m/z 305 [M+H −1], 307 [M+H+1].

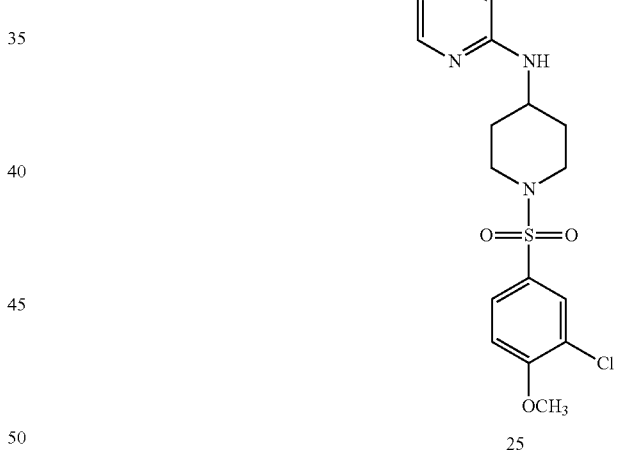

N-(1-((3-Chloro-4-methoxyphenyl)sulfonyl)piperidin-4-yl)-3-nitropyridin-2-amine (25). Et₃N (1.9 mL, 13.64 mmol) was added to a stirred solution of 40 (3.2 g, 10.49 mmol) and 1 (1.65 g, 10.49 mmol) in anhydrous DMSO (160 mL) at rt. The resulting reaction mixture was stirred at 1500 for 4 hr. After the reaction was complete, it was cooled to rt and poured into brine solution and the resulting mixture was extracted with EtOAc. The combined organic layers were dried over anhydrous Na₂SO₄ and concentrated in vacuo to give the crude compound as a yellow solid. This was triturated with Et₂O and hexanes (1:10) to give 4.1 g (91% yield) of 25 as a yellow solid. LCMS m/z 427 [M+H−1], 429 [M+H+1].

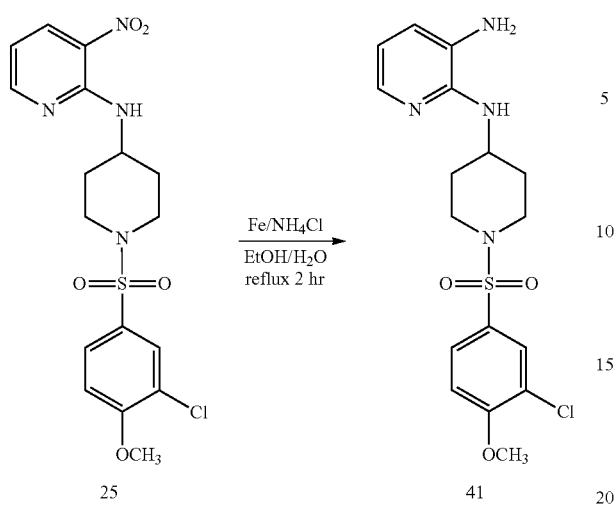

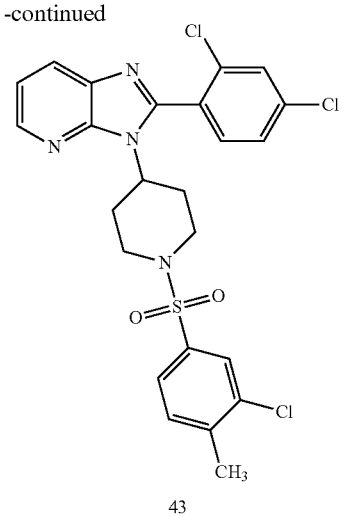

N²-(1-((3-Chloro-4-methoxyphenyl)sulfonyl)piperidin-4-yl)pyridine-2,3-diamine (41). A mixture of 25 (4.1 g, 9.60 mmol), iron powder (2.68 g, 48.02 mmol) and NH₄Cl (0.77 g, 14.40 mmol) in EtOH (40 mL) and H₂O (10 mL) was refluxed for 2 hr. The reaction mixture was filtered through a pad of Celite and the filtrate was concentrated to remove the EtOH. The remaining aqueous mixture was diluted with H₂O and extracted with EtOAc. The organic layer was dried over anhydrous Na₂SO₄ and concentrated in vacuo to give 41 (3.0 g, 79% yield) as a brown solid which was used in the next step without any further purification. LCMS m/z 397 [M+H−1], 399 [M+H+1].

3-(1-((3-Chloro-4-methoxyphenyl)sulfonyl)piperidin-4-yl)-2-(2,4-dichlorophenyl)-3H-imidazo[4,5-b]pyridine (43). A solution of 41 (0.2 g, 0.503 mmol) and 42 (0.0881 g, 0.503 mmol) in HOAc (6 mL) was heated refluxed for 6 hr. After the reaction was complete, the reaction mixture was cooled to rt basified with saturated NaHCO₃ solution. The resulting mixture was extracted with EtOAc and the organic layer was dried over anhydrous Na₂SO₄ then concentrated in vacuo to give the crude product as a yellow solid. This was purified by flash column chromatography using 100-200 mesh silica gel. The desired product was eluted in 50% EtOAc in pet-ether to obtain 0.059 g (21%) of pure 43 as a pale yellow solid. ¹H NMR (DMSO-d₆) δ 8.41-8.39 (dd, J=4.65 Hz, 1H), 8.14-8.11 (dd, J=8.1 Hz, 1H), 7.85-7.84 (d, J=1.8 Hz, 1H), 7.75-7.57 (m, 4H), 7.38-7.33 (m, 2H), 4.02-3.96 (m, 1H), 3.96 (s, 3H), 3.77-3.74 (d, J=9.9 Hz, 2H), 3.0 (br s, 2H), 2.42 (br s, 2H), 1.87 (br s, 2H). LCMS m/z 551 [M+H−1], 553 [M+H+1], 555 [M+H+3], 557 [M+H+5].

Example 13

2-(3-Chloropyridin-4-yl)-3-(1-((2,2-difluorobenzo[d][1,3]dioxol-5-yl)sulfonyl)piperidin-4-yl)-5-methyl-3H-imidazo[4,5-b]pyridine (51)

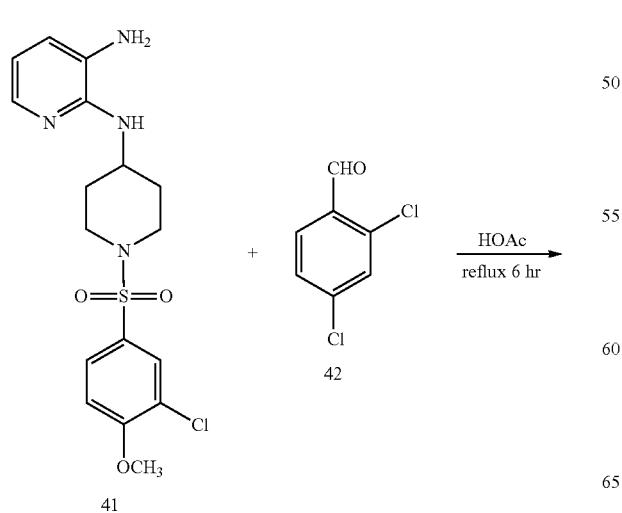

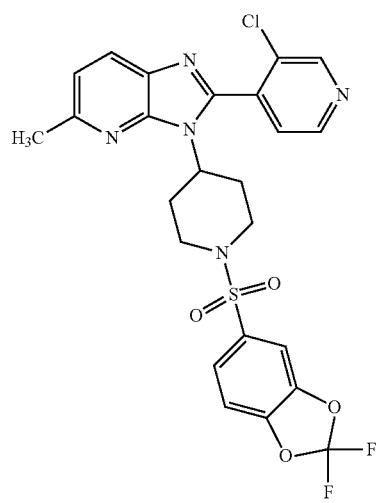 [SMILES: Cc1ccc2nc(-c3ccncc3Cl)n(C3CCN(S(=O)(=O)c4ccc5c(c4)OC(F)(F)O5)CC3)c2n1]

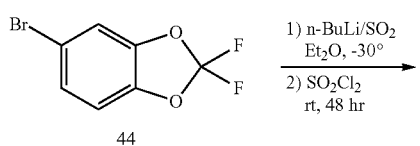

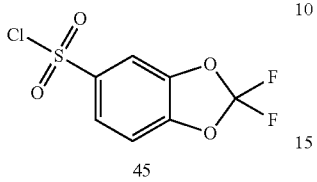

2,2-Difluorobenzo[d][1,3]dioxole-5-sulfonyl chloride (45). N-BuLi (1.6 M) (16.8 mL, 42.194 mmol) was added dropwise to a stirred solution of 44 (10 g, 42.194 mmol) in anhydrous Et₂O (100 mL) at −30°. The reaction mixture was stirred for 10 min and then SO₂Cl₂ (3.41 mL, 42.19 mmol) was added dropwise. The resulting mixture was stirred at −30° for 1 hr, then warmed to rt and stirred at rt for 48 hr. The resulting reaction mixture was used in the next step without workup or purification. ¹H NMR (DMSO-d₆) δ 7.92-7.89 (dd, J=8.4 HZ, J=2.0 Hz, 1H), 7.76 (d, J=2.0 Hz, 1H), 7.30 (d, J=8.8 Hz, 1H). IR (KBr pellet) 1387, 1167 cm⁻¹.

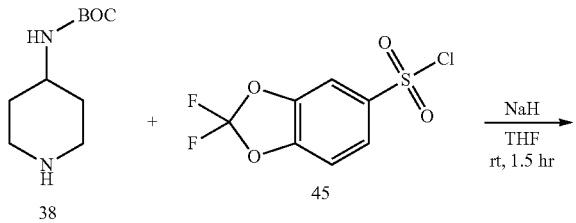

tert-Butyl (1-((2,2-difluorobenzo[d][1,3]dioxol-5-yl)sulfonyl)piperidin-4-yl)carbamate (46). NaH (3.5 g, 74.89 mmol) was added to a stirred solution of 38 (7.5 g, 37.44 mmol) in anhydrous THF (80 mL) at 0° C. The reaction mixture was stirred for 15 min, then 45 (9.31 g, 37.44 mmol) was added dropwise. The resulting mixture was warmed to rt and stirred at rt for 1 hr. Ice-cold H₂O was added and the resulting mixture was extracted with EtOAc. The combined organic layers were dried over Na₂SO₄ and concentrated in vacuo to give the product 46 (8 g, 51% yield) as an off white solid, which was suitable for use in the next step without purification. LCMS m/z 419 [M−H].

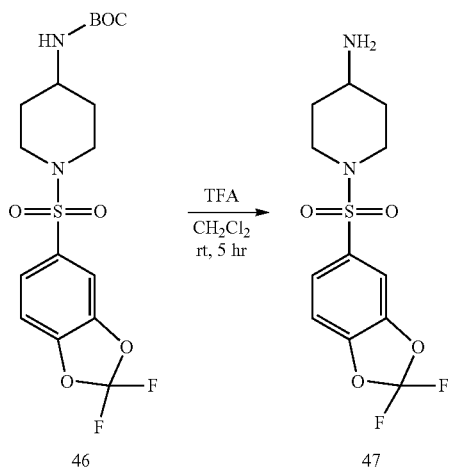 [SMILES: CC(C)(C)OC(=O)NC1CCN(S(=O)(=O)c2ccc3c(c2)OC(F)(F)O3)CC1 ; NC1CCN(S(=O)(=O)c2ccc3c(c2)OC(F)(F)O3)CC1]

1-((2,2-difluorobenzo[d][1,3]dioxol-5-yl)sulfonyl0piperidin-4-amine (47). TFA (24 mL) was added to a stirred solution of 46 (8 g, 19.02 mmol) in anhydrous CH₂Cl₂ (80 mL) at 0° C. The reaction mixture was allowed to warm to rt and stirred for 5 hr. The reaction mixture was basified with saturated NaHCO₃ solution, then extracted with CH₂Cl₂. The organic layer was washed with H₂O, followed by brine solution and dried over anhydrous Na₂SO₄. The organic layer concentrated in vacuo to give 47 (5 g, 83% yield) as an off white solid. This was used in the next step as is without any further purification. LCMS m/z 321 [M+H].

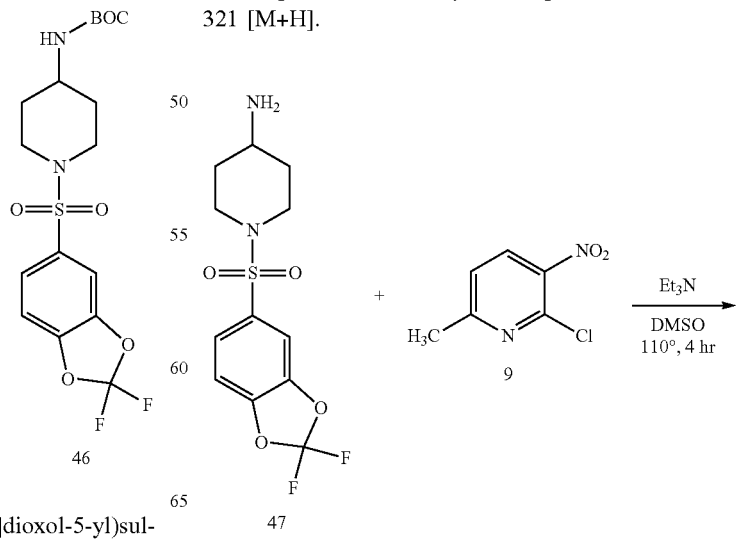

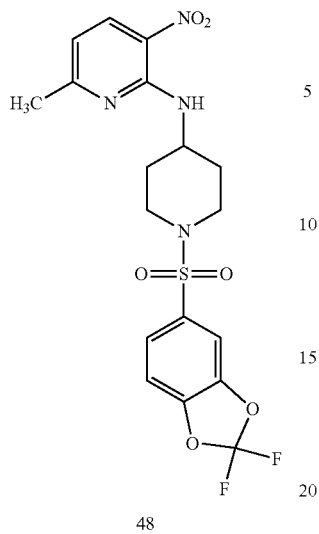

48

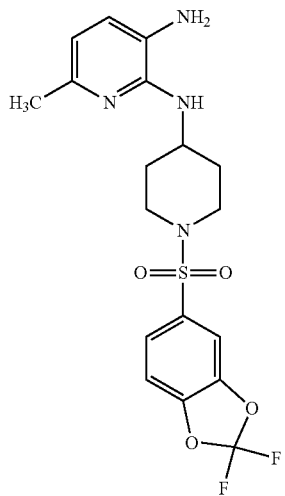

49

N-(1-((2,2-Difluorobenzo[d][1,3]dioxol-5-yl)sulfonyl)piperidin-4-yl)-6-methyl-3-nitropyridin-2-amine (48). Et₃N (2.8 mL, 20.31 mmol) was added to a stirred solution of 47 (5 g, 15.62 mmol) and 9 (2.6 g, 15.62 mmol) in anhydrous DMSO (26 mL) at rt. The resulting reaction mixture was stirred at 110° for 4 hr. After the reaction was complete, it was cooled to rt and poured into brine solution and the resulting mixture was extracted with EtOAc. The combined organic layers were dried over anhydrous Na₂SO₄ and concentrated in vacuo to give 48 (2.5 g, 85% yield) as a yellow solid. This was used in the next step as is without any further purification. LCMS m/z 457 [M+H].

N²-(1-((2,2-difluorobenzo[d][1,3]dioxol-5-yl)sulfonyl) piperidin-4-yl)-6-methylpyridine-2,3-diamine (49). A mixture of 48 (2.5 g, 5.4774 mmol), iron powder (1.52 g, 27.38 mmol) and NH₄Cl (0.43 g, 8,216 mmol) in EtOH (25 mL) and H₂O (7 mL) was refluxed for 2 hr. The reaction mixture was filtered through a pad of Celite and the filtrate was concentrated to remove the EtOH. The remaining aqueous mixture was diluted with H₂O and extracted with EtOAc. The organic layer was dried over anhydrous Na₂SO₄ and concentrated in vacuo to give 49 (1.5 g, 64% yield) as a brown liquid which was used in the next step without any further purification. LCMS m/z 427 [M+H].

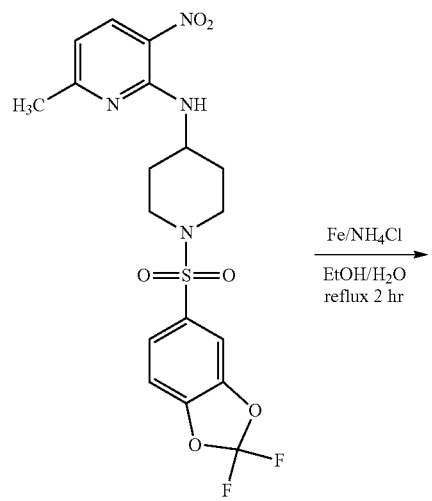

48

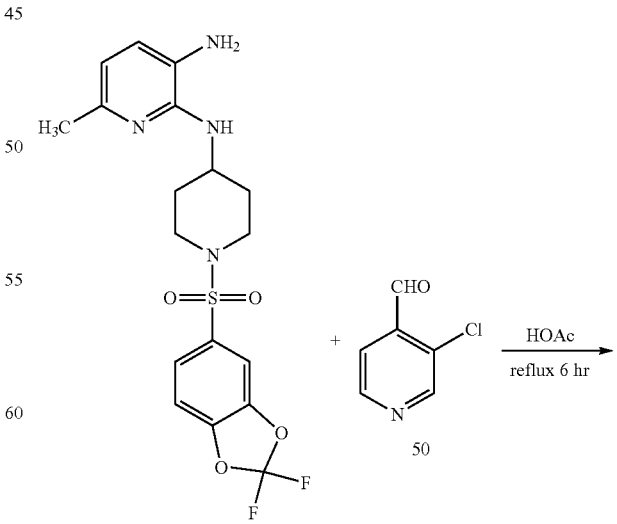

49

-continued

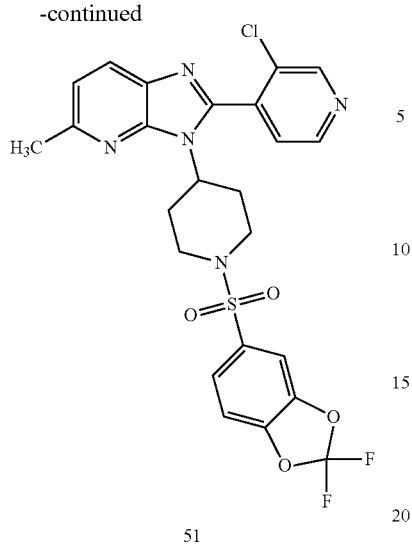

51

2-(3-Chloropyridin-4-yl)-3-(1-((2,2-difluorobenzo[d][1,3]dioxol-5-yl)sulfonyl)piperidin-4-yl)-5-methyl-3H-imidazo[4,5-b]pyridine (51). A solution of 49 (0.100 g, 0.234 mmol) and 50 (0.0332 g, 0.2343 mmol) in HOAc (3 mL) was heated refluxed for 6 hr. After the reaction was complete, the reaction mixture was cooled to rt basified with saturated NaHCO$_3$ solution. The resulting mixture was extracted with EtOAc and the organic layer was dried over anhydrous Na$_2$SO$_4$ then concentrated in vacuo to give the crude product as a yellow solid. This was purified by flash column chromatography using 100-200 mesh silica gel. The desired product was eluted in 50% EtOAc in pet-ether to obtain 0.015 g (12%) of pure 51 as an off white solid.

$^1$H NMR (DMSO-d$_6$) δ 8.88-8.85 (d, J=9.9 Hz, 1H), 8.73-8.71 (d, J=4.8 Hz, 1H), 8.04-8.01 (d, J=8.1 Hz, 1H), 7.85 (s, 1H), 7.76-7.65 (m, 3H), 7.25-7.23 (d, J=8.1 Hz, 1H), 3.98-3.87 (m, 1H), 3.77-3.73 (d, J=11.1 Hz, 2H), 2.96-288 (t, J=11.4 Hz, 2H), 2.63-2.62 (d, J=4.8 Hz, 2H), 2.42 (s, 3H), 1.96-1.89 (t, J=10.8 Hz, 2H). LCMS m/z 548 [M+H−1], 550 [M +H+1].

Example 14

3-(1-(Benzo[d][1,3]dioxol-5-ylsulfonyl)piperidin-4-yl)-2-(3-chloropyridin-4-yl)-5-methyl-3H-imidazo[4,5-b]pyridine (56)

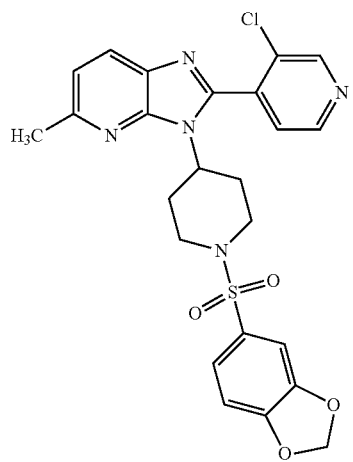 [SMILES: Cc1ccc2nc(-c3ccncc3Cl)n(C3CCN(S(=O)(=O)c4ccc5c(c4)OCO5)CC3)c2n1]

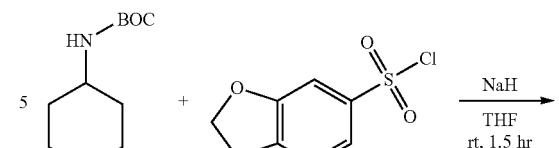

52 tert-Butyl (1-(benzo[d][1,3]dioxol-5-ylsulfonyl)piperidin-4-yl)carbamate (52). NaH (0.23 g, 4.9939 mmol) was added to a stirred solution of 38 (0.5 g, 2.49 mmol) in anhydrous THF (15 mL) at 0° C. The reaction mixture was stirred for 15 min, then 7 (0.55 g, 2.49 mmol) was added dropwise. The resulting mixture was warmed to rt and stirred at rt for 1 hr. Ice-cold H$_2$O was added and the resulting mixture was extracted with EtOAc. The combined organic layers were dried over Na$_2$SO$_4$ and concentrated in vacuo to give the product as an off white solid. This was washed with n-hexane to give pure 52 (0.8 g, 83% yield) as an off white solid. LCMS m/z 385 [M+H].

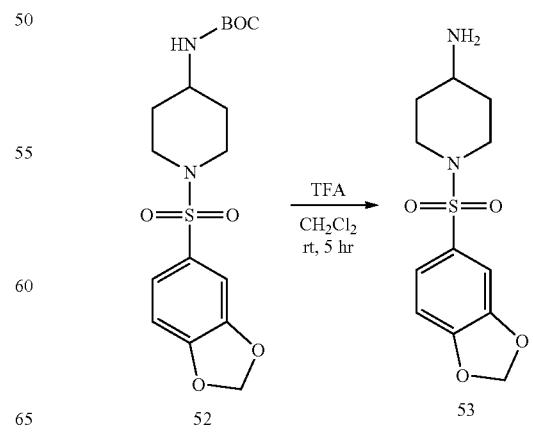

1-(Benzo[d][1,3]dioxol-5-yl)sulfonyl)piperidin-4-amine (53). TFA (2 mL) was added to a stirred solution of 52 (0.8 g, 2.08 mmol) in anhydrous CH$_2$Cl$_2$ (10 mL) at 0° C. The reaction mixture was allowed to warm to rt and stirred for 5 hr. The reaction mixture was basified with saturated NaHCO$_3$ solution, then extracted with CH$_2$Cl$_2$. The organic layer was washed with H$_2$O, followed by brine solution and dried over anhydrous Na$_2$SO$_4$. The organic layer concentrated in vacuo to give 53 (0.4 g, 68% yield) as an off white solid. This was used in the next step as is without any further purification. LCMS m/z 285 [M+H].

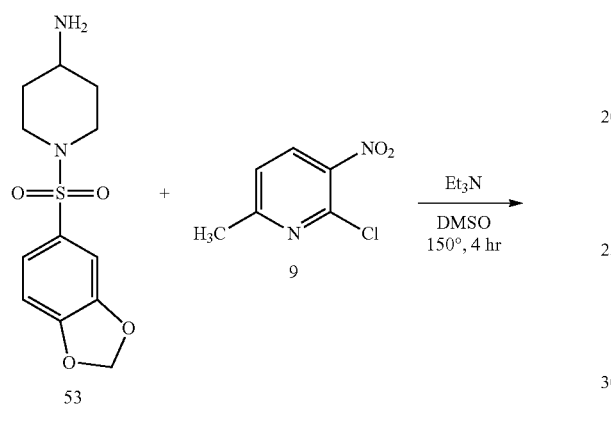

N-(1-(Benzo[d][1,3]dioxol-5-ylsulfonyl)piperidin-4-yl)-6-methyl-3-nitropyridin-2-amine (54). Et$_3$N (0.25 mL, 1.828 mmol) was added to a stirred solution of 53 (0.4 g, 1.406 mmol) and 9 (0.24 g, 1.406 mmol) in anhydrous DMSO (15 mL) at rt. The resulting reaction mixture was stirred at 1500 for 4 hr. After the reaction was complete, it was cooled to rt and poured into brine solution and the resulting mixture was extracted with EtOAc. The combined organic layers were dried over anhydrous Na$_2$SO$_4$ and concentrated in vacuo to give the crude product as a yellow solid. This was washed with Et$_2$O and n-hexane (1:10) to give 0.5 g (85% yield) of 54 as a yellow solid. LCMS m/z 421 [M+H].

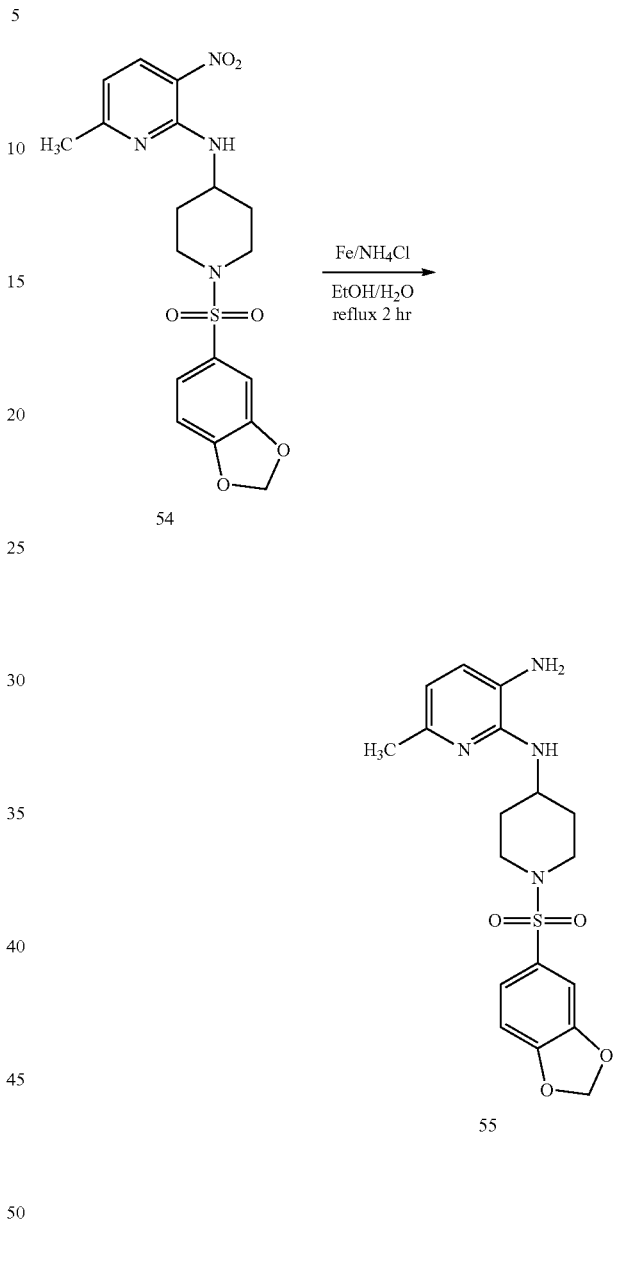

N$^2$-(1-(Benzo[d][1,3]dioxol-5-ylsulfonyl)piperidin-4-yl)-6-methylpyridine-2,3-diamine (55). A mixture of 54 (0.5 g, 1.233 mmol), iron powder (0.34 g, 6.166 mmol) and NH$_4$Cl (0.099 g, 1.849 mmol) in EtOH (10 mL) and H$_2$O (3 mL) was refluxed for 2 hr. The reaction mixture was filtered through a pad of Celite and the filtrate was concentrated to remove the EtOH. The remaining aqueous mixture was diluted with H$_2$O and extracted with EtOAc. The organic layer was dried over anhydrous Na$_2$SO$_4$ and concentrated in vacuo to give 55 (0.15 g, 31% yield) as a brown solid which was used in the next step without any further purification. LCMS m/z 391 [M+H].

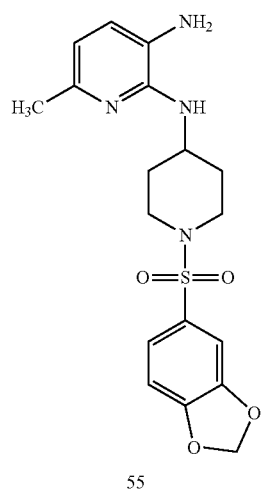

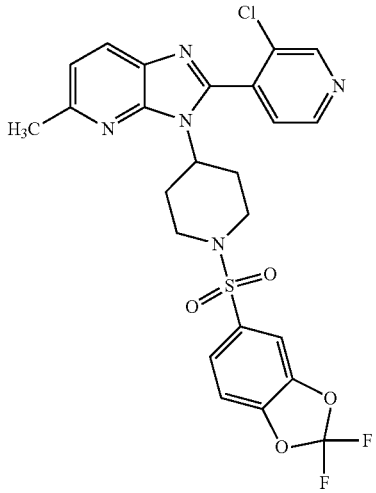 [SMILES: Cc1ccc2nc(-c3ccncc3Cl)n(C3CCN(S(=O)(=O)c4ccc5c(c4)OC(F)(F)O5)CC3)c2n1]

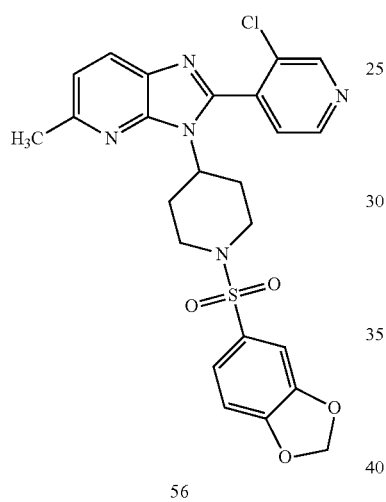

Example 15

2-(2-Chloropyridin-3-yl)-3-(1-((2,2-difluorobenzo[d][1,3]dioxol-5-yl)sulfonyl)piperidin-4-yl)-5-methyl-3H-imidazo[4,5-b]pyridine (58)

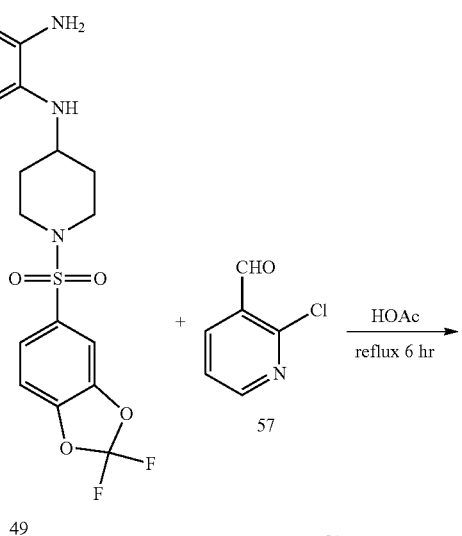

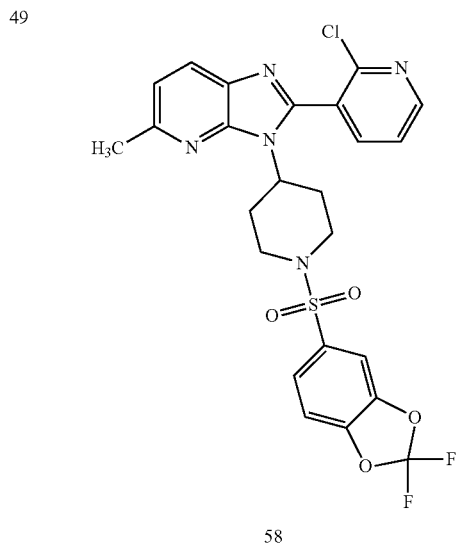

3-(1-(Benzo[d][1,3]dioxol-5-ylsulfonyl)piperidin-4-yl)-2-(3-chloropyridin-4-yl)-5-methyl-3H-imidazo[4,5-b]pyridine (56). A solution of 55 (0.075 g, 0.192 mmol) and 50 (0.0272 g, 0.192 mmol) in HOAc (3 mL) was heated refluxed for 6 hr. After the reaction was complete, the reaction mixture was cooled to rt basified with saturated NaHCO$_3$ solution. The resulting mixture was extracted with EtOAc and the organic layer was dried over anhydrous Na$_2$SO$_4$ then concentrated in vacuo to give the crude product as a yellow solid. This was purified by flash column chromatography using 100-200 mesh silica gel. The desired product was eluted in 50% EtOAc in pet-ether to obtain 0.011 g (11%) of pure 56 as a pale yellow solid. $^1$H NMR (DMSO-d$_6$) δ 8.84 (s, 1H), 8.70-8.68 (d, J=4.8 Hz, 1H), 8.03-8.01 (d, J=8.1 Hz, 1H), 7.68-7.66 (d, J =4.8 Hz, 1H), 7.29-7.21 (m, 3H), 7.13-7.10 (d, J=8.4 Hz, 1H), 6.17 (s, 2H), 3.98 (br s, 1H), 3.73-3.69 (d, J=11.1 Hz, 2H), 2.86 (br s, 2H), 2.64 (s, 3H), 2.38-2.26 (m, 2H), 1.91-1.88 (d, J=11.4 Hz, 2H). LCMS m/z 512 [M+H−1], 514 [M+H+1].

2-(2-Chloropyridin-3-yl)-3-(1-((2,2-difluorobenzo[d][1,3]dioxol-5-yl)sulfonyl)piperidin-4-yl)-5-methyl-3H-imidazo[4,5-b]pyridine (58). A solution of 49 (0.100 g, 0.234 mmol) and 57 (0.0332 g, 0.2343 mmol) in HOAc (3 mL) was refluxed for 6 hr. After the reaction was complete, the reaction mixture was cooled to rt basified with saturated NaHCO$_3$ solution. The resulting mixture was extracted with EtOAc and the organic layer was dried over anhydrous Na$_2$SO$_4$ then concentrated in vacuo to give the crude product as a yellow solid. This was purified by preparative HPLC to give 0.014 g (12%) of pure 58 as an off white solid. $^1$H NMR (DMSO-d$_6$) δ 8.61-8.64 (dd, J=11.4 Hz, 1H), 8.10-8.12 (d, J=7.2 Hz, 1H), 7.99-8.01 (d, J =8 Hz, 1H), 7.84 (s, 1H), 7.57-7.65 (m, 3H), 7.22-7.23 (d, J=7.6 Hz, 1H), 4.01 (m, 1H), 3.74-3.78 (m, 2H), 2.92-3.01 (m, 2H), 2.63, (s, 3H), 2.45 (m, 2H), 1.91 (m, 2H). LCMS m/z 548 [M +H−1], 550 [M+H+1].

Example 175

3-(2-chlorophenyl)-1-(1-((4-ethylphenyl)sulfonyl)piperidin-4-yl)-1-(6-methylpyridin-2-yl)urea (64)

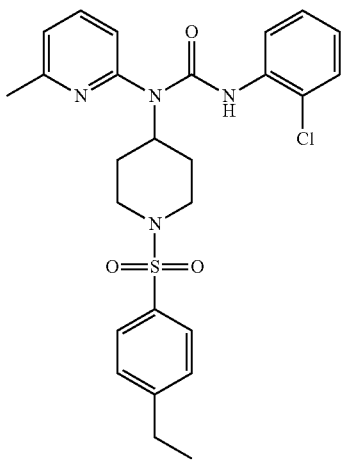 [SMILES: CCc1ccc(S(=O)(=O)N2CCC(N(C(=O)Nc3ccccc3Cl)c3cccc(C)n3)CC2)cc1]

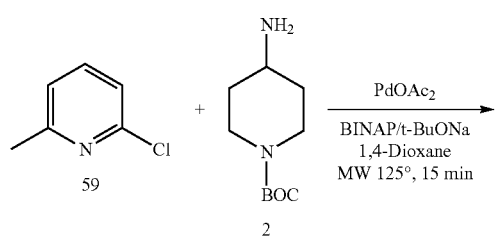

tert-Butyl 4-((6-methylpyridin-2-yl)amino)piperidine-1-carboxylate (60). In a microwave vessel 59 (1.8 mL, 16.47 mmol), 2 (3.910 g, 19.52 mmol), BINAP (96 mg, 0.154 mmol) and t-BuONa (1.896 g, 19.73 mmol) were combined with 1,4-dioxane (10 mL). N$_2$ was bubbled through this heterogeneous mixture for 5 minutes and Pd(OAc)$_2$ (35 mg, 0.156 mmol) was added. This reaction mixture was irradiated in the microwave (125°, 15 min) then diluted with brine and extracted with EtOAc (3×). The combined organic extracts were dried over anhydrous Na$_2$SO$_4$ and concentrated in vacuo to give 3.273 g of 60 (65% yield) as an orange solid. This material was carried on without further purification. $^1$H NMR (CDCl$_3$) δ 7.31 (t, J=7.81, 1H), 6.42 (d, J=7.32 Hz, 1H), 6.17 (d, J=8.30 Hz, 1H), 4.38 (d, J=7.81 Hz, 1H), 4.08-3.92 (m, 2H), 3.69-3.58 (m, 1H), 2.94 (br s, 2H), 2.34 (s, 3H), 2.05-1.96 (m, 2H), 1.45 (s, 9H), 1.35 (d, J=9.77 Hz, 2H).

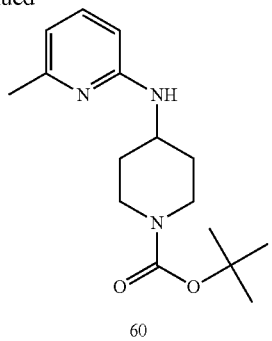

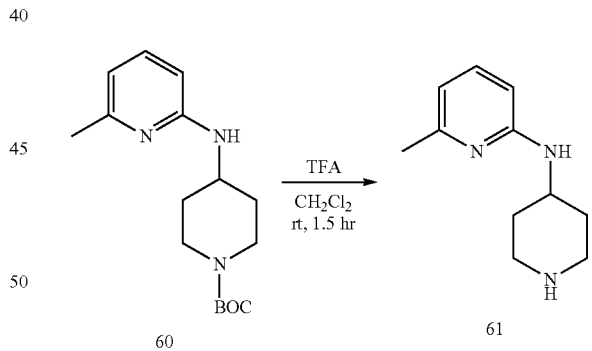

6-Methyl-N-(piperidin-4-yl)pyridin-2-amine (61). TFA (10 mL) was added to a stirred solution of 60 (3.273 g, 11.23 mmol) in anhydrous CH$_2$Cl$_2$ (25 mL) at rt. The resulting orange solution was stirred at rt for 90 min and then concentrated in vacuo to give a yellow oil. This was taken up in 1M HCl and extracted with CH$_2$Cl$_2$ (3×) then the pH of the aqueous layer was adjusted to 12 (litmus) with solid KOH and extracted again with CH$_2$Cl$_2$ (3×). The combined basic organic extracts were dried anhydrous Na$_2$SO$_4$ and concentrated in vacuo to give 1.819 g (85% yield) of pure 61 as an off-white solid. This was used in the next step without further purification ¹H NMR (CDCl₃) δ 7.32 (t, J=7.81 Hz, 1H), 6.42 (d, J=7.32 Hz, 1H), 6.18 (d, J=8.30 Hz, 1H), 4.44 (d, J=7.81 Hz, 1H), 3.58-3.49 (m, 1H), 3.11 (dt, J=3.54, 12.94 Hz, 2H), 2.66-2.77 (m, 2H), 2.35 (s, 3H), 2.08-2.00 (m, 2H), 1.42-1.30 (m, 2H).

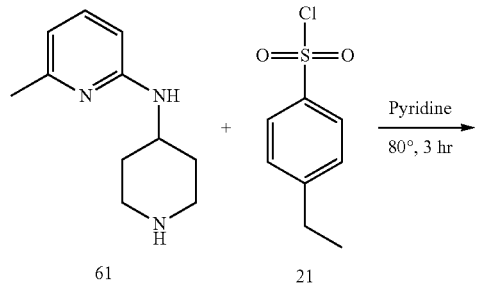

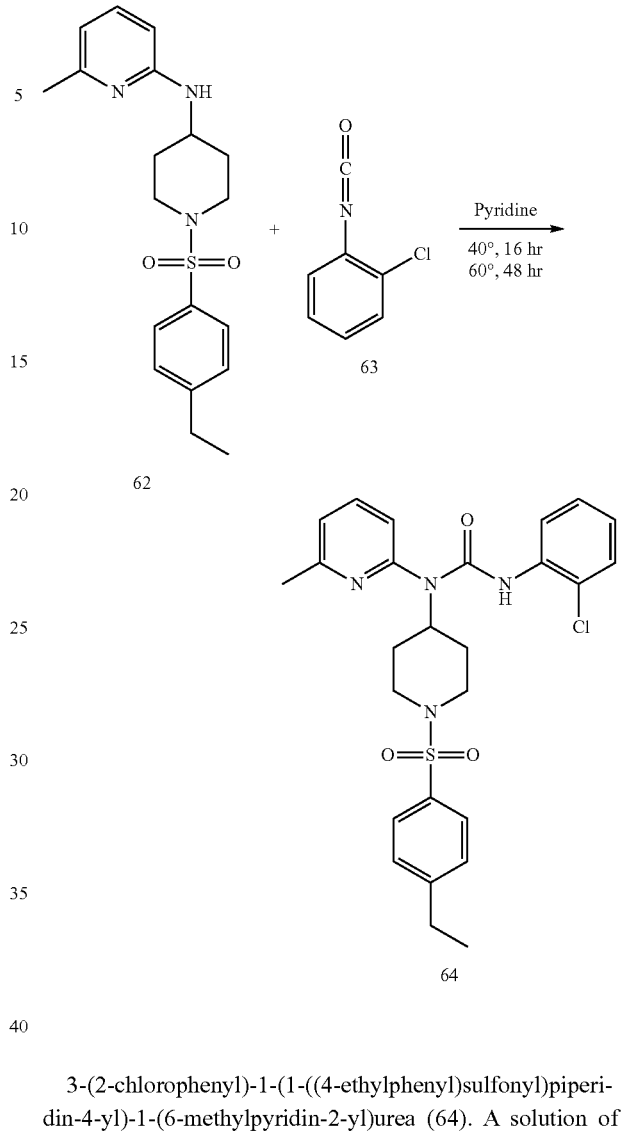

N-(1-((4-ethylphenyl)sulfonyl)piperidin-4-yl)-6-methyl-pyridin-2-amine (62). A solution of 61 (521 mg, 2.72 mmol)) and 21 (0.55 mL, 3.07 mmol) in pyridine (5 mL) was heated at 800 for 3 hr. The reaction was allowed to cool to rt then poured into H₂O. The solid was collected and washed with H₂O (3×) and dried. It was then taken up in CH₂Cl₂ and washed with brine (3×). The combined organic extracts were dried over anhydrous Na₂SO₄ and concentrated in vacuo to give a crude white solid. This was taken up in CHCl₃ and purified by flash chromatography on silica gel. The desired product was collected to give 0.763 g (78% yield) of pure 62 as a white solid. ¹H NMR (CDCl₃) δ 1.33-1.27 (m, 3H), 1.65-1.55 (m, 3H), 2.14-2.07 (m, 2H), 2.33 (s, 3H), 2.68-2.61 (m, 2H), 2.76 (q, J=7.65 Hz, 2H), 3.63-3.53 (m, 3H), 4.33-4.26 (m, 1H), 6.12 (d, J=8.30 Hz, 1H), 6.43 (d, J=7.32 Hz, 1H), 7.32-7.27 (m, 1H), 7.37 (d, J=8.30 Hz, 2H), 7.71-7.67 (m, 7H). LCMS m/z (ES+) 361.

3-(2-chlorophenyl)-1-(1-((4-ethylphenyl)sulfonyl)piperidin-4-yl)-1-(6-methylpyridin-2-yl)urea (64). A solution of 62 (52 mg, 0.145 mmol) and 63 (25 μL, 0.207 mmol) in pyridine (700 μL) was heated at 400 for 16 hr. Additional 63 (0.1 mL) was added and the reaction was heated at 600 for 48 hr, after which it was diluted with H₂O and extracted with EtOAc (3×). The combined organic extracts were washed with brine then dried over anhydrous Na₂SO₄ and concentrated in vacuo to give a colorless oil. This was taken up in CHCl₃, the ppt filtered and the filtrate was purified with flash chromatography on silica gel, eluting with hexane/EtOAc. The desired fractions were concentrated in vacuo to give 0.038 g (51% yield) of pure 64. ¹H NMR (CDCl₃) δ ppm 1.33-1.27 (m, 3H), 1.86 (dq, J=12.45, 4.15 Hz, 2H), 2.00 (dd, J=11.72, 1.95 Hz, 2H), 2.37 (dt, J=11.96, 2.44 Hz, 2H), 2.75 (q, J=7.81 Hz, 2H), 3.87 (dt, J=11.72, 1.95 Hz, 2H), 4.33 (tt, J=12.33, 3.54 Hz, 1H), 6.90 (dt, J=7.81, 1.47 Hz, 1H), 7.05 (d, J=7.81 Hz, 1H) 7.25-7.16 (m, 2H), 7.36 (d, J=8.30 Hz, 2H), 7.68-7.63 (m, 2H), 7.74 (t, J=7.81 Hz, 1H), 8.12 (s, 3.1), 8.18 (dd, J=8.55, 1.71 Hz, 1H). LCMS m/z (ES+) 514.

Example 207

2-Chloro-N-(1-((4-ethylphenyl)sulfonyl)piperidin-4-yl)-N-(4-methoxyphenyl)benzamide (70)

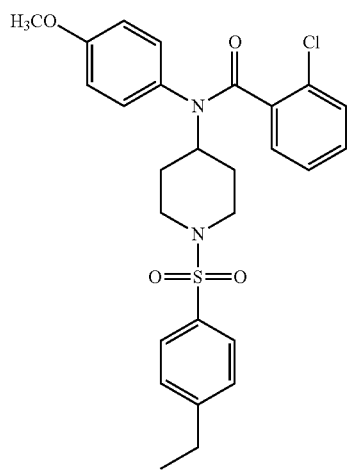 [SMILES: CCc1ccc(S(=O)(=O)N2CCC(N(C(=O)c3ccccc3Cl)c3ccc(OC)cc3)CC2)cc1]

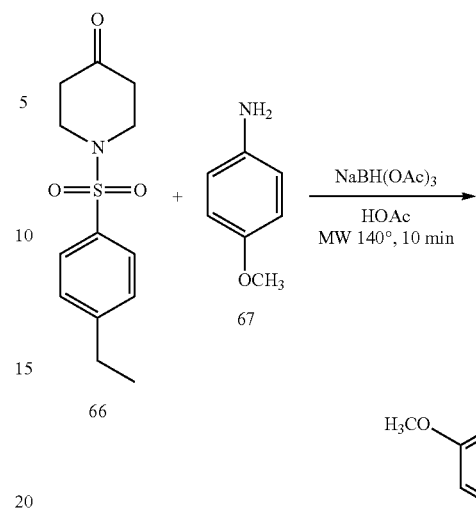

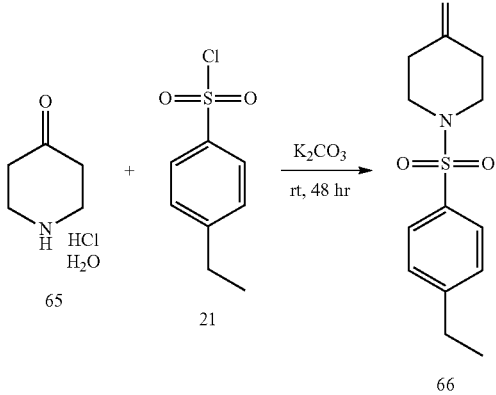

1-((4-Ethylphenyl)sulfonyl)piperidin-4-one (66). A solution of 21 (2.22 mL, 13.76 mmol) in CH$_2$Cl$_2$ (8.0 mL) was added to a mixture of 65 (2.0 g, 13.11 mmol) and K$_2$CO$_3$ (4.35 g, 31.5 mmol) in H$_2$O (13.3 mL) and CH$_2$Cl$_2$ at rt. The resulting mixture was stirred at rt for 48 hr, then extracted with CH$_2$Cl$_2$, then saturated aqueous NaHCO$_3$ solution. The combined organic layers were dried over MgSO$_4$ and evaporated in vacuo to give 3.39 g (97% yield) of 66 as a white solid. This material was used without purification in the next step. $^1$H NMR (CDCl$_3$) δ 7.70 (d, J=8.30 Hz, 2H), 7.37 (d, J=8.30 Hz, 2H), 3.39 (t, J=6.10 Hz, 4H), 2.73 (q, J=7.65 Hz, 2H), 2.54 (t, J=6.10 Hz, 4H), 1.27 (t, J=7.81 Hz, 3H). LCMS m/z 268 [M+H].

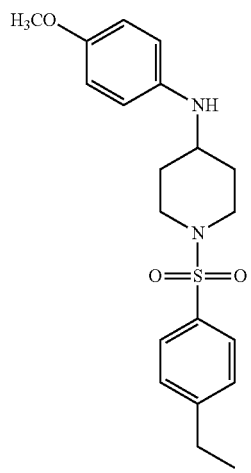

1-((4-Ethylphenyl)sulfonyl)-N-(4-methoxyphenyl)piperidin-4-amine (68). A mixture of 66 (0.535 g, 2.00 mmol), 67 (0.123 g, 1.00 mmol), NaBH(OAc)$_3$ (0.530 g, 2.50 mmol) and HOAc (0.17 mL, 3.00 mmol) in DCE (2.00 mL) was microwaved at 1400 for 10 minutes. The resulting mixture was quenched with saturated aqueous NaHCO$_3$ solution then extracted with CH$_2$Cl$_2$. The combined extracts were dried over MgSO$_4$ and concentrated in vacuo to give the crude product. This was purified by flash chromatography on silica gel, eluting with 50% EtOAc in hexane to give 0.328 g (88%) of pure 68. LCMS m/z 375 [M+H].

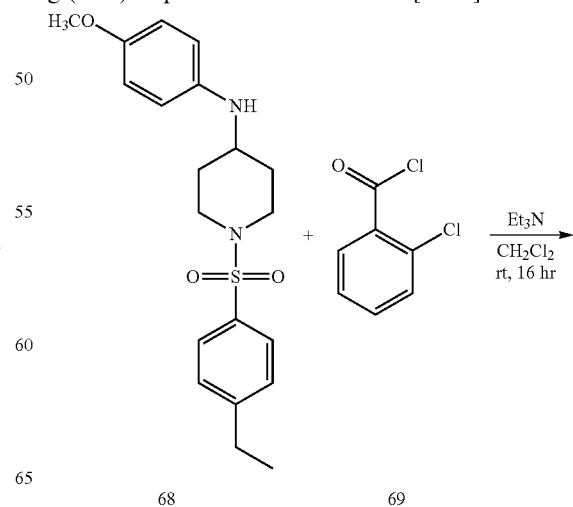

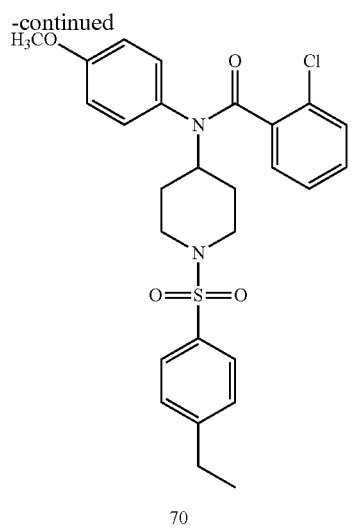

70

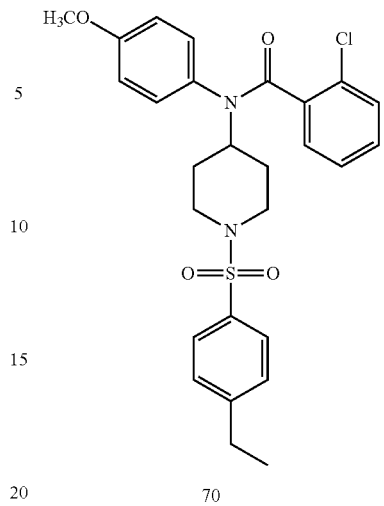

70

2-Chloro-N-(1-((4-ethylphenyl)sulfonyl)piperidin-4-yl)-N-(4-methoxyphenyl)benzamide (70). A mixture of 68 (0.179 g, 0.477 mmol), 69 (0.125 g, 0.715 mmol), and Et₃N (0.33 mL, 2.383 mmol) in anhydrous CH₂Cl₂ (0.95 mL) was stirred at rt for 16 hr. The reaction was quenched with saturated aqueous NaHCO₃ solution then extracted with CH₂Cl₂. The combined extracts were dried over MgSO₄ and concentrated in vacuo to give the crude product. This was purified by flash chromatography on silica gel, eluting with 50% EtOAc in hexane to give 0.150 g (62%) of pure 70. ¹H NMR (CDCl₃) δ 7.65 (d, J=8.30 Hz, 2H), 7.35 (d, J=8.30 Hz, 2H), 7.15 (d, J=7.81 Hz, 1H), 7.10-6.93 (m, 5H), 6.67 (d, J=7.81 Hz, 2H), 4.75-4.60 (m, 1H), 3.86 (d, J=10.25 Hz, 2H), 3.72 (s, 3H), 2.75 (q, J=7.65 Hz, 2H), 2.42 (t, J=11.96 Hz, 2H), 1.97 (d, J=11.72 Hz, 2H), 1.66-1.50 (m, 2H), 1.29 (t, J=7.57 Hz, 3H). LCMS m/z 513 [M+H−1], 515 [M+H+1].

Example 214

2-Chloro-N-(1-((4-ethylphenyl)sulfonyl)piperidin-4-yl)-N-(4-methoxyphenyl)benzothioamide (71)

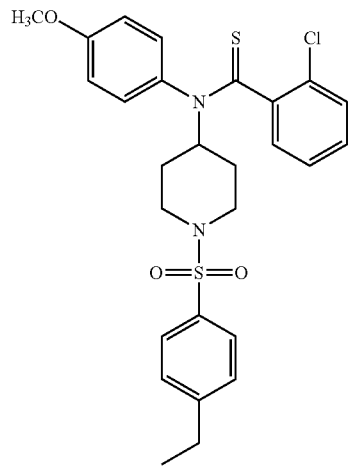

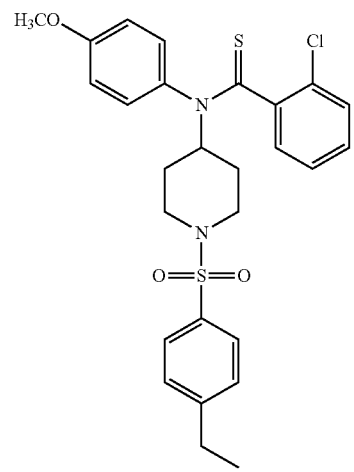

71

2-Chloro-N-(1-((4-ethylphenyl)sulfonyl)piperidin-4-yl)-N-(4-methoxyphenyl)benzothioamide (71). A mixture of 70 (0.122 g, 0.237 mmol) and P₄S₁₀ (0.053 g, 0.119 mmol) in anhydrous CH₂Cl₂ (2.3 mL) was microwaved at 1200 for 70 min. The reaction mixture was quenched with H₂O and after stirring for 10 minutes, extracted with CH₂Cl₂. The extract was dried over MgSO₄ and concentrated in vacuo to give crude product. This was purified by flash chromatography on silica gel, eluting with 40% EtOAc in hexane to give 0.054 g (43%) of pure 71. ¹H NMR (CDCl₃) δ 7.65 (d, J=8.30 Hz, 2H), 7.36 (d, J=8.30 Hz, 2H), 7.19 (d, J=8.79 Hz, 1H), 7.06 (d, J=7.81 Hz, 1H), 7.00 (br. s., 2H), 6.98-6.92 (m, 1H), 6.79-6.62 (m, 3H), 5.60-5.46 (m, 1H), 3.94-3.81 (m, 2H), 3.72 (s, 3H), 2.75 (q, J=7.65 Hz, 2H), 2.43 (q, J=9.77 Hz, 2H), 2.26 (d, J=12.70 Hz, 1H), 2.10-2.00 (m, 1H), 1.69-1.59 (m, J=3.91, 12.21 Hz, 1H), 1.55-1.47 (m, 1H), 1.30 (t, J=7.57 Hz, 3H). m/z 529 [M+H−1], 531 [M+H+1].

Example 220

2-Chloro-N-(1-((2-methylbenzo[d]oxazol-6-yl)sulfonyl)piperidin-4-yl)-N-(m-tolyl)benzenesulfonamide (80)

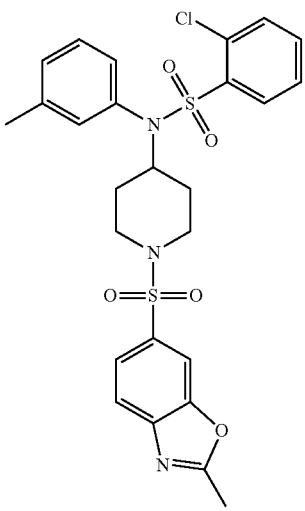 [SMILES: Cc1cccc(N(C2CCN(S(=O)(=O)c3ccc4nc(C)oc4c3)CC2)S(=O)(=O)c2ccccc2Cl)c1]

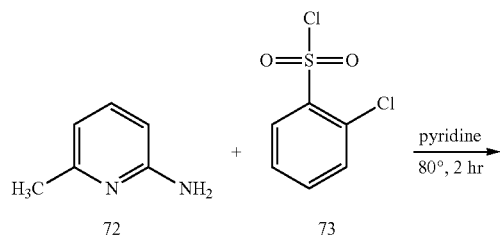

2-Chloro-N-(6-methylpyridin-2-yl)benzenesulfonamide (74). To a stirred solution of 72 (0.50 g, 4.62 mmol) in pyridine (1 mL) was added 73 (0.97 g, 4.62 mmol) at rt. The resulting mixture was stirred at 800 for 2 hr. The reaction mixture was cooled to rt. and ice-cold H$_2$O was added. The solid that separated was collected and dried in vacuo to give 0.80 g (61% yield) of 74 as an off white solid. LCMS m/z 283 [M+H−1], 285 [M+H+1].

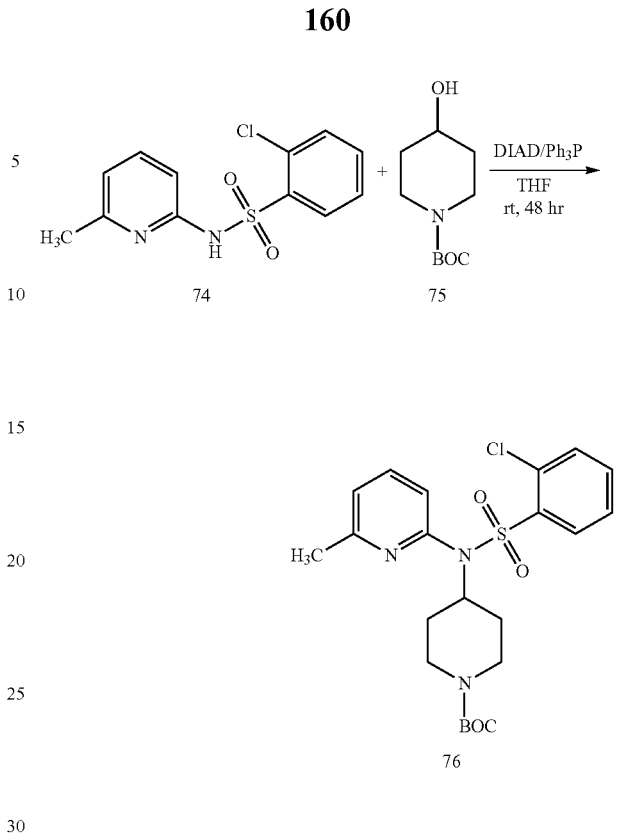

tert-Butyl 4-((2-chloro-N-(6-methylpyridin-2-yl)phenyl)sulfonamido)piperidine-1-carboxylate (76). To a stirred solution of 75 (0.38 g, 1.88 mmol) in anhydrous THF (15 mL) was added 74 (0.53 g, 1.88 mmol) and then Ph$_3$P (0.74 g, 2.83 mmol) at rt. The reaction mixture was cooled to 0° and stirred for 10 min, then DIAD (0.55 mL) was added dropwise over a period of 5 min. The reaction mixture was warmed to rt and stirred at rt for 48 hr. The reaction mixture was quenched by the addition of ice-cold H$_2$O and the resulting mixture was extracted with EtOAc (2×20 mL). The combined organic layers were dried over anhydrous Na$_2$SO$_4$ and concentrated in vacuo to give 1.00 g of crude product 76, which was used in the next step without any further purification.

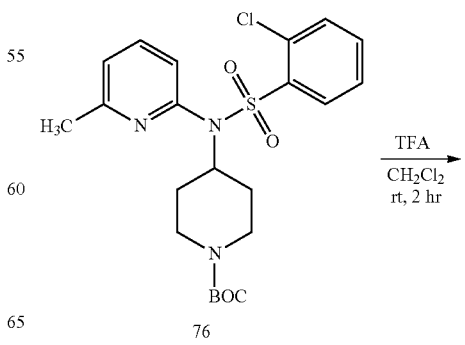

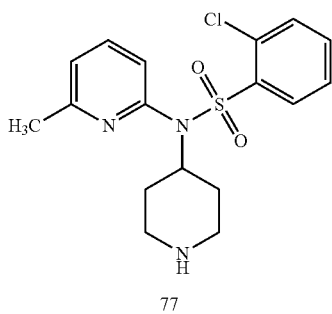

77

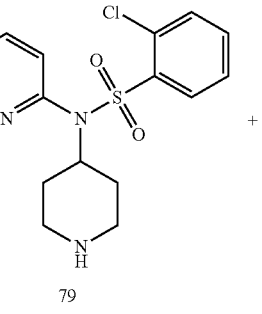

79

2-Chloro-N-(6-methylpyridin-2-yl)-N-(piperidin-4-yl)benzenesulfonamide (77). To a solution of 76 (0.50 g, 1.07 mmol) in anhydrous CH$_2$Cl$_2$ (10 mL) was added TFA (0.33 mL, 3.47 mmol) at 0°. The reaction mixture was warmed to rt and stirred at rt for 2 hr. The reaction mixture was basified with saturated aqueous Na$_2$CO$_3$ solution and extracted with CH$_2$Cl$_2$ (2×25 mL). The combined organic layers were dried over anhydrous Na$_2$SO$_4$ and concentrated in vacuo to obtain the crude compound. This was purified by flash chromatography, eluting with 20% MeOH in CH$_2$Cl$_2$ to give 0.100 g ((26% yield) of pure 77 as an off-white solid. LCMS m/z 366 [M+H−1], 368 [M+H+1].

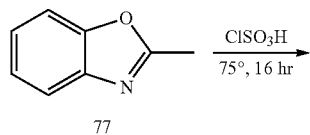

77 → ClSO$_3$H, 75°, 16 hr

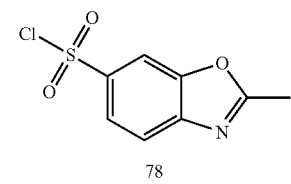

78

2-Methylbenzo[d]oxazole-6-sulfonyl chloride (78). To a stirred solution of chlorosulfonic acid (5 mL) was added compound-77 (2.00 g, 15.02 mmol) slowly in portions over a period of 30 min. at rt. The resulting mixture was heated at 750 for 16 hr. The reaction mixture was cooled to rt and quenched by the addition of ice-cold H$_2$O, and the solid that separated was collected and dried in vacuo to give 0.95 g (27% yield) of 78 as a white solid. This compound was use in the next step without further purification.

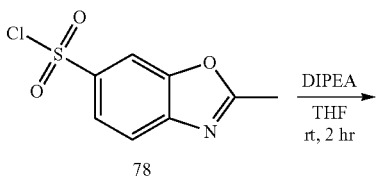

78 → DIPEA, THF, rt, 2 hr

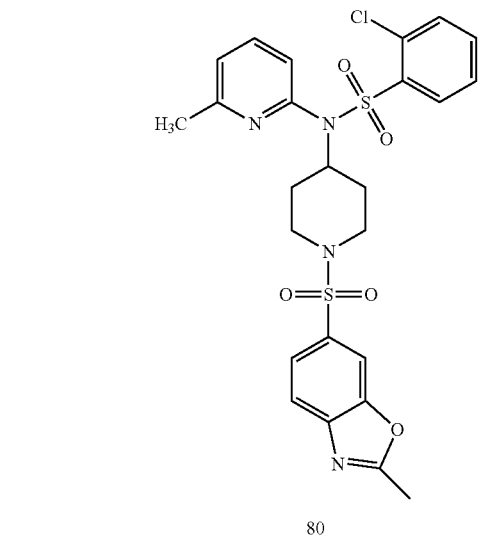

80

2-Chloro-N-(1-((2-methylbenzo[d]oxazol-6-yl)sulfonyl)piperidin-4-yl)-N-(6-methylpyridin-2-yl)benzenesulfonamide (80). A solution of 79 (0.05 g, 0.13 mmol), 78 (0.03 g, 0.13 mmol) and DIPEA (0.04 mL, 0.27 mmol) in anhydrous THF was stirred at rt for 2 h. The reaction mixture was quenched by the addition of H$_2$O and the resulting mixture was extracted with EtOAc (2×20 mL). The organic layers were combined, dried over anhydrous Na$_2$SO$_4$ and concentrated in vacuo to give the crude 80. This was washed with Et$_2$O to give 0.023 g (30% yield) of pure 80 as an off white solid. LCMS m/z 561 [M+H−1], 563 [M+H+1]. $^1$H NMR (DMSO-d$_6$) δ 8.02 (d, J=1.7 Hz, 1H), 7.97-7.89 (m, 1H), 7.88-7.78 (m, 1H), 7.65 (m, 4H), 7.52-7.43 (m, 1H), 7.19 (d, J=8.1 Hz, 1H), 6.80 (d, J=7.8 Hz, 1H), 4.12 (s, 1H), 3.72 (d, J=11.6 Hz, 2H), 2.70 (s, 3H), 2.5-2.49 (m, 2H), 2.31 (s, 3H), 1.82 (d, J=12.3 Hz, 2H), 1.45-1.40 (m, 2H).

Example 222

2-Chloro-N-(1-((4-ethylphenyl)sulfonyl)piperidin-4-yl)-N-(6-methoxypyridin-2-yl)benzenesulfonamide (85)

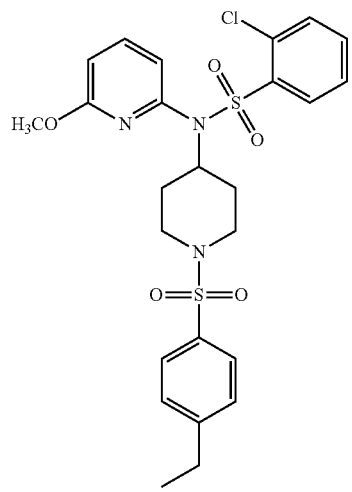 [SMILES: CCc1ccc(S(=O)(=O)N2CCC(N(c3cccc(OC)n3)S(=O)(=O)c3ccccc3Cl)CC2)cc1]

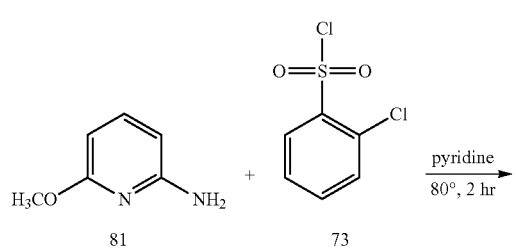

2-Chloro-N-(6-methoxypyridin-2-yl)benzenesulfonamide (82). To a stirred solution of 81 (0.50 g, 4.02 mmol) in pyridine (1 mL) was added 73 (0.84 g, 4.02 mmol) at rt. The resulting mixture was stirred at 800 for 2 hr. The reaction mixture was cooled to rt. and ice-cold H$_2$O was added. The solid that separated was collected and dried in vacuo to give 0.80 g (67% yield) of 82 as an off white solid. $^1$H NMR (CDCl$_3$) δ 8.17 (d, J=7.2 Hz, 1H), 7.49 (d, J=4 Hz, 2H), 7.43 (dd, J=8.0 Hz, J=8.0 Hz, 2H), 7.40-7.37 (m, 1H), 6.72 (d, J=8.0 Hz, 1H), 6.39 (d, J=8.4 Hz, 1H), 3.75 (s, 3H).

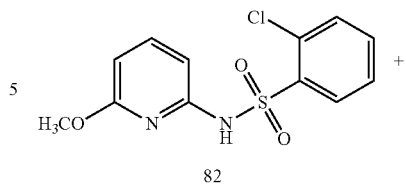

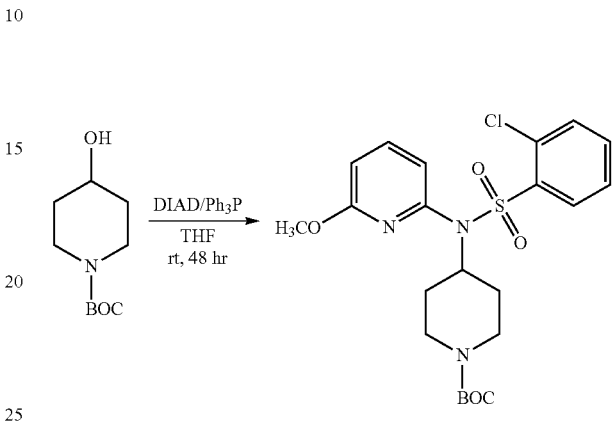

tert-Butyl 4-((2-chloro-N-(6-methoxypyridin-2-yl)phenyl)sulfonamido)piperidine-1-carboxylate (83). To a stirred solution of 75 (0.380 g, 1.88 mmol) in anhydrous THF (15 mL) was added 82 (0.56 g, 1.88 mmol) and then Ph$_3$P (0.74 g, 2.83 mmol) at rt. The reaction mixture was cooled to 0° and stirred for 10 min, then DIAD (0.55 mL) was added dropwise over a period of 5 min. The reaction mixture was warmed to rt and stirred at rt for 48 hr. The reaction mixture was quenched by the addition of ice-cold H$_2$O and the resulting mixture was extracted with EtOAc (2×20 mL). The combined organic layers were dried over anhydrous Na$_2$SO$_4$ and concentrated in vacuo to give 1.00 g of crude product 83 which was used in the next step without any further purification. LCMS m/z 482 [M+H−1], 484 [M+H+1].

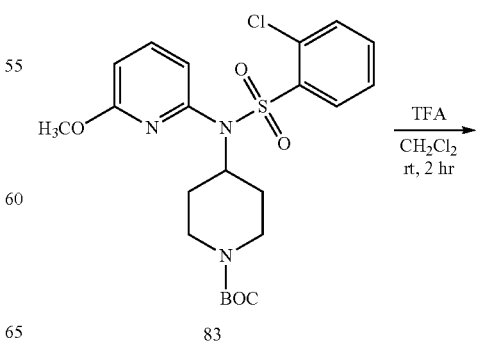

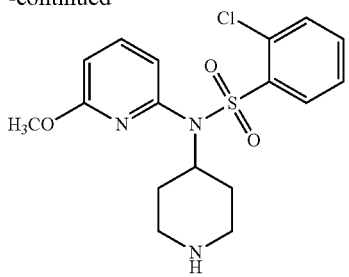

2-Chloro-N-(6-methoxypyridin-2-yl)-N-(piperidin-4-yl)benzenesulfonamide (84). To a solution of 83 (0.50 g, 1.03 mmol) in anhydrous CH$_2$Cl$_2$ (10 mL) was added TFA (0.32 mL, 3.33 mmol) at 0°. The reaction mixture was warmed to rt and stirred at rt for 2 hr. The reaction mixture was basified with saturated aqueous Na$_2$CO$_3$ solution and extracted with CH$_2$Cl$_2$ (2×25 mL). The combined organic layers were dried over anhydrous Na$_2$SO$_4$ and concentrated in vacuo to obtain the crude compound. This was purified by flash chromatography, eluting with 20% MeOH in CH$_2$Cl$_2$ to give 0.100 g (26% yield) of pure 84 as an off-white solid. LCMS m/z 382 [M+H−1], 384 [M+H+1].

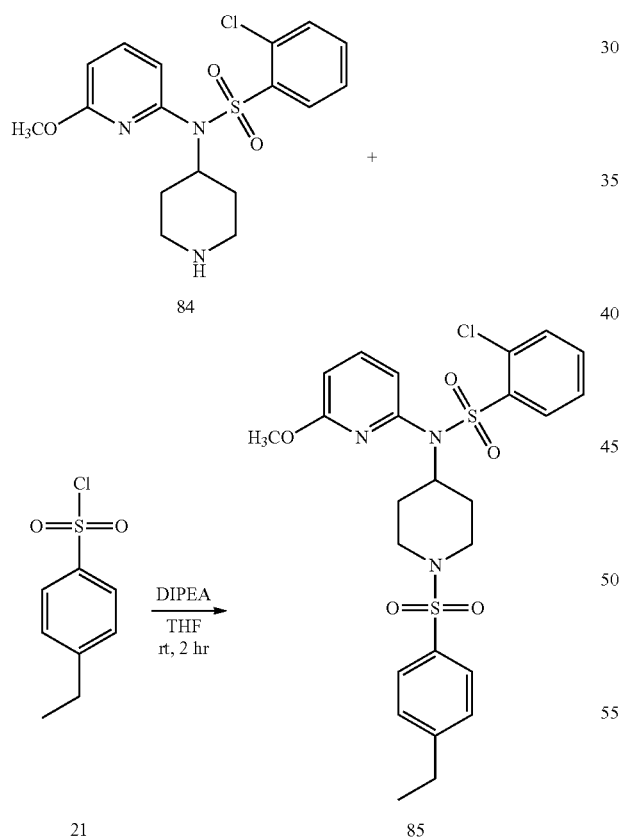

2-Chloro-N-(1-((4-ethylphenyl)sulfonyl)piperidin-4-yl)-N-(6-methoxypyridin-2-yl)benzenesulfonamide (85). A solution of 84 (0.10 g, 0.26 mmol), 21 (0.53 g, 0.26 mmol) and DIPEA (0.07 mL, 0.52 mmol) in anhydrous THF (5 mL) was stirred at rt for 2 h. The reaction mixture was quenched by the addition of H$_2$O and the resulting mixture was extracted with EtOAc (2×20 mL). The organic layers were combined, dried over anhydrous Na$_2$SO$_4$ and concentrated in vacuo to give the crude product 85. This was washed with Et$_2$O to give 0.066 g (46% yield) of pure 85 as an off white solid. LCMS m/z 550 [M+H−1], 552 [M+H+1]. $^1$H NMR (DMSO-d$_6$) δ 7.95 (dd, J=7.9, 1.6 Hz, 1H), 7.76-7.57 (m, 5H), 7.51-7.45 (m, 1H), 7.42 (d, J=8.0 Hz, 2H), 6.81 (d, J=8.2 Hz, 1H), 6.71 (d, J=7.5 Hz, 1H), 4.19 (m, 1H), 3.67 (d, J=12.1 Hz, 2H), 3.52 (s, 3H), 2.70 (q, J=7.7 Hz, 2H), 2.50 (m, 2H), 1.90 (d, J=12.4 Hz, 2H), 1.52 (q, J=11.6 Hz, 2H), 1.21 (t, J=7.6 Hz, 3H).

Example 210

2-Chloro-N-(1-((4-ethylphenyl)sulfonyl)piperidin-4-yl)-N-(pyridin-2-yl)benzenesulfonamide (90)

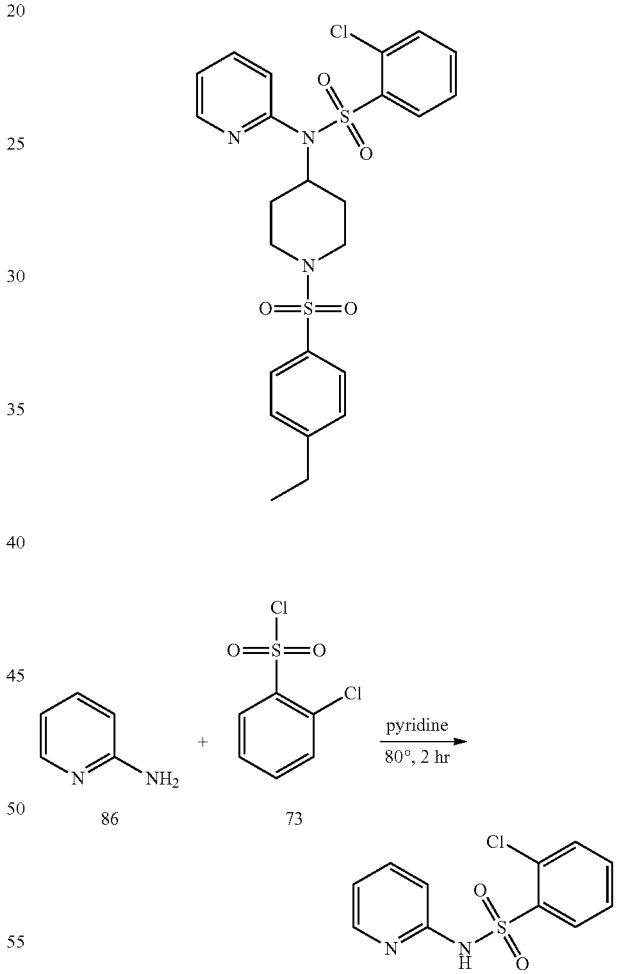

2-Chloro-N-(pyridin-2-yl)benzenesulfonamide (87). To a stirred solution of 86 (0.25 g, 2.65 mmol) in pyridine (0.5 mL) was added 73 (0.55 g, 2.65 mmol) at rt. The resulting mixture was stirred at 800 for 2 hr. The reaction mixture was cooled to rt. and ice-cold H$_2$O was added. The solid that separated was collected and dried in vacuo to give 0.51 g (72% yield) of 87 as an off white solid. LCMS m/z 269 [M+H−1], 271 [M+H+1].

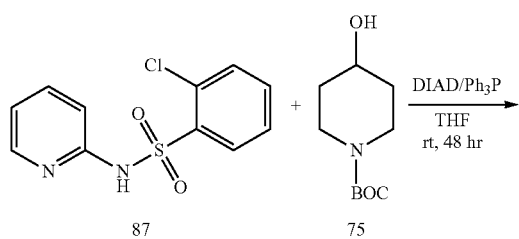

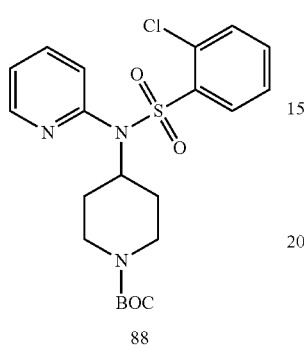

tert-Butyl 4-((2-chloro-N-(pyridin-2-yl)phenyl)sulfonamido)piperidine-1-carboxylate (88). To a stirred solution of 75 (0.40 g, 1.98 mmol) in anhydrous THF (15 mL) was added 87 (0.53 g, 1.98 mmol) and then Ph₃P (0.74 g, 2.83 mmol) at rt. The reaction mixture was cooled to 0° and stirred for 10 min, then DIAD (0.55 mL) was added dropwise over a period of 5 min. The reaction mixture was warmed to rt and stirred at rt for 48 hr. The reaction mixture was quenched by the addition of ice-cold H₂O and the resulting mixture was extracted with EtOAc (2×20 mL). The combined organic layers were dried over anhydrous Na₂SO₄ and concentrated in vacuo to give 1.00 g of crude product 88 which was used in the next step without any further purification.

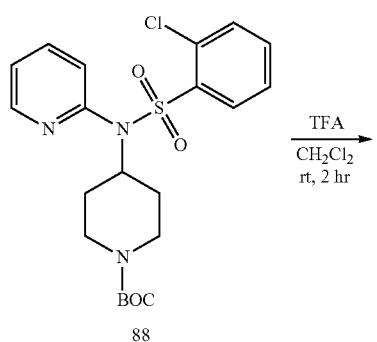

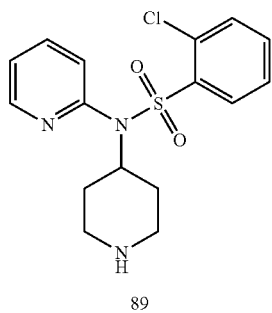

2-Chloro-N-(piperidin-4-yl)-N-(pyridin-2-yl)benzenesulfonamide (89). To a solution of 88 (0.60 g, 1.33 mmol) in anhydrous CH₂Cl₂ (10 mL) was added TFA (0.41 mL, 4.27 mmol) at 0°. The reaction mixture was warmed to rt and stirred at rt for 2 hr. The reaction mixture was basified with saturated aqueous Na₂CO₃ solution and extracted with CH₂Cl₂ (2×25 mL). The combined organic layers were dried over anhydrous Na₂SO₄ and concentrated in vacuo to obtain the crude compound. This was purified by flash chromatography, eluting with 20% MeOH in CH₂Cl₂ to give 0.10 g (22% yield) of pure 89 as an off-white solid. LCMS m/z 352 [M+H−1], 354 [M+H+1].

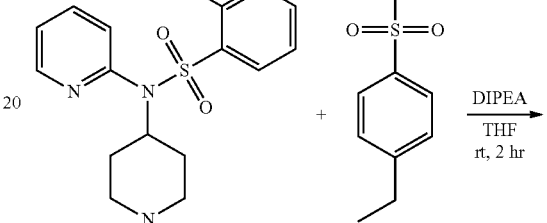

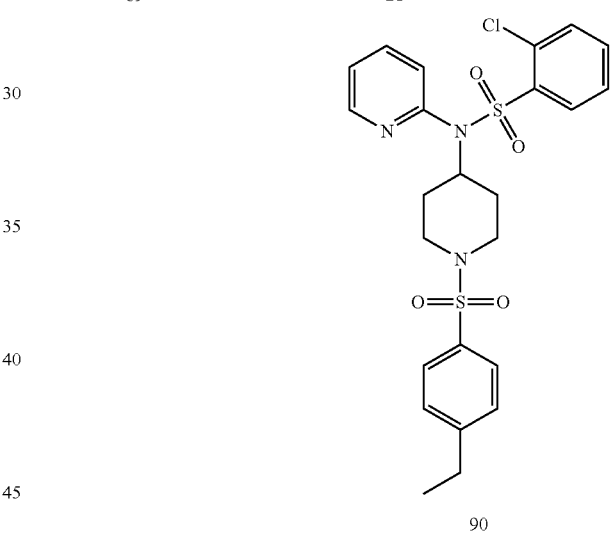

2-Chloro-N-(1-((4-ethylphenyl)sulfonyl)piperidin-4-yl)-N-(pyridin-2-yl)benzenesulfonamide (90). A solution of 89 (0.10 g, 0.28 mmol), 21 (0.53 g, 0.26 mmol) and DIPEA (0.07 mL, 0.56 mmol) in anhydrous THF (5 mL) was stirred at rt for 2 h. The reaction mixture was quenched by the addition of H₂O and the resulting mixture was extracted with EtOAc (2×20 mL). The organic layers were combined, dried over anhydrous Na₂SO₄ and concentrated in vacuo to give the crude product 90. This was washed with Et₂O to give 0.132 g (90% yield) of pure 90 as an off white solid. LCMS m/z 520 [M+H−1], 522 [M+H+1]. $^1$H NMR (DMSO-d₆) δ 8.42-8.44 (m, 1H), 7.94 (dd, J=7.9, 1.5 Hz, 1H), 7.84 (dt, J=7.7, 2.1 Hz, 1H), 7.71-7.62 (m, 2H), 7.61-7.56 (m, 2H), 7.48 (ddd, J=8.3, 7.0, 1.7 Hz, 1H), 7.45-7.37 (m, 3H), 7.10 (d, J=7.9 Hz, 1H), 4.31-4.00 (m, 1H), 3.65 (d, J=11.9 Hz, 2H), 2.70 (q, J=7.6 Hz, 2H), 2.47-2.26 (m, 2H), 1.87 (d, J=12.3 Hz, 2H), 1.49 (dt, J=13.4, 9.4 Hz, 2H), 1.21 (t, J=7.6 Hz, 3H).

TABLE 2
Additional examples were prepared as according to the described methods above, or similar methods, or were purchased from commercial vendors.
| No. | Structure | Example | LCMS m/z [M + H] | SCHEME |
|---|---|---|---|---|
| 1. | 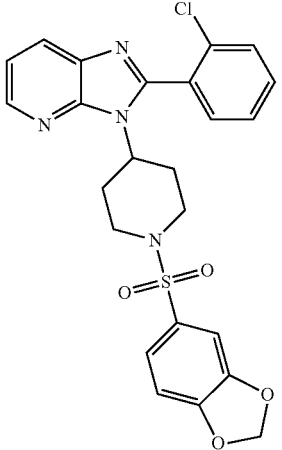 [SMILES: O=S(=O)(c1ccc2c(c1)OCO2)N1CCC(n2c(-c3ccccc3Cl)nc3cccnc32)CC1] | Example 1 | m/z 497 [M + H − 1], 499 [M + H + 1] | 1 |
| 2. | 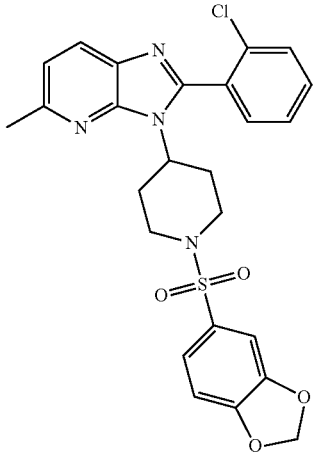 [SMILES: Cc1ccc2nc(-c3ccccc3Cl)n(C3CCN(S(=O)(=O)c4ccc5c(c4)OCO5)CC3)c2n1] | Example 2 | m/z 511 [M + H − 1], 513 [M + H + 1] | 1 |
| 3. | 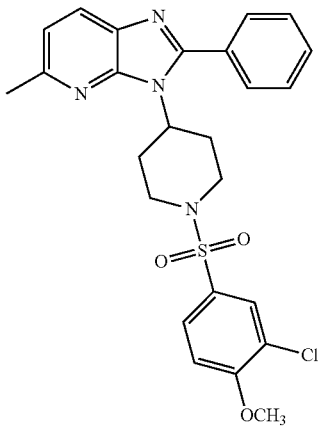 [SMILES: COc1ccc(S(=O)(=O)N2CCC(n3c(-c4ccccc4)nc4ccc(C)nc43)CC2)cc1Cl] | Example 3 | m/z 497 [M + H − 1], 499 [M + H + 1] | 1 |

TABLE 2-continued
Additional examples were prepared as according to the described methods above, or similar methods, or were purchased from commercial vendors.
| No. | Structure | Example | LCMS m/z [M + H] | SCHEME |
|---|---|---|---|---|
| 4. | 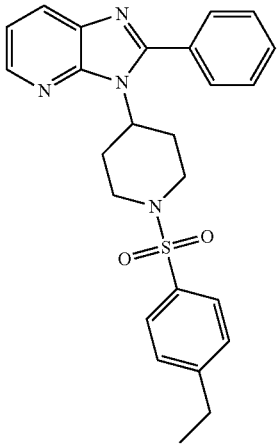 [SMILES: CCc1ccc(S(=O)(=O)N2CCC(n3c(-c4ccccc4)nc4cccnc43)CC2)cc1] | Example 4 | m/z 447 [M + H] | 1 |
| 5. | 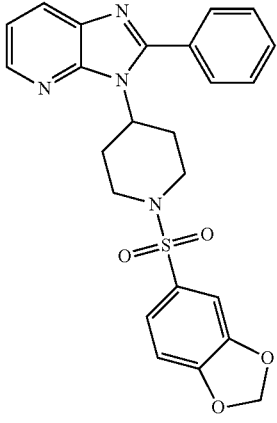 [SMILES: O=S(=O)(c1ccc2c(c1)OCO2)N1CCC(n2c(-c3ccccc3)nc3cccnc32)CC1] | Example 5 | m/z 463 [M + H] | 1 |
| 6. | 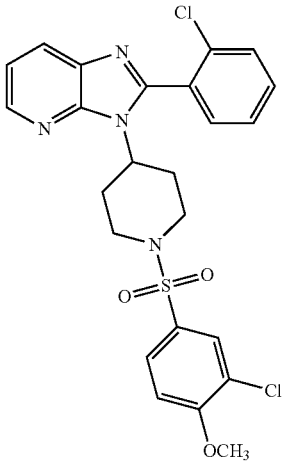 | Example 6 | m/z 517 [M + H − 1], 519 [M + H + 1], 521 [M + H + 3] | 2 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 7. | 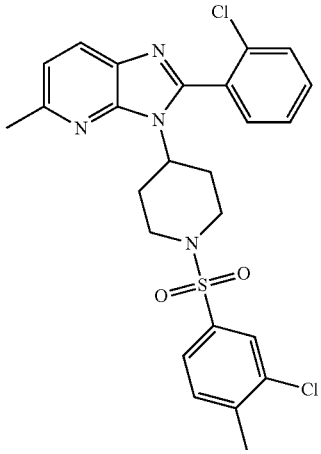 [SMILES: Cc1ccc2nc(-c3ccccc3Cl)n(C3CCN(S(=O)(=O)c4ccc(C)c(Cl)c4)CC3)c2n1] | Example 7 | m/z 515 [M + H − 1], 517 [M + H + 1], 519 [M + H + 3] | 1 |
| 8. | 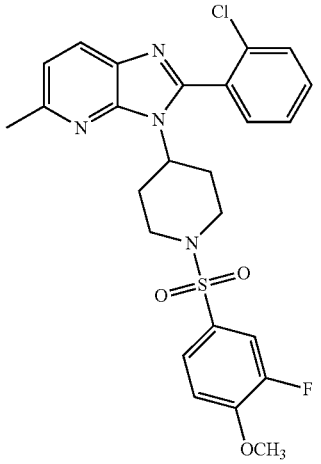 [SMILES: COc1ccc(S(=O)(=O)N2CCC(n3c(-c4ccccc4Cl)nc4ccc(C)nc43)CC2)cc1F] | Example 8 | m/z 515 [M + H − 1], 517 [M + H + 1] | 1 |
| 9. | 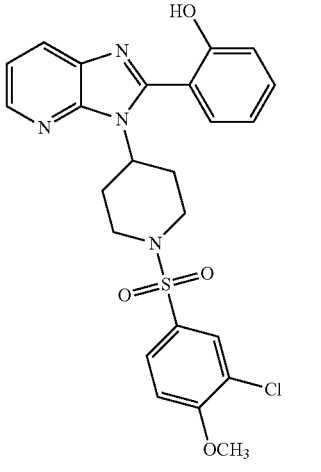 | Example 9 | m/z 499 [M + H − 1], 501 [M + H + 1] | 2 |

TABLE 2-continued

*Additional examples were prepared as according to the described methods above, or similar methods, or were purchased from commercial vendors.*

| No. | Example | LCMS m/z [M + H] | SCHEME |
|---|---|---|---|
| 10. | Example 10 | m/z 501 [M + H − 1], 503 [M + H + 1] 505 [M + H + 3] | 1 |
| 11. | Example 11 | m/z 501 [M + H − 1], 503 [M + H + 1] | 1 |
| 12. | Example 12 | m/z 551 [M + H − 1], 553 [M + H + 1], 555 [M + H + 3], 557 [M + H + 5] | 3 |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 13. | (structure) | Example 13 | m/z 548 [M + H − 1], 550 [M + H + 1] | 3 |
| 14. | (structure) | Example 14 | m/z 512 [M + H − 1], 514 [M + H + 1] | 3 |
| 15. | (structure) | Example 15 | m/z 548 [M + H − 1], 550 [M + H + 1] | 3 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 16. | Example 16 | m/z 483 [M + H − 1], 485 [M + H + 1] | 1 |
| 17. | Example 17 | m/z 433 [M + H] | Commercial |
| 18. | Example 18 | m/z 467 [M + H] | 1 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 19. | | Example 19 | m/z 449 [M + H] | 1 |
| 20. | | Example 20 | m/z 467 [M + H − 1], 469 [M + H + 1] | 1 |
| 21. | | Example 21 | m/z 447 [M + H − 1], 449 [M + H + 1] | 1a |

TABLE 2-continued

Additional examples were prepared as according to the described methods above, or similar methods, or were purchased from commercial vendors.

| No. | Structure | Example | LCMS m/z [M + H] | SCHEME |
| --- | --- | --- | --- | --- |
| 22. | | Example 22 | m/z 517 [M + H − 1], 519 [M + H + 1], 521 [M + H + 3] | 2 |
| 23. | | Example 23 | m/z 497 [M + H − 1], 499 [M + H + 1] | 2 |
| 24. | | Example 24 | m/z 497 [M + H − 1], 499 [M + H + 1] | 2 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 25. | 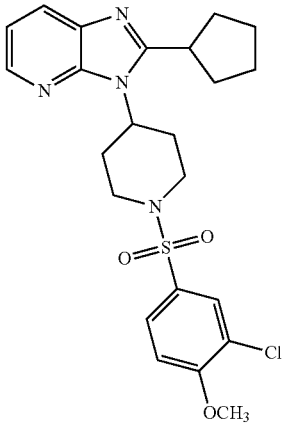 [SMILES: COc1ccc(S(=O)(=O)N2CCC(n3c(C4CCCC4)nc4cccnc43)CC2)cc1Cl] | Example 25 | m/z 475 [M + H − 1], 477 [M + H + 1] | 2 |
| 26. | 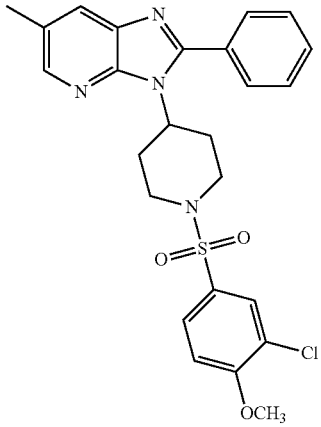 [SMILES: COc1ccc(S(=O)(=O)N2CCC(n3c(-c4ccccc4)nc4cc(C)cnc43)CC2)cc1Cl] | Example 26 | m/z 497 [M + H − 1], 499 [M + H + 1] | 1 |
| 27. | 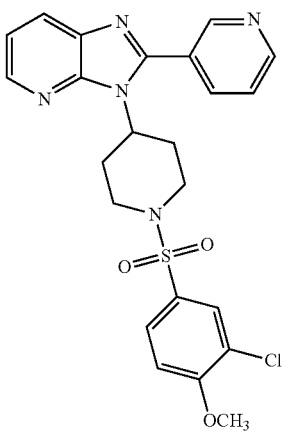 [SMILES: COc1ccc(S(=O)(=O)N2CCC(n3c(-c4cccnc4)nc4cccnc43)CC2)cc1Cl] | Example 27 | m/z 484 [M + H − 1], 486 [M + H + 1] | 2 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 28. | | Example 28 | m/z 484 [M + H − 1], 486 [M + H + 1] | 2 |
| 29. | | Example 29 | m/z 517 [M + H − 1], 519 [M + H + 1], 521 [M + H + 3] | 2 |
| 30. | | Example 30 | m/z 497 [M + H − 1], 499 [M + H + 1] | 2 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 31. | Example 31 | m/z 489 [M + H − 1], 491 [M + H + 1] | 2 |
| 32. | Example 32 | m/z 473 [M + H − 1], 475 [M + H + 1] | 2 |
| 33. | Example 33 | m/z 523 [M + H − 1], 525 [M + H + 1] | 2 |

TABLE 2-continued

*Additional examples were prepared as according to the described methods above, or similar methods, or were purchased from commercial vendors.*

| No. | | Example | LCMS m/z [M + H] | SCHEME |
|---|---|---|---|---|
| 34. | | Example 34 | m/z 523 [M + H − 1], 525 [M + H + 1] | 2 |
| 35. | | Example 35 | m/z 517 [M + H − 1], 519 [M + H + 1], 521 [M + H + 3] | 3 |
| 36. | | Example 36 | m/z 517 [M + H − 1], 519 [M + H + 1], 521 [M + H + 3] | 3 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 37. | | Example 37 | m/z 483 [M + H − 1], 485 [M + H + 1] | 1 |
| 38. | | Example 38 | m/z 534 [M + H − 1], 536 [M + H + 1] | 1b |
| 39. | | Example 39 | m/z 533 [M + H − 1], 535 [M + H + 1] | 3a |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 40. | | Example 40 | m/z 534 [M + H − 1], 536 [M + H + 1] | 3a |
| 41. | | Example 41 | m/z 482 [M + H − 1], 484 [M + H + 1] | 3a |
| 42. | | Example 42 | m/z 512 [M + H − 1], 514 [M + H + 1] | 3a |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 43. | 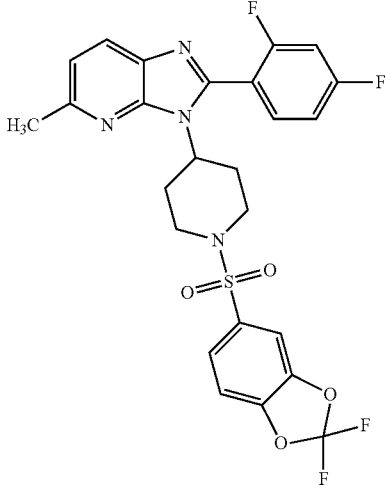 [SMILES: Cc1ccc2nc(-c3ccc(F)cc3F)n(C3CCN(S(=O)(=O)c4ccc5c(c4)OC(F)(F)O5)CC3)c2n1] | Example 43 | m/z 549 [M + H] | 1b |
| 44. | 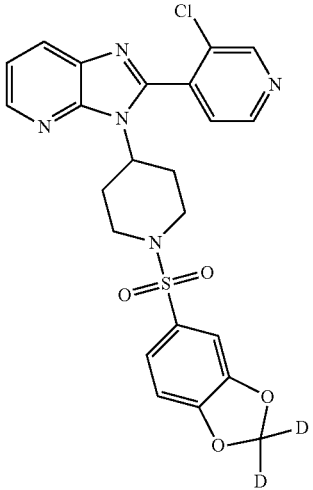 [SMILES: [2H]C1([2H])Oc2ccc(S(=O)(=O)N3CCC(n4c(-c5ccncc5Cl)nc5cccnc54)CC3)cc2O1] | Example 44 | m/z 500 [M + H − 1], 502 [M + H + 1] | 1b |
| 45. | 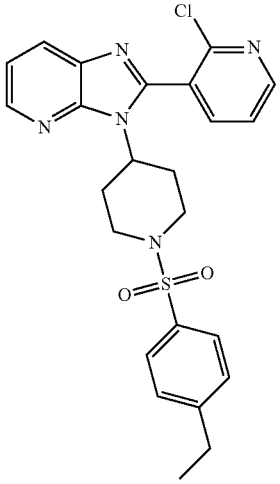 [SMILES: CCc1ccc(S(=O)(=O)N2CCC(n3c(-c4cccnc4Cl)nc4cccnc43)CC2)cc1] | Example 45 | m/z 482 [M + H − 1], 484 [M + H + 1] | 3a |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 46. | | Example 46 | m/z 519 [M + H − 1], 521 [M + H + 1] | 3a |
| 47. | | Example 47 | m/z 483 [M + H] | 3a |
| 48. | | Example 48 | m/z 499 [M + H] | 1b |

TABLE 2-continued
Additional examples were prepared as according to the described methods above, or similar methods, or were purchased from commercial vendors.
| No. | Example | LCMS m/z [M + H] | SCHEME |
|---|---|---|---|
| 49. 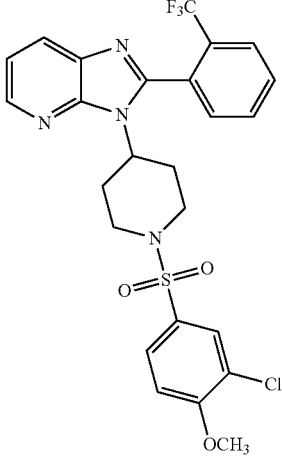 [SMILES: COc1ccc(S(=O)(=O)N2CCC(n3c(-c4ccccc4C(F)(F)F)nc4cccnc43)CC2)cc1Cl] | Example 49 | m/z 551 [M + H − 1], 553 [M + H + 1] | 1 |
| 50. 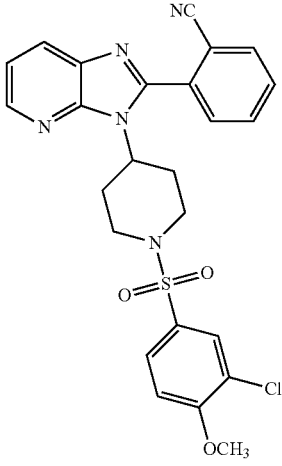 | Example 50 | m/z 508 [M + H − 1], 510 [M + H + 1] | 1 |
| 51. 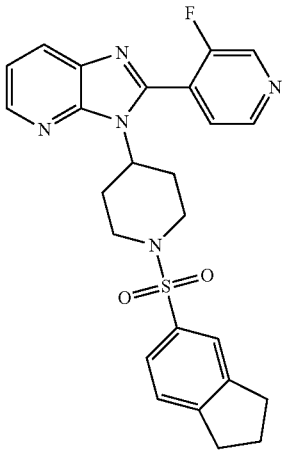 [SMILES: O=S(=O)(c1ccc2c(c1)CCC2)N1CCC(n2c(-c3ccncc3F)nc3cccnc32)CC1] | Example 51 | m/z 478 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 52. | Example 52 | m/z 518 [M + H] | 3a |
| 53. | Example 53 | m/z 519 [M + H − 1], 521 [M + H + 1] | 1 |
| 54. | Example 54 | m/z 548 [M + H − 1], 550 [M + H + 1] | 3 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 55. | Example 55 | m/z 513 [M + H − 1], 515 [M + H + 1] | 1 |
| 56. | Example 56 | m/z 520 [M + H − 1], 522 [M + H + 1] | 3a |
| 57. | Example 57 | m/z 527 [M + H − 1], 529 [M + H + 1] | 1 |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 58. | | Example 58 | m/z 548 [M + H − 1], 550 [M + H + 1], 552 [M + H + 3] | 3a |
| 59. | | Example 59 | m/z 467 [M + H − 1], 469 [M + H + 1] | 1 |
| 60. | | Example 60 | m/z 501 [M + H − 1], 503 [M + H + 1] | 1 |

TABLE 2-continued

*Additional examples were prepared as according to the described methods above, or similar methods, or were purchased from commercial vendors.*

| No. | Structure | Example | LCMS m/z [M + H] | SCHEME |
|---|---|---|---|---|
| 61. | | Example 61 | m/z 447 [M + H] | 1 |
| 62. | | Example 62 | m/z 477 [M + H] | 1 |
| 63. | | Example 63 | m/z 481 [M + H − 1], 483 [M + H + 1] | 1 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 64. | | Example 64 | m/z 481 [M + H] | 1 |
| 65. | | Example 65 | m/z 481 [M + H − 1], 483 [M + H + 1] | 1 |
| 66. | | Example 66 | m/z 537 [M + H − 1], 539 [M + H + 1] | 1 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 67. | Example 67 | m/z 428 [M + H] | 1 |
| 68. | Example 68 | m/z 449 [M + H] | 1 |
| 69. | Example 69 | m/z 461 [M + H] | 1 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 70. | Example 70 | m/z 510 [M + H − 1], 512 [M + H + 1] | 1 |
| 71. | Example 71 | m/z 478 [M + H − 1], 480 [M + H + 1] | 1 |
| 72. | Example 72 | m/z 409 [M + H] | 1 |

TABLE 2-continued

*Additional examples were prepared as according to the described methods above, or similar methods, or were purchased from commercial vendors.*

| No. | Structure | Example | LCMS m/z [M + H] | SCHEME |
|---|---|---|---|---|
| 73. | | Example 73 | m/z 463 [M + H] | 1 |
| 74. | | Example 74 | m/z 517 [M + H] | 1 |
| 75. | | Example 75 | m/z 473 [M + H − 1], 475 [M + H + 1] | 1 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 76. | 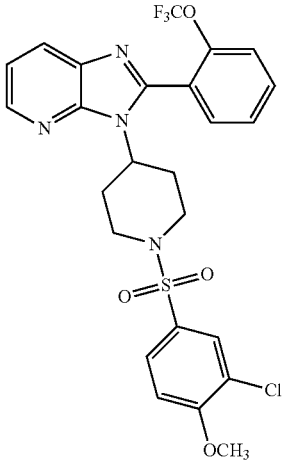 [SMILES: COc1ccc(S(=O)(=O)N2CCC(n3c(-c4ccccc4OC(F)(F)F)nc4cccnc43)CC2)cc1Cl] | Example 76 | m/z 567 [M + H − 1], 569 [M + H + 1] | 1 |
| 77. | 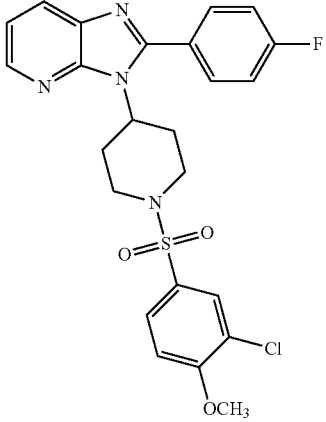 [SMILES: COc1ccc(S(=O)(=O)N2CCC(n3c(-c4ccc(F)cc4)nc4cccnc43)CC2)cc1Cl] | Example 77 | m/z 501 [M + H − 1], 503 [M + H + 1] | 1 |
| 78. | 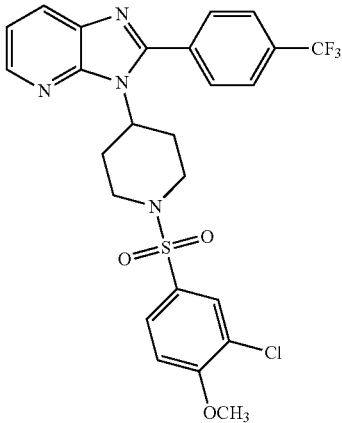 [SMILES: COc1ccc(S(=O)(=O)N2CCC(n3c(-c4ccc(C(F)(F)F)cc4)nc4cccnc43)CC2)cc1Cl] | Example 78 | m/z 551 [M + H − 1], 553 [M + H + 1] | 1 |

TABLE 2-continued
Additional examples were prepared as according to the described methods above, or similar methods, or were purchased from commercial vendors.
| No. | Example | LCMS m/z [M + H] | SCHEME |
|---|---|---|---|
| 79. 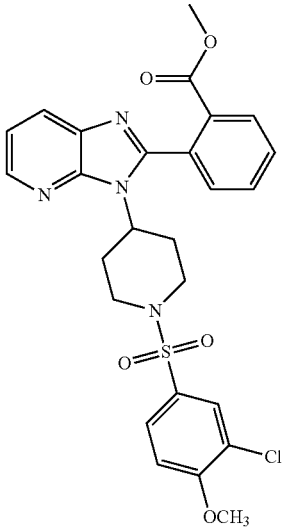 [SMILES: COC(=O)c1ccccc1-c1nc2cccnc2n1C1CCN(S(=O)(=O)c2ccc(OC)c(Cl)c2)CC1] | Example 79 | m/z 541 [M + H − 1], 543 [M + H + 1] | 1 |
| 80. 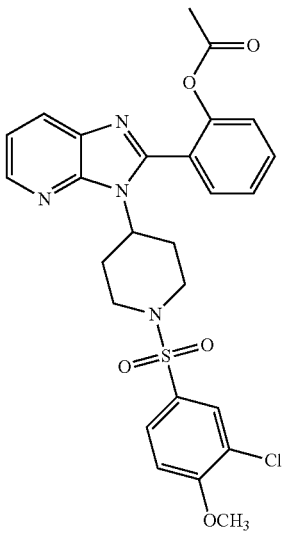 [SMILES: COc1ccc(S(=O)(=O)N2CCC(n3c(-c4ccccc4OC(C)=O)nc4cccnc43)CC2)cc1Cl] | Example 80 | m/z 541 [M + H − 1], 543 [M + H + 1] | 1 |
| 81. 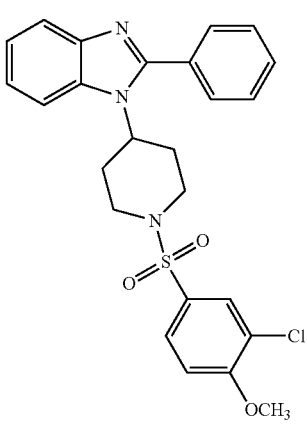 | Example 81 | m/z 482 [M + H − 1], 484 [M + H + 1] | 1b |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 82. | 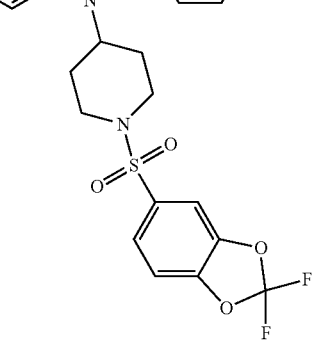 | Example 82 | m/z 498 [M + H] | 1b |
| 83. | 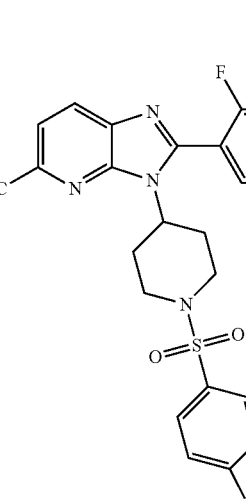 | Example 83 | m/z 531 [M + H] | 1b |
| 84. | 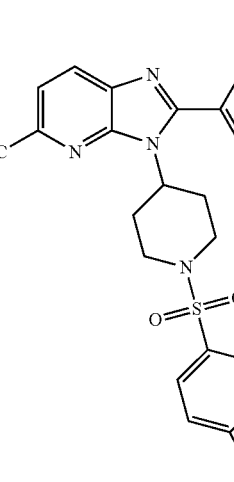 | Example 84 | m/z 532 [M + H] | 1b |

TABLE 2-continued

Additional examples were prepared as according to the described methods above, or similar methods, or were purchased from commercial vendors.

| No. | Example | LCMS m/z [M + H] | SCHEME |
|---|---|---|---|
| 85. | Example 85 | m/z 527 [M + H − 1], 529 [M + H + 1] | 1b |
| 86. | Example 86 | m/z 547 [M + H − 1], 549 [M + H + 1] | 3 |
| 87. | Example 87 | m/z 593 [M + H] | 1b |

TABLE 2-continued

Additional examples were prepared as according to the described methods above, or similar methods, or were purchased from commercial vendors.

| No. | Example | LCMS m/z [M + H] | SCHEME |
|---|---|---|---|
| 88. | Example 88 | m/z 518 [M + H − 1], 520 [M + H + 1], 522 [M + H + 3] | 3a |
| 89. | Example 89 | m/z 518 [M + H − 1], 520 [M + H + 1], 522 [M + H + 3] | 3a |
| 90. | Example 90 | m/z 518 [M + H − 1], 520 [M + H + 1], 522 [M + H + 3] | 3a |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 91. | 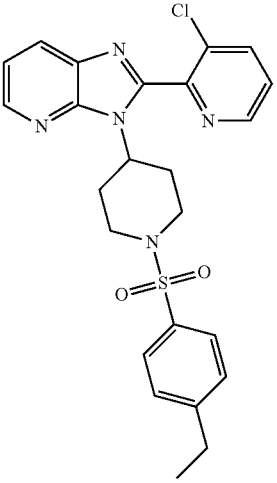 [SMILES: CCc1ccc(S(=O)(=O)N2CCC(n3c(-c4ncccc4Cl)nc4cccnc43)CC2)cc1] | Example 91 | m/z 482 [M + H − 1], 484 [M + H + 1] | 3a |
| 92. | 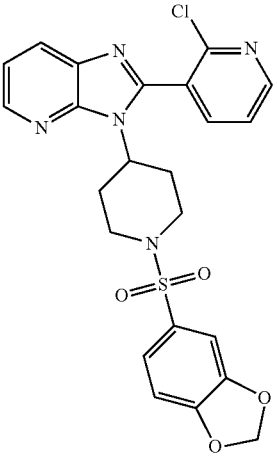 | Example 92 | m/z 498 [M + H − 1], 500 [M + H + 1] | 3a |
| 93. | 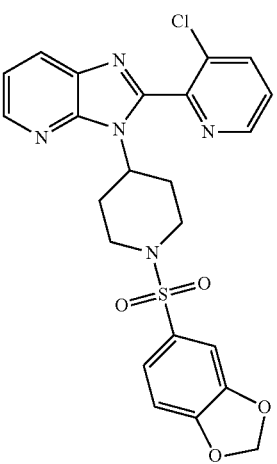 [SMILES: O=S(=O)(c1ccc2c(c1)OCO2)N1CCC(n2c(-c3ncccc3Cl)nc3cccnc32)CC1] | Example 93 | m/z 498 [M + H − 1], 500 [M + H + 1] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 94. | Example 94 | m/z 520 [M + H − 1], 522 [M + H + 1] | 3a |
| 95. | Example 95 | m/z 493 [M + H − 1], 495 [M + H + 1] | 3a |
| 96. | Example 96 | m/z 492 [M + H − 1], 494 [M + H + 1] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 97. | Example 97 | m/z 513 [M + H] | 3a |
| 98. | Example 98 | m/z 482 [M + H − 1], 484 [M + H + 1] | 4 |
| 99. | Example 99 | m/z 498 [M + H] | 4 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 100. | Example 100 | m/z 531 [M + H] | 3a |
| 101. | Example 101 | m/z 512 [M + H − 1], 514 [M + H + 1] | 3a |
| 102. | Example 102 | m/z 534 [M + H − 1], 536 [M + H + 1] | 3a |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 103. | | Example 103 | m/z 481 [M + H − 1], 483 [M + H + 1] | 4 |
| 104. | | Example 104 | m/z 497 [M + H] | 4 |
| 105. | | Example 105 | m/z 500 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 106. | Example 106 | m/z 536 [M + H] | 3a |
| 107. | Example 107 | m/z 482 [M + H] | 3a |
| 108. | Example 108 | m/z 499 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 109. | Example 109 | m/z 535 [M + H] | 3a |
| 110. | Example 110 | m/z 466 [M + H] | 3a |
| 111. | Example 111 | m/z [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 112. | Example 112 | m/z 532 [M + H] | 3a |
| 113. | Example 113 | m/z 480 [M + H] | 3a |
| 114. | Example 114 | m/z 515 [M + H] | 3a |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 115. | | Example 115 | m/z 463 [M + H] | 3a |
| 116. | | Example 116 | m/z 518 [M + H] | 3a |
| 117. | | Example 117 | m/z 480 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 118. | Example 118 | m/z 564 [M + H − 1], 566 [M + H + 1] | 3a |
| 119. | Example 119 | m/z 518 [M + H] | 3a |
| 120. | Example 120 | m/z 466 [M + H] | 3a |

TABLE 2-continued

Additional examples were prepared as according to the described methods above, or similar methods, or were purchased from commercial vendors.

| No. | Structure | Example | LCMS m/z [M + H] | SCHEME |
|-----|-----------|---------|------------------|--------|
| 121. | | Example 121 | m/z 497 [M + H] | 3a |
| 122. | | Example 122 | m/z 495 [M + H] | 3a |
| 123. | | Example 123 | m/z 482 [M + H] | 3a |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 124. | | Example 124 | m/z 583 [M + H] | 3a |
| 125. | | Example 125 | m/z 585 [M + H] | 3a |
| 126. | | Example 126 | m/z 565 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 127. | Example 127 | m/z 548 [M + H] | 3a |
| 128. | Example 128 | m/z 501 [M + H] | 3a |
| 129. | Example 129 | m/z 505 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 130. | Example 130 | m/z 517 [M + H] | 3a |
| 131. | Example 131 | m/z 449 [M + H] | 3a |
| 132. | Example 132 | m/z 509 [M + H] | 3a |

TABLE 2-continued

Additional examples were prepared as according to the described methods above, or similar methods, or were purchased from commercial vendors.

| No. | Example | LCMS m/z [M + H] | SCHEME |
|---|---|---|---|
| 133. | Example 133 | m/z 493 [M + H] | 3a |
| 134. | Example 134 | m/z 510 [M + H] | 3a |
| 135. | Example 135 | m/z 500 [M + H − 1], 502 [M + H + 1] | 1c |

TABLE 2-continued

Additional examples were prepared as according to the described methods above, or similar methods, or were purchased from commercial vendors.

| No. | Example | LCMS m/z [M + H] | SCHEME |
|---|---|---|---|
| 136. | Example 136 | m/z 484 [M + H] | 1b |
| 137. | Example 137 | m/z 534 [M + H − 1], 536 [M + H + 1] | 3a |
| 138. | Example 138 | m/z 496 [M + H] | 3a |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 139. | 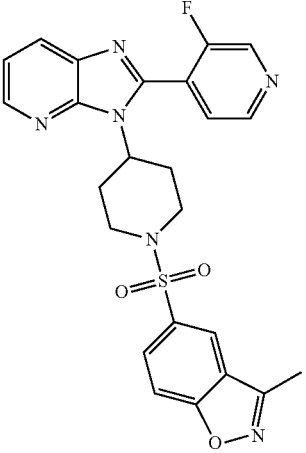 [SMILES: Cc1noc2ccc(S(=O)(=O)N3CCC(n4c(-c5ccncc5F)nc5cccnc54)CC3)cc12] | Example 139 | m/z 493 [M + H] | 1b |
| 140. | 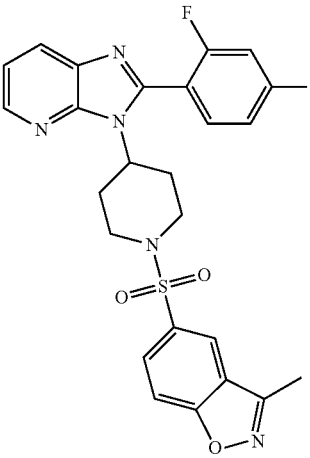 | Example 140 | m/z 510 [M + H] | 1b |
| 141. | 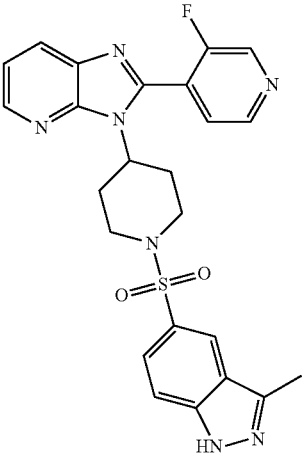 [SMILES: Cc1n[nH]c2ccc(S(=O)(=O)N3CCC(n4c(-c5ccncc5F)nc5cccnc54)CC3)cc12] | Example 141 | m/z 492 [M + H] | 1b |

TABLE 2-continued

Additional examples were prepared as according to the described methods above, or similar methods, or were purchased from commercial vendors.

| No. | Example | LCMS m/z [M + H] | SCHEME |
|-----|---------|------------------|--------|
| 142. | Example 142 | m/z 491 [M + H] | 1b |
| 143. | Example 143 | m/z 508 [M + H] | 1b |
| 144. | Example 144 | m/z 509 [M + H] | 1b |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 145. | 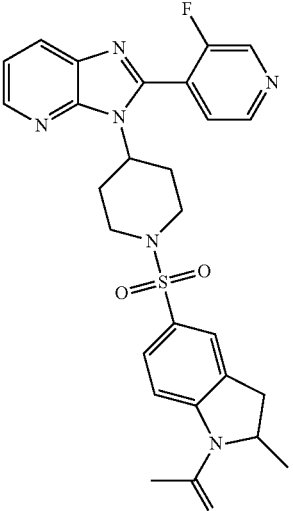 | Example 145 | m/z 535 [M + H] | 1b |
| 146. | 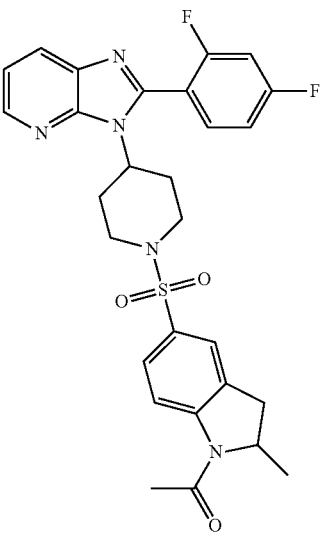 [SMILES: CC(=O)N1c2ccc(S(=O)(=O)N3CCC(n4c(-c5ccc(F)cc5F)nc5cccnc54)CC3)cc2CC1C] | Example 146 | m/z 552 [M + H] | 1b |
| 147. | 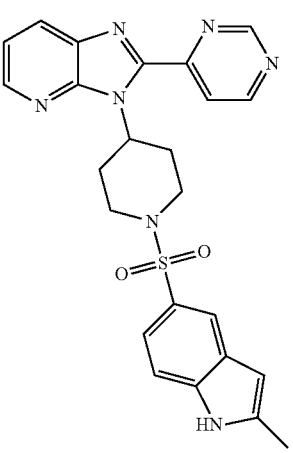 [SMILES: Cc1cc2cc(S(=O)(=O)N3CCC(n4c(-c5ccncn5)nc5cccnc54)CC3)ccc2[nH]1] | Example 147 | m/z 474 [M + H] | 1b |

TABLE 2-continued

Additional examples were prepared as according to the described methods above, or similar methods, or were purchased from commercial vendors.

| No. | Example | LCMS m/z [M + H] | SCHEME |
|---|---|---|---|
| 148. | Example 148 | m/z 493 [M + H] | 1b |
| 149. | Example 149 | m/z 510 [M + H] | 1b |
| 150. | Example 150 | m/z 547 [M + H] | 10 |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 151. | | Example 151 | m/z 495 [M + H] | 10 |
| 152. | | Example 152 | m/z 518 [M + H] | 1b |
| 153. | | Example 153 | m/z 562 [M + H − 1], 564 [M + H + 1] | 10 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 154. | Example 154 | m/z 563 [M + H − 1], 565 [M + H + 1] | 10 |
| 155. | Example 155 | m/z 510 [M + H − 1], 512 [M + H + 1] | 10 |
| 156. | Example 156 | m/z 511 [M + H − 1], 513 [M + H + 1] | 10 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 157. | Example 157 | m/z 545 [M + H − 1], 547 [M + H + 1], [M + H + 3] | 1b |
| 158. | Example 158 | m/z 529 [M + H − 1], 531 [M + H + 1] | 1b |
| 159. | Example 159 | m/z 546 [M + H − 1], 548 [M + H + 1] | 1b |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 160. | | Example 160 | m/z 538 [M + H − 1], 540 [M + H + 1] | 10 |
| 161. | | Example 161 | m/z 493 [M + H − 1], 495 [M + H + 1] | 1b |
| 162. | | Example 162 | m/z 477 [M + H] | 1b |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 163. | | Example 163 | m/z 523 [M + H] | 10 |
| 164. | | Example 164 | m/z 540 [M + H] | 10 |
| 165. | | Example 165 | m/z 532 [M + H] | 1b |

TABLE 2-continued

Additional examples were prepared as according to the described methods above, or similar methods, or were purchased from commercial vendors.

| No. | Example | LCMS m/z [M + H] | SCHEME |
|---|---|---|---|
| 166. | Example 166 | m/z 548 [M + H − 1], 550 [M + H + 1] | 1b |
| 167. | Example 167 | m/z 496 [M + H − 1], 498 [M + H + 1] | 10 |
| 168. | Example 168 | m/z 497 [M + H − 1], 499 [M + H + 1] | 10 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 169. | Example 169 | m/z 496 [M + H] | 3 |
| 170. | Example 170 | m/z 512 [M + H − 1], 514 [M + H + 1] | 3 |
| 171. | Example 171 | m/z 470 [M + H] | 12 |

TABLE 2-continued

*Additional examples were prepared as according to the described methods above, or similar methods, or were purchased from commercial vendors.*

| No. | Structure | Example | LCMS m/z [M + H] | SCHEME |
|---|---|---|---|---|
| 172. | | Example 172 | m/z 466 [M + H] | 12 |
| 173. | | Example 173 | m/z 450 [M + H] | 12 |
| 174. | | Example 174 | m/z 500 [M + H − 1], 502 [M + H + 1] | 12 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 175. | | Example 175 | m/z 513 [ES+ − 1], 515 [ES+ + 1] | 11 |
| 176. | | Example 176 | m/z 549 [ES+ − 1], 551 [ES+ + 1], 553 [ES+ + 3] | 11 |
| 177. | | Example 177 | m/z 499 [ES+ − 1], 501 [ES+ + 1] | 11 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 178. | (structure) | Example 178 | m/z 535 [ES+ − 1], 537 [ES+ + 1] 539 [ES+ + 3] | 11 |
| 179. | (structure) | Example 179 | m/z 480 [ES+] | 11 |
| 180. | (structure) | Example 180 | m/z 466 [ES+] | 11 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 181. | 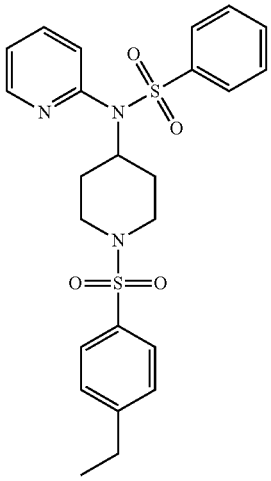 [SMILES: CCc1ccc(S(=O)(=O)N2CCC(N(c3ccccn3)S(=O)(=O)c3ccccc3)CC2)cc1] | Example 181 | m/z 487 [ES+] | 13 |
| 182. | 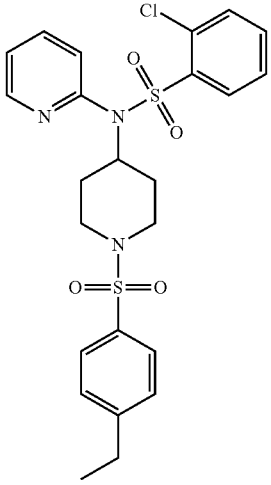 [SMILES: CCc1ccc(S(=O)(=O)N2CCC(N(c3ccccn3)S(=O)(=O)c3ccccc3Cl)CC2)cc1] | Example 182 | m/z 520 [ES+ − 1], 522 [ES+ + 1] | 13 |
| 183. | 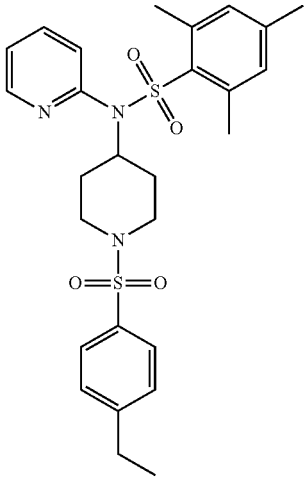 [SMILES: CCc1ccc(S(=O)(=O)N2CCC(N(c3ccccn3)S(=O)(=O)c3c(C)cc(C)cc3C)CC2)cc1] | Example 183 | m/z 528 [ES+] | 13 |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 184. | | Example 184 | m/z 564 [ES+] | 13 |
| 185. | | Example 185 | m/z 581 [ES+] | 13 |
| 186. | | Example 186 | m/z 501 [ES+] | 13 |

TABLE 2-continued

Additional examples were prepared as according to the described methods above, or similar methods, or were purchased from commercial vendors.

| No. | Structure | Example | LCMS m/z [M + H] | SCHEME |
|-----|-----------|---------|------------------|--------|
| 187. | | Example 187 | m/z 536 [ES+ − 1], 538 [ES+ + 1] | 13 |
| 188. | | Example 188 | m/z 552 [ES+] | 13 |
| 189. | | Example 189 | m/z 534 [ES+ − 1], 536 [ES+ + 1] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 190. | Example 190 | m/z 570 [ES+ − 1], 572 [ES+ + 1] 574 [ES+ + 3] | 13 |
| 191. | Example 191 | m/z 586 [ES+ − 1], 588 [ES+ + 1] | 13 |
| 192. | Example 192 | m/z 542 [ES+] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 193. | Example 193 | m/z 578 [ES+ − 1], 580 [ES+ + 1] | 13 |
| 194. | Example 194 | m/z 594 [ES+] | 13 |
| 195. | Example 195 | m/z 466 [M + H] | 12a |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 196. | | Example 196 | m/z 484 [M + H − 1], 486 [M + H + 1] | 12 |
| 197. | | Example 197 | m/z 500 [M + H − 1], 502 [M + H + 1] | 12 |
| 198. | | Example 198 | m/z 520 [M + H − 1], 522 [M + H + 1], 524 [M + H + 3] | 12 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 199. | Example 199 | m/z 485 [M + H − 1], 487 [M + H + 1] | 12 |
| 200. | Example 200 | m/z 518 [M + H − 1], 520 [M + H + 1] | 12 |
| 201. | Example 201 | m/z 498 [M + H − 1], 500 [M + H + 1] | 12 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 202. | | Example 202 | m/z 514 [M + H − 1], 516 [M + H + 1] | 12 |
| 203. | | Example 203 | m/z 504 [M + H − 1], 506 [M + H + 1] | 12 |
| 204. | | Example 204 | m/z 502 [M + H] | 12 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 205. | Example 205 | m/z 516 [M + H] | 12 |
| 206. | Example 206 | m/z 534 [M + H − 1], 536 [M + H + 1], 538 [M + H + 3] | 12 |
| 207. | Example 207 | m/z 513 [M + H − 1], 515 [M + H + 1] | 12 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 208. | 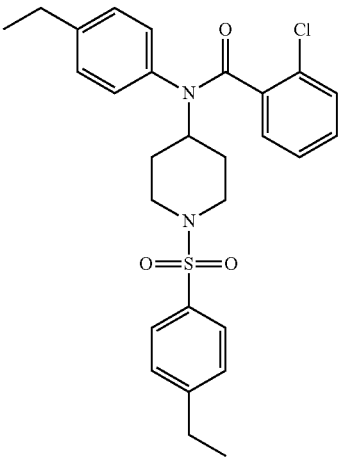 [SMILES: CCc1ccc(N(C(=O)c2ccccc2Cl)C2CCN(S(=O)(=O)c3ccc(CC)cc3)CC2)cc1] | Example 208 | m/z 511 [M + H − 1], 513 [M + H + 1] | 12 |
| 209. | 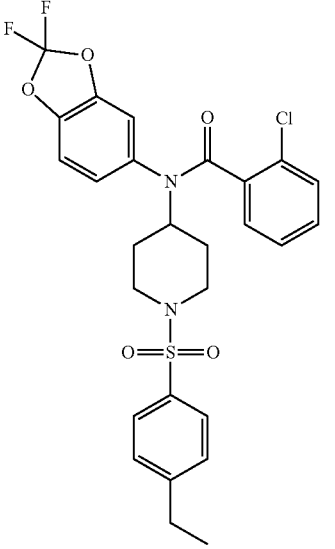 [SMILES: CCc1ccc(S(=O)(=O)N2CCC(N(C(=O)c3ccccc3Cl)c3ccc4c(c3)OC(F)(F)O4)CC2)cc1] | Example 209 | m/z 563 [M + H − 1], 565 [M + H + 1] | 12 |
| 210. | 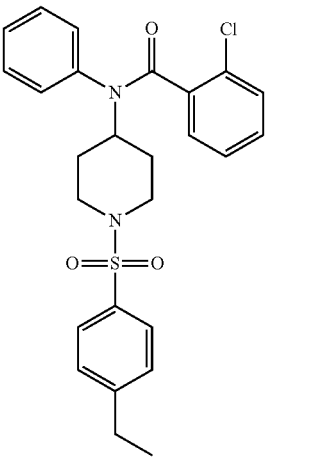 [SMILES: CCc1ccc(S(=O)(=O)N2CCC(N(C(=O)c3ccccc3Cl)c3ccccc3)CC2)cc1] | Example 210 | m/z 483 [M + H − 1], 485 [M + H + 1] | 12 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 211. | 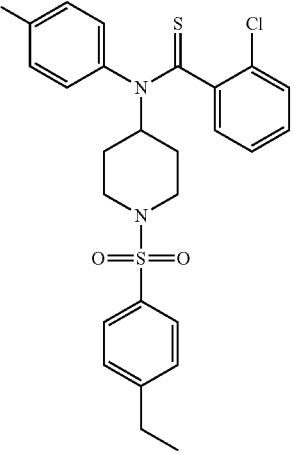 | Example 211 | m/z 529 [M + H − 1], 531 [M + H + 1] | 12a |
| 212. | 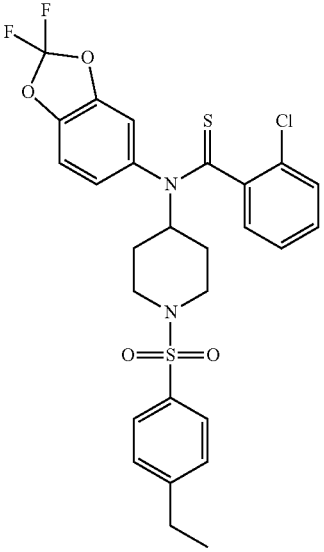 | Example 212 | m/z 579 [M + H − 1], 581 [M + H + 1] | 12a |
| 213. | 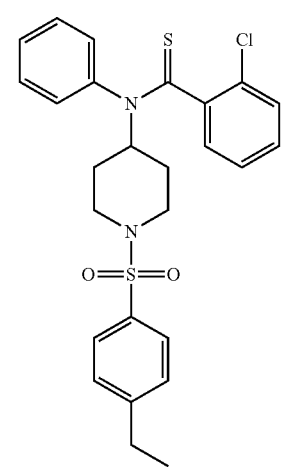 [SMILES: CCc1ccc(S(=O)(=O)N2CCC(N(C(=S)c3ccccc3Cl)c3ccccc3)CC2)cc1] | Example 213 | m/z 499 [M + H − 1], 501 [M + H + 1] | 12a |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 214. | [structure: 4-bromophenyl-N-(1-(4-ethylphenylsulfonyl)piperidin-4-yl)-2-chlorobenzamide] | Example 214 | m/z 561 [M + H − 1], 563 [M + H + 1], 565 [M + H + 3] | 12 |
| 215. | [structure: 4-fluorophenyl-N-(1-(4-ethylphenylsulfonyl)piperidin-4-yl)-2-chlorobenzamide] | Example 215 | m/z 501 [M + H − 1], 503 [M + H + 1] | 12 |
| 216. | [structure: 4-iodophenyl-N-(1-(4-ethylphenylsulfonyl)piperidin-4-yl)-2-chlorobenzamide] | Example 216 | m/z 609 [M + H − 1], 611 [M + H + 1] | 12 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 217. | Example 217 | m/z 517 [M + H − 1], 519 [M + H + 1], 521 [M + H + 3] | 12 |
| 218. | Example 218 | m/z 550 [M + H − 1], 552 [M + H + 1] | 13 |
| 219. | Example 219 | m/z 602 [M + H − 1], 604 [M + H + 1] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 220. | Example 220 | m/z 561 [M + H − 1], 563 [M + H + 1] | 13 |
| 221. | Example 221 | m/z 534 [M + H − 1], 536 [M + H + 1] | 13 |
| 222. | Example 222 | m/z 550 [M + H − 1], 552 [M + H + 1] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 223. | Example 223 | m/z 561 [M + H − 1], 563 [M + H + 1] | 13 |
| 224. | Example 224 | m/z 520 [M + H − 1], 522 [M + H + 1] | 13 |
| 225. | Example 225 | m/z 500 [M + H] | 13 |

TABLE 2-continued

*Additional examples were prepared as according to the described methods above, or similar methods, or were purchased from commercial vendors.*

| No. | Structure | Example | LCMS m/z [M + H] | SCHEME |
|---|---|---|---|---|
| 226. | | Example 226 | m/z 500 [M + H] | 13 |
| 227. | | Example 227 | m/z 534 [M + H − 1], 536 [M + H + 1] | 13 |
| 228. | | Example 228 | m/z 577 [M + H − 1], 579 [M + H + 1] | 13 |

TABLE 2-continued

Additional examples were prepared as according to the described methods above, or similar methods, or were purchased from commercial vendors.

| No. | | Example | LCMS m/z [M + H] | SCHEME |
|---|---|---|---|---|
| 229. | | Example 229 | m/z 500 [M + H] | 13 |
| 230. | | Example 230 | m/z 554 [M + H − 1], 556 [M + H + 1], 558 [M + H + 3] | 13 |
| 231. | | Example 231 | m/z 526 [M + H − 1], 528 [M + H + 1] | 13 |

TABLE 2-continued

*Additional examples were prepared as according to the described methods above, or similar methods, or were purchased from commercial vendors.*

| No. | | Example | LCMS m/z [M + H] | SCHEME |
|---|---|---|---|---|
| 232. | [structure] | Example 232 | m/z 554 [M + H − 1], 556 [M + H + 1], 558 [M + H + 3] | 13 |
| 233. | [structure] | Example 233 | m/z 554 [M + H − 1], 556 [M + H + 1], 558 [M + H + 3] | 13 |
| 234. | [structure] | Example 234 | m/z 520 [M + H − 1], 522 [M + H + 1] | 13 |

TABLE 2-continued

Additional examples were prepared as according to the described methods above, or similar methods, or were purchased from commercial vendors.

| No. | Example | LCMS m/z [M + H] | SCHEME |
| --- | --- | --- | --- |
| 235. | Example 235 | m/z 520 [M + H − 1], 522 [M + H + 1] | 13 |
| 236. | Example 236 | m/z 549 [M + H − 1], 551 [M + H + 1] | 13 |
| 237. | Example 237 | m/z 533 [M + H − 1], 535 [M + H + 1] | 13 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 238. | 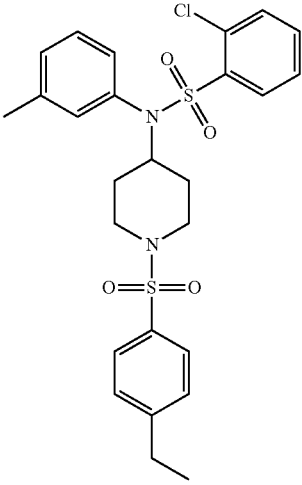 [SMILES: CCc1ccc(S(=O)(=O)N2CCC(N(c3cccc(C)c3)S(=O)(=O)c3ccccc3Cl)CC2)cc1] | Example 238 | m/z 533 [M + H − 1], 535 [M + H + 1] | 13 |
| 239. | 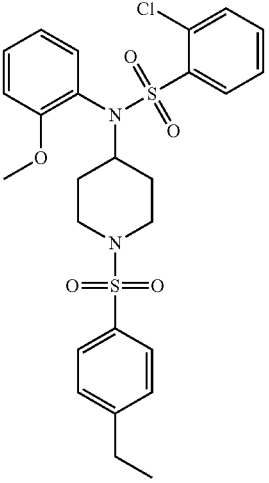 [SMILES: CCc1ccc(S(=O)(=O)N2CCC(N(c3ccccc3OC)S(=O)(=O)c3ccccc3Cl)CC2)cc1] | Example 239 | m/z 549 [M + H − 1], 551 [M + H + 1] | 13 |
| 240. | 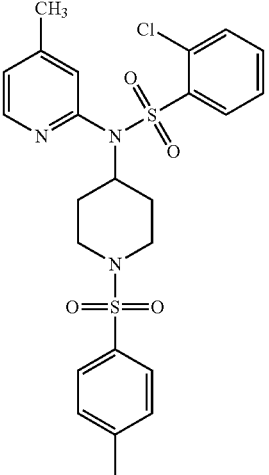 | Example 240 | m/z 534 [M + H − 1], 536 [M + H + 1] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 241. | Example 241 | m/z 537 [M + H − 1], 539 [M + H + 1] | 13 |
| 242. | Example 242 | m/z 521 [M + H − 1], 523 [M + H + 1] | 13 |
| 243. | Example 243 | m/z 588 [M + H − 1], 590 [M + H + 1] | 13 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 244. | 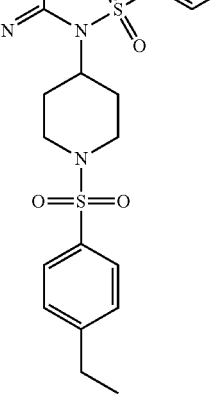 | Example 244 | m/z 550 [M + H − 1], 552 [M + H + 1] | 13 |
| 245. | 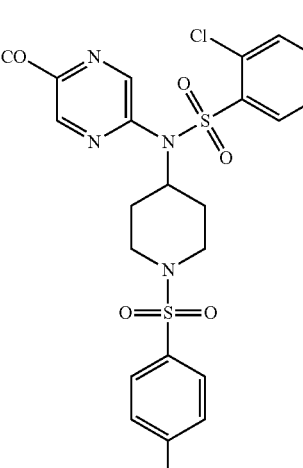 | Example 245 | m/z 551 [M + H − 1], 553 [M + H + 1] | 13 |
| 246. | 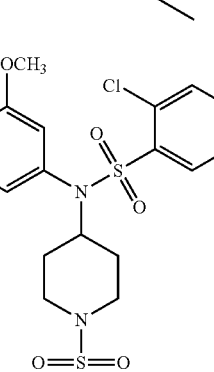 | Example 246 | m/z 549 [M + H − 1], 551 [M + H + 1] | 13 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 247. | Example 247 | m/z 550 [M + H − 1], 552 [M + H + 1] | 13 |
| 248. | Example 248 | m/z 521 [M + H − 1], 523 [M + H + 1] | 13 |
| 249. | Example 249 | m/z 521 [M + H − 1], 523 [M + H + 1] | 13 |

Assays for Detecting and Measuring the Effect of Compounds on F508del CFTR Channels CFTR-YFP Assay-CFTR Corrector Protocol:

This protocol is designed to selectively screen small molecule compounds for F508del CFTR corrector activities in the YFP (yellow fluorescent protein) flux assay. In this protocol, the cells are incubated with testing compounds for 24 hours, washed with PBS, stimulated with forskolin and a standard potentiator, and fluorescence in each plate well is measured kinetically read on a 384-well plate reader, such as the Hamamatsu FDSS-6000.

YFP fluorescence intensity values are acquired at high speed before and after iodide buffer is injected to the assay cells. Iodide enters the cells via active CFTR channels in the plasma membrane, and quenches the YFP fluorescence. The rate of fluorescence quenching is proportionate to the total CFTR activity in the cell membrane. F508del CFTR correctors increase the number of CFTR molecules in the testing cell plasma membrane, and thereby accelerate YFP quenching.

This method was initially developed for bench top plate readers (Galietta, J, Jayaraman, S and Verkman, AS. Cell-based assay for high-throughput quantitative screening of CFTR chloride transport agonists. Am. J. Physiol Cell Physiol (2001), 281: C1734), and was adapted to the HTS format (Sui J, Cotard S, Andersen J, Zhu P, Staunton J, Lee M, Lin S. Optimization of a Yellow fluorescent protein-based iodide influx high-throughput screening assay for cystic fibrosis transmembrane conductance regulator (CFTR) modulators. Assay Drug Dev Technol. (2010), 8: 656-668).

Fisher Rat Thyroid (FRT) cells stably expressing both human F508del CFTR and a halide-sensitive yellow fluorescent protein (YFP-H148Q/I152L 25,22) (Galietta et al. Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 µg/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 µM in either a 2-fold or 3-fold dilution series. Cells were incubated in a cell culture incubator at 37° C. with 5% $CO_2$ for 24-26 h. Assay plates were washed with DPBS media (Thermo, cat#SH30028.02) to remove unbound cells and compound. Stimulation media (25 µL) containing 20 µM Forskolin & 30 µM P3 [6-(Ethyl-phenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

CFTR-YFP Assay-CFTR Potentiator Protocol:

This protocol is designed to selectively screen small molecule compounds for F508del CFTR potentiator activities in the YFP (yellow fluorescent protein) flux assay. Such compounds act acutely to stimulate CFTR already expressed on the membrane surface. In this protocol, the cells are incubated at 27° C. for 24 hours to homogeneously boost F508del CFTR expression in the cell membrane (low temperature correction), washed with PBS, treated with test compound, and CFTR activity is stimulated with forskolin for 1-2 hr. Measurement of ion flux is initiated by addition of iodide-containing buffer, and YFP quenching is kinetically recorded using a 384-well plate reader, such as the Hamamatsu FDSS-6000.

YFP fluorescence intensity values are acquired at high speed over a 1 min time course before and after iodide buffer is injected to the assay cells. Iodide enters the cells via active CFTR channels in the plasma membrane, and quenches the YFP fluorescence. The rate of fluorescence quenching is proportionate to total CFTR activity in the cell membrane. F508del-CFTR potentiators increase CFTR open probability or CFTR-mediated ion conductivity, and this enhanced CFTR mediated iodide flux in the test cell plasma membrane accelerates YFP quenching.

This method was initially developed for bench top plate readers (Galietta, J, Jayaraman, S and Verkman, AS. Cell-based assay for high-throughput quantitative screening of CFTR chloride transport agonists. Am. J. Physiol Cell Physiol (2001), 281: C1734), and was adapted to the HTS format (Sui J, Cotard S, Andersen J, Zhu P, Staunton J, Lee M, Lin S. Optimization of a Yellow fluorescent protein-based iodide influx high-throughput screening assay for cystic fibrosis transmembrane conductance regulator (CFTR) modulators. Assay Drug Dev Technol. (2010), 8: 656-668).

Fisher Rat Thyroid (FRT) cells stably expressing both human F508del CFTR and a halide-sensitive yellow fluorescent protein (YFP-H148Q/I152L 25,22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 g/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat#SH30028.02) to remove unbound cells. Test compound was applied to the cells at varying concentrations ranging from 2 nM-40 µM in either a 2-fold or 3-fold dilution series in DPBS and stimulated with 20 µM Forskolin (final concentration) in Hams F-12 coon's modified media. Plates were incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay, test compounds were applied to the basolateral surface of the cells at various test concentrations (n=3 or n=4 replicates per test condition).

Ussing Assay

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage were stabilized and adjusted before application of voltage clamp.

Compounds were added in the following order.

| Step | Chamber |
|---|---|
| 3.0 uM Benzamil for 20 minutes | apical addition only |
| 10 uM Forskolin for 20 minutes | apical + basolateral addition |
| 10 uM Genestein for 20 minutes | apical + basolateral addition |
| 10 uM CFTR-172 for 20 minutes | apical + basolateral addition |
| 20 uM Bumetanide for 30 minutes | basolateral addition only |

The short circuit current and transepithelial resistances (typically >300 Ω-cm2) from each chamber was recorded every 10 seconds on stored on a PC using Acquire and Analyze (Physiologic Instruments).

Analysis

Efficacy of test compounds was compared using the average of the forskolin response and the CFTR-172 inhibited current response of the test compound divided by the average of the forskolin response and the CFTR-172 inhibited current elicited by the positive control. Normalized scores were tabulated for all compounds and concentrations.

TABLE 3

| CFTR-YFP Corrector Protocol: | | |
|---|---|---|
| Example | $EC_{50}$ | $E_{MAX}$ |
| Example 1 | III | II |
| Example 2 | III | II |
| Example 3 | III | II |
| Example 4 | I | II |
| Example 5 | III | II |
| Example 6 | III | II |
| Example 7 | III | II |
| Example 8 | III | II |
| Example 9 | III | II |

TABLE 3-continued

| CFTR-YFP Corrector Protocol: | | |
|---|---|---|
| Example | $EC_{50}$ | $E_{MAX}$ |
| Example 10 | III | II |
| Example 11 | III | II |
| Example 12 | III | I |
| Example 13 | III | II |
| Example 14 | I | I |
| Example 15 | III | II |
| Example 16 | II | III |
| Example 17 | III | II |
| Example 18 | III | II |
| Example 19 | III | II |
| Example 20 | III | II |
| Example 21 | I | I |
| Example 22 | III | II |
| Example 23 | III | III |
| Example 24 | III | II |
| Example 25 | III | II |
| Example 26 | III | II |
| Example 27 | III | II |
| Example 28 | III | II |
| Example 29 | III | I |
| Example 30 | III | II |
| Example 31 | III | II |
| Example 32 | I | II |
| Example 33 | II | II |
| Example 34 | III | II |
| Example 35 | III | II |
| Example 36 | III | I |
| Example 37 | III | II |
| Example 38 | III | III |
| Example 39 | III | II |
| Example 40 | III | II |
| Example 41 | III | II |
| Example 42 | III | II |
| Example 43 | III | II |
| Example 44 | III | II |
| Example 45 | III | II |
| Example 46 | III | II |
| Example 47 | III | II |
| Example 48 | III | II |
| Example 49 | III | II |
| Example 50 | III | II |
| Example 51 | III | II |
| Example 52 | III | II |
| Example 53 | III | II |
| Example 54 | III | II |
| Example 55 | III | II |
| Example 56 | III | II |
| Example 57 | III | II |
| Example 58 | III | I |
| Example 59 | III | II |
| Example 60 | III | II |
| Example 61 | III | II |
| Example 62 | III | II |
| Example 63 | III | II |
| Example 64 | III | II |
| Example 65 | III | II |
| Example 66 | III | I |
| Example 67 | I | I |
| Example 68 | III | I |
| Example 69 | III | I |
| Example 70 | III | I |
| Example 71 | III | I |
| Example 72 | III | I |
| Example 73 | III | II |
| Example 74 | III | II |
| Example 75 | II | II |
| Example 76 | III | II |
| Example 77 | III | II |
| Example 78 | III | I |
| Example 79 | III | II |
| Example 80 | III | II |
| Example 81 | III | II |

TABLE 3-continued

CFTR-YFP Corrector Protocol:

| Example | $EC_{50}$ | $E_{MAX}$ |
|---|---|---|
| Example 82 | III | II |
| Example 83 | III | II |
| Example 84 | III | II |
| Example 85 | I | I |
| Example 86 | III | II |
| Example 87 | I | I |
| Example 88 | I | II |
| Example 89 | II | III |
| Example 90 | II | II |
| Example 91 | III | II |
| Example 92 | III | II |
| Example 93 | III | II |
| Example 94 | III | I |
| Example 95 | II | I |
| Example 96 | III | II |
| Example 97 | III | II |
| Example 98 | III | I |
| Example 99 | III | II |
| Example 100 | III | I |
| Example 101 | III | I |
| Example 102 | III | II |
| Example 103 | III | I |
| Example 104 | III | II |
| Example 105 | III | II |
| Example 106 | III | I |
| Example 107 | III | II |
| Example 108 | III | II |
| Example 109 | III | II |
| Example 110 | III | II |
| Example 111 | III | II |
| Example 112 | III | III |
| Example 113 | III | II |
| Example 114 | III | II |
| Example 115 | III | II |
| Example 116 | III | III |
| Example 117 | III | II |
| Example 118 | III | II |
| Example 119 | III | III |
| Example 120 | III | III |
| Example 121 | III | II |
| Example 122 | III | III |
| Example 123 | III | I |
| Example 124 | III | II |
| Example 125 | III | II |
| Example 126 | III | II |
| Example 127 | III | II |
| Example 128 | III | I |
| Example 129 | III | I |
| Example 130 | III | II |
| Example 131 | III | I |
| Example 132 | III | II |
| Example 133 | III | III |
| Example 134 | III | II |
| Example 135 | II | I |
| Example 136 | III | I |
| Example 137 | II | I |
| Example 138 | I | II |
| Example 139 | I | I |
| Example 140 | I | I |
| Example 141 | III | I |
| Example 142 | III | I |
| Example 143 | III | I |
| Example 144 | III | I |
| Example 145 | III | I |
| Example 146 | III | I |
| Example 147 | III | I |
| Example 148 | III | I |
| Example 149 | III | I |
| Example 150 | II | II |
| Example 151 | III | II |
| Example 152 | II | I |
| Example 153 | III | II |
| Example 154 | III | II |
| Example 155 | III | II |
| Example 156 | III | II |
| Example 157 | III | I |
| Example 158 | II | I |
| Example 159 | III | I |
| Example 160 | III | II |
| Example 161 | II | I |
| Example 162 | III | I |
| Example 163 | III | III |
| Example 164 | III | III |
| Example 165 | III | II |
| Example 166 | III | II |
| Example 167 | I | I |
| Example 168 | III | II |
| Example 169 | III | II |
| Example 170 | I | I |
| Example 171 | III | I |
| Example 172 | III | I |
| Example 173 | III | II |
| Example 174 | I | I |
| Example 175 | III | I |
| Example 176 | III | I |
| Example 177 | III | I |
| Example 178 | III | I |
| Example 179 | III | I |
| Example 180 | II | I |
| Example 181 | III | II |
| Example 182 | III | I |
| Example 183 | III | II |
| Example 184 | III | I |
| Example 185 | III | II |
| Example 186 | III | I |
| Example 187 | III | I |
| Example 188 | III | I |
| Example 189 | III | II |
| Example 190 | III | I |
| Example 191 | II | I |
| Example 192 | III | II |
| Example 193 | III | II |
| Example 194 | III | II |
| Example 195 | III | II |
| Example 196 | II | II |
| Example 197 | III | I |
| Example 198 | III | I |
| Example 199 | III | I |
| Example 200 | III | I |
| Example 201 | III | II |
| Example 202 | III | I |
| Example 203 | III | 1 |
| Example 204 | III | I |
| Example 205 | III | I |
| Example 206 | II | I |
| Example 207 | II | II |
| Example 208 | II | II |
| Example 209 | III | II |
| Example 210 | II | II |
| Example 211 | II | II |
| Example 212 | II | II |
| Example 213 | II | I |
| Example 214 | III | I |
| Example 215 | II | I |
| Example 216 | III | I |
| Example 217 | III | I |
| Example 218 | III | I |
| Example 219 | III | I |
| Example 220 | III | II |
| Example 221 | III | II |
| Example 222 | III | I |
| Example 223 | II | I |
| Example 224 | III | I |
| Example 225 | III | I |
| Example 226 | III | I |
| Example 227 | III | I |
| Example 228 | II | I |
| Example 229 | III | I |
| Example 230 | III | II |
| Example 231 | III | II |

TABLE 3-continued

CFTR-YFP Corrector Protocol:

| Example | $EC_{50}$ | $E_{MAX}$ |
|---|---|---|
| Example 232 | III | I |
| Example 233 | III | II |
| Example 234 | III | II |
| Example 235 | III | II |
| Example 236 | III | I |
| Example 237 | III | I |
| Example 238 | III | II |
| Example 239 | III | I |
| Example 240 | III | I |
| Example 241 | III | I |
| Example 242 | III | I |
| Example 243 | II | I |
| Example 244 | II | II |
| Example 245 | III | II |
| Example 246 | II | II |
| Example 247 | III | II |
| Example 248 | III | II |
| Example 249 | III | II |

$EC_{50}$: "III" refers to an $EC_{50}$ <10 µM, "II" refers to $EC_{50}$ range of 10-20 µM, "I" refers to $EC_{50}$ >20 µM % Efficacy is reported as the $E_{MAX}$ normalized to the positive control. "III" refers to $E_{MAX}$ >80%, "II" refers to a range of 80%-30%, "I" refers to a range of 30%-10%.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound selected from Table 4 or a pharmaceutically acceptable salt thereof:

TABLE 4

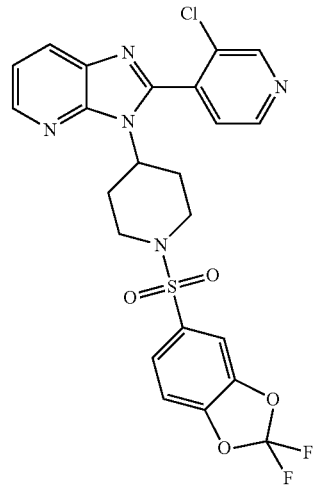 [SMILES: O=S(=O)(c1ccc2c(c1)OC(F)(F)O2)N1CCC(n2c(-c3ccncc3Cl)nc3cccnc32)CC1]

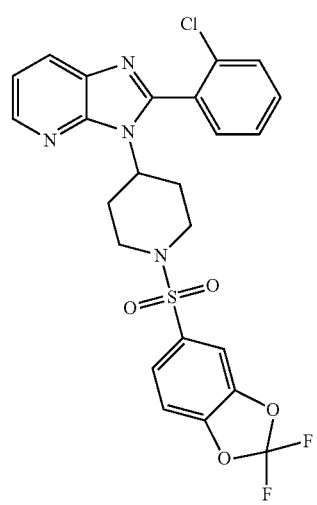 [SMILES: O=S(=O)(c1ccc2c(c1)OC(F)(F)O2)N1CCC(n2c(-c3ccccc3Cl)nc3cccnc32)CC1]

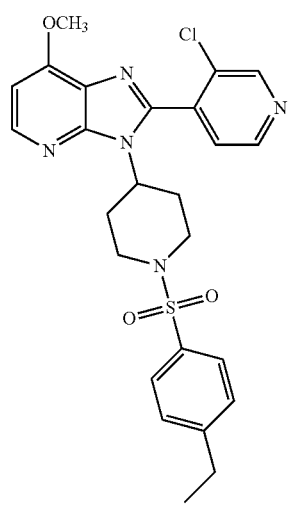 [SMILES: CCc1ccc(S(=O)(=O)N2CCC(n3c(-c4ccncc4Cl)nc4c(OC)ccnc43)CC2)cc1]

TABLE 4-continued
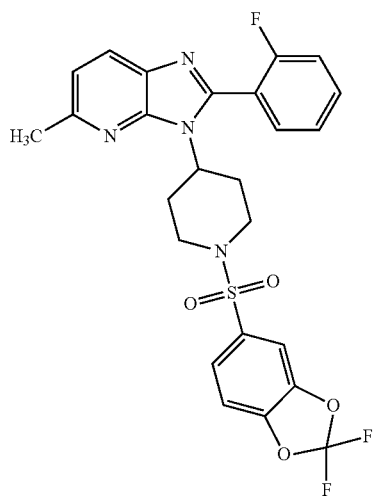 [SMILES: Cc1ccc2nc(-c3ccccc3F)n(C3CCN(S(=O)(=O)c4ccc5c(c4)OC(F)(F)O5)CC3)c2n1]
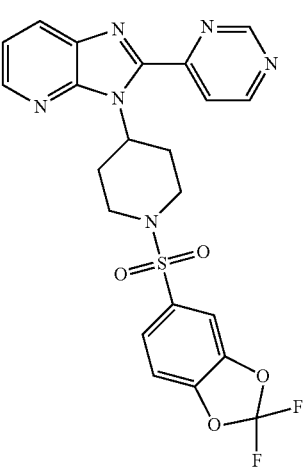 [SMILES: O=S(=O)(c1ccc2c(c1)OC(F)(F)O2)N1CCC(n2c(-c3ccncn3)nc3cccnc32)CC1]
TABLE 4-continued
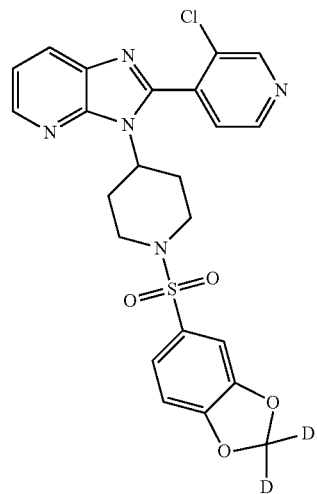 [SMILES: [2H]C1([2H])Oc2ccc(S(=O)(=O)N3CCC(n4c(-c5ccncc5Cl)nc5cccnc54)CC3)cc2O1]
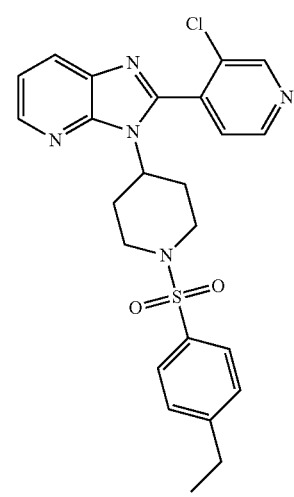
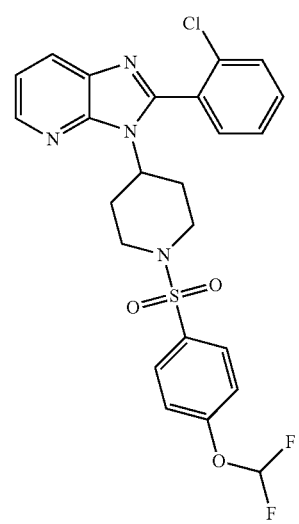 [SMILES: O=S(=O)(c1ccc(OC(F)F)cc1)N1CCC(n2c(-c3ccccc3Cl)nc3cccnc32)CC1]

TABLE 4-continued
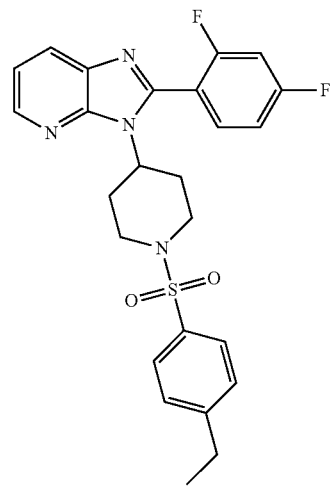 [SMILES: CCc1ccc(S(=O)(=O)N2CCC(n3c(-c4ccc(F)cc4F)nc4cccnc43)CC2)cc1]
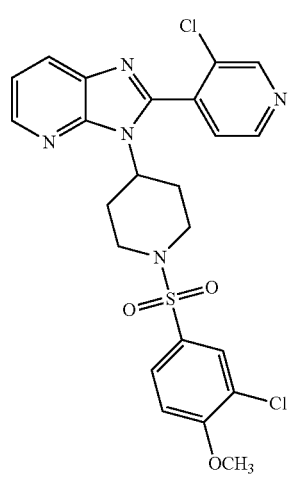 [SMILES: COc1ccc(S(=O)(=O)N2CCC(n3c(-c4ccncc4Cl)nc4cccnc43)CC2)cc1Cl]
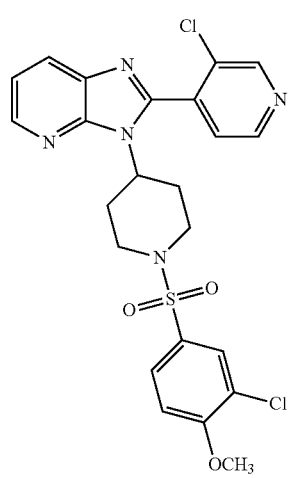 [SMILES: COc1ccc(S(=O)(=O)N2CCC(n3c(-c4ccncc4Cl)nc4cccnc43)CC2)cc1Cl]
TABLE 4-continued
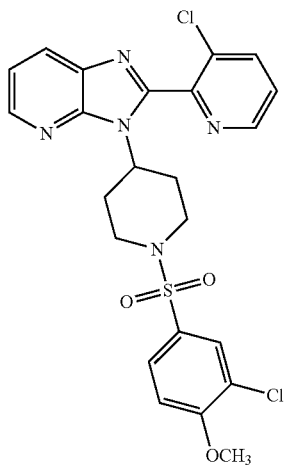 [SMILES: COc1ccc(S(=O)(=O)N2CCC(n3c(-c4ncccc4Cl)nc4cccnc43)CC2)cc1Cl]
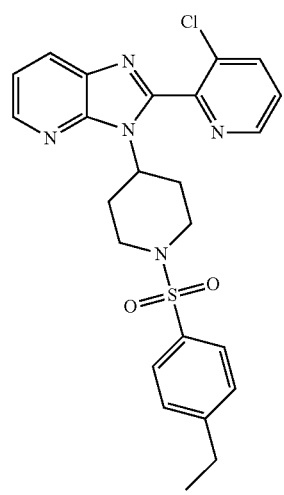 [SMILES: CCc1ccc(S(=O)(=O)N2CCC(n3c(-c4ncccc4Cl)nc4cccnc43)CC2)cc1]
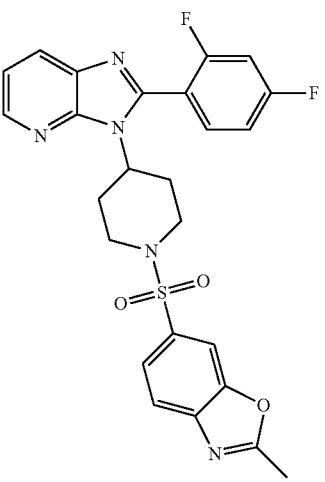 [SMILES: Cc1nc2ccc(S(=O)(=O)N3CCC(n4c(-c5ccc(F)cc5F)nc5cccnc54)CC3)cc2o1]

TABLE 4-continued
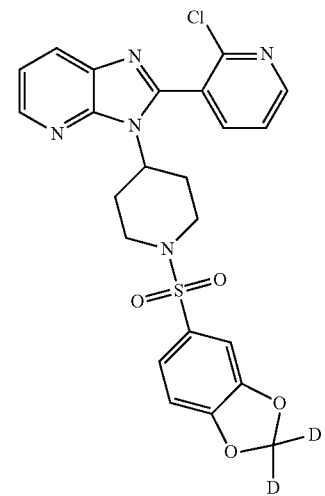 [SMILES: [2H]C1([2H])Oc2ccc(S(=O)(=O)N3CCC(n4c(-c5cccnc5Cl)nc5cccnc54)CC3)cc2O1]
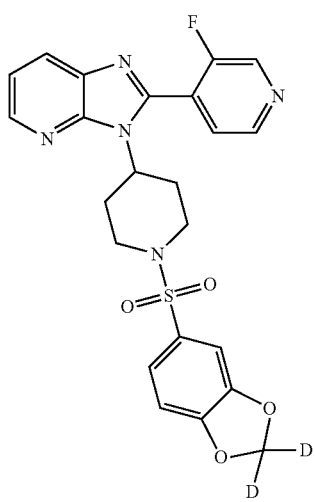 [SMILES: [2H]C1([2H])Oc2ccc(S(=O)(=O)N3CCC(n4c(-c5ccncc5F)nc5cccnc54)CC3)cc2O1]
TABLE 4-continued
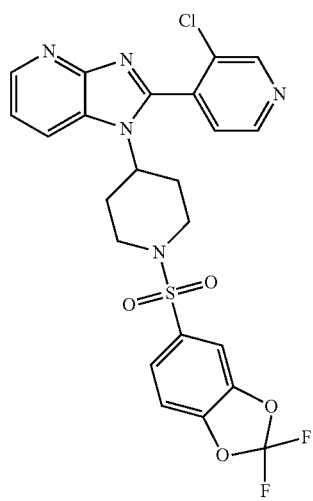 [SMILES: O=S(=O)(c1ccc2c(c1)OC(F)(F)O2)N1CCC(n2c(-c3ccncc3Cl)nc3ncccc32)CC1]
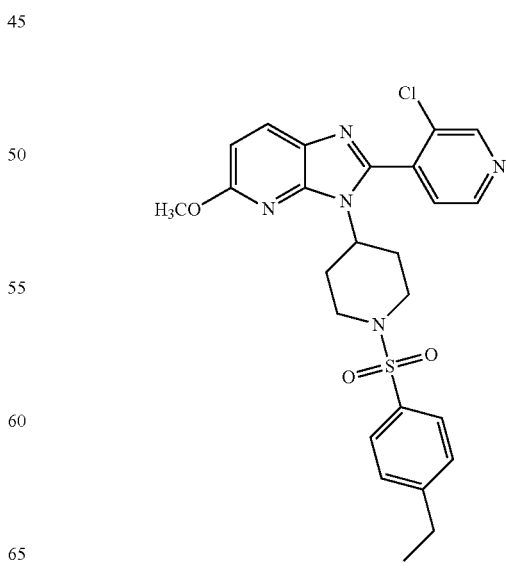

TABLE 4-continued
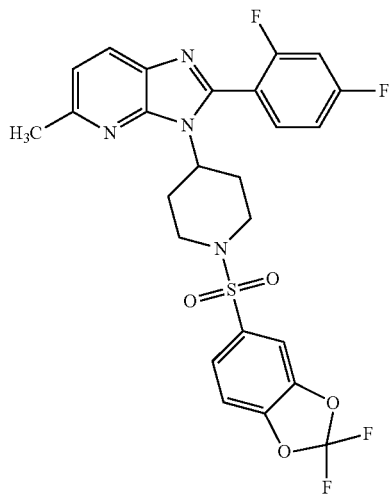 [SMILES: Cc1ccc2nc(-c3ccc(F)cc3F)n(C3CCN(S(=O)(=O)c4ccc5c(c4)OC(F)(F)O5)CC3)c2n1]
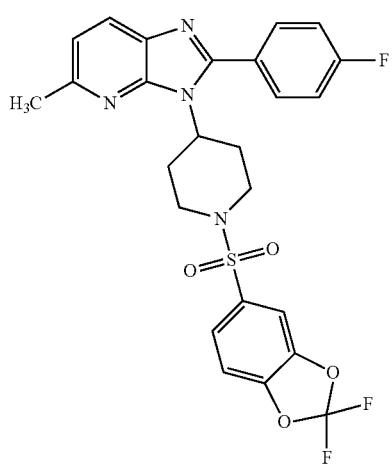 [SMILES: Cc1ccc2nc(-c3ccc(F)cc3)n(C3CCN(S(=O)(=O)c4ccc5c(c4)OC(F)(F)O5)CC3)c2n1]
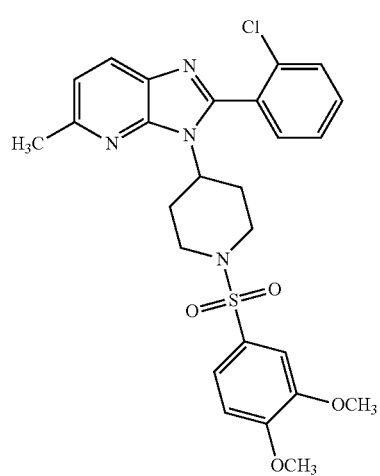 [SMILES: COc1ccc(S(=O)(=O)N2CCC(n3c(-c4ccccc4Cl)nc4ccc(C)nc43)CC2)cc1OC]
TABLE 4-continued
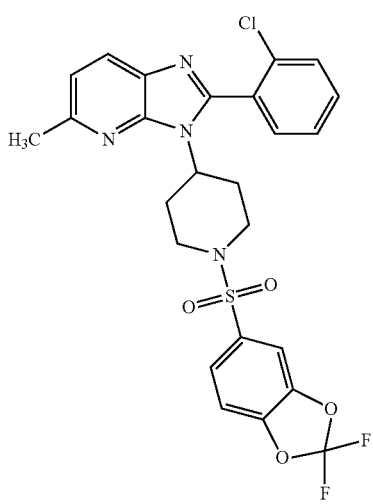 [SMILES: Cc1ccc2nc(-c3ccccc3Cl)n(C3CCN(S(=O)(=O)c4ccc5c(c4)OC(F)(F)O5)CC3)c2n1]
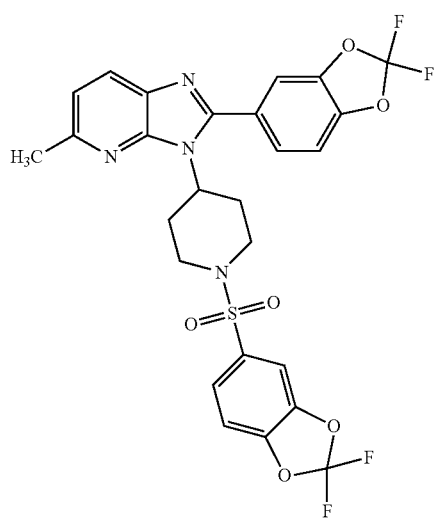 [SMILES: Cc1ccc2nc(-c3ccc4c(c3)OC(F)(F)O4)n(C3CCN(S(=O)(=O)c4ccc5c(c4)OC(F)(F)O5)CC3)c2n1]
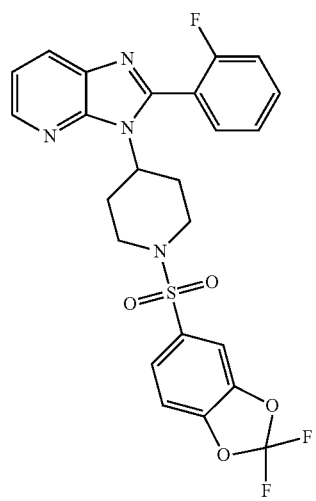 [SMILES: O=S(=O)(c1ccc2c(c1)OC(F)(F)O2)N1CCC(n2c(-c3ccccc3F)nc3cccnc32)CC1]

TABLE 4-continued
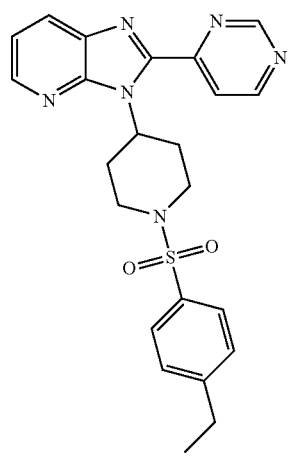 [SMILES: CCc1ccc(S(=O)(=O)N2CCC(n3c(-c4ccncn4)nc4cccnc43)CC2)cc1]
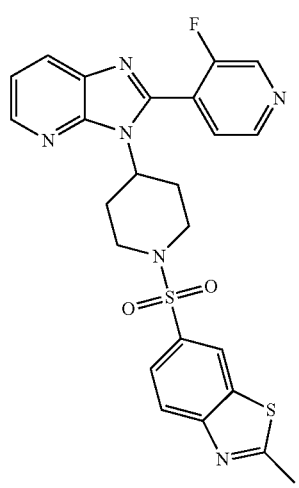 [SMILES: Cc1nc2ccc(S(=O)(=O)N3CCC(n4c(-c5ccncc5F)nc5cccnc54)CC3)cc2s1]
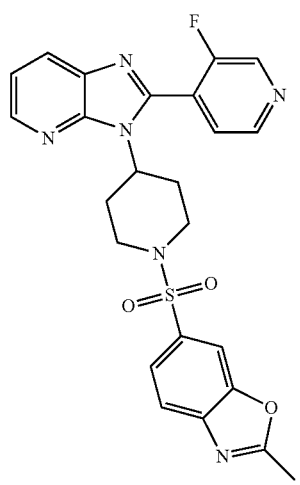
TABLE 4-continued
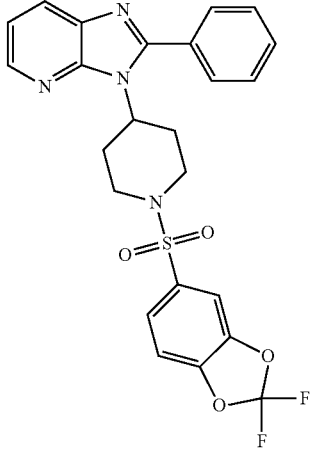 [SMILES: O=S(=O)(c1ccc2c(c1)OC(F)(F)O2)N1CCC(n2c(-c3ccccc3)nc3cccnc32)CC1]
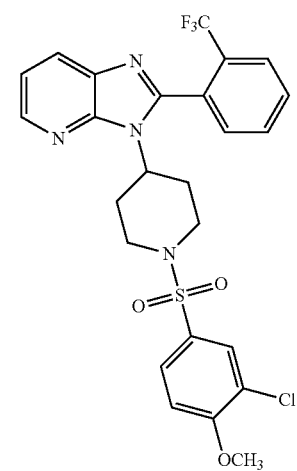
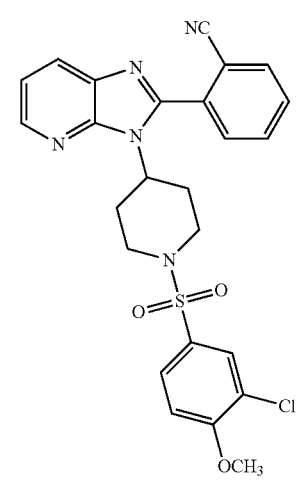

353
TABLE 4-continued

354
TABLE 4-continued

TABLE 4-continued
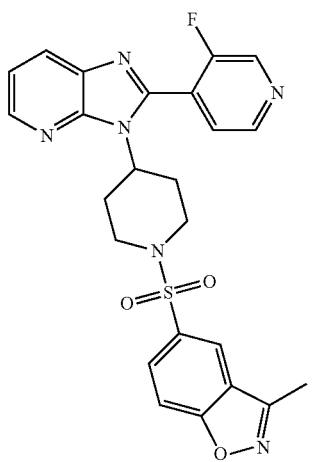 [SMILES: Cc1noc2ccc(S(=O)(=O)N3CCC(n4c(-c5ccncc5F)nc5cccnc54)CC3)cc12]
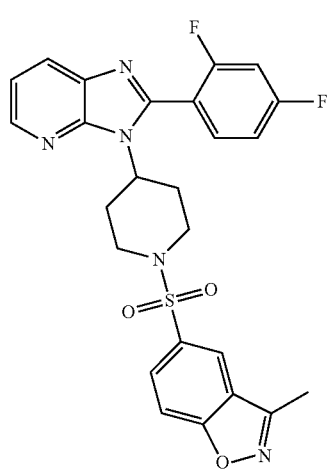 [SMILES: Cc1noc2ccc(S(=O)(=O)N3CCC(n4c(-c5ccc(F)cc5F)nc5cccnc54)CC3)cc12]
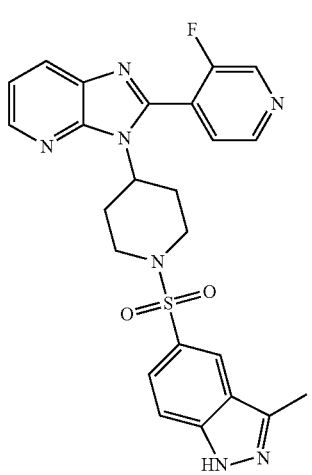 [SMILES: Cc1n[nH]c2ccc(S(=O)(=O)N3CCC(n4c(-c5ccncc5F)nc5cccnc54)CC3)cc12]
TABLE 4-continued
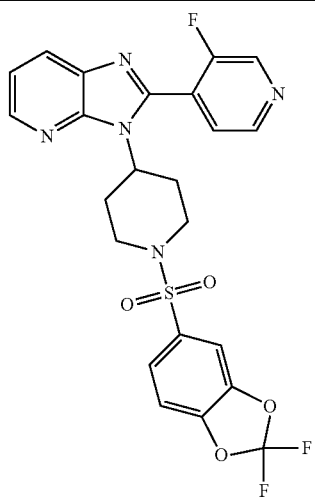
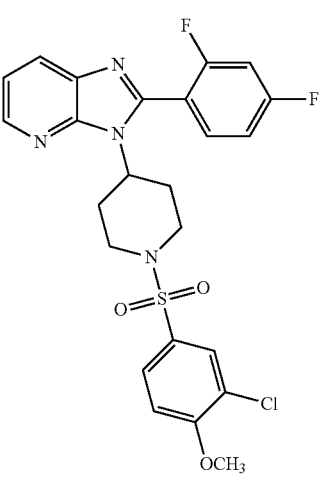 [SMILES: COc1ccc(S(=O)(=O)N2CCC(n3c(-c4ccc(F)cc4F)nc4cccnc43)CC2)cc1Cl]
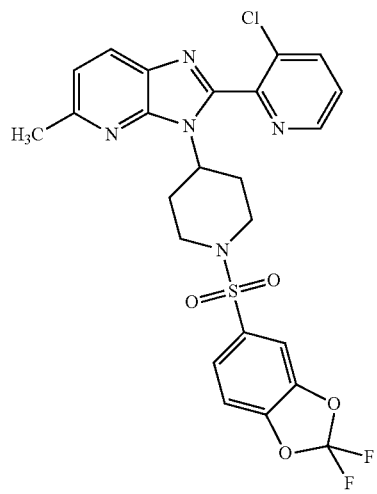 [SMILES: Cc1ccc2nc(-c3ncccc3Cl)n(C3CCN(S(=O)(=O)c4ccc5c(c4)OC(F)(F)O5)CC3)c2n1]

TABLE 4-continued
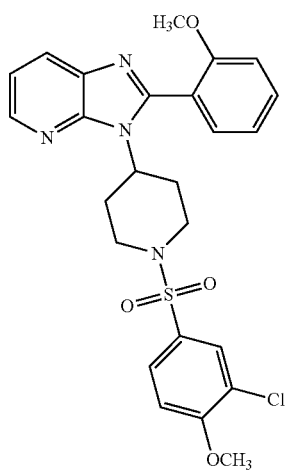
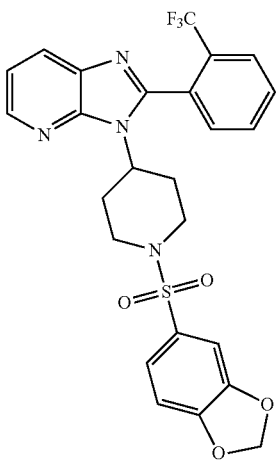
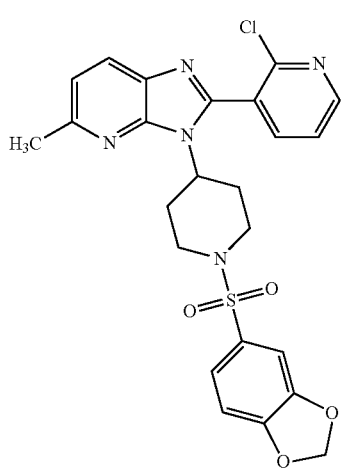 [SMILES: Cc1ccc2nc(-c3cccnc3Cl)n(C3CCN(S(=O)(=O)c4ccc5c(c4)OCO5)CC3)c2n1]
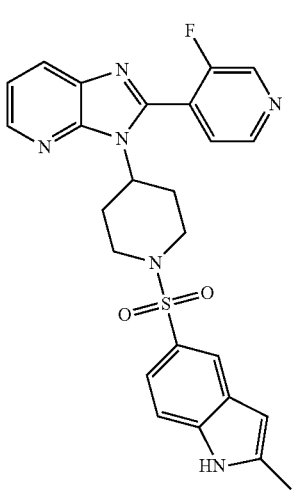 [SMILES: Cc1cc2cc(S(=O)(=O)N3CCC(n4c(-c5ccncc5F)nc5cccnc54)CC3)ccc2[nH]1]

TABLE 4-continued
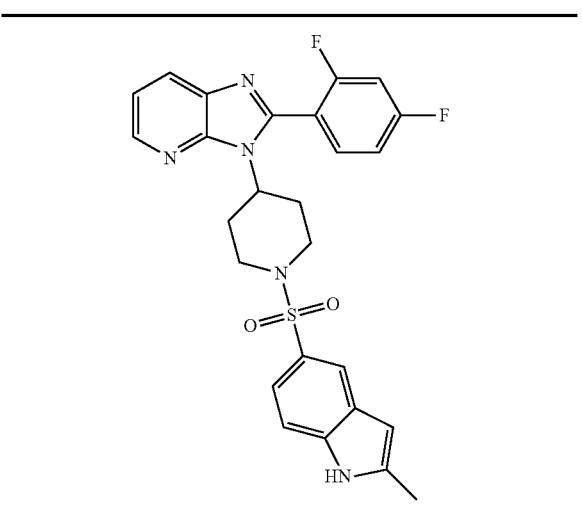
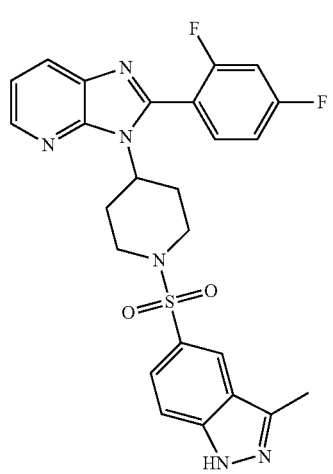 [SMILES: Cc1n[nH]c2ccc(S(=O)(=O)N3CCC(n4c(-c5ccc(F)cc5F)nc5cccnc54)CC3)cc12]
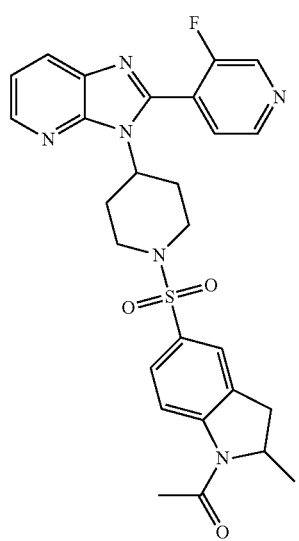 [SMILES: CC(=O)N1c2ccc(S(=O)(=O)N3CCC(n4c(-c5ccncc5F)nc5cccnc54)CC3)cc2CC1C]
TABLE 4-continued
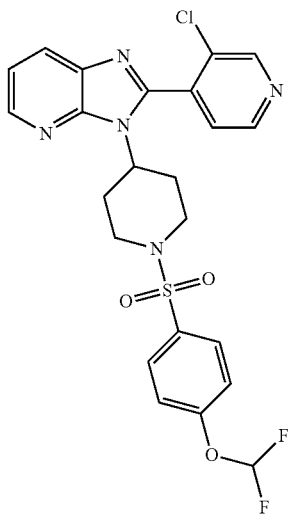
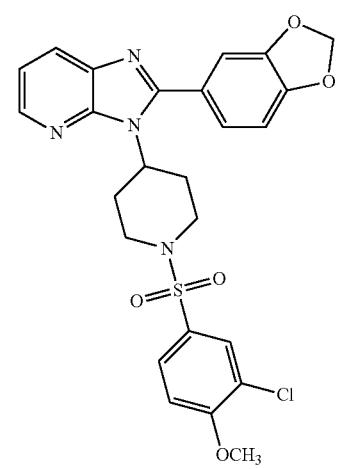 [SMILES: COc1ccc(S(=O)(=O)N2CCC(n3c(-c4ccc5c(c4)OCO5)nc4cccnc43)CC2)cc1Cl]
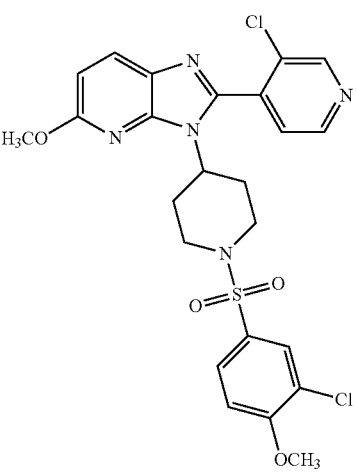 [SMILES: COc1ccc2nc(-c3ccncc3Cl)n(C3CCN(S(=O)(=O)c4ccc(OC)c(Cl)c4)CC3)c2n1]

TABLE 4-continued
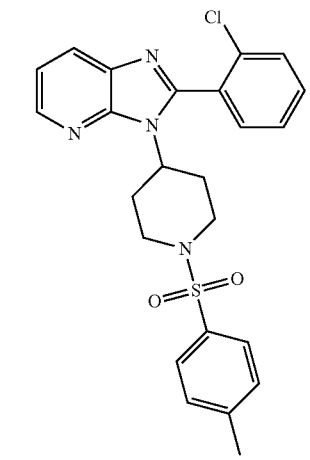 [SMILES: Cc1ccc(S(=O)(=O)N2CCC(n3c(-c4ccccc4Cl)nc4cccnc43)CC2)cc1]
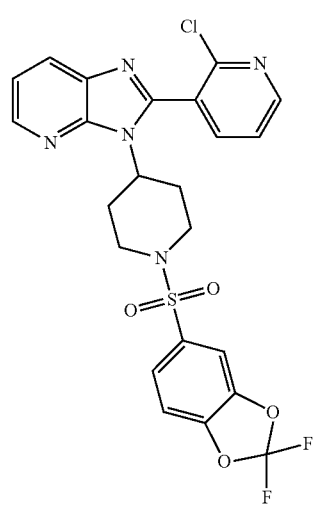
TABLE 4-continued
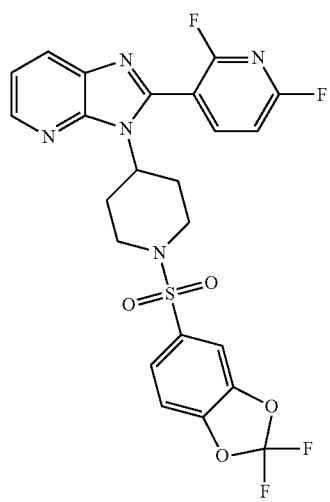
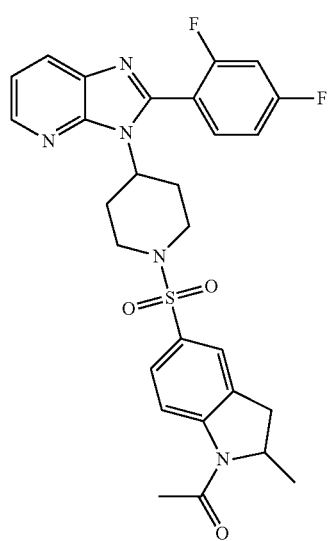 [SMILES: CC(=O)N1c2ccc(S(=O)(=O)N3CCC(n4c(-c5ccc(F)cc5F)nc5cccnc54)CC3)cc2CC1C]

TABLE 4-continued
363
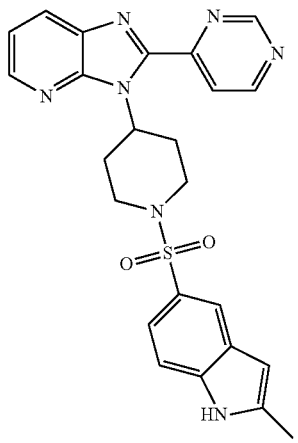 [SMILES: Cc1cc2cc(S(=O)(=O)N3CCC(n4c(-c5ccncn5)nc5cccnc54)CC3)ccc2[nH]1]
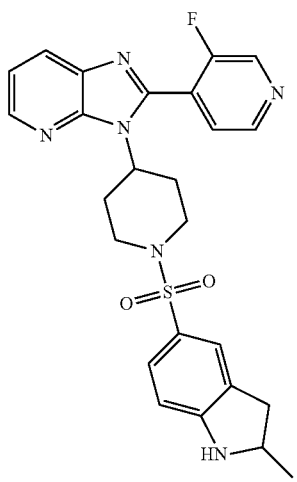 [SMILES: CC1Cc2cc(S(=O)(=O)N3CCC(n4c(-c5ccncc5F)nc5cccnc54)CC3)ccc2N1]
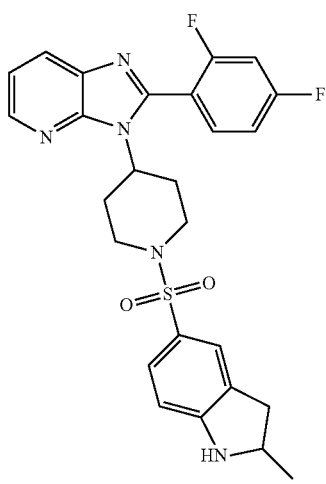 [SMILES: CC1Cc2cc(S(=O)(=O)N3CCC(n4c(-c5ccc(F)cc5F)nc5cccnc54)CC3)ccc2N1]
TABLE 4-continued
364
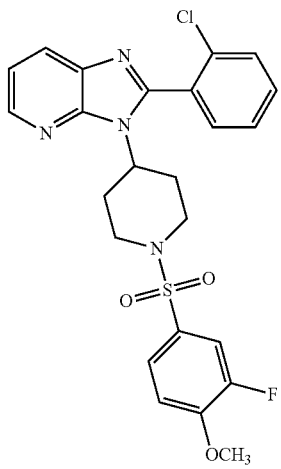 [SMILES: COc1ccc(S(=O)(=O)N2CCC(n3c(-c4ccccc4Cl)nc4cccnc43)CC2)cc1F]
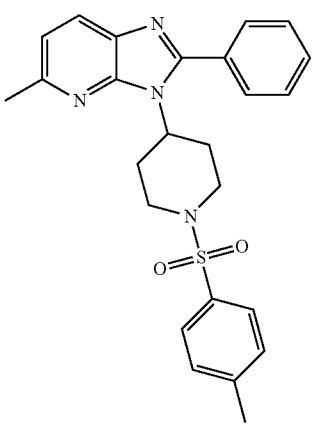 [SMILES: Cc1ccc(S(=O)(=O)N2CCC(n3c(-c4ccccc4)nc4ccc(C)nc43)CC2)cc1]
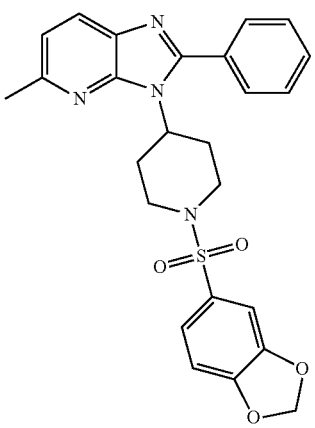 [SMILES: Cc1ccc2nc(-c3ccccc3)n(C3CCN(S(=O)(=O)c4ccc5c(c4)OCO5)CC3)c2n1]

TABLE 4-continued
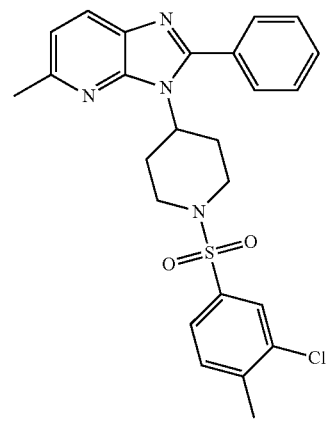 [SMILES: Cc1ccc2nc(-c3ccccc3)n(C3CCN(S(=O)(=O)c4ccc(C)c(Cl)c4)CC3)c2n1]
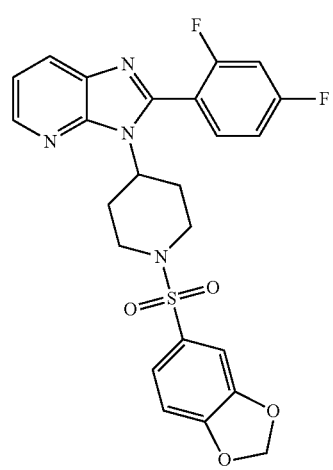 [SMILES: O=S(=O)(c1ccc2c(c1)OCO2)N1CCC(n2c(-c3ccc(F)cc3F)nc3cccnc32)CC1]
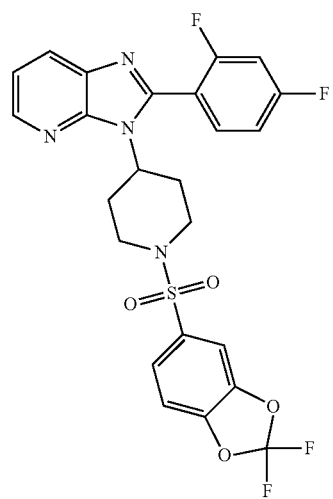
TABLE 4-continued
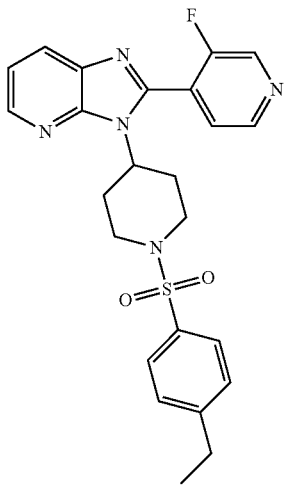 [SMILES: CCc1ccc(S(=O)(=O)N2CCC(n3c(-c4ccncc4F)nc4cccnc43)CC2)cc1]
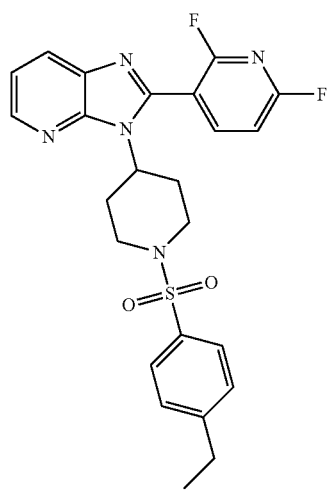 [SMILES: CCc1ccc(S(=O)(=O)N2CCC(n3c(-c4ccc(F)nc4F)nc4cccnc43)CC2)cc1]
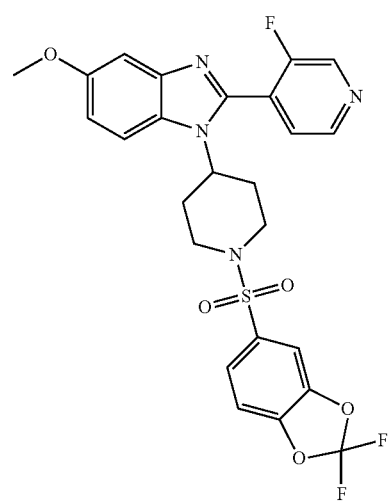 [SMILES: COc1ccc2c(c1)nc(-c1ccncc1F)n2C1CCN(S(=O)(=O)c2ccc3c(c2)OC(F)(F)O3)CC1]

TABLE 4-continued
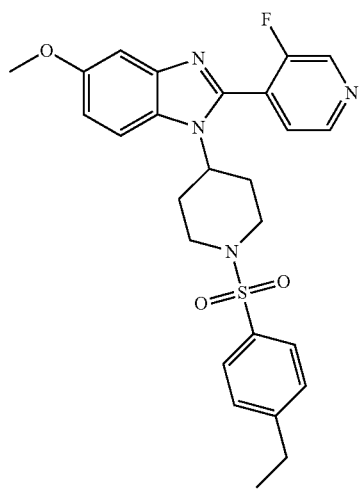 [SMILES: CCc1ccc(S(=O)(=O)N2CCC(n3c(-c4ccncc4F)nc4cc(OC)ccc43)CC2)cc1]
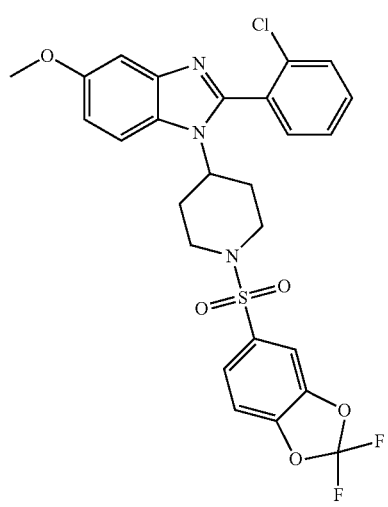 [SMILES: COc1ccc2c(c1)nc(-c1ccccc1Cl)n2C1CCN(S(=O)(=O)c2ccc3c(c2)OC(F)(F)O3)CC1]
TABLE 4-continued
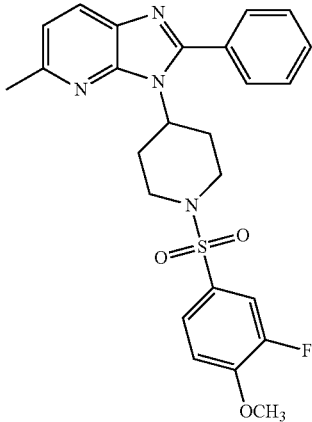 [SMILES: COc1ccc(S(=O)(=O)N2CCC(n3c(-c4ccccc4)nc4ccc(C)nc43)CC2)cc1F]
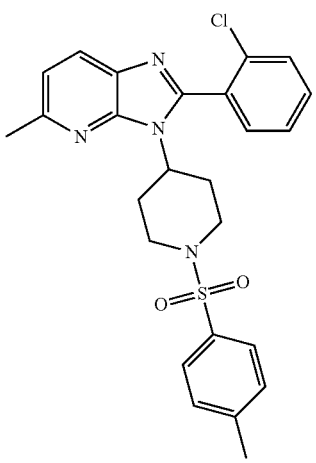 [SMILES: Cc1ccc(S(=O)(=O)N2CCC(n3c(-c4ccccc4Cl)nc4ccc(C)nc43)CC2)cc1]
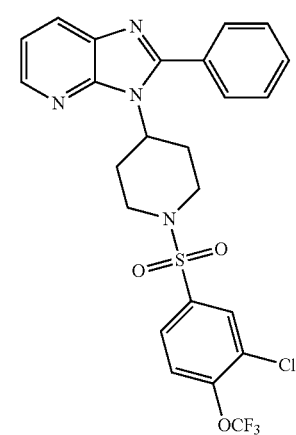 [SMILES: O=S(=O)(c1ccc(OC(F)(F)F)c(Cl)c1)N1CCC(n2c(-c3ccccc3)nc3cccnc32)CC1]

TABLE 4-continued
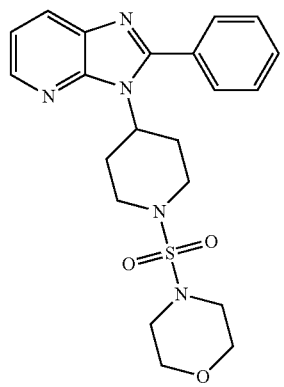 [SMILES: O=S(=O)(N1CCOCC1)N1CCC(n2c(-c3ccccc3)nc3cccnc32)CC1]
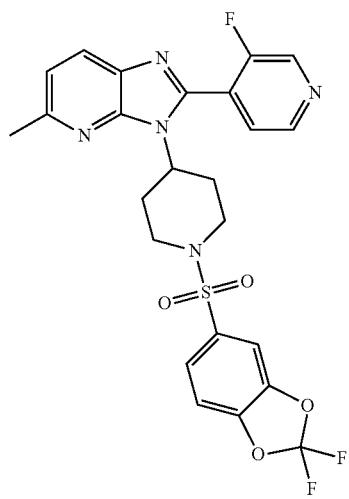 [SMILES: Cc1ccc2nc(-c3ccncc3F)n(C3CCN(S(=O)(=O)c4ccc5c(c4)OC(F)(F)O5)CC3)c2n1]
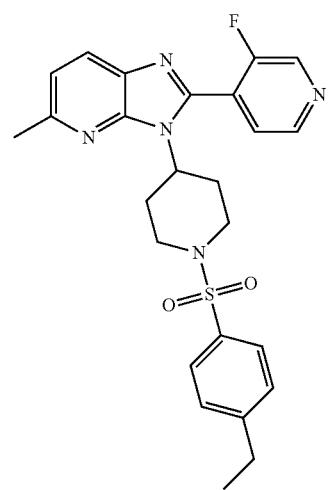 [SMILES: CCc1ccc(S(=O)(=O)N2CCC(n3c(-c4ccncc4F)nc4ccc(C)nc43)CC2)cc1]
TABLE 4-continued
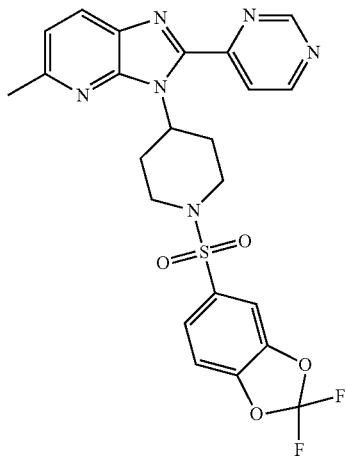 [SMILES: Cc1ccc2nc(-c3ccncn3)n(C3CCN(S(=O)(=O)c4ccc5c(c4)OC(F)(F)O5)CC3)c2n1]
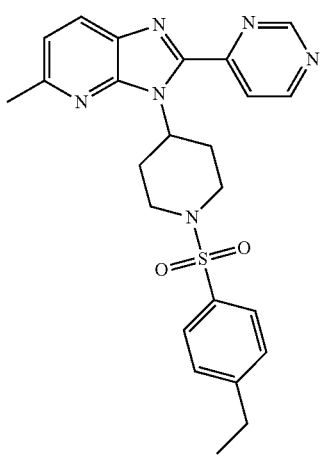 [SMILES: CCc1ccc(S(=O)(=O)N2CCC(n3c(-c4ccncn4)nc4ccc(C)nc43)CC2)cc1]
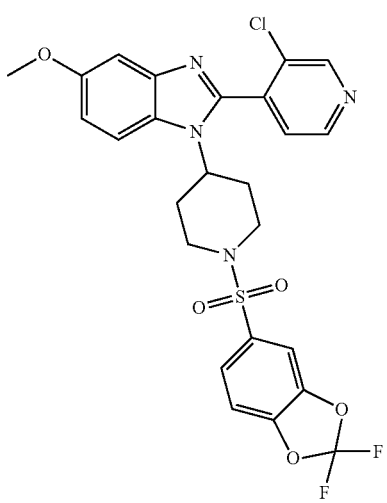 [SMILES: COc1ccc2c(c1)nc(-c1ccncc1Cl)n2C1CCN(S(=O)(=O)c2ccc3c(c2)OC(F)(F)O3)CC1]

TABLE 4-continued
371
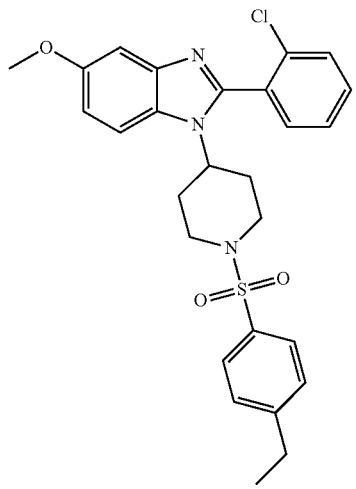 [SMILES: CCc1ccc(S(=O)(=O)N2CCC(n3c(-c4ccccc4Cl)nc4cc(OC)ccc43)CC2)cc1]
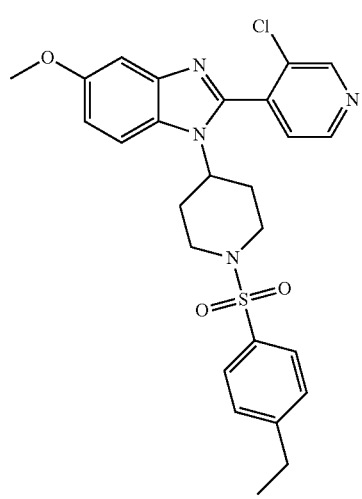 [SMILES: CCc1ccc(S(=O)(=O)N2CCC(n3c(-c4ccncc4Cl)nc4cc(OC)ccc43)CC2)cc1]
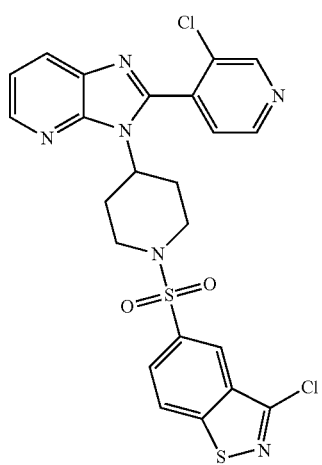
TABLE 4-continued
372
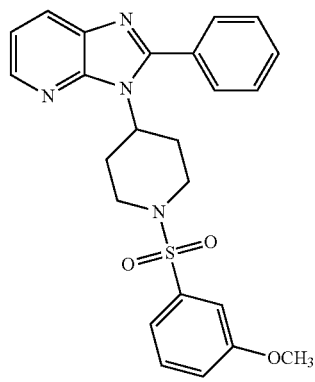 [SMILES: COc1cccc(S(=O)(=O)N2CCC(n3c(-c4ccccc4)nc4cccnc43)CC2)c1]
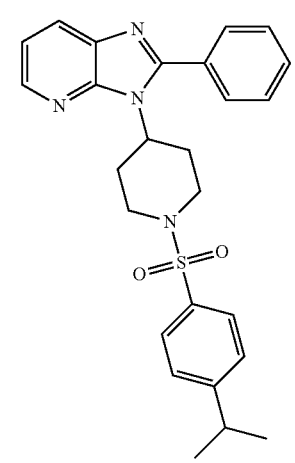 [SMILES: CC(C)c1ccc(S(=O)(=O)N2CCC(n3c(-c4ccccc4)nc4cccnc43)CC2)cc1]
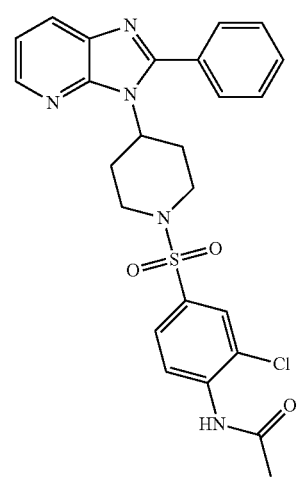 [SMILES: CC(=O)Nc1ccc(S(=O)(=O)N2CCC(n3c(-c4ccccc4)nc4cccnc43)CC2)cc1Cl]

TABLE 4-continued
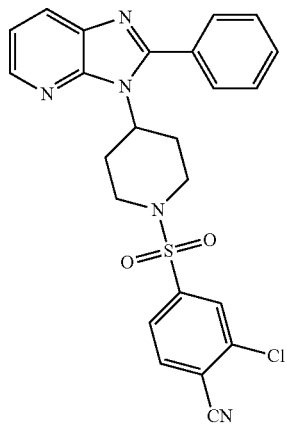 [SMILES: N#Cc1ccc(S(=O)(=O)N2CCC(n3c(-c4ccccc4)nc4cccnc43)CC2)cc1Cl]
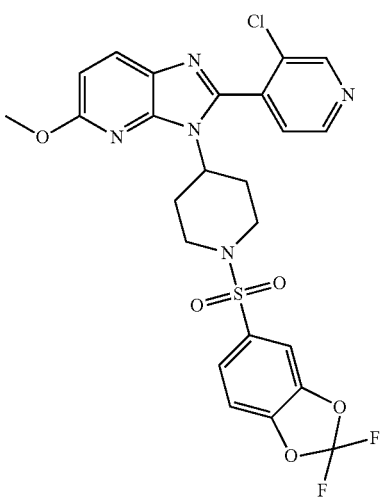
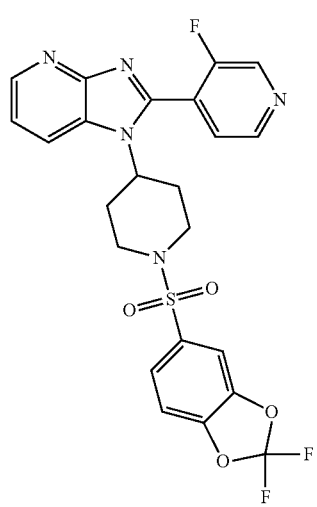 [SMILES: O=S(=O)(c1ccc2c(c1)OC(F)(F)O2)N1CCC(n2c(-c3ccncc3F)nc3ncccc32)CC1]
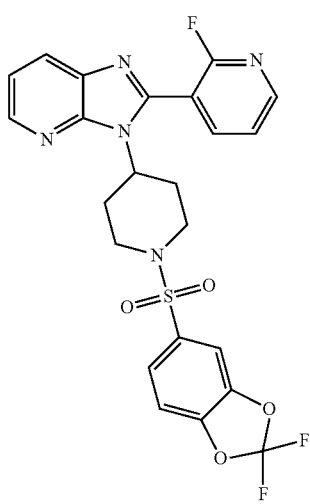
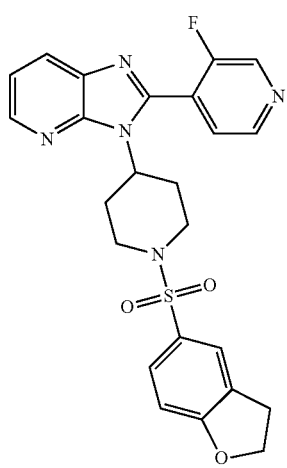 [SMILES: O=S(=O)(c1ccc2c(c1)CCO2)N1CCC(n2c(-c3ccncc3F)nc3cccnc32)CC1]
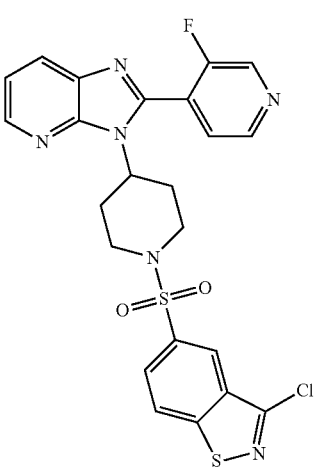 [SMILES: O=S(=O)(c1ccc2snc(Cl)c2c1)N1CCC(n2c(-c3ccncc3F)nc3cccnc32)CC1]

TABLE 4-continued
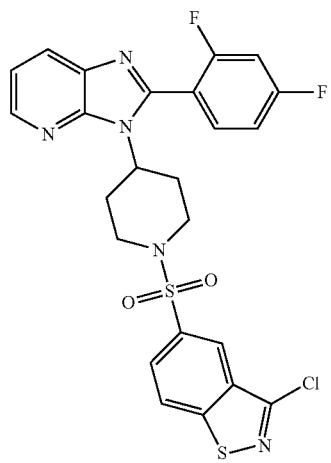
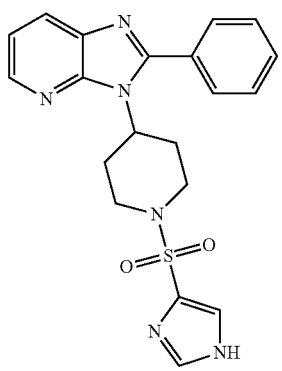 [SMILES: O=S(=O)(c1c[nH]cn1)N1CCC(n2c(-c3ccccc3)nc3cccnc32)CC1]
TABLE 4-continued
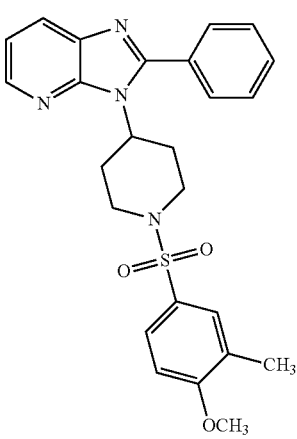 [SMILES: COc1ccc(S(=O)(=O)N2CCC(n3c(-c4ccccc4)nc4cccnc43)CC2)cc1C]
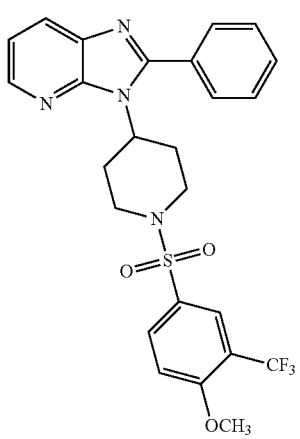 [SMILES: COc1ccc(S(=O)(=O)N2CCC(n3c(-c4ccccc4)nc4cccnc43)CC2)cc1C(F)(F)F]

TABLE 4-continued
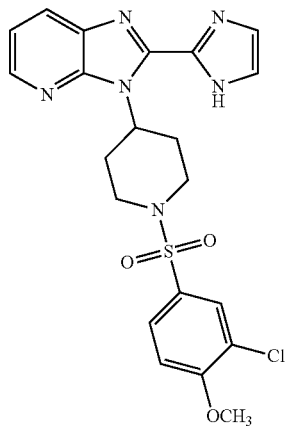 [SMILES: COc1ccc(S(=O)(=O)N2CCC(n3c(-c4ncc[nH]4)nc4cccnc43)CC2)cc1Cl]
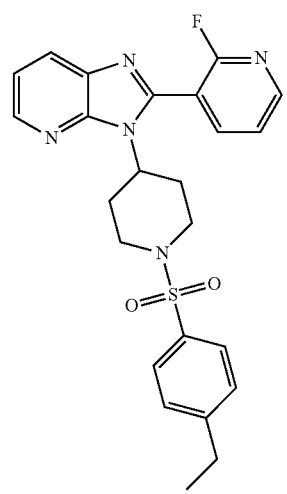 [SMILES: CCc1ccc(S(=O)(=O)N2CCC(n3c(-c4cccnc4F)nc4cccnc43)CC2)cc1]
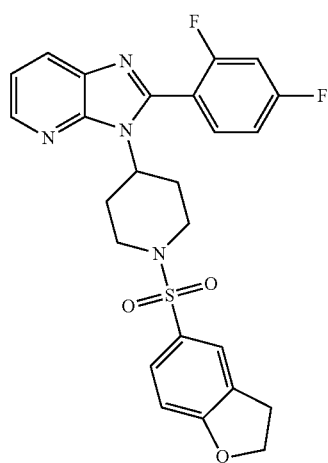 [SMILES: O=S(=O)(c1ccc2c(c1)CCO2)N1CCC(n2c(-c3ccc(F)cc3F)nc3cccnc32)CC1]
TABLE 4-continued
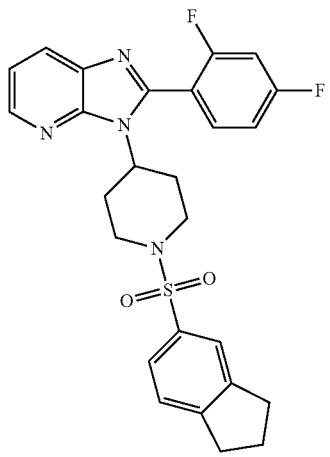 [SMILES: O=S(=O)(c1ccc2c(c1)CCC2)N1CCC(n2c(-c3ccc(F)cc3F)nc3cccnc32)CC1]
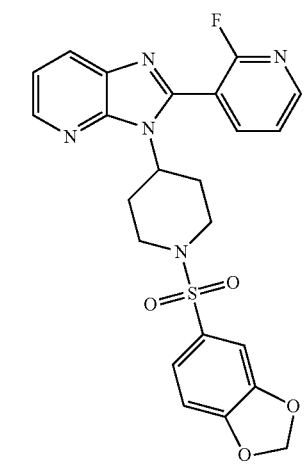 [SMILES: O=S(=O)(c1ccc2c(c1)OCO2)N1CCC(n2c(-c3cccnc3F)nc3cccnc32)CC1]
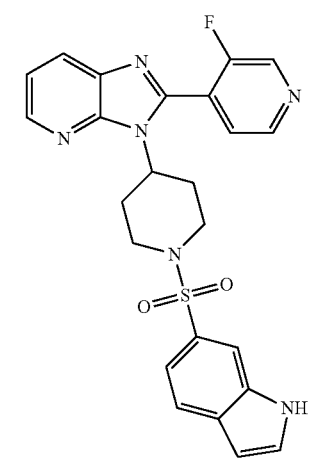

TABLE 4-continued
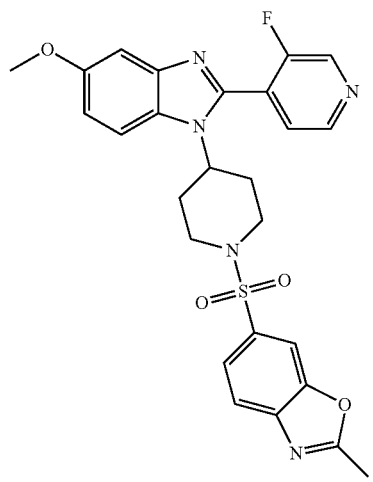
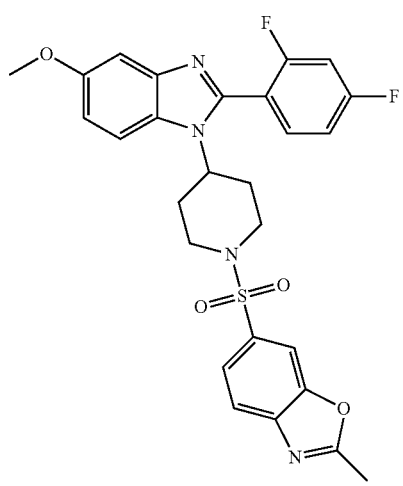 [SMILES: COc1ccc2c(c1)nc(-c1ccc(F)cc1F)n2C1CCN(S(=O)(=O)c2ccc3nc(C)oc3c2)CC1]
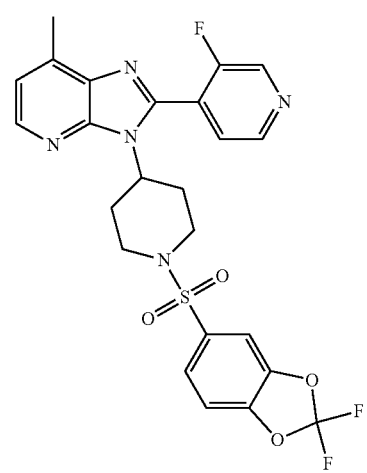 [SMILES: Cc1ccnc2c1nc(-c1ccncc1F)n2C1CCN(S(=O)(=O)c2ccc3c(c2)OC(F)(F)O3)CC1]
TABLE 4-continued
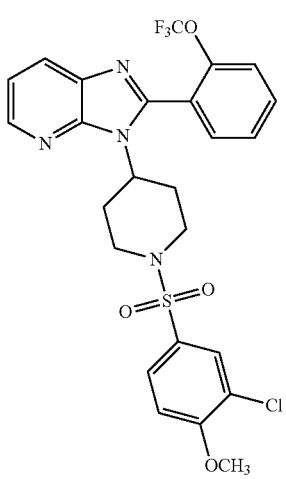
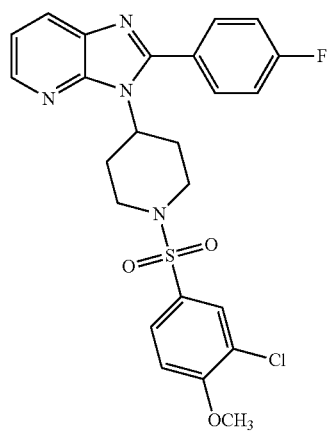 [SMILES: COc1ccc(S(=O)(=O)N2CCC(n3c(-c4ccc(F)cc4)nc4cccnc43)CC2)cc1Cl]
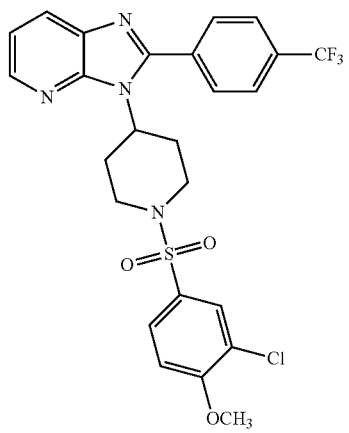 [SMILES: COc1ccc(S(=O)(=O)N2CCC(n3c(-c4ccc(C(F)(F)F)cc4)nc4cccnc43)CC2)cc1Cl]

TABLE 4-continued

TABLE 4-continued
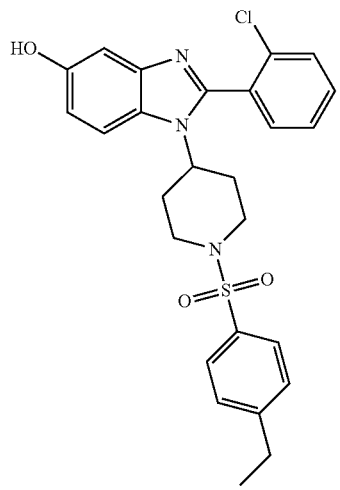 [SMILES: CCc1ccc(S(=O)(=O)N2CCC(n3c(-c4ccccc4Cl)nc4cc(O)ccc43)CC2)cc1]
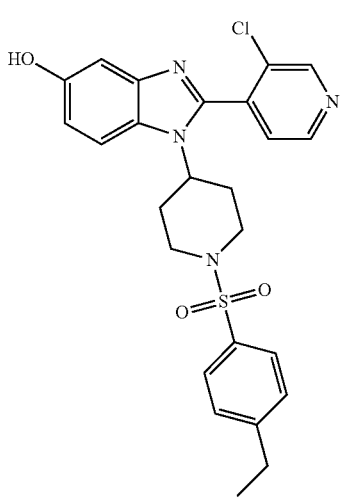 [SMILES: CCc1ccc(S(=O)(=O)N2CCC(n3c(-c4ccncc4Cl)nc4cc(O)ccc43)CC2)cc1]
TABLE 4-continued
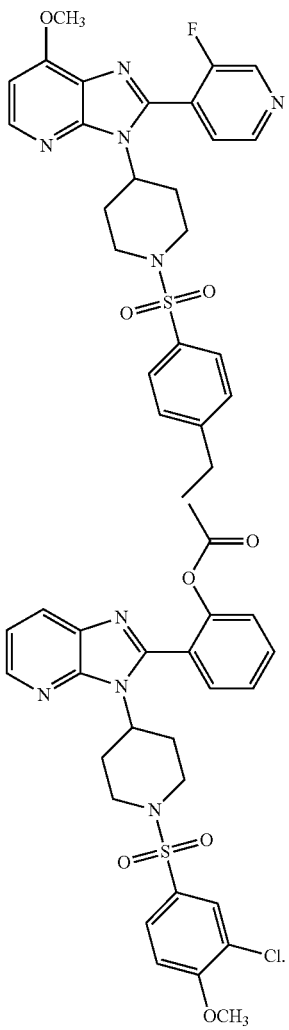
2. A pharmaceutical composition comprising a compound according to claim 1, or a pharmaceutically acceptable salt thereof, and a pharmaceutically acceptable carrier or excipient.
* * * * *